(12) United States Patent
Stansfield et al.

(10) Patent No.: US 11,186,589 B2
(45) Date of Patent: Nov. 30, 2021

(54) CYANOINDOLINE DERIVATIVES AS NIK INHIBITORS

(71) Applicant: Janssen Pharmaceutica NV, Beerse (BE)

(72) Inventors: Ian Stansfield, Issy-les Moulineaux (FR); Olivier Alexis Georges Querolle, Issy-les Moulineaux (FR); Yannick Aime Eddy Ligny, Issy-les Moulineaux (FR); Gerhard Max Gross, Beerse (BE); Edgar Jacoby, Beerse (BE); Lieven Meerpoel, Beerse (BE); Simon Richard Green, Harlow (GB); George Hynd, Harlow (GB); Janusz Jozef Kulagowski, Harlow (GB); Calum Macleod, Harlow (GB); Samuel Edward Mann, Harlow (GB)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/783,810

(22) Filed: Feb. 6, 2020

(65) Prior Publication Data
US 2021/0032267 A1 Feb. 4, 2021

Related U.S. Application Data

(63) Continuation of application No. 16/309,080, filed as application No. PCT/EP2017/066125 on Jun. 29, 2017, now abandoned.

(30) Foreign Application Priority Data

Jun. 30, 2016 (EP) .................................. 16177131
Jun. 30, 2016 (EP) .................................. 16177142
Jun. 30, 2016 (EP) .................................. 16177147

(51) Int. Cl.
| | |
|---|---|
| C07D 498/04 | (2006.01) |
| C07D 405/14 | (2006.01) |
| C07D 471/04 | (2006.01) |
| C07D 487/04 | (2006.01) |
| C07D 405/04 | (2006.01) |
| C07D 491/04 | (2006.01) |
| C07D 403/12 | (2006.01) |
| A61P 35/00 | (2006.01) |
| C07D 401/14 | (2006.01) |
| C07D 403/14 | (2006.01) |
| C07D 491/052 | (2006.01) |

(52) U.S. Cl.
CPC ............ *C07D 498/04* (2013.01); *A61P 35/00* (2018.01); *C07D 401/14* (2013.01); *C07D 403/12* (2013.01); *C07D 403/14* (2013.01); *C07D 405/04* (2013.01); *C07D 405/14* (2013.01); *C07D 471/04* (2013.01); *C07D 487/04* (2013.01); *C07D 491/04* (2013.01); *C07D 491/052* (2013.01)

(58) Field of Classification Search
CPC .. C07D 498/04; C07D 401/14; C07D 403/12; C07D 403/14; C07D 405/04; C07D 405/14; C07D 471/04; C07D 487/04; C07D 491/04; C07D 491/052; A61P 35/00
USPC ...................................................... 514/211.1
See application file for complete search history.

(56) References Cited

U.S. PATENT DOCUMENTS

2019/0119299 A1  4/2019  Stansfield et al.

FOREIGN PATENT DOCUMENTS

| | | |
|---|---|---|
| JP | 2003511378 A | 3/2003 |
| JP | 2014510794 A | 5/2014 |
| WO | WO 2001/025220 A1 | 4/2001 |
| WO | WO-0160816 A1 | 8/2001 |
| WO | WO-0164643 A2 | 9/2001 |
| WO | WO-02079197 A1 | 10/2002 |
| WO | WO-02102313 A2 | 12/2002 |
| WO | WO-03030909 A1 | 4/2003 |
| WO | WO-2009158011 A1 | 12/2009 |
| WO | WO-2009158571 A1 | 12/2009 |
| WO | WO-2010042337 A1 | 4/2010 |
| WO | WO-2011022440 A2 | 2/2011 |
| WO | WO-2011153553 A2 | 12/2011 |
| WO | WO-2012016217 A1 | 2/2012 |
| WO | WO 2012/142329 A1 | 10/2012 |
| WO | WO-2014174021 A1 | 10/2014 |
| WO | WO-2015030847 A1 | 3/2015 |
| WO | WO-2015044267 A1 | 4/2015 |
| WO | WO-2015044269 A1 | 4/2015 |

(Continued)

OTHER PUBLICATIONS

Cancer [online], [retrieved on Jul. 6, 2007] Retrieved from the Internet, URL: http://www.nlm.nih.gov/medlineplus/cancer.html (Year: 2007).*

(Continued)

*Primary Examiner* — Kristin A Vajda

(57) ABSTRACT

The present invention relates to pharmaceutical agents useful for therapy and/or prophylaxis in a mammal, and in particular to inhibitors of NF-κB-inducing kinase (NIK—also known as MAP3K14) useful for treating diseases such as cancer, inflammatory disorders, metabolic disorders and autoimmune disorders. The invention is also directed to pharmaceutical compositions comprising such compounds, and to the use of such compounds or pharmaceutical compositions for the prevention or treatment of diseases such as cancer, inflammatory disorders, metabolic disorders including obesity and diabetes, and autoimmune disorders.

20 Claims, No Drawings

(56) References Cited

FOREIGN PATENT DOCUMENTS

| | | |
|---|---|---|
| WO | WO-2015154039 A2 | 10/2015 |
| WO | WO-2015176135 A1 | 11/2015 |
| WO | WO-2016022645 A1 | 2/2016 |
| WO | WO 2016/049211 A1 | 3/2016 |
| WO | WO-2017114510 A1 | 7/2017 |
| WO | WO-2017125530 A1 | 7/2017 |
| WO | WO-2017125534 A1 | 7/2017 |
| WO | WO-2017161028 A1 | 9/2017 |
| WO | WO-2018002217 A1 | 1/2018 |
| WO | WO-2018002219 A1 | 1/2018 |

OTHER PUBLICATIONS

Lala et al., Role of nitric oxide in tumor progression: Lessons from experimental tumors, Cancer and Metastasis Reviews (1998), 17 , 91-106 (Year: 1998).*

Golub et al., Molecular Classification of Cancer: Class Discovery and Class Prediction by Gene Expression Monitoring, Science (1999), vol. 286, 531-537 (Year: 1999).*

F. Herrington, et al., "Modulation of NF-κB Signaling as a Therapeutic Target in Autoimmunity", Journal of Biomolecular Screening, (2016), vol. 21, No. 3, pp. 223-242.

G. McMahon, "VEGF Receptor Signaling in Tumor Angiogenesis", The Oncologist, (2000), vol. 5, suppl. 1, pp. 3-10.

H.M. Pinedo, et al., "Translational Research: The Role of VEGF in Tumor Angiogenesis", The Oncologist, (2000), vol. 5, suppl. 1, pp. 1-2.

D. Vrabel, et al., "The impact of NF-κB signaling on pathogenesis and current treatment strategies in multiple myeloma", Blood Reviews, (2019), vol. 34, pp. 56-66.

T.W. Greene and P.G.M. Wuts, Protective Groups in Organic Synthesis, $4^{th}$ ed., Wiley, Hoboken, New Jersey, 2007.

Allen et al. NLRP12 suppresses colon inflammation and tumorigenesis through the negative regulation of noncanonical NF-κB signaling. Immunity. 36: 742-754 (2012).

Annuziata et al. Frequent engagement of the classical and alternative NF-κB pathways by diverse genetic abnormalities in multiple myeloma. Cancer Cell. 12: 115-130 (2007).

Aya et al. NF-κB-inducing kinase controls lymphocyte and osteoclast activities in inflammatory arthritis. J. Clin. Invest. 115: 1848-1854 (2005).

Bhattacharyya et al. Tumor necrosis factor alpha-induced inflammation is increased but apoptosis is inhibited by common food additive carrageenan. J Biol. Chem. 285: 39511-39522 (2011).

Bitar et al. Inflammation and apoptosis in aortic tissues of aged type II diabetes: Amelioration with α-lipoic acid through phosphatidylinositol 3-kinase/Akt-dependent mechanism. Life Sci. 86: 844-853 (2010).

Bushell et al., Genetic inactivation of TRAF3 in canine and human B-cell lymphoma. Blood. 125: 999-1005 (2015).

Choudhary et al. NF-κB-lnducing Kinase (NIK) mediates skeletal muscle insulin resistance: blockade by adiponectin. Endocrinology. 152: 3622-3627 (2011).

Chung et al. NF-κB Inducing Kinase, NIK mediates cigarette smoke/TNFa-induced histone acetylation and inflammation through differential activation of IKKs. PLoS ONE. 6(8): e23488. doi:10.1371/journal.pone.0023488 (2011).

Demchenko et al. Classical and/or alternative NF-κB pathway activation in multiple myeloma. Blood. 115: 3541-3552 (2010).

Gennaro et al. Remington's Pharmaceutical Sciences (18th ed., Mack Publishing Company, 1990, see especially Part 8 : Pharmaceutical preparations and their Manufacture (1990).

Hughes et al., 4-Aryl-5-cyano-2-aminopyrimidines as VEGF-R2 inhibitors: synthesis and biological evaluation.Bioorg Med Chem Lett. 17(12):3266-3270 (2007).

International Application No. PCT/EP2017/066120 International Preliminary Report on Patentability dated Jan. 1, 2019.

Keats et al. Promiscuous mutations activate the noncanonical NF-κB pathway in multiple myeloma. Cancer Cell. 12: 131-144 (2007).

Nishina et al. NIK is involved in constitutive activation of the alternative NF-jB pathway and proliferation of pancreatic cancer cells. Biochemical and Biophysical Research Communications. 388: 96-101 (2009).

Pham et al. Constitutive BR3 receptor signaling in diffuse, large B-cell lymphomas stabilizes nuclear factor-B-inducing kinase while activating both canonical and alternative nuclear factor-B pathways. Blood. 117:200-210 (2011).

Rahal et al., Pharmacological and genomic profiling identifies NF-κB-targeted treatment strategies for mantle cell lymphoma. Nature Medicine. 20(1): 87-92 (2014).

Ranuncolo et al. Hodgkin lymphoma requires stabilized NIK and constitutive RelB expression for survival. Blood First Edition Paper. DOI 10.1182/blood-2012-01-405951; 120(18): 3756-3763 (2012).

Rosebeck et al. Cleavage of NIK by the API2-MALT1 fusion oncoprotein leads to noncanonical NF-κB activation. Science. 331: 468-472 (2011).

Saitoh et al. Overexpressed NF-B-inducing kinase contributes to the tumorigenesis of adult T-cell leukemia and Hodgkin Reed-Sternberg cells. Blood. 111: 5118-5129 (2008).

Shuto et al. Activation of NF-κB by nontypeable Hemophilus influenzae is mediated by toll-like receptor 2-TAK1-dependent NIK-IKKayb-IkBa and MKK3y6-p38 MAP kinase signaling pathways in epithelial cells. PNAS. 98: 8774-8779 (2001).

International Application No. PCT/EP2017/066125 International Preliminary Report on Patentability dated Jan. 1, 2019.

PCT/EP2017/066125International Search Report and Written Opinion dated Jul. 27, 2017.

PCT/EP2017/051150 International Preliminary Report on Patentability dated Jul. 24, 2018.

PCT/EP2017/051150 International Search Report and Written Opinion dated Mar. 2, 2017.

PCT/EP2017/051160 International Preliminary Report on Patentability dated Jul. 24, 2018.

PCT/EP2017/051160 International Search Report and Written Opinion dated Mar. 9, 2017.

PCT/EP2017/066120 International Search Report and Written Opinion dated Aug. 23, 2017.

Thu and Richmond, NF-κB inducing kinase: a key regulator in the immune system and in cancer. Cytokine Growth F. R. 21: 213-226 (2010).

Thu et al. NF-κB inducing kinase (NIK) modulates melanoma tumorigenesis by regulating expression of pro-survival factors through the b-catenin pathway. Oncogene. 31(20), 2580-2592 (2012).

Wixted et al. A model to identify novel targets involved in oxidative stress-induced apoptosis in human lung epithelial cells by RNA interference. Toxicology In Vitro. 24: 310-318 (2010).

Yamamoto et al. Epigenetic alteration of the NF-κB-inducing kinase (NIK) gene is involved in enhanced NIK expression in basal-like breast cancer. Cancer Science. 101: 2391-2397 (2010).

Yang et al. NIK stabilization in osteoclasts results in osteoporosis and enhanced inflammatory osteolysis. PLoS ONE. 5(11): e15383. doi:10.1371/journal.pone.0015383 (2010).

Zhao et al. NF-κB-lnducing kinase increases renal tubule epithelial inflammation associated with diabetes. Exp. Diabetes Res. 2011: 1-9 (2011).

\* cited by examiner

CYANOINDOLINE DERIVATIVES AS NIK INHIBITORS

CROSS REFERENCE TO RELATED APPLICATIONS

This application is a continuation application of U.S. Ser. No. 16/309,080, filed Dec. 11, 2018, which application is a § 371 US national stage application of International PCT Application No. PCT/EP2017/066125, filed Jun. 29, 2017, which claims the benefit of European Application No. 16177131.6, filed Jun. 30, 2016, European Application No. 16177142.3, filed Jun. 30, 2016, and European Application No. 16177147.2, filed Jun. 30, 2016, each of which applications are incorporated herein by reference in their entirety.

FIELD OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer (in particular B-cell malignancies including leukemias, lymphomas and myeloma), inflammatory disorders, metabolic disorders including obesity and diabetes, and autoimmune disorders. The invention is also directed to pharmaceutical compositions comprising such compounds, and to the use of such compounds or pharmaceutical compositions for the prevention or treatment of diseases such as cancer, inflammatory disorders, metabolic disorders including obesity and diabetes, and autoimmune disorders.

BACKGROUND OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer and inflammatory disorders. Nuclear factor-kappa B (NF-κB) is a transcription factor regulating the expression of various genes involved in the immune response, cell proliferation, adhesion, apoptosis, and carcinogenesis. NF-κB dependent transcriptional activation is a tightly controlled signaling pathway, through sequential events including phosphorylation and protein degradation. NIK is a serine/threonine kinase which regulates NF-κB pathway activation. There are two NF-κB signaling pathways, the canonical and the non-canonical. NIK is indispensable for the non-canonical signaling pathway where it phosphorylates IKKα, leading to the partial proteolysis of p100; liberating p52 which then heterodimerizes with RelB, translocates to the nucleus and mediates gene expression. The non-canonical pathway is activated by only a handful of ligands such as CD40 ligands, B-cell activating factor (BAFF), lymphotoxin β receptor ligands and TNF-related weak inducer of apoptosis (TWEAK) and NIK has been shown to be required for activation of the pathway by these ligands. Because of its key role, NIK expression is tightly regulated. Under normal non-stimulated conditions NIK protein levels are very low, this is due to its interaction with a range of TNF receptor associated factors (TRAF2 and TRAF3), which are ubiquitin ligases and result in degradation of NIK. It is believed that when the non-canonical pathway is stimulated by ligands, the activated receptors now compete for TRAFs, dissociating the TRAF-NIK complexes and thereby increasing the levels of NIK. (Thu and Richmond, *Cytokine Growth F. R.* 2010, 21, 213-226)

Research has shown that blocking the NF-κB signaling pathway in cancer cells can cause cells to stop proliferating, to die and to become more sensitive to the action of other anti-cancer therapies. A role for NIK has been shown in the pathogenesis of both hematological malignancies and solid tumours.

The NF-κB pathway is dysregulated in multiple myeloma due to a range of diverse genetic abnormalities that lead to the engagement of the canonical and non-canonical pathways (Annuziata et al. *Cancer Cell* 2007, 12, 115-130; Keats et al. *Cancer Cell* 2007, 12, 131-144; Demchenko et al. *Blood* 2010, 115, 3541-3552). Myeloma patient samples frequently have increased levels of NIK activity. This can be due to chromosomal amplification, translocations (that result in NIK proteins that have lost TRAF binding domains), mutations (in the TRAF binding domain of NIK) or TRAF loss of function mutations. Researchers have shown that myeloma cell lines can be dependent on NIK for proliferation; in these cell lines if NIK activity is reduced by either shRNA or compound inhibition, this leads to a failure in NF-κB signaling and the induction of cell death (Annuziata, 2007).

In a similar manner, mutations in TRAF and increased levels of NIK have also been seen in samples from Hodgkin lymphoma (HL) patients. Once again proliferation of cell lines derived from HL patients is susceptible to inhibition of NIK function by both shRNA and compounds (Ranuncolo et al. *Blood* First Edition Paper, 2012, DOI 10.1182/blood-2012-01-405951).

NIK levels are also enhanced in adult T cell leukemia (ATL) cells and targeting NIK with shRNA reduced ATL growth in vivo (Saitoh et al. *Blood* 2008, 111, 5118-5129).

It has been demonstrated that the API2-MALT1 fusion oncoprotein created by the recurrent translocation t(11;18)(q21;q21) in mucosa-associated lymphoid tissue (MALT) lymphoma induces proteolytic cleavage of NF-κB-inducing kinase (NIK) at arginine 325. NIK cleavage generates a C-terminal NIK fragment that retains kinase activity and is resistant to proteasomal degradation (due to loss of TRAF binding region). The presence of this truncated NIK leads to constitutive non-canonical NF-κB signaling, enhanced B cell adhesion, and apoptosis resistance. Thus NIK inhibitors could represent a new treatment approach for refractory t(11;18)-positive MALT lymphoma (Rosebeck et al. *Science* 2011, 331, 468-472).

NIK aberrantly accumulates in diffuse large B-cell lymphoma (DLBCL) cells due to constitutive activation of B-cell activation factor (BAFF) through interaction with autochthonous B-lymphocyte stimulator (BLyS) ligand. NIK accumulation in human DLBCL cell lines and patient tumor samples suggested that constitutive NIK kinase activation is likely to be a key signaling mechanism involved in abnormal lymphoma tumor cell proliferation. Growth assays showed that using shRNA to inhibit NIK kinase protein expression in GCB- and ABC-like DLBCL cells decreased lymphoma cell growth in vitro, implicating NIK-induced NF-κB pathway activation as having a significant role in DLBCL proliferation (Pham et al. *Blood* 2011, 117, 200-210).

More recently, also loss-of-function mutations in TRAF3 have been characterized in human and canine DLBCL (Bushell et al., *Blood* 2015, 125, 999-1005).

Recently, similar mutations in the non-canonical NFkB signaling pathway (TRAF2, TRAF3, NIK, BIRC3) were found in ibrutinib-refractory mantle cell lymphoma cell lines (Rahal et al., *Nat Med* 2014, 1, 87-92).

As mentioned a role of NIK in tumour cell proliferation is not restricted to hematological cells, there are reports that NIK protein levels are stabilised in some pancreatic cancer cell lines and as seen in blood cells proliferation of these pancreatic cancer lines are susceptible to NIK siRNA treatment (Nishina et al. *Biochem. Bioph. Res. Co.* 2009, 388, 96-101). Constitutive activation of NF-κB, is preferentially involved in the proliferation of basal-like subtype breast cancer cell lines, including elevated NIK protein levels in specific lines (Yamamoto et al. *Cancer Sci.* 2010, 101, 2391-2397). In melanoma tumours, tissue microarray analysis of NIK expression revealed that there was a statistically significant elevation in NIK expression when compared with benign tissue. Moreover, shRNA techniques were used to knock-down NIK, the resultant NIK-depleted melanoma cell lines exhibited decreased proliferation, increased apoptosis, delayed cell cycle progression and reduced tumor growth in a mouse xenograft model (Thu et al. *Oncogene* 2012, 31(20), 2580-92). A wealth of evidence showed that NF-κB is often constitutively activated in non-small cell lung cancer tissue specimens and cell lines. Depletion of NIK by RNAi induced apoptosis and affected efficiency of anchorage-independent NSCLC cell growth.

In addition research has shown that NF-κB controls the expression of many genes involved in inflammation and that NF-κB signalling is found to be chronically active in many inflammatory diseases, such as rheumatoid arthritis, inflammatory bowel disease, sepsis and others. Thus pharmaceutical agents capable of inhibiting NIK and thereby reducing NF-κB signaling pathway can have a therapeutic benefit for the treatment of diseases and disorders for which over-activation of NF-κB signaling is observed.

Dysregulated NF-κB activity is associated with colonic inflammation and cancer, and it has been shown that Nlrp12 deficient mice were highly susceptible to colitis and colitis-associated colon cancer. In this context work showed that NLRP12 functions as a negative regulator of the NF-κB pathway through its interaction and regulation of NIK and TRAF3, and as a checkpoint of critical pathways associated with inflammation and inflammation-associated tumorigenesis (Allen et al. *Immunity* 2012, 36, 742-754).

Tumor necrosis factor (TNF)-α, is secreted in response to inflammatory stimuli in diseases such as rheumatoid arthritis and inflammatory bowel disease. In a series of experiments in colonic epithelial cells and mouse embryonic fibroblasts, TNF-α mediates both apoptosis and inflammation, stimulating an inflammatory cascade through the non-canonical pathway of NF-κB activation, leading to increased nuclear RelB and p52. TNF-α induced the ubiquitination of TRAFs, which interacts with NIK, leading to increased levels of phospho-NIK (Bhattacharyya et al. *J Biol. Chem.* 2011, 285, 39511-39522).

Inflammatory responses are a key component of chronic obstructive pulmonary disease (COPD) as such it has been shown that NIK plays a key role in exacerbating the disease following infection with the Gram-negative bacterium non-typeable *Hemophilus influenza* (Shuto et al. *PNAS* 2001, 98, 8774-8779). Likewise cigarette smoke (CS) contains numerous reactive oxygen/nitrogen species, reactive aldehydes, and quinones, which are considered to be some of the most important causes of the pathogenesis of chronic inflammatory lung diseases, such as COPD and lung cancer. Increased levels of NIK and p-IKKα have been observed in peripheral lungs of smokers and patients with COPD. In addition it has been shown that endogenous NIK is recruited to promoter sites of pro-inflammatory genes to induce post-translational modification of histones, thereby modifying gene expression profiles, in response to CS or TNFα (Chung et al. *PLoS ONE* 2011, 6(8): e23488. doi:10.1371/journal.pone.0023488). A shRNA screen was used in an in vitro model of oxidative stress induced cell death (as a model of COPD) to interrogate a human drugable genome siRNA library in order to identify genes that modulate the cellular response to stress. NIK was one of the genes identified in this screen as a potential new therapeutic target to modulate epithelial apoptosis in chronic lung diseases (Wixted et al. *Toxicol. In Vitro* 2010, 24, 310-318).

Diabetic individuals can be troubled by a range of additional manifestations associated with inflammation. One such complication is cardiovascular disease and it has been shown that there are elevated levels of p-NIK, p-IKK-α/β and p-IκB-α in diabetic aortic tissues (Bitar et al. *Life Sci.* 2010, 86, 844-853). In a similar manner, NIK has been shown to regulate proinflammatory responses of renal proximal tubular epithelial cells via mechanisms involving TRAF3. This suggests a role for NF-κB noncanonical pathway activation in modulating diabetes-induced inflammation in renal tubular epithelium (Zhao et al. *Exp. Diabetes Res.* 2011, 1-9. doi:10.1155/2011/192564). The same group has shown that NIK plays a critical role in noncanonical NF-κB pathway activation, induced skeletal muscle insulin resistance in vitro, suggesting that NIK could be an important therapeutic target for the treatment of insulin resistance associated with inflammation in obesity and type 2 diabetes (Choudhary et al. *Endocrinology* 2011, 152, 3622-3627).

NF-κB is an important component of both autoimmunity and bone destruction in rheumatoid arthritis (RA). Mice lacking functional NIK have no peripheral lymph nodes, defective B and T cells, and impaired receptor activator of NF-κB ligand-stimulated osteoclastogenesis. Aya et al. (*J. Clin. Invest.* 2005, 115, 1848-1854) investigated the role of NIK in murine models of inflammatory arthritis using Nik−/− mice. The serum transfer arthritis model was initiated by preformed antibodies and required only intact neutrophil and complement systems in recipients. While Nik−/− mice had inflammation equivalent to that of Nik+/+ controls, they showed significantly less periarticular osteoclastogenesis and less bone erosion. In contrast, Nik−/− mice were completely resistant to antigen-induced arthritis (AIA), which requires intact antigen presentation and lymphocyte function but not lymph nodes. Additionally, transfer of Nik+/+ splenocytes or T cells to Rag2−/− mice conferred susceptibility to AIA, while transfer of Nik−/− cells did not. Nik−/− mice were also resistant to a genetic, spontaneous form of arthritis, generated in mice expressing both the KRN T cell receptor and H-2 g7. The same group used transgenic mice with OC-lineage expression of NIK lacking its TRAF3 binding domain (NT3), to demonstrate that constitutive activation of NIK drives enhanced osteoclastogenesis and bone resorption, both in basal conditions and in response to inflammatory stimuli (Yang et al. *PLoS ONE* 2010, 5(11): e15383. doi:10.1371/journal.pone.0015383). Thus this group concluded that NIK is important in the immune and bone-destructive components of inflammatory arthritis and represents a possible therapeutic target for these diseases.

It has also been hypothesized that manipulating levels of NIK in T cells may have therapeutic value. Decreasing NIK activity in T cells might significantly ameliorate autoimmune responses and alloresponses, like GVHD (Graft Versus Host Disease) and transplant rejection, without crippling the immune system as severely as do inhibitors of canonical NF-κB activation.

WO2003030909 describes the preparation of 2- and 4-aminopyrimidines N-substituted by a bicyclic ring for use as kinase inhibitors in the treatment of cancer.

WO2002079197 describes 4-aryl-substituted 2-pyrimidinamines and 2-pyridinamines, useful as inhibitors of c-Jun N-terminal kinases (JNK) and other protein kinases.

WO2014174021, WO2015044267 and WO2015044269 describe NIK inhibitors for the treatment of cancer.

WO2010042337 describes 6-azaindole aminopyrimidine derivatives having NIK inhibitory activity.

SUMMARY OF THE INVENTION

The present invention concerns novel compounds of Formula (I)

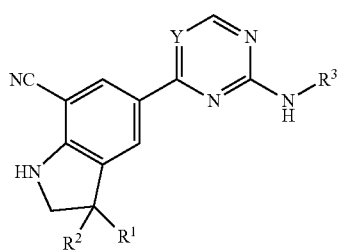

(I)

tautomers and stereoisomeric forms thereof, wherein
$R^1$ represents $C_{1-4}$alkyl;
$R^2$ represents $C_{1-6}$alkyl, $C_{1-6}$alkyl substituted with one $R^5$, or $C_{1-6}$alkyl substituted with one, two or three fluoro atoms;
Y represents $CR^4$ or N;
$R^4$ represents hydrogen or halo;
$R^5$ represents $Het^{3a}$, —$NR^{6a}R^{6b}$, or —$OR^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;
$R^{1a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of —NH$_2$, —COOH, and $Het^6$;
$R^{16a}$ and $R^{16b}$ each independently represents hydrogen, $C_{1-4}$alkyl or $C_{3-6}$cycloalkyl;
$R^3$ represents
a) a fused bicyclic ring system of formula (1a-1) or (1a-2):

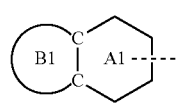

(1a-1)

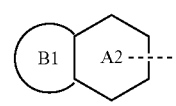

(1a-2)

ring A1 represents phenyl or a 6-membered heteroaromatic ring containing 1 or 2 N-atoms;
ring A2 represents 2-oxo-1,2-dihydropyridin-3-yl;
ring B1 represents a 4- to 7-membered saturated heterocyclyl containing one or two heteroatoms each independently selected from O, S, S(=O)$_p$ and N;
wherein (1a-1) and (1a-2) may optionally be substituted on the ring carbon atoms with in total one, two or three substituents each independently selected from the group consisting of halo; cyano; oxo; —OH; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$ alkyl; —O—$C_{1-4}$alkyl substituted with one, two or three halo atoms; —O—$C_{1-4}$alkyl-$R^{12}$; $C_{3-6}$ cycloalkyl; —O—$C_{3-6}$cycloalkyl; $Het^{1a}$; —O-$Het^{1b}$; $R^{18}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;
wherein ring A2 may optionally be substituted, where possible, on the N-atom with a substituent selected from the group consisting of $C_{1-6}$alkyl; $C_{3-6}$cycloalkyl; $Het^{1a}$; $R^{18}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when $Het^{1a}$ or $R^{18}$ are directly attached to the N-atom of ring A2, said $Het^{1a}$ or $R^{18}$ are attached to the N-atom via a ring carbon atom; and wherein ring B1 may optionally be substituted, where possible, on one or two ring N-atoms with a substituent each independently selected from the group consisting of $C_{1-6}$alkyl; $C_{3-6}$cycloalkyl; $Het^{1a}$; $R^{18}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; —(C=O)—$C_{1-4}$alkyl; —C(=O)$NR^{14g}R^{14h}$; —C(=O)—$C_{1-4}$alkyl-$NR^{14i}R^{14j}$; —C(=O)—C(=O)—$NR^{14k}R^{14l}$; $C_{2-6}$alkenyl; and $C_{2-6}$alkenyl substituted with one $R^{13}$; provided that when $Het^{1a}$ or $R^{18}$ are directly attached to the N-atom of ring B1, said $Het^{1a}$ or $R^{18}$ are attached to the N-atom via a ring carbon atom; or
b) a fused bicyclic ring system of formula (2a-1):

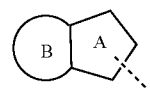

(2a-1)

ring A represents pyrazolyl optionally substituted with one substituent selected from the group consisting of $C_{1-4}$alkyl, —$C_{1-4}$alkyl-O—$C_{1-4}$alkyl, and $C_{1-4}$alkyl substituted with one, two or three halo atoms;
ring B represents a $C_{5-7}$cycloalkyl or a 5- to 7-membered saturated heterocyclyl containing one or two heteroatoms each independently selected from O and N;
wherein said $C_{5-7}$cycloalkyl or 5- to 7-membered saturated heterocyclyl may optionally be substituted on one or two ring carbon atoms with one or two substituents each independently selected from the group consisting of $C_{1-4}$alkyl, —$C_{1-4}$alkyl-O—$C_{1-4}$alkyl and —$C_{1-4}$alkyl-OH, or one ring carbon atom may optionally be substituted with oxo; and wherein said 5- to 7-membered saturated heterocyclyl may optionally be substituted on one or two ring N-atoms with a substituent each independently selected from the group consisting of $C_{1-6}$ alkyl; $C_{3-6}$cycloalkyl; $C_{1-4}$alkyl substituted with one, two or three halo atoms; $C_{1-4}$alkyl substituted with one, two or three —OH substituents; $C_{1-4}$alkyl substituted with one $R^{13}$; —(C(=O)—$C_{1-4}$alkyl; —C(=O) $NR^{14g}R^{14h}$; —C(=O)—$C_{1-4}$alkyl-$NR^{14i}R^{14j}$; or c) a fused 6- to 11-membered bicyclic heteroaromatic ring system containing one or two heteroatoms each independently selected from O, S, and N;

wherein said fused 6- to 11-membered bicyclic heteroaromatic ring system may optionally be substituted on the ring carbon atoms with in total one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; —P(=O)—($C_{1-4}$alkyl)$_2$; —NH—C(=O)—$C_{1-4}$alkyl; —NH—C(=O)—$Het^1$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; and wherein said fused 6- to 11-membered bicyclic heteroaromatic ring system may optionally be substituted, where possible, on one ring N-atom with a substituent selected from the group consisting of $C_{1-6}$alkyl; $C_{3-6}$cycloalkyl; $Het^{1a}$; $R^{18}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; —(C(=O)—$C_{1-4}$alkyl; —C(=O) $NR^{14g}R^{14h}$; —C(=O)—$C_{1-4}$alkyl-$NR^{14i}R^{14j}$; —C(=O)—C(=O)—$NR^{14k}R^{14l}$; $C_{2-6}$alkenyl; and $C_{2-6}$alkenyl substituted with one $R^{13}$; provided that when $Het^{1a}$ or $R^{18}$ are directly attached to a N-atom, said $Het^{1a}$ or $R^{18}$ are attached to the N-atom via a ring carbon atom;

$R^{10}$ represents —OH, —O—$C_{1-4}$alkyl, —$NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$Het^2$ represents a heterocyclyl of formula (b-1)

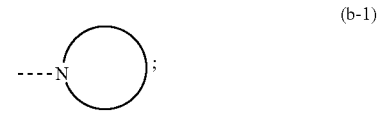

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$ alkyl, —O—$C_{1-4}$alkyl, —$NH_2$, —NH($C_{1-4}$alkyl), —N($C_{1-4}$alkyl)$_2$, and $C_{1-4}$alkyl-OH;

$R^{11b}$ represents hydrogen; $Het^{1e}$; $C_{1-4}$alkyl; $C_{1-4}$alkyl-$Het^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, —S(=O)$_2$—$C_{1-4}$alkyl, —S(=O)(=N—$R^{20c}$)—$C_{1-4}$alkyl, or —C(=O)—$Het^{1f}$;

$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, —S(=O) (=N—$R^{2b}$)—$C_{1-4}$alkyl, $C_{3-6}$cycloalkyl, $Ar^2$, or $Het^{1c}$;

$Ar^1$ represents phenyl optionally substituted with one hydroxy;

$Ar^2$ represents phenyl optionally substituted with one $C_{1-4}$alkyl; or a 5- or 6-membered heteroaromatic ring containing one, two or three heteroatoms each independently selected from O, S, and N;

$Het^{3a}$, $Het^{3b}$, $Het^5$, $Het^6$ and $Het^{1f}$ each independently represents a heterocyclyl of formula (c-1)

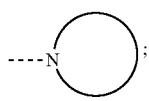

(c-1) represents a N-linked 4- to 7-membered monocyclic saturated heterocyclyl optionally containing one additional heteroatom selected from O, S, S(=O)$_p$ and N;
wherein in case (c-1) contains one additional N-atom, said additional N-atom may optionally be substituted with C$_{1-4}$alkyl or C$_{3-6}$cycloalkyl; and
wherein (c-1) may optionally be substituted on one or two ring C-atoms atoms with one or two substituents each independently selected from the group consisting of halo, C$_{1-4}$alkyl, and C$_{3-6}$cycloalkyl;
$R^{11a}$, $R^{14a}$, $R^{14c}$, $R^{14g}$, $R^{14i}$, $R^{14k}$, $R^{15a}$, $R^{17a}$ and $R^{19a}$ each independently represents hydrogen or C$_{1-4}$ alkyl;
$R^{14b}$, $R^{14d}$, $R^{14h}$, $R^{14j}$, $R^{14l}$, $R^{15b}$, $R^{17b}$ and $R^{19b}$ each independently represents hydrogen; C$_{1-4}$alkyl; C$_{3-6}$cycloalkyl; or C$_{1-4}$alkyl substituted with one substituent selected from the group consisting of halo, —OH and —O—C$_{1-4}$alkyl;
$R^{20}$, $R^{20b}$ and $R^{20c}$ each independently represents hydrogen; C$_{1-4}$alkyl; C$_{3-6}$cycloalkyl; or C$_{1-4}$alkyl substituted with one substituent selected from the group consisting of —OH and —O—C$_{1-4}$ alkyl;
p represents 1 or 2;
and the pharmaceutically acceptable addition salts, and the solvates thereof.

The present invention also relates to a pharmaceutical composition comprising a therapeutically effective amount of a compound of Formula (I), a pharmaceutically acceptable addition salt, or a solvate thereof, and a pharmaceutically acceptable carrier or excipient.

Additionally, the invention relates to a compound of Formula (I), a pharmaceutically acceptable addition salt, or a solvate thereof, for use as a medicament, and to a compound of Formula (I), a pharmaceutically acceptable addition salt, or a solvate thereof, for use in the treatment or in the prevention of cancer, inflammatory disorders, autoimmune disorders, and metabolic disorders such as diabetes and obesity.

In a particular embodiment, the invention relates to a compound of Formula (I), a pharmaceutically acceptable addition salt, or a solvate thereof, for use in the treatment or in the prevention of a haematological malignancy or solid tumour.

In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma. In another specific embodiment of the present invention, the solid tumour is selected from the group consisting of pancreatic cancer, breast cancer, melanoma and non-small cell lung cancer.

The invention also relates to the use of a compound of Formula (I), a pharmaceutically acceptable addition salt, or a solvate thereof, in combination with an additional pharmaceutical agent for use in the treatment or prevention of cancer, inflammatory disorders, autoimmune disorders, and metabolic disorders such as diabetes and obesity.

Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable addition salt, or a solvate thereof.

The invention also relates to a product comprising a compound of Formula (I), a pharmaceutically acceptable addition salt, or a solvate thereof, and an additional pharmaceutical agent, as a combined preparation for simultaneous, separate or sequential use in the treatment or prevention of cancer, inflammatory disorders, autoimmune disorders, and metabolic disorders such as diabetes and obesity.

Additionally, the invention relates to a method of treating or preventing a cell proliferative disease in a warm-blooded animal which comprises administering to the said animal an effective amount of a compound of Formula (I), a pharmaceutically acceptable addition salt, or a solvate thereof, as defined herein, or a pharmaceutical composition or combination as defined herein.

Some of the compounds of the present invention may undergo metabolism to a more active form in vivo (prodrugs).

DETAILED DESCRIPTION OF THE INVENTION

The term 'halo' or 'halogen' as used herein represents fluoro, chloro, bromo and iodo.

The prefix 'C$_{x-y}$' (where x and y are integers) as used herein refers to the number of carbon atoms in a given group. Thus, a C$_{1-6}$alkyl group contains from 1 to 6 carbon atoms, a C$_{3-6}$cycloalkyl group contains from 3 to 6 carbon atoms, and so on.

The term 'C$_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term 'C$_{1-6}$alkyl' as used herein as a group or part of a group represents a straight or branched chain saturated hydrocarbon radical having from 1 to 6 carbon atoms such as the groups defined for C$_{1-4}$alkyl and n-pentyl, n-hexyl, 2-methylbutyl and the like.

The term "C$_{2-6}$alkenyl" as used herein as a group or part of a group represents a straight or branched chain hydrocarbon group containing from 2 to 6 carbon atoms and containing a carbon carbon double bond such as, but not limited to, ethenyl, propenyl, butenyl, pentenyl, 1-propen-2-yl, hexenyl and the like.

The term 'C$_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

In general, whenever the term "substituted" is used in the present invention, it is meant, unless otherwise is indicated or is clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

The skilled person will understand that the term "optionally substituted" means that the atom or radical indicated in the expression using "optionally substituted" may or may not be substituted (this means substituted or unsubstituted respectively).

When two or more substituents are present on a moiety they may, where possible and unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom (e.g. a hydrogen on a nitrogen atom may be replaced by a substituent), for example in saturated heterocyclyl groups or 5-membered aromatic rings as used in the definition of $R^{18}$.

C(O) or C(=O) represents a carbonyl moiety.

S(=O)$_2$ or SO$_2$ represents a sulfonyl moiety.

"oxo" means =O; for example piperidine substituted with oxo in position 2 is represented by the following structure

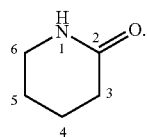

The skilled person will understand that —S(=O)(=N—$R^{20a}$)—C$_{1-4}$alkyl corresponds with

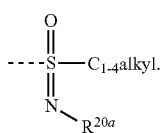

Within the context of this invention 'saturated' means 'fully saturated', if not otherwise specified.

Het$^{1a}$, Het$^{1c}$ and Het$^{1d}$, may be attached to the remainder of the molecule of Formula (I) through any available ring carbon or nitrogen atom as appropriate, if not otherwise specified.

The 5-membered aromatic ring containing one, two or three N-atoms as referred to in the definition of $R^{18}$, may be attached to the remainder of the molecule of Formula (I) through any available ring carbon or nitrogen atom as, if not otherwise specified.

It will be clear that in case a saturated cyclic moiety is substituted on two ring carbon atoms with one substituent, in total two carbon-linked substituents are present on the saturated cyclic moiety (one substituent on each carbon atom).

It will be clear that in case a saturated cyclic moiety is substituted on two ring carbon atoms with two substituents, in total four carbon-linked substituents are present on the saturated cyclic moiety (two substituents on each carbon atom).

It will be clear that in case a saturated cyclic moiety is substituted on three ring carbon atoms with two substituents, in total six carbon-linked substituents are present on the saturated cyclic moiety (two substituents on each carbon atom).

It will be clear that in case a saturated cyclic moiety is substituted on two ring N-atoms with a substituent, in total two N-linked substituents are present on the saturated cyclic moiety (a substituent on each N-atom).

It will be clear that a saturated cyclic moiety may, where possible, have substituents on both carbon and N-atoms, unless otherwise is indicated or is clear from the context.

Within the context of this invention, bicyclic saturated heterocyclyl groups include fused, spiro and bridged saturated heterocycles.

Fused bicyclic groups are two cycles that share two atoms and the bond between these atoms.

Spiro bicyclic groups are two cycles that are joined at a single atom.

Bridged bicyclic groups are two cycles that share more than two atoms.

Examples of N-linked 6- to 11-membered fused bicyclic saturated heterocyclyl groups, include, but are not limited to

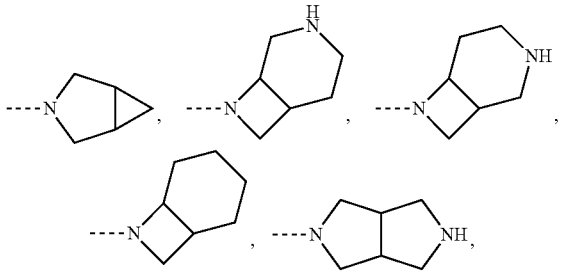

and the like.

Examples of N-linked 6- to 11-membered spiro bicyclic saturated heterocyclyl groups, include, but are not limited to

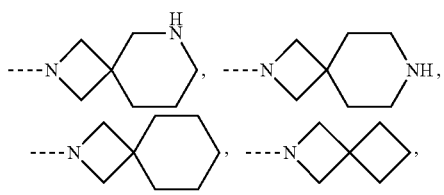

and the like.

Examples of N-linked 6- to 11-membered bridged bicyclic saturated heterocyclyl groups, include, but are not limited to

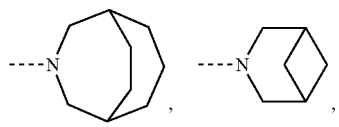

and the like.

The skilled person will realize that the definition of Het$^{1a}$, Het$^{1c}$ and Het$^{1d}$ also includes C-linked bicycles (attached to the remainder of the molecule of Formula (I) through any available ring carbon atom).

It should be understood that the exemplified bicyclic saturated heterocyclyl groups referred to above may optionally be substituted, where possible, on carbon and/or nitrogen atoms according to any of the embodiments.

Non-limiting examples of 4- to 7-membered monocyclic saturated heterocyclyl moieties containing one or two heteroatoms each independently selected from O, S, S(=O)$_p$ and N (as in the definition of Het$^{1a}$, Het$^{1c}$, and Het$^{1d}$) are shown below:

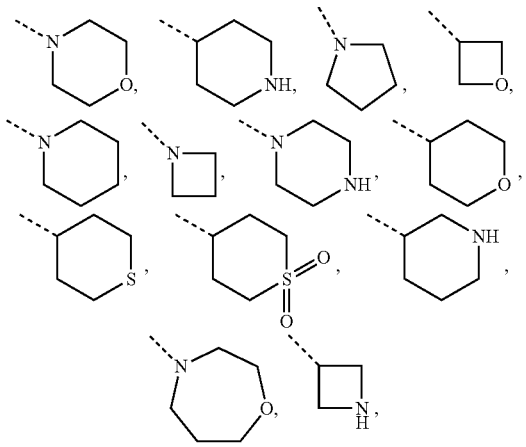

and the like.

Each of which may optionally be substituted, where possible, on carbon and/or nitrogen atoms according to any of the embodiments.

Non-limiting examples of 4- to 7-membered monocyclic saturated heterocyclyl moieties, attached to the remainder of the molecule of Formula (I) through any available ring carbon atom (C-linked), and containing one or two heteroatoms each independently selected from O, S, S(=O)$_p$ and N (as in the definition of Het$^{1b}$, Het$^{1e}$, Het$^{1g}$ and Het$^4$) are shown below

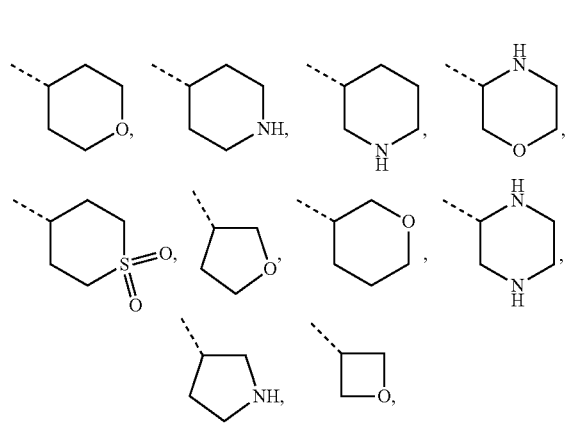

and the like.

Each of which may optionally be substituted, where possible, on carbon and/or nitrogen atoms according to any of the embodiments.

Non-limiting examples of N-linked 4- to 7-membered monocyclic saturated heterocyclyl moieties optionally containing one additional heteroatom selected from O, S, S(=O)$_p$ and N (as in the definition of (b-1) and (c-1)) are shown below:

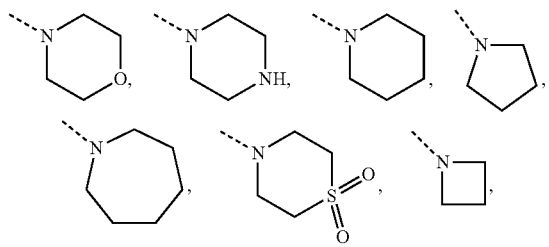

and the like.

Each of which may optionally be substituted, where possible, on carbon and/or nitrogen atoms according to any of the embodiments.

Non-limiting examples of 5-membered aromatic ring containing one, two or three N-atoms as referred to in the definition of R$^{18}$ are shown below

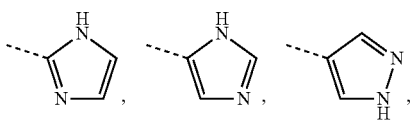

and the like.

Each of which may optionally be substituted, where possible, on carbon and/or nitrogen atoms according to any of the embodiments.

The skilled person will realize that typical fused 6- to 11-membered bicyclic heteroaromatic ring systems containing one or two heteroatoms each independently selected from O, S, and N (as in the definition of R$^3$), will be fused 7- to 11-membered bicyclic heteroaromatic ring systems containing one or two heteroatoms each independently selected from O, S, and N. Non-limiting examples are shown below

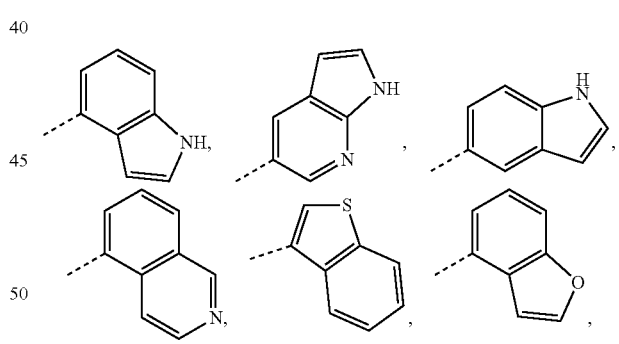

and the like.

Each of which may optionally be substituted, where possible, on carbon atoms and/or one nitrogen atom according to any of the embodiments.

Non-limiting examples of the fused bicyclic ring system of formula (1a-1):

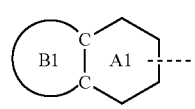

(1a-1)

are shown below

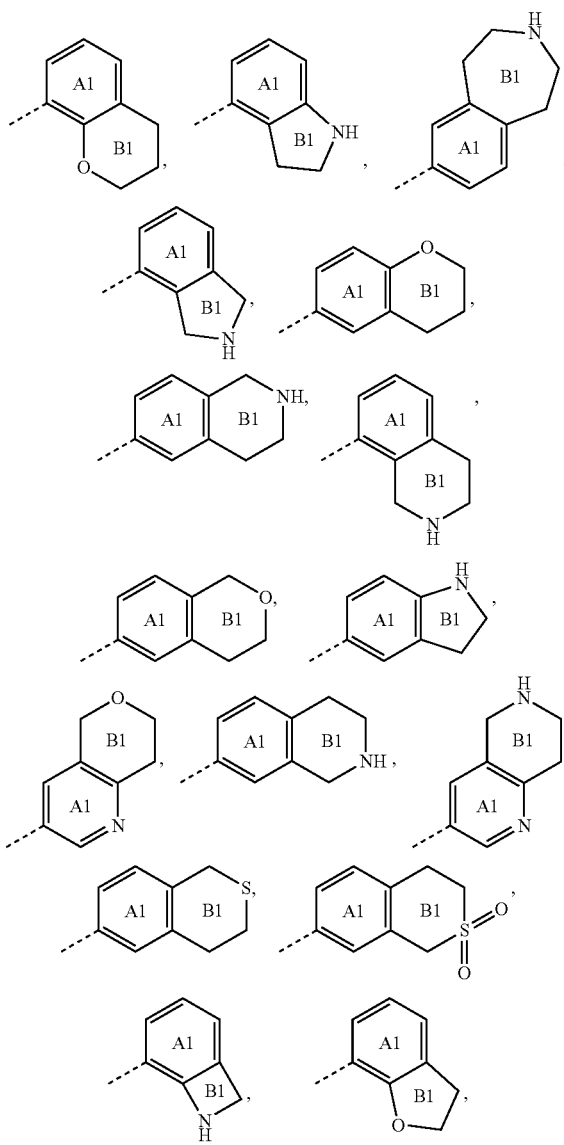

and the like.

Each of which may optionally be substituted, where possible, on carbon and/or nitrogen atoms according to any of the embodiments.

Non-limiting examples of the fused bicyclic ring system of formula (1a-1)

(1a-2)

are shown below and the like

Each of which may optionally be substituted, where possible, on carbon and/or nitrogen atoms according to any of the embodiments.

Non-limiting examples of the fused bicyclic ring system of formula (2a-1)

(2a-1)

are shown below:

Each of which may optionally be substituted, where possible, on carbon and/or nitrogen atoms according to any of the embodiments.

The skilled person will understand that in case $R^3$ represents a fused bicyclic ring system of formula (1a-1), (1a-1) is attached to the remainder of the molecule of Formula (I) (—NH-moiety) via ring A1.

The skilled person will understand that in case $R^3$ represents a fused bicyclic ring system of formula (1a-2), (1a-2) is attached to the remainder of the molecule of Formula (I) (—NH-moiety) via a ring carbon atom of ring A2.

The skilled person will understand that in case $R^3$ represents a fused bicyclic ring system of formula (2a-1), (2a-1) is attached to the remainder of the molecule of Formula (I) (—NH-moiety) via a ring carbon atom of ring A.

Whenever substituents are represented by chemical structure, "---" represents the bond of attachment to the remainder of the molecule of Formula (I).

Lines (such as "---") drawn into ring systems indicate that the bond may be attached to any of the suitable ring atoms.

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable addition salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

For example

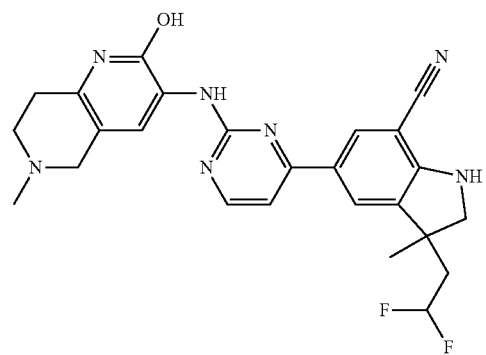 [SMILES: CN1CCc2nc(O)c(Nc3nccc(-c4cc(C#N)c5c(c4)C(C)(CC(F)F)CN5)n3)cc2C1]

also covers the other tautomeric form

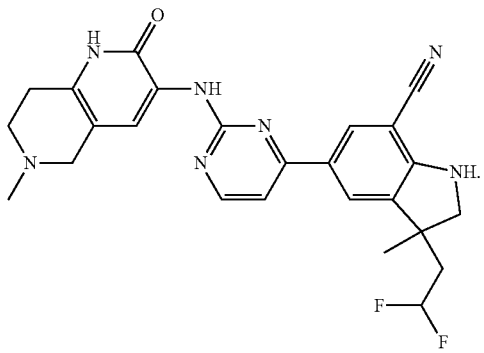 [SMILES: CN1CCc2[nH]c(=O)c(Nc3nccc(-c4cc(C#N)c5c(c4)C(C)(CC(F)F)CN5)n3)cc2C1]

Pharmaceutically-acceptable addition salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base addition salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}$H, $^{3}$H, $^{11}$C, $^{13}$C, $^{14}$C, $^{13}$N, $^{15}$O, $^{17}$O, $^{18}$O, $^{32}$P, $^{33}$P, $^{35}$S, $^{18}$F, $^{36}$Cl, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^{2}$H, $^{3}$H, $^{11}$C and $^{18}$F. More preferably, the radioactive isotope is $^{2}$H. In particular, deuterated compounds are intended to be included within the scope of the present invention.

Certain isotopically-labeled compounds of the present invention (e.g., those labeled with $^{3}$H and $^{14}$C) are useful in compound and for substrate tissue distribution assays. Tritiated ($^{3}$H) and carbon-14 ($^{14}$C) isotopes are useful for their ease of preparation and detectability. Further, substitution with heavier isotopes such as deuterium (i.e., $^{2}$H may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy.

The present invention relates in particular to compounds of Formula (I) as defined herein, tautomers and stereoisomeric forms thereof, wherein $R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen or halo;
$R^5$ represents $Het^{3a}$, —$NR^{6a}R^{6b}$, or —$OR^7$;
$R^{6a}$ represents hydrogen or $C_{1-4}$alkyl;
$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of —NH$_2$, —COOH, and $Het^6$;

$R^{16a}$ and $R^{16b}$ each independently represents hydrogen, $C_{1-4}$alkyl or $C_{3-6}$cycloalkyl;

$R^3$ represents a fused bicyclic ring system of formula (1a-1)

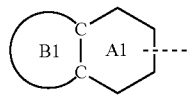

(1a-1)

ring A1 represents phenyl or a 6-membered heteroaromatic ring containing 1 or 2 N-atoms;

ring B1 represents a 4- to 7-membered saturated heterocyclyl containing one or two heteroatoms each independently selected from O, S, S(=O)$_p$ and N;

wherein (1a-1) may optionally be substituted on the ring carbon atoms with in total one, two or three substituents each independently selected from the group consisting of halo; cyano; oxo; $C_{1-6}$ alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$ cycloalkyl; $Het^{1a}$; —O-$Het^{1b}$; $R^{18}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; and wherein ring B1 may optionally be substituted, where possible, on one or two ring N-atoms with a substituent each independently selected from the group consisting of $C_{1-6}$alkyl; $C_{3-6}$cycloalkyl; $Het^{1a}$; $R^{18}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; —(C=O)—$C_{1-4}$alkyl; —C(=O)$NR^{14g}R^{14h}$; —C(=O)—$C_{1-4}$alkyl-$NR^{14i}R^{14j}$; —C(=O)—C(=O)—$NR^{14k}R^{14l}$; $C_{2-6}$alkenyl; and $C_{2-6}$alkenyl substituted with one $R^{13}$; provided that when $Het^{1a}$ or $R^{18}$ are directly attached to the N-atom of ring B, said $Het^{1a}$ or $R^{18}$ are attached to the N-atom via a ring carbon atom;

$R^{10}$ represents —OH, —O—$C_{1-4}$alkyl, —$NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^2$ represents a heterocyclyl of formula (b-1)

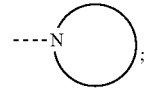

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$ alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; $Het^{1e}$; $C_{1-4}$alkyl; $C_{1-4}$alkyl-$Het^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)N$R^{15a}R^{15b}$, —N$R^{19a}R^{19b}$, $C_{3-6}$cycloalkyl, Het$^{1d}$, —S(=O)$_2$—$C_{1-4}$alkyl, —S(=O)(=N—$R^{20c}$)—$C_{1-4}$alkyl, or —C(=O)—Het$^{1f}$;

$R^{12}$ represents —OH, —O—$C_{1-4}$alkyl, —N$R^{14a}R^{14b}$, —C(=O)N$R^{14c}R^{14d}$, —S(=O)$_2$—$C_{1-4}$alkyl, —S(=O)(=N—$R^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1)

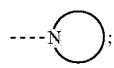 (c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{14g}$, $R^{14i}$, $R^{14k}$, $R^{15a}$, $R^{17a}$ and $R^{19a}$ each independently represents hydrogen or $C_{1-4}$ alkyl;

$R^{14b}$, $R^{14d}$, $R^{14h}$, $R^{14j}$, $R^{14l}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$, $R^{20b}$ and $R^{20c}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$ alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, $C_{1-6}$alkyl substituted with one $R^5$, or $C_{1-6}$alkyl substituted with one, two or three fluoro atoms;

Y represents C$R^4$ or N;

$R^4$ represents hydrogen or halo;

$R^5$ represents Het$^{3a}$, —N$R^{6a}R^{6b}$, or —O$R^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—Het$^4$; —S(=O)$_2$—$C_{1-4}$alkyl; —C(=O)—$C_{1-4}$alkyl substituted with one substituent selected from the group consisting of —OH and —N$R^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-N$R^{8a}R^{8b}$, —C(=O)—$R^9$, —S(=O)$_2$—OH, —P(=O)$_2$—OH, —(C=O)—CH(NH$_2$)—$C_{1-4}$alkyl-Ar$^1$, or —$C_{1-4}$alkyl-Het$^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of —NH$_2$, —COOH, and Het$^6$;

$R^{16a}$ and $R^{16b}$ each independently represents hydrogen, $C_{1-4}$alkyl or $C_{3-6}$cycloalkyl;

$R^3$ represents a fused bicyclic ring system of formula (1a-1) or (1a-2)

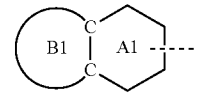 (1a-1)

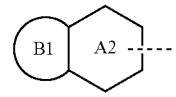 (1a-2)

ring A1 represents phenyl or a 6-membered heteroaromatic ring containing 1 or 2 N-atoms;

ring A2 represents 2-oxo-1,2-dihydropyridin-3-yl;

ring B1 represents a 4- to 7-membered saturated heterocyclyl containing one or two heteroatoms each independently selected from O, S, S(=O)$_p$ and N;

wherein (1a-1) and (1a-2) may optionally be substituted on the ring carbon atoms with in total one, two or three substituents each independently selected from the group consisting of halo; cyano; oxo; —OH; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$ alkyl; —O—$C_{1-4}$alkyl substituted with one, two or three halo atoms; —O—$C_{1-4}$alkyl-$R^{12}$; $C_{3-6}$ cycloalkyl; —O—$C_{3-6}$cycloalkyl; Het$^{1a}$; —O-Het$^{1b}$; $R^{18}$; —P(=O)—($C_{1-4}$alkyl)$_2$; —NH—C(=O)—$C_{1-4}$alkyl; —NH—C(=O)—Het$^9$; —N$R^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;

wherein ring A2 may optionally be substituted, where possible, on the N-atom with a substituent selected from the group consisting of $C_{1-6}$alkyl; $C_{3-6}$cycloalkyl; Het$^a$; $R^{18}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when Het$^{1a}$ or $R^{18}$ are directly attached to the N-atom of ring A2, said Het$^{1a}$ or $R^{18}$ are attached to the N-atom via a ring carbon atom; and wherein ring B1 may optionally be substituted, where possible, on one or two ring N-atoms with a substituent each independently selected from the group consisting of $C_{1-6}$alkyl; $C_{3-6}$cycloalkyl; Het$^{1a}$; $R^{18}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; —(C=O)—$C_{1-4}$alkyl; —C(=O)N$R^{14g}R^{14h}$; —C(=O)—$C_{1-4}$alkyl-N$R^{14i}R^{14j}$; —C(=O)—C(=O)—N$R^{14k}R^{14l}$; $C_{2-6}$alkenyl; and $C_{2-6}$alkenyl substituted with one R; provided that when Het$^{1a}$ or $R^{18}$ are directly attached to the N-atom of ring B1, said Het$^{1a}$ or $R^{18}$ are attached to the N-atom via a ring carbon atom;

$R^{10}$ represents —OH, —O—$C_{1-4}$alkyl, —N$R^{11a}R^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^{1b}$, Het$^{1e}$, Het$^{1g}$ and Het$^4$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$ and Het$^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^2$ represents a heterocyclyl of formula (b-1)

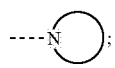

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$ alkyl, —O—$C_{1-4}$alkyl, —NH$_2$, —NH($C_{1-4}$alkyl), —N($C_{1-4}$alkyl)$_2$, and $C_{1-4}$alkyl-OH;

R$^{11b}$ represents hydrogen; Het$^{1e}$; $C_{1-4}$alkyl; $C_{1-4}$alkyl-Het$^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

R$^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, —S(=O)$_2$—$C_{1-4}$alkyl, —S(=O)(=N—R$^{20c}$)—$C_{1-4}$alkyl, or —C(=O)—Het$^{1f}$;

R$^{12}$ represents —OH, —O—$C_{1-4}$alkyl, —NR$^{14a}$R$^{14b}$, C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl; or a 5- or 6-membered heteroaromatic ring containing one, two or three heteroatoms each independently selected from O, S, and N;

Het$^{3a}$, Het$^{3b}$, Het$^5$, Het$^6$ and Het$^{1f}$ each independently represents a heterocyclyl of formula (c-1)

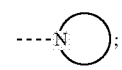

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

R$^{11a}$, R$^{14a}$, R$^{14c}$, R$^{14g}$, R$^{14i}$, R$^{14k}$, R$^{15a}$, R$^{17a}$ and R$^{19a}$ each independently represents hydrogen or $C_{1-4}$ alkyl;

R$^{14b}$, R$^{14d}$, R$^{14h}$, R$^{14j}$, R$^{14l}$, R$^{15b}$, R$^{17b}$ and R$^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

R$^{20a}$, R$^{20b}$ and R$^{20c}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$ alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein R$^1$ represents $C_{1-4}$alkyl;

R$^2$ represents $C_{1-6}$alkyl, $C_{1-6}$alkyl substituted with one R$^5$, or $C_{1-6}$alkyl substituted with one, two or three fluoro atoms;

Y represents CR$^4$ or N;

R$^4$ represents hydrogen or halo;

R$^5$ represents —OR$^7$;

R$^7$ represents hydrogen;

$R^3$ represents a) a fused bicyclic ring system of formula (1a-1) or (1a-2)

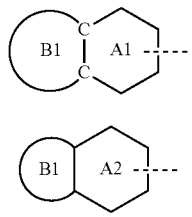

(1a-1)

(1a-2)

ring A1 represents phenyl or a 6-membered heteroaromatic ring containing 1 or 2 N-atoms;
ring A2 represents 2-oxo-1,2-dihydropyridin-3-yl;
ring B1 represents a 4- to 7-membered saturated heterocyclyl containing one or two heteroatoms each independently selected from O and N;
wherein (1a-1) and (1a-2) may optionally be substituted on the ring carbon atoms with in total one, two or three substituents each independently selected from the group consisting of halo; oxo; —OH; $C_{1-6}$alkyl; —O—$C_{1-4}$alkyl; —C(=O)—$R^{10}$; —O—$C_{1-4}$alkyl-$R^{12}$; —O—$C_{3-6}$cycloalkyl; —$NR^{17a}R^{17b}$; $C_{1-4}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$;
wherein ring A2 may optionally be substituted, where possible, on the N-atom with a substituent selected from the group consisting of $C_{1-6}$alkyl; and $C_{1-4}$alkyl substituted with one $R^{13}$; and
wherein ring B1 may optionally be substituted, where possible, on one or two ring N-atoms with a substituent each independently selected from the group consisting of $C_{1-6}$alkyl; $C_{3-6}$cycloalkyl; $C_{1-4}$alkyl substituted with one, two or three —OH substituents; $C_{1-4}$alkyl substituted with one $R^{13}$; —(C=O)—$C_{1-4}$alkyl; —C(=O)$NR^{14g}R^{14h}$; —C(=O)—$C_{1-4}$alkyl-$NR^{14k}R^{14i}$; —C(=O)—C(=O)—$NR^{14k}R^{14l}$; or b) a fused bicyclic ring system of formula (2a-1)

(2a-1)

ring A represents pyrazolyl optionally substituted with one substituent selected from the group consisting of $C_{1-4}$alkyl, and —$C_{1-4}$alkyl-O—$C_{1-4}$alkyl;
ring B represents a $C_{5-7}$cycloalkyl or a 5- to 7-membered saturated heterocyclyl containing one or two heteroatoms each independently selected from O and N;
wherein said $C_{5-7}$cycloalkyl or 5- to 7-membered saturated heterocyclyl may optionally be substituted on one or two ring carbon atoms with one or two substituents each independently selected from the group consisting of $C_{1-4}$alkyl, —$C_{1-4}$alkyl-O—$C_{1-4}$alkyl and —$C_{1-4}$alkyl-OH, or one ring carbon atom may optionally be substituted with oxo; and wherein said 5- to 7-membered saturated heterocyclyl may optionally be substituted on one or two ring N-atoms with $C_{1-6}$alkyl; or c) a fused 7- to 11-membered bicyclic heteroaromatic ring system containing one or two heteroatoms each independently selected from O, S, and N;

wherein said fused 7- to 11-membered bicyclic heteroaromatic ring system may optionally be substituted on the ring carbon atoms with in total one, two or three substituents each independently selected from the group consisting of halo; —$C_{1-4}$alkyl; and —C(=O)—$R^{10}$; and wherein said fused 7- to 11-membered bicyclic heteroaromatic ring system may optionally be substituted, where possible, on one ring N-atom with a substituent selected from the group consisting of $C_{1-4}$alkyl substituted with one, two or three —OH substituents; and $C_{1-4}$alkyl substituted with one $R^{13}$;

$R^{10}$ represents —$NR^{11a}R^{11b}$;
$Het^{1d}$ represents a 4- to 7-membered monocyclic saturated heterocyclyl containing one or two heteroatoms each independently selected from O, S, S(=O)$_p$ and N;
$R^{11b}$ represents $C_{1-4}$alkyl;
$R^{13}$ represents —O—$C_{1-4}$alkyl, —C(=O)$NR^{15a}R^{15b}$, $C_{3-6}$cycloalkyl, or $Het^{1d}$;
$R^2$ represents $C_{3-6}$cycloalkyl;
$R^{11a}$, $R^{14g}$, $R^{14i}$, $R^{14k}$, $R^{15a}$, and $R^{17a}$ each independently represents hydrogen or $C_{1-4}$alkyl;
$R^{14h}$, $R^{14j}$, $R^{14l}$, $R^{15b}$, and $R^{17b}$ each independently represents hydrogen or $C_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, $C_{1-6}$alkyl substituted with one $R^5$, or $C_{1-6}$alkyl substituted with one, two or three fluoro atoms;
Y represents $CR^4$ or N;
$R^4$ represents hydrogen or halo;
$R^5$ represents —$OR^7$;
$R^7$ represents hydrogen;
$R^3$ represents a fused bicyclic ring system of formula (1a-1) or (1a-2)

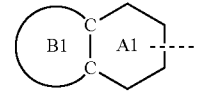

(1a-1)

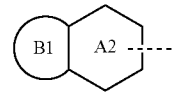

(1a-2)

ring A1 represents phenyl or a 6-membered heteroaromatic ring containing 1 or 2 N-atoms;
ring A2 represents 2-oxo-1,2-dihydropyridin-3-yl;
ring B1 represents a 4- to 7-membered saturated heterocyclyl containing one or two heteroatoms each independently selected from O and N;
wherein (1a-1) and (1a-2) may optionally be substituted on the ring carbon atoms with in total one, two or three substituents each independently selected from the group consisting of halo; oxo; —OH; $C_{1-6}$alkyl; —O—$C_{1-4}$alkyl; —C(=O)—$R^{10}$; —O—$C_{1-4}$alkyl-$R^{12}$; —O—$C_{3-6}$cycloalkyl; —$NR^{17a}R^{17b}$; $C_{1-4}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$;
wherein ring A2 may optionally be substituted, where possible, on the N-atom with a substituent selected from the group consisting of $C_{1-6}$alkyl; and $C_{1-4}$alkyl substituted with one $R^{13}$; and wherein ring B1 may optionally be substituted, where possible, on one or two ring N-atoms with a substituent each independently selected from the group consisting of $C_{1-6}$alkyl; $C_{3-6}$cycloalkyl; $C_{1-4}$alkyl substituted with one, two or three —OH substituents; $C_{1-4}$alkyl substituted with one $R^{13}$; —(C=O)—$C_{1-4}$alkyl; —C(=O)NR$^{14g}$R$^{14h}$; —C(=O)—$C_{1-4}$alkyl-NR$^{14i}$R$^{14j}$; —C(=O)—C(=O)—NR$^{14k}$R$^{14l}$;
$R^{10}$ represents —NR$^{11a}$R$^{11b}$;
$R^{11b}$ represents $C_{1-4}$alkyl;
$R^{13}$ represents —O—$C_{1-4}$alkyl, —C(=O)NR$^{15a}$R$^{15b}$, or $C_{3-6}$cycloalkyl;
$R^{12}$ represents $C_{3-6}$cycloalkyl;
$R^{11a}$, $R^{14g}$, $R^{14i}$, $R^{14k}$, $R^{15a}$, and $R^{17a}$ each independently represents hydrogen or $C_{1-4}$alkyl;
$R^{14h}$, $R^{14j}$, $R^{14l}$, $R^{15b}$, and $R^{17b}$ each independently represents hydrogen or $C_{1-4}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents CR$^4$;
$R^4$ represents hydrogen or halo;
$R^5$ represents -OR$^7$;
$R^7$ represents hydrogen, $C_{1-4}$alkyl, —$C_{1-4}$alkyl-NR$^{8a}$R$^{8b}$, —C(=O)—R$^9$, —(C=O)—CH(NH$_2$)— or $C_{1-4}$ alkyl-Ar$^1$;
$R^{1a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of —NH$_2$, and —COOH;
$R^3$ represents a fused bicyclic ring system of formula (1a-1)

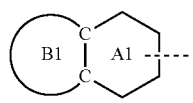

(1a-1)

ring A1 represents phenyl or a 6-membered heteroaromatic ring containing 1 or 2 N-atoms;
ring B1 represents a 4- to 7-membered saturated heterocyclyl containing one or two heteroatoms each independently selected from O, S, S(=O)$_p$ and N;
wherein (1a-1) may optionally be substituted on the ring carbon atoms with in total one, two or three substituents each independently selected from the group consisting of halo; cyano; oxo; $C_{1-6}$ alkyl; —O—$C_{1-4}$alkyl; —C(=O)—R$^{10}$; —S(=O)$_2$—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; —NH—C(=O)—$C_{1-4}$alkyl; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$; and
wherein ring B1 may optionally be substituted, where possible, on one or two ring N-atoms with a substituent each independently selected from the group consisting of $C_{1-6}$alkyl; $C_{3-6}$cycloalkyl; $C_{1-4}$alkyl substituted with one, two or three halo atoms; $C_{1-4}$alkyl substituted with one, two or three —OH substituents; $C_{1-4}$alkyl substituted with one $R^{13}$; —(C=O)—$C_{1-4}$alkyl; —C(=O)NR$^{14g}$R$^{14h}$; —C(=O)— $C_{1-4}$alkyl-NR$^{14i}$R$^{14j}$; —C(=O)—C(=O)—NR$^{14k}$R$^{14l}$; $C_{2-6}$alkenyl; and $C_{2-6}$alkenyl substituted with one $R^{13}$;
$R^{10}$ represents —OH, —O—$C_{1-4}$alkyl, or —NR$^{11a}$R$^{11b}$;
$R^{11b}$ represents hydrogen; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;
$R^{13}$ represents —O—$C_{1-4}$alkyl, —C(=O)NR$^{15a}$R$^{15b}$, —NR$^{19a}$R$^{19b}$, $C_{3-6}$cycloalkyl, or —S(=O)$_2$—$C_{1-4}$alkyl;
$R^{12}$ represents —OH, —O—$C_{1-4}$alkyl, —NR$^{14a}$R$^{14b}$, C(=O)NR$^{14c}$R$^{14d}$, —S(=O)$_2$—$C_{1-4}$alkyl, $C_{3-6}$cycloalkyl, or Ar$^2$;
Ar$^1$ represents phenyl optionally substituted with one hydroxy;
Ar$^2$ represents phenyl optionally substituted with one $C_{1-4}$alkyl;
$R^{11a}$, $R^{14a}$, $R^{14c}$, $R^{14g}$, $R^{14i}$, $R^{14k}$, $R^{15a}$, $R^{17a}$ and $R^{19a}$ each independently represents hydrogen or $C_{1-4}$ alkyl;
$R^{14b}$, $R^{14d}$, $R^{14h}$, $R^{14j}$, $R^{14l}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;
$R^{20a}$, $R^{20b}$ and $R^{20c}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$ alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;
$R^2$ represents $C_{1-6}$alkyl, or $C_{1-6}$alkyl substituted with one $R^5$;
Y represents CR$^4$;
$R^4$ represents hydrogen;
$R^5$ represents —OR$^7$;
$R^7$ represents hydrogen;
$R^3$ represents a fused bicyclic ring system of formula (1a-1)

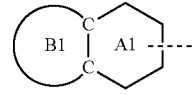

(1a-1)

ring A1 represents phenyl or a 6-membered heteroaromatic ring containing 1 or 2 N-atoms;
ring B1 represents a 4- to 7-membered saturated heterocyclyl containing one or two heteroatoms each independently selected from O and N;
wherein (1a-1) may optionally be substituted on the ring carbon atoms with in total one, two or three substituents each independently selected from the group consisting of halo; $C_{1-6}$alkyl; —O—$C_{1-4}$alkyl; —C(=O)—R$^{10}$; —O—$C_{1-4}$alkyl-R$^{12}$; —NR$^{17a}$R$^{17b}$; $C_{1-4}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$; and
wherein ring B1 may optionally be substituted, where possible, on one or two ring N-atoms with a substituent each independently selected from the group consisting of $C_{1-6}$alkyl; $C_{1-4}$alkyl substituted with one $R^{13}$; —(C=O)—$C_{1-4}$alkyl; —C(=O)—$C_{1-4}$alkyl-$NR^{14i}R^{14j}$; and —C(=O)—C(=O)—$NR^{14k}R^{14l}$;
$R^{10}$ represents —$NR^{11a}R^{11b}$;
$R^{11b}$ represents $C_{1-4}$alkyl;
$R^{13}$ represents —O—$C_{1-4}$alkyl, —C(=O)$NR^{15a}R^{15}$, or $C_{3-6}$cycloalkyl;
$R^{12}$ represents $C_{3-6}$cycloalkyl;
$R^{11a}$, $R^{14i}$, $R^{14k}$, $R^{15a}$, and $R^{17a}$ each independently represents hydrogen or $C_{1-4}$alkyl;
$R^{14j}$, $R^{14l}$, $R^{15b}$, and $R^{17b}$ each independently represents hydrogen or $C_{1-4}$alkyl; and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused bicyclic ring system of formula (1a-1)

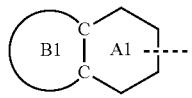

(1a-1)

ring A1 represents phenyl or a 6-membered heteroaromatic ring containing 1 N-atom;
ring B1 represents a 4- to 7-membered saturated heterocyclyl containing one heteroatom selected from O and N;
wherein (1a-1) may optionally be substituted on the ring carbon atoms with in total one, two or three substituents each independently selected from the group consisting of —O—$C_{1-4}$alkyl; —O—$C_{1-4}$alkyl-$R^{12}$; and $C_{1-4}$alkyl substituted with one $R^{13}$; and
wherein ring B1 may optionally be substituted, where possible, on one N-atom with a $C_{1-6}$alkyl substituent;
$R^{13}$ represents $C_{3-6}$cycloalkyl;
$R^{12}$ represents $C_{3-6}$cycloalkyl; and the pharmaceutically acceptable addition salts, and the solvates thereof.

The present invention relates in particular to compounds of Formula (I) as defined herein, tautomers and stereoisomeric forms thereof, wherein
$R^1$ represents methyl;
$R^2$ represents methyl substituted with one $R^5$;
Y represents $CR^4$;
$R^4$ represents hydrogen;
$R^5$ represents —$OR^7$;
$R^7$ represents hydrogen;
$R^3$ represents a fused bicyclic ring system selected from the following structures

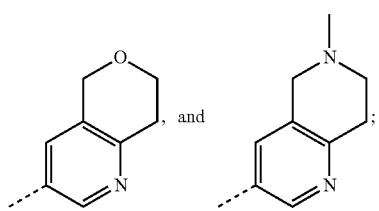

wherein said fused bicyclic ring system may optionally be substituted on the ring carbon atoms with in total one, two or three substituents each independently selected from the group consisting of —O—$C_{1-4}$alkyl; —O—$C_{1-4}$alkyl-$R^{12}$; and $C_{1-4}$alkyl substituted with one $R^{13}$;
$R^{13}$ represents $C_{3-6}$cycloalkyl;
$R^{12}$ represents $C_{3-6}$cycloalkyl;
and the pharmaceutically acceptable addition salts, and the solvates thereof.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(a) Y represents $CR^4$; and $R^4$ represents hydrogen;
(b) $R^5$ represents —$OR^7$;
(c) $R^7$ represents hydrogen;
(d) $R^3$ represents a fused bicyclic ring system of formula (1a-1)

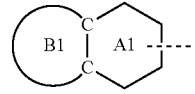

(1a-1)

ring A1 represents phenyl or a 6-membered heteroaromatic ring containing 1 or 2 N-atoms;
ring B1 represents a 4- to 7-membered saturated heterocyclyl containing one or two heteroatoms each independently selected from O and N;
wherein (1a-1) may optionally be substituted on the ring carbon atoms with in total one, two or three substituents each independently selected from the group consisting of halo; $C_{1-6}$alkyl; —O—$C_{1-4}$alkyl; —C(=O)—$R^{10}$; —O—$C_{1-4}$alkyl-$R^{12}$; —$NR^{17a}R^{17b}$; $C_{1-4}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$; and
wherein ring B1 may optionally be substituted, where possible, on one or two ring N-atoms with a substituent each independently selected from the group consisting of $C_{1-6}$alkyl; $C_{1-4}$alkyl substituted with one $R^{13}$; —(C=O)—$C_{1-4}$alkyl; —C(=O)—$C_{1-4}$alkyl-$NR^{14i}R^{14j}$; —C(=O)—C(=O)—$NR^{14k}R^{14l}$;
(e) $R^{10}$ represents —$NR^{11a}R^{11b}$;
(f) $R^{11b}$ represents $C_{1-4}$alkyl;
(g) $R^{13}$ represents —O—$C_{1-4}$alkyl, —C(=O)$NR^{15a}R^{15}$, or $C_{3-6}$cycloalkyl;
(h) $R^{12}$ represents $C_{3-6}$cycloalkyl;
(i) $R^{11a}$, $R^{14i}$, $R^{14k}$, $R^{15a}$, and $R^{17a}$ each independently represents hydrogen or $C_{1-4}$alkyl;
(j) $R^{14j}$, $R^{14l}$, $R^{15b}$, and $R^{17b}$ each independently represents hydrogen or $C_{1-4}$alkyl.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(a) $R^1$ represents methyl;
$R^2$ represents methyl substituted with one $R^5$;
(b) Y represents $CR^4$; and $R^4$ represents hydrogen;
(c) $R^5$ represents —$OR^7$;
(d) $R^7$ represents hydrogen;

(e) R³ represents a fused bicyclic ring system selected from the following structures

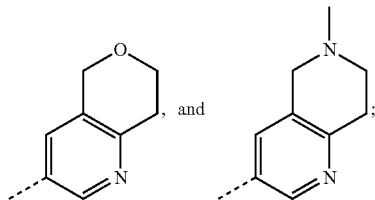, and wherein said fused bicyclic ring system may optionally be substituted on the ring carbon atoms with in total one, two or three substituents each independently selected from the group consisting of —O—$C_{1-4}$alkyl; —O—$C_{1-4}$alkyl-$R^{12}$; and $C_{1-4}$alkyl substituted with one $R^{13}$;
(f) $R^{13}$ represents $C_{3-6}$cycloalkyl;
(g) $R^{12}$ represents $C_{3-6}$cycloalkyl.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(a) $R^1$ represents methyl;
$R^2$ represents methyl substituted with one $R^5$;
(b) Y represents N;
(c) $R^5$ represents —$OR^7$;
(d) $R^7$ represents hydrogen;
(e) $R^3$ represents a fused bicyclic ring system selected from the following structures

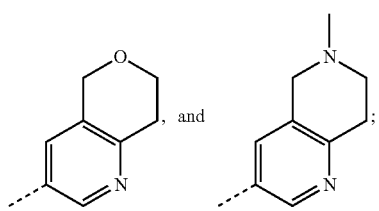, and wherein said fused bicyclic ring system may optionally be substituted on the ring carbon atoms with in total one, two or three substituents each independently selected from the group consisting of —O—$C_{1-4}$alkyl; —O—$C_{1-4}$alkyl-$R^{12}$; and $C_{1-4}$alkyl substituted with one $R^{13}$;
(f) $R^{13}$ represents $C_{3-6}$cycloalkyl;
(g) $R^{12}$ represents $C_{3-6}$cycloalkyl.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(a) $R^1$ represents methyl;
$R^2$ represents methyl substituted with one $R^5$;
(b) Y represents $CR^4$; and $R^4$ represents hydrogen;
(c) $R^5$ represents —$OR^7$;
(d) $R^7$ represents hydrogen;
(e) $R^3$ represents a fused bicyclic ring system selected from the following structures

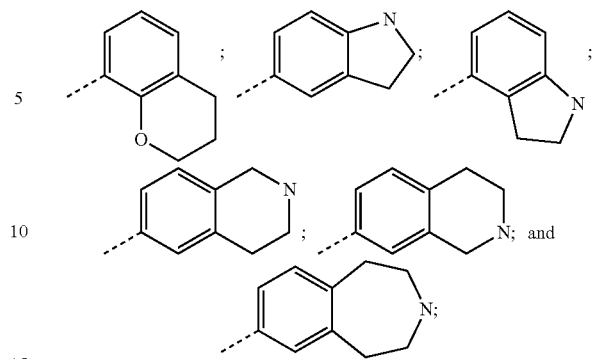

wherein said fused bicyclic ring system may optionally be substituted on the ring carbon atoms with in total one, two or three substituents each independently selected from the group consisting of halo, oxo, $C_{1-6}$alkyl, —O—$C_{1-4}$alkyl; —O—$C_{1-4}$alkyl-$R^{12}$; —$NR^{17a}R^{17b}$; $C_{1-4}$alkyl substituted with one, two or three —OH substituents; and $C_{1-4}$alkyl substituted with one $R^{13}$; and wherein said fused bicyclic ring system may optionally be substituted on the ring N-atom with a substituent each independently selected from the group consisting of $C_{1-6}$alkyl; —(C═O)—$C_{1-4}$alkyl; —C(═O)—$C_{1-4}$alkyl-$NR^{14i}R^{14j}$; and —C(═O)—C(═O)—$NR^{14k}R^{14l}$;
(g) $R^{14i}$, $R^{14k}$, $R^{14j}$, $R^{14l}$, $R^{17a}$, and $R^{17b}$ each independently represents hydrogen or $C_{1-4}$alkyl;
(h) $R^{13}$ represents $C_{3-6}$cycloalkyl;
(i) $R^{12}$ represents $C_{3-6}$cycloalkyl.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused bicyclic ring system of formula (1a-2)

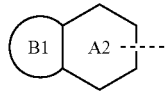 (1a-2)

ring A2 represents 2-oxo-1,2-dihydropyridin-3-yl;
ring B1 represents a 4- to 7-membered saturated heterocyclyl containing one or two heteroatoms each independently selected from O and N;
wherein (1a-2) may optionally be substituted on the ring carbon atoms with in total one, two or three substituents each independently selected from the group consisting of halo; $C_{1-6}$alkyl; —O—$C_{1-4}$alkyl; —C(═O)—$R^{10}$; $C_{1-4}$alkyl substituted with one, two or three —OH substituents; and $C_{1-4}$ alkyl substituted with one $R^{13}$;
wherein ring A2 may optionally be substituted, where possible, on the N-atom with a substituent selected from the group consisting of $C_{1-6}$alkyl; $C_{3-6}$cycloalkyl; and $C_{1-4}$alkyl substituted with one $R^{13}$; and
wherein ring B1 may optionally be substituted, where possible, on one or two ring N-atoms with a substituent each independently selected from the group consisting of $C_{1-6}$alkyl; —(C=O)—$C_{1-4}$ alkyl; —C(=O)—$C_{1-4}$alkyl-$NR^{14i}R^{14j}$; and —C(=O)—C(=O)—$NR^{14k}R^{14l}$;

$R^{10}$ represents —$NR^{11a}R^{11b}$;

$R^{11b}$ represents $C_{1-4}$alkyl;

$R^{13}$ represents —O—$C_{1-4}$alkyl, —C(=O)$NR^{15a}R^{15b}$, or $C_{3-6}$cycloalkyl;

$R^{11a}$, $R^{14i}$, $R^{14k}$, and $R^{15a}$ each independently represents hydrogen or $C_{1-4}$alkyl;

$R^{14j}$, $R^{14l}$, and $R^{15b}$ each independently represents hydrogen or $C_{1-4}$alkyl;

and the pharmaceutically acceptable addition salts, and the solvates thereof.

The present invention also relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen or halo;

$R^5$ represents $Het^{3a}$, —$NR^{6a}R^{6b}$, or —$OR^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —C(=O)—CH(NH$_2$)—$C_{1-4}$alkyl-$Ar^1$, or —$C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of —NH$_2$, —COOH, and $Het^6$;

$R^{16a}$ and $R^{16b}$ each independently represents hydrogen, $C_{1-4}$alkyl or $C_{3-6}$cycloalkyl;

$R^3$ represents a fused bicyclic ring system of formula (2a-1)

(2a-1)

ring A represents pyrazolyl optionally substituted with one substituent selected from the group consisting of $C_{1-4}$alkyl, —$C_{1-4}$alkyl-O—$C_{1-4}$alkyl, and $C_{1-4}$alkyl substituted with one, two or three halo atoms;

ring B represents a $C_{5-7}$cycloalkyl or a 5- to 7-membered saturated heterocyclyl containing one or two heteroatoms each independently selected from O and N;

wherein said $C_{5-7}$cycloalkyl or 5- to 7-membered saturated heterocyclyl may optionally be substituted on one ring carbon atom with one or two $C_{1-4}$alkyl substituents, or one ring carbon atom may optionally be substituted with oxo; and wherein said 5- to 7-membered saturated heterocyclyl may optionally be substituted on one or two ring N-atoms with a substituent each independently selected from the group consisting of $C_{1-6}$ alkyl; $C_{3-6}$cycloalkyl; $C_{1-4}$alkyl substituted with one, two or three halo atoms; $C_{1-4}$alkyl substituted with one, two or three —OH substituents; $C_{1-4}$alkyl substituted with one $R^{13}$; —(C=O)—$C_{1-4}$alkyl; —C(=O)$NR^{14g}R^{14h}$; —C(=O)—$C_{1-4}$alkyl-$NR^{14i}R^{14j}$;

$Het^4$ represents a 4- to 7-membered monocyclic saturated heterocyclyl, attached to the remainder of the molecule of Formula (II) through any available ring carbon atom, said $Het^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, —S(=O)$_2$—$C_{1-4}$alkyl, —S(=O)(=N—$R^{20c}$)—$C_{1-4}$alkyl, or —C(=O)—$Het^{1f}$;

$Ar^1$ represents phenyl optionally substituted with one hydroxy;

$Het^{3a}$, $Het^{3b}$, $Het^6$ and $Het^{1f}$ each independently represents a heterocyclyl of formula (c-1)

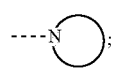

(c-1)

(c-1) represents a N-linked 4- to 7-membered monocyclic saturated heterocyclyl optionally containing one additional heteroatom selected from O, S, S(=O)$_p$ and N;

wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$Het^{1d}$ represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$ alkyl, —$NH_2$, —NH($C_{1-4}$alkyl), and —N($C_{1-4}$alkyl)$_2$;

$R^{14g}$, $R^{14i}$, $R^{15a}$, and $R^{19a}$ each independently represents hydrogen or $C_{1-4}$alkyl;

$R^{14h}$, $R^{14j}$, $R^{15b}$, and $R^{9b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20c}$ represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, $C_{1-6}$alkyl substituted with one $R^5$, or $C_{1-6}$alkyl substituted with one, two or three fluoro atoms;

Y represents $CR^4$ or N;

$R^4$ represents hydrogen or halo;

$R^5$ represents $Het^{3a}$, —$NR^{6a}R^{6b}$, or —$OR^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH($NH_2$)—$C_{1-4}$alkyl-$Ar^1$, or —$C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of —$NH_2$, —COOH, and $Het^6$;

$R^{16a}$ and $R^{16b}$ each independently represents hydrogen, $C_{1-4}$alkyl or $C_{3-6}$cycloalkyl;

$R^3$ represents a fused bicyclic ring system of formula (2a-1)

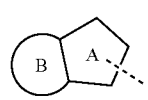

(2a-1)

ring A represents pyrazolyl optionally substituted with one substituent selected from the group consisting of $C_{1-4}$alkyl, —$C_{1-4}$alkyl-O—$C_{1-4}$alkyl, and $C_{1-4}$alkyl substituted with one, two or three halo atoms;

ring B represents a $C_{5-7}$cycloalkyl or a 5- to 7-membered saturated heterocyclyl containing one or two heteroatoms each independently selected from O and N;

wherein said $C_{5-7}$cycloalkyl or 5- to 7-membered saturated heterocyclyl may optionally be substituted on one ring carbon atom with one or two substituents each independently selected from the group consisting of $C_{1-4}$alkyl, —$C_{1-4}$alkyl-O—$C_{1-4}$alkyl and —$C_{1-4}$alkyl-OH, or one ring carbon atom may optionally be substituted with oxo; and wherein said 5- to 7-membered saturated heterocyclyl may optionally be substituted on one or two ring N-atoms with a substituent each independently selected from the group consisting of $C_{1-6}$ alkyl; $C_{3-6}$cycloalkyl; $C_{1-4}$alkyl substituted with one, two or three halo atoms; $C_{1-4}$alkyl substituted with one, two or three —OH substituents; $C_{1-4}$alkyl substituted with one $R^{13}$; —(C=O)—$C_{1-4}$alkyl; —C(=O)$NR^{14g}R^{14h}$; —C(=O)—$C_{1-4}$alkyl-$NR^{14i}R^{14j}$;

$Het^4$ represents a 4- to 7-membered monocyclic saturated heterocyclyl, attached to the remainder of the molecule of Formula (I) through any available ring carbon atom, said $Het^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, —S(=O)$_2$—$C_{1-4}$alkyl, —S(=O)(=N—$R^{20c}$)—$C_{1-4}$alkyl, $Ar^2$ or —C(=O)—$Het^{1f}$;

$Ar^1$ represents phenyl optionally substituted with one hydroxy;

$Ar^2$ represents phenyl or a 5- or 6-membered heteroaromatic ring containing one, two or three heteroatoms each independently selected from O, S, and N;

$Het^{3a}$, $Het^{3b}$, $Het^6$ and $Het^{1f}$ each independently represents a heterocyclyl of formula (c-1)

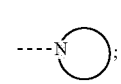

(c-1)

(c-1) represents a N-linked 4- to 7-membered monocyclic saturated heterocyclyl optionally containing one additional heteroatom selected from O, S, S(=O)$_p$ and N;

wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$Het^{1d}$ represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$ alkyl, —$NH_2$, —$NH(C_{1-4}$alkyl), and —$N(C_{1-4}$alkyl$)_2$;
$R^{14g}$, $R^{14i}$, $R^{15a}$, and $R^{19a}$ each independently represents hydrogen or $C_{1-4}$alkyl;
$R^{14h}$, $R^{14j}$, $R^{15b}$, and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;
$R^{20c}$ represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen or halo;
$R^5$ represents —$OR^7$;
$R^7$ represents hydrogen, $C_{1-4}$alkyl, —$C_{1-4}$alkyl-$NR^{8a}R^{8b}$, —C(=O)—$R^9$, —C(=O)—CH($NH_2$)— or $C_{1-4}$ alkyl-$Ar^1$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of —$NH_2$, and —COOH;
$R^3$ represents a fused bicyclic ring system of formula (2a-1)

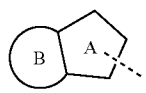

(2a-1)

ring A represents pyrazolyl optionally substituted with one substituent selected from the group consisting of $C_{1-4}$alkyl, —$C_{1-4}$alkyl-O—$C_{1-4}$alkyl, and $C_{1-4}$alkyl substituted with one, two or three halo atoms;
ring B represents a $C_{5-7}$cycloalkyl or a 5- to 7-membered saturated heterocyclyl containing one or two heteroatoms each independently selected from O and N;
wherein said $C_{5-7}$cycloalkyl or 5- to 7-membered saturated heterocyclyl may optionally be substituted on one ring carbon atom with one or two $C_{1-4}$alkyl substituents, or one ring carbon atom may optionally be substituted with oxo; and
wherein said 5- to 7-membered saturated heterocyclyl may optionally be substituted on one or two ring N-atoms with a substituent each independently selected from the group consisting of $C_{1-6}$ alkyl; $C_{3-6}$cycloalkyl; $C_{1-4}$alkyl substituted with one, two or three halo atoms; $C_{1-4}$alkyl substituted with one, two or three —OH substituents; $C_{1-4}$alkyl substituted with one $R^{13}$; —(C=O)—$C_{1-4}$alkyl; —C(=O)NR$^{14g}$R$^{14h}$; —C(=O)—$C_{1-4}$alkyl-NR$^{14i}$R$^{14j}$;
$R^{13}$ represents —O—$C_{1-4}$alkyl, —C(=O)NR$^{15a}$R$^{15b}$, NR$^{19a}$R$^{19b}$, or $C_{3-6}$cycloalkyl;

$Ar^1$ represents phenyl optionally substituted with one hydroxy;
$R^{14g}$, $R^{14i}$, $R^{15a}$, and $R^{19a}$ each independently represents hydrogen or $C_{1-4}$alkyl;
$R^{14h}$, $R^{14j}$, $R^{15b}$, and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused bicyclic ring system of formula (2a-1)

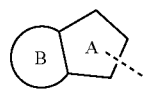

(2a-1)

ring A represents pyrazolyl optionally substituted with one substituent selected from the group consisting of $C_{1-4}$alkyl, and —$C_{1-4}$alkyl-O—$C_{1-4}$alkyl;
ring B represents a $C_{5-7}$cycloalkyl or a 5- to 7-membered saturated heterocyclyl containing one or two heteroatoms each independently selected from O and N;
wherein said $C_{5-7}$cycloalkyl or 5- to 7-membered saturated heterocyclyl may optionally be substituted on one or two ring carbon atoms with one or two substituents each independently selected from the group consisting of $C_{1-4}$alkyl, —$C_{1-4}$alkyl-O—$C_{1-4}$alkyl and —$C_{1-4}$alkyl-OH, or one ring carbon atom may optionally be substituted with oxo; and
wherein said 5- to 7-membered saturated heterocyclyl may optionally be substituted on one or two ring N-atoms with $C_{1-6}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused bicyclic ring system of formula (2a-1)

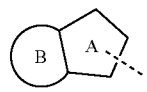

(2a-1)

ring A represents pyrazolyl optionally substituted with one substituent selected from the group consisting of $C_{1-4}$alkyl, and —$C_{1-4}$alkyl-O—$C_{1-4}$alkyl;

ring B represents a $C_{5-7}$cycloalkyl or a 5- to 7-membered saturated heterocyclyl containing one or two heteroatoms each independently selected from O and N;
wherein said $C_{5-7}$cycloalkyl or 5- to 7-membered saturated heterocyclyl may optionally be substituted on one ring carbon atom with one or two $C_{1-4}$alkyl substituents, or one ring carbon atom may optionally be substituted with oxo; and
wherein said 5- to 7-membered saturated heterocyclyl may optionally be substituted on one or two ring N-atoms with a $C_{1-6}$alkyl substituent;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused bicyclic ring system of formula (2a-1):

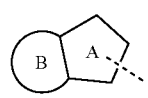

(2a-1)

ring A represents pyrazolyl;
ring B represents a 6-membered saturated heterocyclyl containing one heteroatom selected from O and N;
wherein said 6-membered saturated heterocyclyl may optionally be substituted on one ring carbon atom with one $C_{1-4}$alkyl substituent, or one ring carbon atom may optionally be substituted with oxo; and
wherein said 5- to 7-membered saturated heterocyclyl may optionally be substituted on one N-atom with a $C_{1-6}$alkyl substituent;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused bicyclic ring system selected from the following structures

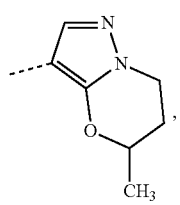 , 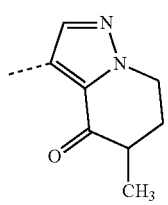 and

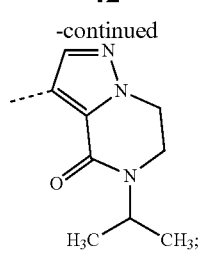

and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused bicyclic ring system of formula (2a-1)

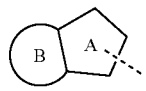

(2a-1)

ring A represents pyrazolyl optionally substituted with one substituent selected from the group consisting of $C_{1-4}$alkyl, and —$C_{1-4}$alkyl-O—$C_{1-4}$alkyl;
ring B represents a $C_{5-7}$cycloalkyl or a 5- to 7-membered saturated heterocyclyl containing one or two heteroatoms each independently selected from O and N;
wherein said $C_{5-7}$cycloalkyl or 5- to 7-membered saturated heterocyclyl may optionally be substituted on one or two ring carbon atoms with one or two substituents each independently selected from the group consisting of $C_{1-4}$alkyl, —$C_{1-4}$alkyl-O—$C_{1-4}$alkyl and —$C_{1-4}$alkyl-OH, or one ring carbon atom may optionally be substituted with oxo; and
wherein said 5- to 7-membered saturated heterocyclyl may optionally be substituted on one or two ring N-atoms with a substituent each independently selected from the group consisting of $C_{1-6}$ alkyl; $C_{3-6}$cycloalkyl; $C_{1-4}$alkyl substituted with one, two or three halo atoms; $C_{1-4}$alkyl substituted with one, two or three —OH substituents; and $C_{1-4}$alkyl substituted with one $R^{13}$;
$R^{13}$ represents $Ar^2$;
$Ar^2$ represents phenyl;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused bicyclic ring system selected from the following structures

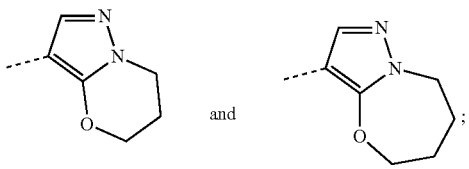

wherein said fused bicyclic ring may optionally be substituted on one or two ring carbon atoms with one or two substituents each independently selected from the group consisting of $C_{1-4}$alkyl;
and the pharmaceutically acceptable addition salts, and the solvates thereof.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:

(a) $R^2$ represents $C_{1-6}$alkyl substituted with one $R^5$;
(b) Y represents $CR^4$; and $R^4$ represents hydrogen;
(c) $R^5$ represents —$OR^7$;
(d) $R^7$ represents hydrogen;
(e) $R^3$ represents a fused bicyclic ring system of formula (2a-1)

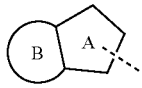

(2a-1)

ring A represents pyrazolyl optionally substituted with one substituent selected from the group consisting of $C_{1-4}$alkyl, and —$C_{1-4}$alkyl-O—$C_{1-4}$alkyl;
ring B represents a $C_{5-7}$cycloalkyl or a 5- to 7-membered saturated heterocyclyl containing one or two heteroatoms each independently selected from O and N;
wherein said $C_{5-7}$cycloalkyl or 5- to 7-membered saturated heterocyclyl may optionally be substituted on one ring carbon atom with one or two $C_{1-4}$alkyl substituents, or one ring carbon atom may optionally be substituted with oxo; and
wherein said 5- to 7-membered saturated heterocyclyl may optionally be substituted on one or two ring N-atoms with a $C_{1-6}$alkyl substituent.

The present invention also relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen or halo;
$R^5$ represents $Het^{3a}$, —$NR^{6a}R^{6b}$, or —$OR^7$;
$R^{6a}$ represents hydrogen or $C_{1-4}$alkyl;
$R^{6b}$ represents hydrogen; $C_{1-4}$alkyl; $C_{3-6}$cycloalkyl; —$C(=O)$—$C_{1-4}$alkyl; —$C(=O)$—$Het^4$; —$S(=O)_2$—$C_{1-4}$alkyl; —$C(=O)$—$C_{1-4}$alkyl substituted with one substituent selected from the group consisting of —OH and —$NR^{16a}R^{16b}$; or $C_{1-4}$alkyl substituted with one substituent selected from the group consisting of —OH and —$S(=O)_2$—$C_{1-4}$alkyl;

$R^7$ represents hydrogen, $C_{1-4}$alkyl, —$C_{1-4}$alkyl-$NR^{8a}R^{8b}$, —$C(=O)$—$R^9$, —$S(=O)_2$—OH, —$P(=O)_2$—OH, —$(C=O)$—$CH(NH_2)$—$C_{1-4}$alkyl-$Ar^1$, or —$C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of —$NH_2$, —COOH, and $Het^6$;
$R^{16a}$ and $R^{16b}$ each independently represents hydrogen, $C_{1-4}$alkyl or $C_{3-6}$cycloalkyl;
$R^3$ represents a fused 6- to 11-membered bicyclic heteroaromatic ring system containing one or two heteroatoms each independently selected from O, S, and N;
wherein said fused 6- to 11-membered bicyclic heteroaromatic ring system may optionally be substituted on the ring carbon atoms with in total one, two or three substituents each independently selected from the group consisting of halo; cyano; $C_{1-6}$alkyl; —O—$C_{1-4}$alkyl; —$C(=O)$—$R^{10}$; —$S(=O)_2$—$C_{1-4}$alkyl; —$S(=O)(=N$—$R^{20a})$—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; —$P(=O)$—($C_{1-4}$alkyl)$_2$; —NH—$C(=O)$—$C_{1-4}$alkyl; —NH—$C(=O)$—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; and
wherein said fused 6- to 11-membered bicyclic heteroaromatic ring system may optionally be substituted, where possible, on one ring N-atom with a substituent selected from the group consisting of $C_{1-6}$alkyl; $C_{3-6}$cycloalkyl; $Het^{1a}$; $R^{18}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; —$(C=O)$—$C_{1-4}$alkyl; —$C(=O)$$NR^{14g}R^{14h}$, —$C(=O)$—$C_{1-4}$alkyl-$NR^{14i}R^{14j}$; —$C(=O)$—$C(=O)$—$NR^{14k}R^{14l}$; $C_{2-6}$alkenyl; and $C_{2-6}$alkenyl substituted with one $R^{13}$;
provided that when $Het^{1a}$ or $R^{18}$ are directly attached to the N-atom of ring B, said $Het^{1a}$ or $R^{18}$ are attached to the N-atom via a ring carbon atom;
$R^{10}$ represents —OH, —O—$C_{1-4}$alkyl, —$NR^{11a}R^{11b}$ or $Het^2$;
$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl; $Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N; or a 6- to 11-membered bicyclic saturated heterocyclyl, including fused, spiro and bridged cycles, containing one, two or three heteroatoms each independently selected from O, S, $S(=O)_p$ and N;
wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$Het^2$ represents a heterocyclyl of formula (b-1)

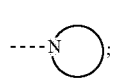
(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —$NH_2$, —NH($C_{1-4}$alkyl), —N($C_{1-4}$alkyl)$_2$, and $C_{1-4}$alkyl-OH;

$R^{11b}$ represents hydrogen; $Het^{1e}$; $C_{1-4}$alkyl; $C_{1-4}$alkyl-$Het^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)NR$^{15a}$R$^{15b}$, —NR$^{19a}$R$^{19b}$, $C_{3-6}$cycloalkyl, $Het^{1d}$, —S(=O)$_2$—$C_{1-4}$alkyl, —S(=O)(=N—$R^{20c}$)—$C_{1-4}$alkyl, or —C(=O)—$Het^{1f}$;

$R^{12}$ represents —OH, —O—$C_{1-4}$alkyl, —NR$^{14a}$R$^{14b}$, C(=O)NR$^{14c}$R$^{14d}$, —S(=O)$_2$—$C_{1-4}$alkyl, —S(=O)(=N—$R^{20b}$)—$C_{1-4}$alkyl, $C_{3-6}$cycloalkyl, $Ar^2$, or $Het^{1c}$;

$Ar^1$ represents phenyl optionally substituted with one hydroxy;

$Ar^2$ represents phenyl optionally substituted with one $C_{1-4}$alkyl;

$Het^{3a}$, $Het^{3b}$, $Het^5$, $Het^6$ and $Het^{1f}$ each independently represents a heterocyclyl of formula (c-1)

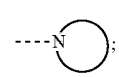
(c-1)

(c-1) represents a N-linked 4- to 7-membered monocyclic saturated heterocyclyl optionally containing one additional heteroatom selected from O, S, S(=O)$_p$ and N;

wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{14g}$, $R^{14i}$, $R^{14k}$, $R^{15a}$, $R^{17a}$ and $R^{19a}$ each independently represents hydrogen or $C_{1-4}$ alkyl;

$R^{14b}$, $R^{14d}$, $R^{14h}$, $R^{14i}$, $R^{14l}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20}$, $R^{20b}$ and $R^{20c}$ each independently represents hydrogen; $C_{1-4}$alkyl; $C_{3-6}$cycloalkyl; or $C_{1-4}$ alkyl substituted with one substituent selected from the group consisting of —OH and —O—$C_{1-4}$ alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, $C_{1-6}$alkyl substituted with one $R^5$, or $C_{1-6}$alkyl substituted with one, two or three fluoro atoms;

Y represents CR$^4$ or N;

$R^4$ represents hydrogen or halo;

$R^5$ represents $Het^{3a}$, —NR$^{6a}$R$^{6b}$, or —OR$^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-NR$^{8a}$R$^{8b}$, —C(=O)—$R^9$, —S(=O)$_2$—OH, —P(=O)$_2$—OH, —(C=O)—CH(NH$_2$)—$C_{1-4}$alkyl-Ar$^1$, or —$C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of —$NH_2$, —COOH, and $Het^6$;

$R^{16a}$ and $R^{16b}$ each independently represents hydrogen, $C_{1-4}$alkyl or $C_{3-6}$cycloalkyl;

$R^3$ represents a fused 6- to 11-membered bicyclic heteroaromatic ring system containing one or two heteroatoms each independently selected from O, S, and N;

wherein said fused 6- to 11-membered bicyclic heteroaromatic ring system may optionally be substituted on the ring carbon atoms with in total one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl;

—O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; Het$^{1a}$; —O-Het$^{1b}$; R$^{18}$; —P(=O)—(C$_{1-4}$alkyl)$_2$; —NH—C(=O)—C$_{1-4}$alkyl; —NH—C(=O)—Het$^{1g}$; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; and C$_{2-6}$alkenyl substituted with one R$^{13}$; and wherein said fused 6- to 11-membered bicyclic heteroaromatic ring system may optionally be substituted, where possible, on one ring N-atom with a substituent selected from the group consisting of C$_{1-6}$alkyl; C$_{3-6}$cycloalkyl; Het$^{1a}$; R$^{18}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; —(C=O)—C$_{1-4}$alkyl; —C(=O)NR$^{14g}$R$^{14h}$; —C(=O)—C$_{1-4}$alkyl-NR$^{14i}$R$^{14j}$; —C(=O)—C(=O)—NR$^{14k}$R$^{14l}$; C$_{2-6}$alkenyl; and C$_{2-6}$alkenyl substituted with one R$^{13}$;

provided that when Het$^{1a}$ or R$^{18}$ are directly attached to the N-atom of a ring, said Het$^{1a}$ or R$^{18}$ are attached to the N-atom via a ring carbon atom;

R$^{10}$ represents —OH, —O—C$_{1-4}$alkyl, —NR$^{11a}$R$^{11b}$ or Het$^2$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^{1b}$, Het$^{1e}$, Het$^{1g}$ and Het$^4$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$ and Het$^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^2$ represents a heterocyclyl of formula (b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with C$_{1-4}$alkyl; and wherein (b-1) may optionally be substituted on one, two or three ring C-atoms with one or two substituents each independently selected from the group consisting of halo, —OH, cyano, C$_{1-4}$alkyl, —O—C$_{1-4}$alkyl, —NH$_2$, —NH(C$_{1-4}$alkyl), —N(C$_{1-4}$alkyl)$_2$, and C$_{1-4}$alkyl-OH;

R$^{11b}$ represents hydrogen; Het$^{1e}$; C$_{1-4}$alkyl; C$_{1-4}$alkyl-Het$^5$; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;

R$^{13}$ represents —O—C$_{1-4}$alkyl, —C(=O)NR$^{15a}$R$^{15b}$, —NR$^{19a}$R$^{19b}$, C$_{3-6}$cycloalkyl, Het$^{1d}$, —S(=O)$_2$—C$_{1-4}$alkyl, —S(=O)(=N—R$^{20c}$)—C$_{1-4}$alkyl, or —C(=O)—Het$^{1f}$;

R$^{12}$ represents —OH, —O—C$_{1-4}$alkyl, —NR$^{14a}$R$^{14b}$, C(=O)NR$^{14c}$R$^{14d}$, —S(=O)$_2$—C$_{1-4}$alkyl, —S(=O)(=N—R$^{20b}$)—C$_{1-4}$alkyl, C$_{3-6}$cycloalkyl, Ar$^2$, or Het$^{1c}$;

Ar$^1$ represents phenyl optionally substituted with one hydroxy;

Ar$^2$ represents phenyl optionally substituted with one C$_{1-4}$alkyl;

Het$^{3a}$, Het$^{3b}$, Het$^5$, Het$^6$ and Het$^{1f}$ each independently represents a heterocyclyl of formula (c-1)

(c-1) represents a N-linked 4- to 7-membered monocyclic saturated heterocyclyl optionally containing one additional heteroatom selected from O, S, S(=O)$_p$ and N;

wherein in case (c-1) contains one additional N-atom, said additional N-atom may optionally be substituted with C$_{1-4}$alkyl or C$_{3-6}$cycloalkyl; and wherein (c-1) may optionally be substituted on one or two ring C-atoms atoms with one or two substituents each independently selected from the group consisting of halo, C$_{1-4}$alkyl, and C$_{3-6}$cycloalkyl;

R$^{11a}$, R$^{14a}$, R$^{14c}$, R$^{14g}$, R$^{14i}$, R$^{14k}$, R$^{15a}$, R$^{17a}$ and R$^{19a}$ each independently represents hydrogen or C$_{1-4}$ alkyl;

$R^{14b}$, $R^{14d}$, $R^{14h}$, $R^{14j}$, $R^{14l}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20}$, $R^{20b}$ and $R^{20c}$ each independently represents hydrogen; $C_{1-4}$alkyl; $C_{3-6}$cycloalkyl; or $C_{1-4}$ alkyl substituted with one substituent selected from the group consisting of —OH and —O—$C_{1-4}$ alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, $C_{1-6}$alkyl substituted with one $R^5$, or $C_{1-6}$alkyl substituted with one, two or three fluoro atoms;

Y represents $CR^4$ or N;

$R^4$ represents hydrogen or halo;

$R^5$ represents $Het^{3a}$, —$NR^{6a}R^{6b}$, or —$OR^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH(NH$_2$)—$C_{1-4}$alkyl-$Ar^1$, or —$C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of —NH$_2$, —COOH, and $Het^6$;

$R^{16a}$ and $R^{16b}$ each independently represents hydrogen, $C_{1-4}$alkyl or $C_{3-6}$cycloalkyl;

$R^3$ represents a fused 7- to 11-membered bicyclic heteroaromatic ring system containing one or two heteroatoms each independently selected from O, S, and N;

wherein said fused 7- to 11-membered bicyclic heteroaromatic ring system may optionally be substituted on the ring carbon atoms with in total one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; and wherein said fused 7- to 11-membered bicyclic heteroaromatic ring system may optionally be substituted, where possible, on one ring N-atom with a substituent selected from the group consisting of $C_{1-6}$alkyl; $C_{3-6}$cycloalkyl; $Het^{1a}$; $R^{18}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; —(C=O)—$C_{1-4}$alkyl; —C(=O)$NR^{14g}R^{14h}$, —C(=O)—$C_{1-4}$ alkyl-$NR^{14i}R^{14j}$; —C(=O)—C(=O)—$NR^{14k}R^{14l}$; $C_{2-6}$alkenyl; and $C_{2-6}$alkenyl substituted with one $R^{18}$; provided that when $Het^{1a}$ or $R^{18}$ are directly attached to the N-atom of a ring, said $Het^{1a}$ or $R^{18}$ are attached to the N-atom via a ring carbon atom;

$R^{10}$ represents —OH, —O—$C_{1-4}$alkyl, —$NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N; or a 6- to 11-membered bicyclic saturated heterocyclyl, including fused, spiro and bridged cycles, containing one, two or three heteroatoms each independently selected from O, S, $S(=O)_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, $S(=O)_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

$Het^2$ represents a heterocyclyl of formula (b-1)

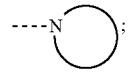

(b-1)

(b-1) represents a N-linked 4- to 7-membered monocyclic saturated heterocyclyl optionally containing one additional heteroatom selected from O, S, $S(=O)_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;
wherein in case (b-1) contains one or two additional N-atoms, said one or two N-atoms may optionally be substituted with C$_{1-4}$alkyl; and
wherein (b-1) may optionally be substituted on one, two or three ring C-atoms with one or two substituents each independently selected from the group consisting of halo, —OH, cyano, C$_{1-4}$ alkyl, —O—C$_{1-4}$alkyl, —NH$_2$, —NH(C$_{1-4}$alkyl), —N(C$_{1-4}$alkyl)$_2$, and C$_{1-4}$alkyl-OH; R$^{11b}$ represents hydrogen; Het$^{1e}$; C$_{1-4}$alkyl; C$_{1-4}$alkyl-Het$^5$; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;
R$^{13}$ represents —O—C$_{1-4}$alkyl, —C(=O)NR$^{15a}$R$^{15b}$, —NR$^{19a}$R$^{19b}$, C$_{3-6}$cycloalkyl, Het$^{1d}$, —S(=O)$_2$—C$_{1-4}$alkyl, —S(=O)(=N—R$^{20c}$)—C$_{1-4}$alkyl, or —C(=O)—Het$^{1f}$;
R$^{12}$ represents —OH, —O—C$_{1-4}$alkyl, —NR$^{14a}$R$^{14b}$, C(=O)NR$^{14c}$R$^{14d}$, —S(=O)$_2$—C$_{1-4}$alkyl, —S(=O)(=N—R$^{20b}$)—C$_{1-4}$alkyl, C$_{3-6}$cycloalkyl, Ar$^2$, or Het$^{1c}$;
Ar$^1$ represents phenyl optionally substituted with one hydroxy;
Ar$^2$ represents phenyl optionally substituted with one C$_{1-4}$alkyl;
Het$^{3a}$, Het$^{3b}$, Het$^5$, Het$^6$ and Het$^{1f}$ each independently represents a heterocyclyl of formula (c-1)

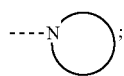
(c-1)

(c-1) represents a N-linked 4- to 7-membered monocyclic saturated heterocyclyl optionally containing one additional heteroatom selected from O, S, S(=O)$_p$ and N;
wherein in case (c-1) contains one additional N-atom, said additional N-atom may optionally be substituted with C$_{1-4}$alkyl or C$_{3-6}$cycloalkyl; and
wherein (c-1) may optionally be substituted on one or two ring C-atoms atoms with one or two substituents each independently selected from the group consisting of halo, C$_{1-4}$alkyl, and C$_{3-6}$cycloalkyl;
R$^{11a}$, R$^{14a}$, R$^{14c}$, R$^{14g}$, R$^{14i}$, R$^{14k}$, R$^{15a}$, R$^{17a}$ and R$^{19a}$ each independently represents hydrogen or C$_{1-4}$ alkyl;
R$^{14b}$, R$^{14d}$, R$^{14h}$, R$^{14i}$, R$^{14l}$, R$^{15b}$, R$^{17b}$ and R$^{19b}$ each independently represents hydrogen; C$_{1-4}$alkyl; C$_{3-6}$cycloalkyl; or C$_{1-4}$alkyl substituted with one substituent selected from the group consisting of halo, —OH and —O—C$_{1-4}$alkyl;
R$^{20}$, R$^{20b}$ and R$^{20c}$ each independently represents hydrogen; C$_{1-4}$alkyl; C$_{3-6}$cycloalkyl; or C$_{1-4}$ alkyl substituted with one substituent selected from the group consisting of —OH and —O—C$_{1-4}$ alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
R$^1$ represents C$_{1-4}$alkyl;
R$^2$ represents C$_{1-6}$alkyl, or C$_{1-6}$alkyl substituted with one R$^5$;
Y represents CR$^4$;
R$^4$ represents hydrogen or halo;
R$^5$ represents —NR$^{6a}$R$^{6b}$ or —OR$^7$;
R$^{6a}$ represents hydrogen or C$_{1-4}$alkyl;
R$^{6b}$ represents hydrogen; C$_{1-4}$alkyl; C$_{3-6}$cycloalkyl; or —C(=O)—C$_{1-4}$alkyl;
R$^7$ represents hydrogen, C$_{1-4}$alkyl, or —C$_{1-4}$alkyl-NR$^{8a}$R$^{8b}$;
R$^{8a}$ represents hydrogen or C$_{1-4}$alkyl;
R$^{8b}$ represents hydrogen, C$_{1-4}$alkyl, or C$_{3-6}$cycloalkyl;
R$^3$ represents a fused 6- to 11-membered bicyclic heteroaromatic ring system containing one or two heteroatoms each independently selected from O, S, and N;
wherein said fused 6- to 11-membered bicyclic heteroaromatic ring system may optionally be substituted on the ring carbon atoms with in total one, two or three substituents each independently selected from the group consisting of halo; cyano; C$_{1-6}$alkyl; —O—C$_{1-4}$alkyl; C$_{1-4}$ alkyl substituted with one, two or three halo atoms; C$_{1-4}$alkyl substituted with one, two or three —OH substituents; C$_{1-4}$alkyl substituted with one R$^{13}$; C$_{2-6}$alkenyl; and C$_{2-6}$alkenyl substituted with one R$^{13}$; and
wherein said fused 6- to 11-membered bicyclic heteroaromatic ring system may optionally be substituted, where possible, on one ring N-atom with a substituent selected from the group consisting of C$_{1-6}$alkyl; C$_{3-6}$cycloalkyl; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; and C$_{2-6}$alkenyl substituted with one R$^{13}$;
Het$^{1d}$ represents a 4- to 7-membered monocyclic saturated heterocyclyl containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and
wherein said 4- to 7-membered monocyclic saturated heterocyclyl may optionally be substituted on one, two or three ring C-atoms with one or two substituents each independently selected from the group consisting of —OH, halo, C$_{1-4}$alkyl, cyano, —O—C$_{1-4}$alkyl, —NH$_2$, —NH(C$_{1-4}$alkyl), and —N(C$_{1-4}$alkyl)$_2$;
R$^{13}$ represents —O—C$_{1-4}$alkyl, —C(=O)NR$^{15a}$R$^{15b}$, —NR$^{19a}$R$^{19b}$, C$_{3-6}$cycloalkyl, or Het$^{1d}$;
R$^{15a}$, and R$^{19a}$ each independently represents hydrogen or C$_{1-4}$alkyl;
R$^{15b}$, and R$^{19b}$ each independently represents hydrogen; C$_{1-4}$alkyl;
C$_{3-6}$cycloalkyl; or C$_{1-4}$alkyl substituted with one substituent selected from the group consisting of halo, —OH and —O—C$_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
R$^1$ represents C$_{1-4}$alkyl;
R$^2$ represents C$_{1-6}$alkyl, or C$_{1-6}$alkyl substituted with one R$^5$;
Y represents CR$^4$;
R$^4$ represents hydrogen;
R$^5$ represents —OR$^7$;

R$^7$ represents hydrogen;
R$^3$ represents a fused 6- to 11-membered bicyclic heteroaromatic ring system containing one or two heteroatoms each independently selected from O, S, and N;
wherein said fused 6- to 11-membered bicyclic heteroaromatic ring system may optionally be substituted on the ring carbon atoms with in total one, two or three halo substituents; and
wherein said fused 6- to 11-membered bicyclic heteroaromatic ring system may optionally be substituted, where possible, on one ring N-atom with a substituent selected from the group consisting of C$_{1-4}$alkyl substituted with one, two or three —OH substituents; C$_{1-4}$alkyl substituted with one R$^{13}$;
Het$^{1d}$ represents a 4- to 7-membered monocyclic saturated heterocyclyl containing one or two heteroatoms each independently selected from O, S, S(=O)$_p$ and N;
R$^{13}$ represents —O—C$_{1-4}$alkyl, —C(=O)NR$^{15a}$R$^{15b}$, or Het$^{1d}$;
R$^{15a}$ represents hydrogen or C$_{1-4}$alkyl;
R$^{15b}$ represents C$_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
R$^1$ represents C$_{1-4}$alkyl;
R$^2$ represents C$_{1-6}$alkyl, or C$_{1-6}$alkyl substituted with one R$^5$;
Y represents CR$^4$;
R$^4$ represents hydrogen;
R$^5$ represents —OR$^7$;
R$^7$ represents hydrogen;
R$^3$ represents a fused 7- to 11-membered bicyclic heteroaromatic ring system containing one or two heteroatoms each independently selected from O, S, and N;
wherein said fused 7- to 11-membered bicyclic heteroaromatic ring system may optionally be substituted on the ring carbon atoms with in total one, two or three halo substituents; and
wherein said fused 7- to 11-membered bicyclic heteroaromatic ring system may optionally be substituted, where possible, on one ring N-atom with a substituent selected from the group consisting of C$_{1-4}$alkyl substituted with one, two or three —OH substituents; C$_{1-4}$alkyl substituted with one R$^{13}$;
Het$^{1d}$ represents a 4- to 7-membered monocyclic saturated heterocyclyl containing one or two heteroatoms each independently selected from O, S, S(=O)$_p$ and N;
R$^{13}$ represents —O—C$_{1-4}$alkyl, —C(=O)NR$^{15a}$R$^{15b}$, or Het$^{1d}$;
R$^{15a}$ represents hydrogen or C$_{1-4}$alkyl;
R$^{15b}$ represents C$_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
R$^1$ represents C$_{1-4}$alkyl;
R$^2$ represents C$_{1-6}$alkyl, or C$_{1-6}$alkyl substituted with one R$^5$;
Y represents CR$^4$;
R$^4$ represents hydrogen;
R$^5$ represents —OR$^7$;
R$^7$ represents hydrogen;
R$^3$ represents a fused 7- to 11-membered bicyclic heteroaromatic ring system containing one or two heteroatoms each independently selected from O, S, and N;
wherein said fused 7- to 11-membered bicyclic heteroaromatic ring system may optionally be substituted on the ring carbon atoms with in total one, two or three substituents each independently selected from the group consisting of halo; —C$_{1-4}$alkyl; and —C(=O)—R$^{10}$; and
wherein said fused 7- to 11-membered bicyclic heteroaromatic ring system may optionally be substituted, where possible, on one ring N-atom with a substituent selected from the group consisting of C$_{1-4}$alkyl substituted with one, two or three —OH substituents; and C$_{1-4}$alkyl substituted with one R$^{13}$;
R$^{10}$ represents —NR$^{11a}$R$^{11b}$;
Het$^{1d}$ represents a 4- to 7-membered monocyclic saturated heterocyclyl containing one or two heteroatoms each independently selected from O, S, S(=O)$_p$ and N;
R$^{11b}$ represents C$_{1-4}$alkyl;
R$^{13}$ represents —O—C$_{1-4}$alkyl, —C(=O)NR$^{15a}$R$^{15b}$, or Het$^{1d}$;
R$^{11a}$ and R$^{15a}$ each independently represents hydrogen or C$_{1-4}$alkyl;
R$^{15b}$ represents C$_{1-4}$alkyl;
p represents 1 or 2;
and the pharmaceutically acceptable addition salts, and the solvates thereof.

The present invention relates in particular to compounds of Formula (I) as defined herein, tautomers and stereoisomeric forms thereof, wherein
R$^1$ represents C$_{1-4}$alkyl;
R$^2$ represents C$_{1-6}$alkyl, or C$_{1-6}$alkyl substituted with one R$^5$;
Y represents CR$^4$;
R$^4$ represents hydrogen;
R$^5$ represents —OR$^7$;
R$^7$ represents hydrogen;
R$^3$ represents a fused 9-membered bicyclic heteroaromatic ring system containing one or two N-atoms;
wherein said fused 9-membered bicyclic heteroaromatic ring system may optionally be substituted on the ring carbon atoms with in total one, two or three halo substituents; and
wherein said fused 9-membered bicyclic heteroaromatic ring system may optionally be substituted, where possible, on one ring N-atom with a substituent selected from the group consisting of C$_{1-4}$alkyl substituted with one, two or three —OH substituents; C$_{1-4}$alkyl substituted with one R$^{13}$;
Het$^{1d}$ represents morpholinyl;
R$^{13}$ represents —O—C$_{1-4}$alkyl, —C(=O)NR$^{15a}$R$^{15b}$, or Het$^{1d}$;
R$^{15a}$ represents hydrogen or C$_{1-4}$alkyl;
R$^{15b}$ represents C$_{1-4}$alkyl;
and the pharmaceutically acceptable addition salts, and the solvates thereof.

The present invention relates in particular to compounds of Formula (I) as defined herein, tautomers and stereoisomeric forms thereof, wherein
R$^1$ represents C$_{1-4}$alkyl;
R$^2$ represents C$_{1-6}$alkyl, or C$_{1-6}$alkyl substituted with one R$^5$;
Y represents CR$^4$;
R$^4$ represents hydrogen;
R$^5$ represents —OR$^7$;
R$^7$ represents hydrogen;
R$^3$ represents a fused 9-membered bicyclic heteroaromatic ring system selected from the following structures

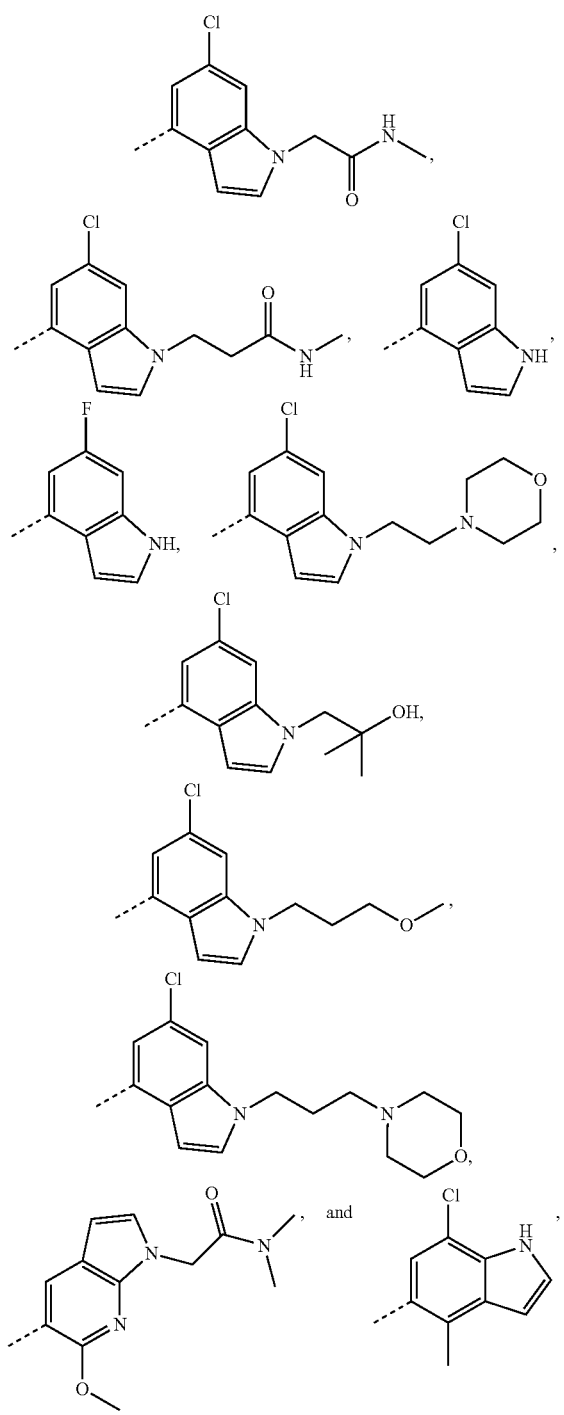

and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused 9-membered bicyclic heteroaromatic ring system selected from the following structures

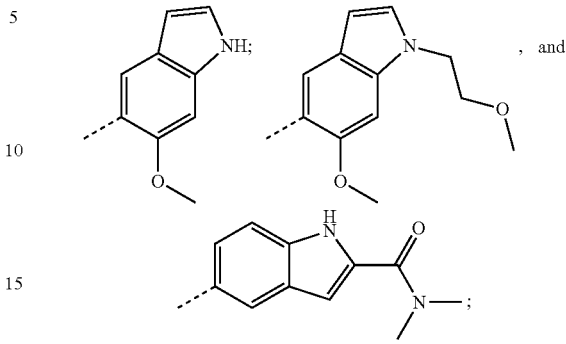

and the pharmaceutically acceptable addition salts, and the solvates thereof.

The present invention also relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents a fused 9-membered bicyclic heteroaromatic ring system containing one N-atom;
wherein said fused 9-membered bicyclic heteroaromatic ring system may optionally be substituted on the ring carbon atoms with in total one, two or three halo substituents; and wherein said fused 9-membered bicyclic heteroaromatic ring system may optionally be substituted, where possible, on one ring N-atom with a substituent selected from the group consisting of $C_{1-4}$alkyl substituted with one, two or three —OH substituents; $C_{1-4}$alkyl substituted with one $R^{13}$;
$R^{13}$ represents —O—$C_{1-4}$alkyl, or —C(=O)$NR^{15a}R^{15b}$;
$R^{15a}$ represents hydrogen or $C_{1-4}$alkyl;
$R^{15b}$ represents $C_{1-4}$alkyl;
and the pharmaceutically acceptable addition salts, and the solvates thereof.

The present invention relates in particular to compounds of Formula (III) as defined herein, tautomers and stereoisomeric forms thereof, wherein
$R^1$ represents methyl;
$R^2$ represents methyl substituted with one $R^5$;
Y represents $CR^4$;
$R^4$ represents hydrogen;
$R^5$ represents —$OR^7$;
$R^7$ represents hydrogen;
$R^3$ represents

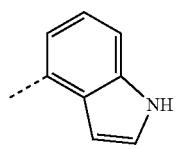

optionally substituted on the ring carbon atoms with in total one, two or three halo substituents; and optionally substituted on the ring N-atom with a substituent selected from the group consisting of $C_{1-4}$alkyl substituted with one, two or three —OH substituents; $C_{1-4}$alkyl substituted with one $R^{13}$;
$R^{13}$ represents —O—$C_{1-4}$alkyl, or —C(=O)NR$^{15a}$R$^{15b}$;
$R^{15a}$ represents hydrogen or $C_{1-4}$alkyl;
$R^{15b}$ represents $C_{1-4}$alkyl;
and the pharmaceutically acceptable addition salts, and the solvates thereof.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(a) Y represents CR$^4$; and R$^4$ represents hydrogen;
(b) R$^5$ represents —OR$^7$;
(c) R$^7$ represents hydrogen;
(d) R$^3$ represents a fused 6- to 11-membered bicyclic heteroaromatic ring system containing one or two heteroatoms each independently selected from O, S, and N;
wherein said fused 6- to 11-membered bicyclic heteroaromatic ring system may optionally be substituted on the ring carbon atoms with in total one, two or three halo substituents; and
wherein said fused 6- to 11-membered bicyclic heteroaromatic ring system may optionally be substituted, where possible, on one ring N-atom with a substituent selected from the group consisting of $C_{1-4}$alkyl substituted with one, two or three —OH substituents; $C_{1-4}$alkyl substituted with one $R^{13}$;
(e) Het$^{1d}$ represents a 4- to 7-membered monocyclic saturated heterocyclyl containing one or two heteroatoms each independently selected from O, S, S(=O)$_p$ and N;
(f) $R^{13}$ represents —O—$C_{1-4}$alkyl, —C(=O)NR$^{15a}$R$^{15b}$, or Het$^{1d}$;
(g) R$^{15a}$ represents hydrogen or $C_{1-4}$alkyl;
(h) R$^{15b}$ represents $C_{1-4}$alkyl.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(a) R$^1$ represents methyl;
(b) R$^2$ represents methyl substituted with one R$^5$;
(c) Y represents CR$^4$; and R$^4$ represents hydrogen;
(d) R$^5$ represents —OR$^7$;
(e) R$^7$ represents hydrogen;
(f) R$^3$ represents

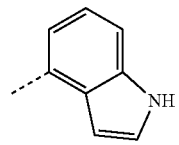

optionally substituted on the ring carbon atoms with in total one, two or three halo substituents; and optionally substituted on the ring N-atom with a substituent selected from the group consisting of $C_{1-4}$alkyl substituted with one, two or three —OH substituents; $C_{1-4}$alkyl substituted with one $R^{13}$;
(g) $R^{13}$ represents —O—$C_{1-4}$alkyl, or —C(=O)NR$^{15a}$R$^{15b}$;
(h) R$^{15a}$ represents hydrogen or $C_{1-4}$alkyl;
(i) R$^{15b}$ represents $C_{1-4}$alkyl.

In an embodiment, the present invention relates to a subgroup of Formula (I), hereby named compounds of Formula (I'):

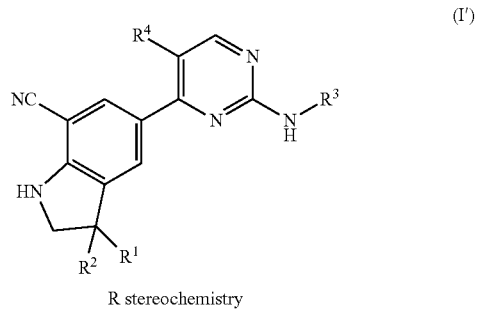

R stereochemistry wherein all variables are defined according to any of the other embodiments.

In an embodiment, the present invention relates to a subgroup of Formula (I), hereby named compounds of Formula (I')

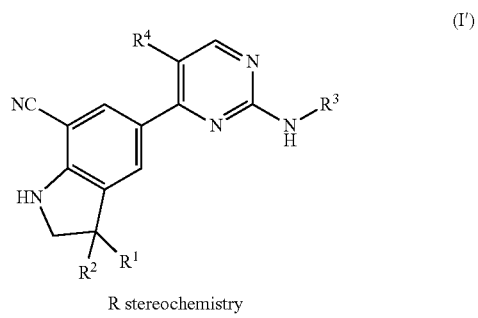

R stereochemistry wherein R$^1$ represents $C_{1-4}$alkyl;
R$^2$ represents $C_{1-6}$alkyl substituted with one R$^5$;
in particular wherein R$^1$ represents $C_{1-4}$alkyl;
R$^2$ represents $C_{1-6}$alkyl substituted with one R$^5$;
R$^5$ represents —OR$^7$;
more in particular wherein R$^1$ represents $C_{1-4}$alkyl;
R$^2$ represents $C_{1-6}$alkyl substituted with one R$^5$;
R$^5$ represents —OR$^7$;
R$^7$ represents hydrogen;
and wherein all other variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein
R$^1$ represents methyl;
R$^2$ represents methyl or —CH$_2$—OH.

In an embodiment, the present invention relates to those compounds of Formula (I) and the pharmaceutically acceptable addition salts, and the solvates thereof, or any subgroup thereof as mentioned in any of the other embodiments, wherein
R$^1$ represents methyl; R$^2$ represents —CH$_2$—OH.

In an embodiment, the present invention relates to those compounds of Formula (I) and the pharmaceutically acceptable addition salts, and the solvates thereof, or any subgroup thereof as mentioned in any of the other embodiments, wherein $R^4$ represents hydrogen or fluoro.

In an embodiment, the present invention relates to those compounds of Formula (I) and the pharmaceutically acceptable addition salts, and the solvates thereof, or any subgroup thereof as mentioned in any of the other embodiments, wherein $R^4$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein
$R^7$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein
$R^5$ represents —$OR^7$; and
$R^7$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein
$R^9$ represents $C_{1-4}$alkyl, or $C_{1-4}$alkyl substituted with one substituent selected from the group consisting of —$NH_2$, —COOH, and $Het^6$.

In an embodiment, the present invention relates to those compounds of Formula (I) and the pharmaceutically acceptable addition salts, and the solvates thereof, or any subgroup thereof as mentioned in any of the other embodiments, wherein $R^{18}$ is attached to the remainder of the molecule of Formula (I) via a carbon atom.

In an embodiment, the present invention relates to those compounds of Formula (I) and the pharmaceutically acceptable addition salts, and the solvates thereof, or any subgroup thereof as mentioned in any of the other embodiments, wherein ring A represents phenyl.

In an embodiment, the present invention relates to those compounds of Formula (I) and the pharmaceutically acceptable addition salts, and the solvates thereof, or any subgroup thereof as mentioned in any of the other embodiments, wherein $R^{18}$ represents

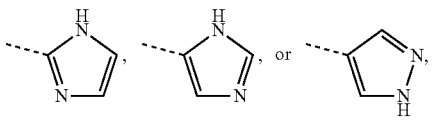

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $R^{18}$ represents

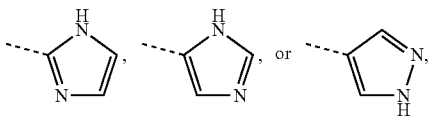

each substituted on the NH with $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents morpholinyl, piperidinyl, pyrrolidinyl, oxetanyl, azetidinyl, piperazinyl, tetrahydro-2H-pyranyl, or hexahydro-1,4-oxazepinyl, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ represent morpholinyl, in particular 1-morpholinyl, optionally substituted where possible on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1d}$ represents morpholinyl, in particular 1-morpholinyl, optionally substituted where possible on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^1$ and $Het^{1d}$ each independently represents

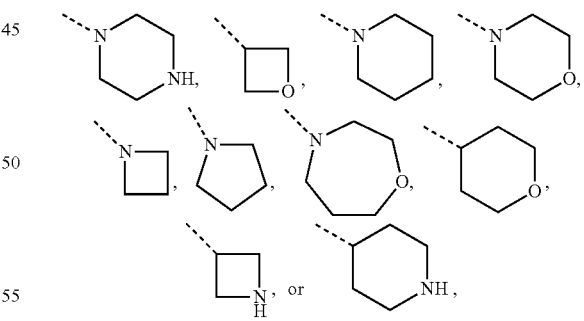

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein
$Het^{1d}$ represents a 4- to 7-membered monocyclic saturated heterocyclyl containing one or two heteroatoms each independently selected from O, S, $S(=O)_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein Het$^{1d}$ represents a 4- to 7-membered monocyclic saturated heterocyclyl containing one or two heteroatoms each independently selected from O, S, S(=O)$_p$ and N; or in case Het$^{1d}$ is attached to the remainder of the molecule of Formula (I) through an N-atom, Het$^{1d}$ may also represent a N-linked 6- to 11-membered bicyclic saturated heterocyclyl, including fused, spiro and bridged cycles, optionally containing one or two additional heteroatoms each independently selected from O, S, S(=O)$_p$ and N;

wherein said 4- to 7-membered monocyclic saturated heterocyclyl or said N-linked 6- to 11-membered bicyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said N-linked 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$ alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein Het$^{1a}$ represents

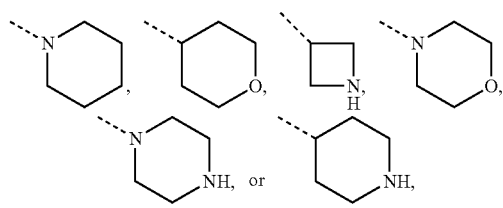

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1c}$ represents

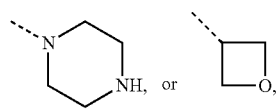

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1d}$ represents

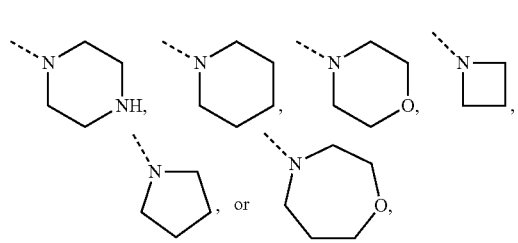

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$, Het$^{1e}$, Het$^{1g}$ and Het$^4$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, attached to the remainder of the molecule of Formula (I) through any available ring carbon atom, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$, Het$^{1e}$, Het$^{1g}$ and Het$^4$ each independently represents piperidinyl, tetrahydro-2H-pyranyl, or pyrrolidinyl, attached to the remainder of the molecule of Formula (I) through any available ring carbon atom, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$, Het$^{1e}$, Het$^{1g}$ and Het$^4$ each independently represents

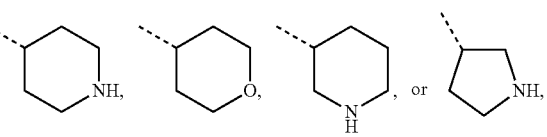

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^4$ represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, attached to the remainder of the molecule of Formula (I) through any available ring carbon atom,
each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^4$ represents piperidinyl, tetrahydro-2H-pyranyl, or pyrrolidinyl, attached to the remainder of the molecule of Formula (I) through any available ring carbon atom,
each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^4$ represents

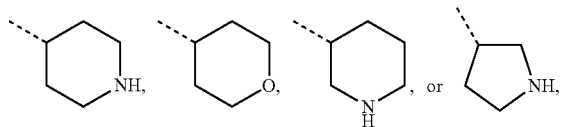

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^1$ represents

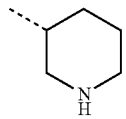

optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$ represents

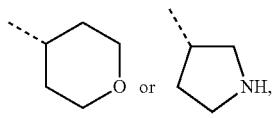

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$ represents

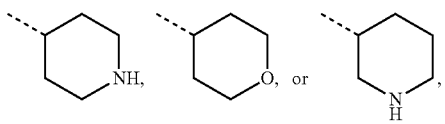

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^2$ represents

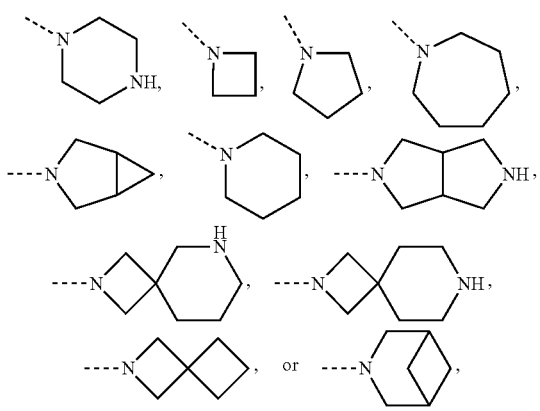

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{3a}$, Het$^{3b}$, Het$^5$, Het$^6$ and Het$^{1f}$ each independently represents

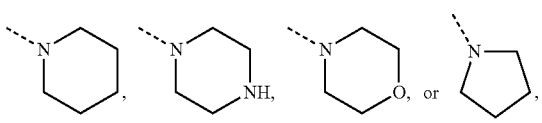

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{3a}$, Het$^{3b}$, Het$^6$ and Het$^{1f}$ each independently represents

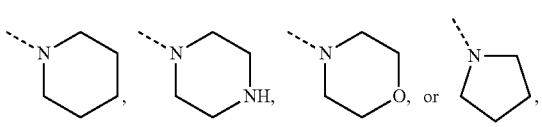

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^4$ represents pyrrolidinyl, piperidinyl, tetrahydropyranyl, azetidinyl, or 1,1-dioxidethiopyranyl; each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^5$ represents

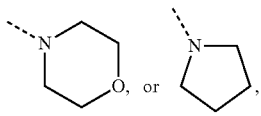

each optionally substituted according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^6$ represents

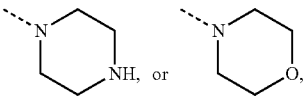

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1f}$ represents

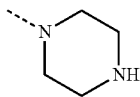

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein
Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and
wherein said 4- to 7-membered monocyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein
Het$^2$ represents a heterocyclyl of formula (b-1)

(b-1) represents a N-linked 4- to 7-membered monocyclic saturated heterocyclyl optionally containing one additional heteroatom selected from O, S, S(=O)$_p$ and N;
wherein in case (b-1) contains one additional N-atom, said N-atom may optionally be substituted with C$_{1-4}$alkyl; and
wherein (b-1) may optionally be substituted on one, two or three ring C-atoms with one or two substituents each independently selected from the group consisting of halo, —OH, cyano, C$_{1-4}$ alkyl, —O—C$_{1-4}$alkyl, —NH$_2$, —NH(C$_{1-4}$alkyl), —N(C$_{1-4}$alkyl)$_2$, and C$_{1-4}$alkyl-OH.

In an embodiment, the present invention relates to those compounds of Formula (I) and the pharmaceutically acceptable addition salts, and the solvates thereof, or any subgroup thereof as mentioned in any of the other embodiments, wherein
Het$^{1a}$ represents a 4- to 7-membered monocyclic saturated heterocyclyl containing one or two heteroatoms each independently selected from O, S, S(=O)$_p$ and N; or a 6- to 1-membered bicyclic saturated heterocyclyl, including fused, spiro and bridged cycles, containing one, two or three heteroatoms each independently selected from O, S, S(=O)$_p$ and N;
wherein said 4- to 7-membered monocyclic saturated heterocyclyl or said 6- to 11-membered bicyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and
wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;
Het$^{1c}$ and Het$^{1d}$ each independently represents a 4- to 7-membered monocyclic saturated heterocyclyl containing one or two heteroatoms each independently selected from O, S, S(=O)$_p$ and N; or in case Het$^{1c}$ and Het$^{1d}$ are attached to the remainder of the molecule of Formula (I) through an N-atom, Het$^{1c}$ and Het$^{1d}$ may also represent a N-linked 6- to 11-membered bicyclic saturated heterocyclyl, including fused, spiro and bridged cycles, optionally containing one or two additional heteroatoms each independently selected from O, S, S(=O)$_p$ and N;

wherein said 4- to 7-membered monocyclic saturated heterocyclyl or said N-linked 6- to 11-membered bicyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl or said N-linked 6- to 11-membered bicyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$ alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein R$^5$ represents —OR$^7$;

R$^7$ represents hydrogen, C$_{1-4}$alkyl, —C$_{1-4}$alkyl-NR$^{8a}$R$^{8b}$, —C(=O)—R$^9$, —(C=O)—CH(NH$_2$)— or C$_{1-4}$ alkyl-Ar$^1$;

R$^9$ represents C$_{1-6}$alkyl, or C$_{1-6}$alkyl substituted with one substituent selected from the group consisting of —NH$_2$, and —COOH;

R$^3$ represents a fused bicyclic ring system of formula (1a-1)

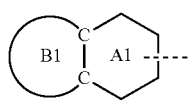

(1a-1)

ring A1 represents phenyl or a 6-membered heteroaromatic ring containing 1 or 2 N-atoms;

ring B1 represents a 4- to 7-membered saturated heterocyclyl containing one or two heteroatoms each independently selected from O, S, S(=O)$_p$ and N;

wherein (1a-1) may optionally be substituted on the ring carbon atoms with in total one, two or three substituents each independently selected from the group consisting of halo; cyano; oxo; C$_{1-6}$ alkyl; —O—C$_{1-4}$alkyl; —C(=O)—R$^{10}$; —S(=O)$_2$—C$_{1-4}$alkyl; —O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; —NH—C(=O)—C$_{1-4}$alkyl; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{2-6}$alkenyl; and C$_{2-6}$alkenyl substituted with one R$^{13}$; and wherein ring B1 may optionally be substituted, where possible, on one or two ring N-atoms with a substituent each independently selected from the group consisting of C$_{1-6}$alkyl; C$_{3-6}$cycloalkyl; C$_{1-4}$alkyl substituted with one, two or three halo atoms; C$_{1-4}$alkyl substituted with one, two or three —OH substituents; C$_{1-4}$alkyl substituted with one R$^{13}$; —(C=O)—C$_{1-4}$alkyl; —C(=O)NR$^{14g}$R$^{14h}$; —C(=O)—C$_{1-4}$alkyl-NR$^{14i}$R$^{14j}$; —C(=O)—C(=O)—NR$^{14k}$R$^{14l}$; C$_{2-6}$alkenyl; and C$_{2-6}$alkenyl substituted with one R$^{13}$;

R$^{10}$ represents —OH, —O—C$_{1-4}$alkyl, or —NR$^{11a}$R$^{11b}$;

R$^{11b}$ represents hydrogen; C$_{1-4}$alkyl; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;

R$^{13}$ represents —O—C$_{1-4}$alkyl, —C(=O)NR$^{15a}$R$^{15b}$, —NR$^{19a}$R$^{19b}$, C$_{3-6}$cycloalkyl, or —S(=O)$_2$—C$_{1-4}$alkyl;

R$^{12}$ represents —OH, —O—C$_{1-4}$alkyl, —NR$^{14a}$R$^{14b}$, C(=O)NR$^{14c}$R$^{14d}$, —S(=O)$_2$—C$_{1-4}$alkyl, C$_{3-6}$cycloalkyl, or Ar$^2$.

In an embodiment, the present invention relates to those compounds of Formula (I) and the pharmaceutically acceptable addition salts, and the solvates thereof, or any subgroup thereof as mentioned in any of the other embodiments, wherein R$^5$ represents —OR$^7$;

R$^7$ represents hydrogen;

R$^3$ represents a fused bicyclic ring system of formula (1a-1)

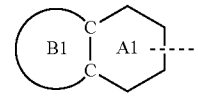

(1a-1)

ring A1 represents phenyl or a 6-membered heteroaromatic ring containing 1 or 2 N-atoms;

ring B1 represents a 4- to 7-membered saturated heterocyclyl containing one or two heteroatoms each independently selected from O and N;

wherein (1a-1) may optionally be substituted on the ring carbon atoms with in total one, two or three substituents each independently selected from the group consisting of halo; C$_{1-6}$alkyl; —O—C$_{1-4}$alkyl; —C(=O)—R$^{10}$; —O—C$_{1-4}$alkyl-R$^{12}$; —NR$^{17a}$R$^{17b}$; C$_{1-4}$alkyl substituted with one, two or three —OH substituents; C$_{1-4}$alkyl substituted with one R$^{13}$; C$_{2-6}$alkenyl; and C$_{2-6}$alkenyl substituted with one R$^{13}$; and wherein ring B1 may optionally be substituted, where possible, on one or two ring N-atoms with a substituent each independently selected from the group consisting of C$_{1-6}$alkyl; C$_{1-4}$alkyl substituted with one R$^{13}$; —(C=O)—C$_{1-4}$alkyl; —C(=O)—C$_{1-4}$alkyl-NR$^{14i}$R$^{14j}$; and —C(=O)—C(=O)—NR$^{14k}$R$^{14l}$;

R$^{10}$ represents —NR$^{11a}$R$^{11b}$;

R$^{11b}$ represents C$_{1-4}$alkyl;

R$^{13}$ represents —O—C$_{1-4}$alkyl, —C(=O)NR$^{15a}$R$^{15b}$, or C$_{3-6}$cycloalkyl;

R$^{12}$ represents C$_{3-6}$cycloalkyl;

R$^{11a}$, R$^{14i}$, R$^{14k}$, R$^{15a}$, and R$^{17a}$ each independently represents hydrogen or C$_{1-4}$alkyl;

R$^{14j}$, R$^{14l}$, R$^{15b}$, and R$^{17b}$ each independently represents hydrogen or C$_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein R$^2$ represents C$_{1-6}$alkyl substituted with one R$^5$;

R$^5$ represents —OR$^7$;

R$^7$ represents hydrogen;

$R^3$ represents a fused bicyclic ring system of formula (1a-1)

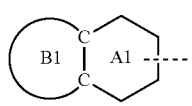

(1a-1)

ring A1 represents phenyl or a 6-membered heteroaromatic ring containing 1 N-atom;
ring B1 represents a 4- to 7-membered saturated heterocyclyl containing one heteroatom selected from O and N;
wherein (1a-1) may optionally be substituted on the ring carbon atoms with in total one, two or three substituents each independently selected from the group consisting of —O—$C_{1-4}$alkyl; —O—$C_{1-4}$alkyl-$R^{12}$; and $C_{1-4}$alkyl substituted with one $R^{13}$; and
wherein ring B may optionally be substituted, where possible, on one N-atom with a $C_{1-6}$alkyl substituent;
$R^{13}$ represents $C_{3-6}$cycloalkyl;
$R^{12}$ represents $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents $C_{1-4}$alkyl;
$R^2$ represents $C_{1-6}$alkyl substituted with one $R^5$;
$R^5$ represents —$OR^7$;
$R^7$ represents hydrogen;
$R^3$ represents a fused bicyclic ring system of formula (2a-1)

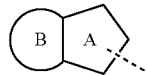

(2a-1)

ring A represents pyrazolyl optionally substituted with one substituent selected from the group consisting of $C_{1-4}$alkyl, and —$C_{1-4}$alkyl-O—$C_{1-4}$alkyl;
ring B represents a $C_{5-7}$cycloalkyl or a 5- to 7-membered saturated heterocyclyl containing one or two heteroatoms each independently selected from O and N;
wherein said $C_{5-7}$cycloalkyl or 5- to 7-membered saturated heterocyclyl may optionally be substituted on one ring carbon atom with one or two $C_{1-4}$alkyl substituents, or one ring carbon atom may optionally be substituted with oxo; and
wherein said 5- to 7-membered saturated heterocyclyl may optionally be substituted on one or two ring N-atoms with a $C_{1-6}$alkyl substituent.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents $C_{1-4}$alkyl;
$R^2$ represents $C_{1-6}$alkyl substituted with one $R^5$;
$R^5$ represents —$OR^7$;
$R^7$ represents hydrogen;
$R^3$ represents a fused bicyclic ring system of formula (2a-1)

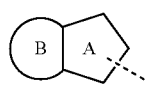

(2a-1)

ring A represents pyrazolyl;
ring B represents a 6-membered saturated heterocyclyl containing one heteroatom selected from O and N;
wherein said 6-membered saturated heterocyclyl may optionally be substituted on one ring carbon atom with one $C_{1-4}$alkyl substituent, or one ring carbon atom may optionally be substituted with oxo; and
wherein said 5- to 7-membered saturated heterocyclyl may optionally be substituted on one N-atom with a $C_{1-6}$alkyl substituent.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents $C_{1-4}$alkyl;
$R^2$ represents $C_{1-6}$alkyl substituted with one $R^5$;
$R^5$ represents —$OR^7$;
$R^7$ represents hydrogen;
$R^3$ represents a fused bicyclic ring system selected from the following structures

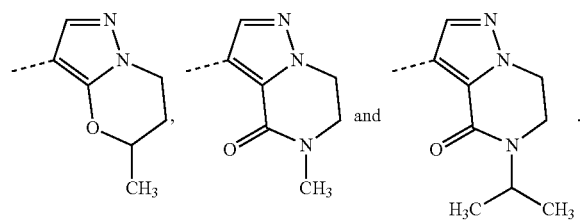

In an embodiment, the present invention relates to those compounds of Formula (I) and the pharmaceutically acceptable addition salts, and the solvates thereof, or any subgroup thereof as mentioned in any of the other embodiments, wherein
$R^5$ represents —$NR^{6a}R^{6b}$, or —$OR^7$;
$R^{6b}$ represents hydrogen; $C_{1-4}$alkyl; $C_{3-6}$cycloalkyl; or —C(=O)—$C_{1-4}$alkyl;
$R^7$ represents hydrogen, $C_{1-4}$alkyl, or —$C_{1-4}$alkyl-$NR^{8a}R^{8b}$;
$R^3$ represents a fused 6- to 11-membered bicyclic heteroaromatic ring system containing one or two heteroatoms each independently selected from O, S, and N;
wherein said fused 6- to 11-membered bicyclic heteroaromatic ring system may optionally be substituted on the ring carbon atoms with in total one, two or three substituents each independently selected from the group consisting of halo; cyano; $C_{1-6}$alkyl; —O—$C_{1-4}$alkyl; $C_{1-4}$ alkyl substituted with one, two or three halo atoms; $C_{1-4}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$; and
wherein said fused 6- to 11-membered bicyclic heteroaromatic ring system may optionally be substituted, where possible, on one ring N-atom with a substituent selected from the group consisting of $C_{1-6}$alkyl; $C_{3-6}$cycloalkyl; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;
$Het^{1d}$ represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —O—$C_{1-4}$alkyl, —$NH_2$, —NH($C_{1-4}$alkyl), and —N($C_{1-4}$alkyl)$_2$;
$R^{13}$ represents —O—$C_{1-4}$alkyl, —C(=O)$NR^{15a}R^{15b}$, —$NR^{19a}R^{19b}$, $C_{3-6}$cycloalkyl, or $Het^{1d}$.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents $C_{1-4}$alkyl;
$R^5$ represents —$OR^7$;
$R^7$ represents hydrogen;
$R^3$ represents a fused 6- to 11-membered bicyclic heteroaromatic ring system containing one or two heteroatoms each independently selected from O, S, and N;
wherein said fused 6- to 11-membered bicyclic heteroaromatic ring system may optionally be substituted on the ring carbon atoms with in total one, two or three halo substituents; and
wherein said fused 6- to 11-membered bicyclic heteroaromatic ring system may optionally be substituted, where possible, on one ring N-atom with a substituent selected from the group consisting of $C_{1-4}$alkyl substituted with one, two or three —OH substituents; $C_{1-4}$alkyl substituted with one $R^{13}$;
$Het^{1d}$ represents a 4- to 7-membered monocyclic saturated heterocyclyl containing one or two heteroatoms each independently selected from O, S, S(=O)$_p$ and N;
$R^{13}$ represents —O—$C_{1-4}$alkyl, —C(=O)$NR^{15a}R^{15b}$, or $Het^{1d}$;
$R^{15a}$ represents hydrogen or $C_{1-4}$alkyl;
$R^{15b}$ represents $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents $C_{1-4}$alkyl;
$R^5$ represents —$OR^7$;
$R^7$ represents hydrogen;
$R^3$ represents a fused 9-membered bicyclic heteroaromatic ring system containing one N-atom;
wherein said fused 6- to 11-membered bicyclic heteroaromatic ring system may optionally be substituted on the ring carbon atoms with in total one, two or three halo substituents; and
wherein said fused 6- to 11-membered bicyclic heteroaromatic ring system may optionally be substituted, where possible, on one ring N-atom with a substituent selected from the group consisting of $C_{1-4}$alkyl substituted with one, two or three —OH substituents; $C_{1-4}$alkyl substituted with one $R^{13}$;
$R^{13}$ represents —O—$C_{1-4}$alkyl, or —C(=O)$NR^{15a}R^{15b}$;
$R^{15a}$ represents hydrogen or $C_{1-4}$alkyl;
$R^{15b}$ represents $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $R^3$ represents an optionally substituted fused bicyclic ring system of formula (1a-1) or (1a-2).

In an embodiment, the present invention relates to those compounds of Formula (I) and the pharmaceutically acceptable addition salts, and the solvates thereof, or any subgroup thereof as mentioned in any of the other embodiments, wherein $R^3$ represents an optionally substituted fused bicyclic ring system of formula (1a-1).

In an embodiment, the present invention relates to those compounds of Formula (I) and the pharmaceutically acceptable addition salts, and the solvates thereof, or any subgroup thereof as mentioned in any of the other embodiments, wherein $R^3$ represents an optionally substituted fused bicyclic ring system of formula (1a-2).

In an embodiment, the present invention relates to those compounds of Formula (I) and the pharmaceutically acceptable addition salts, and the solvates thereof, or any subgroup thereof as mentioned in any of the other embodiments, wherein $R^3$ represents an optionally substituted fused bicyclic ring system of formula (2a-1).

In an embodiment, the present invention relates to those compounds of Formula (I) and the pharmaceutically acceptable addition salts, and the solvates thereof, or any subgroup thereof as mentioned in any of the other embodiments, wherein $R^3$ represents an optionally substituted fused 6- to 11-membered bicyclic heteroaromatic ring system containing one or two heteroatoms each independently selected from O, S, and N.

In an embodiment, the present invention relates to those compounds of Formula (I) and the pharmaceutically acceptable addition salts, and the solvates thereof, or any subgroup thereof as mentioned in any of the other embodiments, wherein $R^3$ represents an optionally substituted fused 7- to 11-membered bicyclic heteroaromatic ring system containing one or two heteroatoms each independently selected from O, S, and N.

In an embodiment, the present invention relates to those compounds of Formula (I) and the pharmaceutically acceptable addition salts, and the solvates thereof, or any subgroup thereof as mentioned in any of the other embodiments, wherein
$R^3$ represents a fused bicyclic ring system selected from the following structures

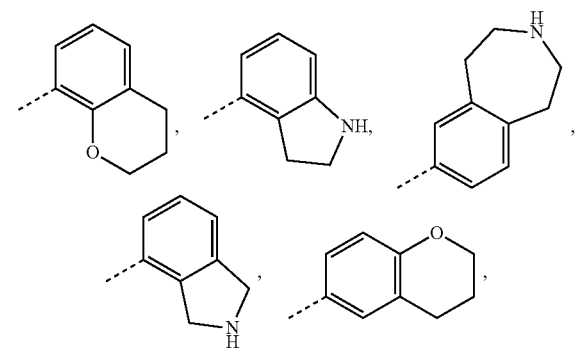

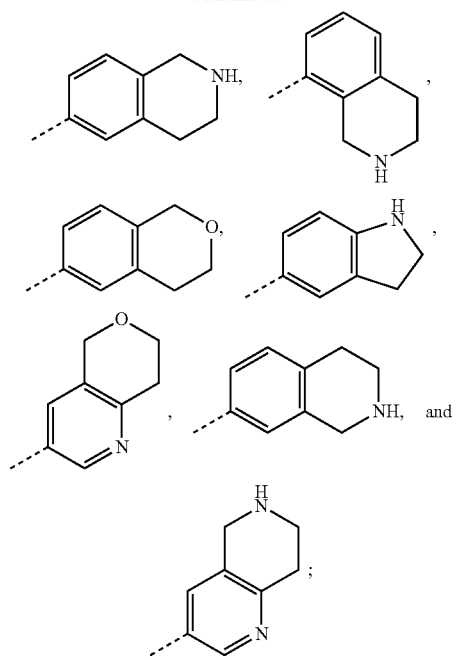

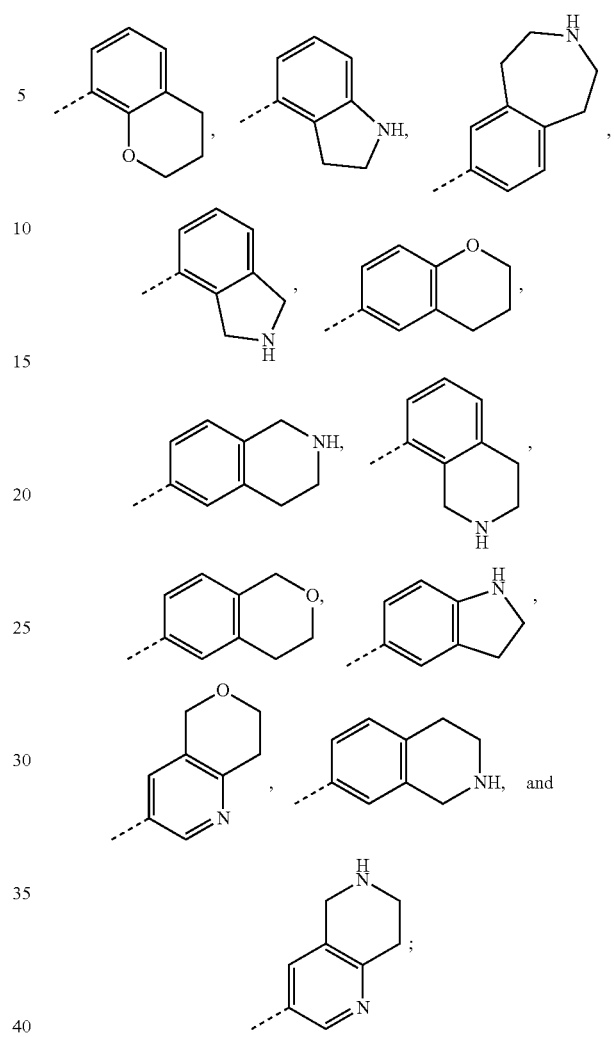

wherein said fused bicyclic ring system may optionally be substituted on the ring carbon atoms with in total one, two or three substituents each independently selected from the group consisting of halo; cyano; $C_{1-6}$alkyl; —O—$C_{1-4}$alkyl; —C(=O)—R; —S(=O)$_2$—$C_{1-4}$alkyl; —S(=O)(=N—R$^{20a}$)—$C_{1-4}$ alkyl; —O—$C_{1-4}$alkyl substituted with one, two or three halo atoms; —O—$C_{1-4}$alkyl-R$^{12}$; $C_{3-6}$ cycloalkyl; —O—$C_{3-6}$cycloalkyl; Het$^{1a}$; —O-Het$^{1b}$; R$^{18}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{11}$; $C_{2-6}$alkenyl; and $C_{2-6}$alkenyl substituted with one R$^{13}$; and wherein said fused bicyclic ring system may optionally be substituted, where possible, on one ring N-atom with a substituent selected from the group consisting of $C_{1-6}$alkyl; $C_{3-6}$cycloalkyl; Het$^{1a}$; R$^{18}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; —(C=O)—$C_{1-4}$alkyl; —C(=O)NR$^{14g}$R$^{14h}$; —C(=O)—$C_{1-4}$alkyl-NR$^{14i}$R$^{14j}$; —C(=O)—C(=O)—NR$^{14k}$R$^{14l}$; $C_{2-6}$alkenyl; and $C_{2-6}$alkenyl substituted with one R$^{13}$; provided that when Het$^{1a}$ or R$^{18}$ are directly attached to a N-atom of said fused bicyclic ring system, said Het$^{1a}$ or R$^{18}$ are attached to the N-atom via a ring carbon atom.

In an embodiment, the present invention relates to those compounds of Formula (I) and the pharmaceutically acceptable addition salts, and the solvates thereof, or any subgroup thereof as mentioned in any of the other embodiments, wherein R$^3$ represents a fused bicyclic ring system selected from the following structures wherein said fused bicyclic ring system may optionally be substituted on the ring carbon atoms with in total one, two or three substituents each independently selected from the group consisting of halo; $C_{1-6}$alkyl; —O—$C_{1-4}$alkyl; —C(=O)—R$^{10}$; —O—$C_{1-4}$alkyl-R$^{12}$; —NR$^{17a}$R$^{17b}$; $C_{1-4}$alkyl substituted with one, two or three —OH substituents; $C_{1-4}$alkyl substituted with one R$^{13}$; $C_{2-6}$alkenyl; and $C_{2-6}$alkenyl substituted with one R$^{13}$; and wherein said fused bicyclic ring system may optionally be substituted, where possible, on one ring N-atom with a substituent selected from the group consisting of $C_{1-6}$alkyl; $C_{1-4}$alkyl substituted with one R; —(C=O)—$C_{1-4}$alkyl; —C(=O)—$C_{1-4}$alkyl-NR$^{14i}$R$^{14j}$; and —C(=O)—C(=O)—NR$^{14k}$R$^{14l}$.

In an embodiment, the present invention relates to those compounds of Formula (I) and the pharmaceutically acceptable addition salts, and the solvates thereof, or any subgroup thereof as mentioned in any of the other embodiments, wherein R$^3$ represents a fused bicyclic ring system selected from the following structures 75
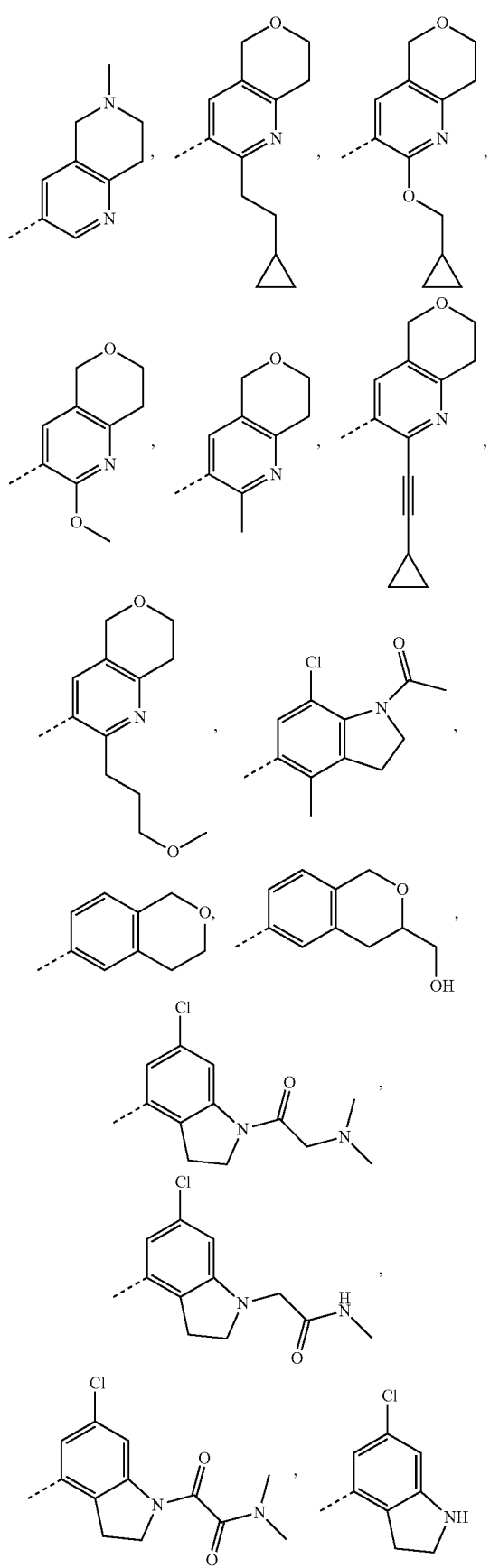
76
-continued
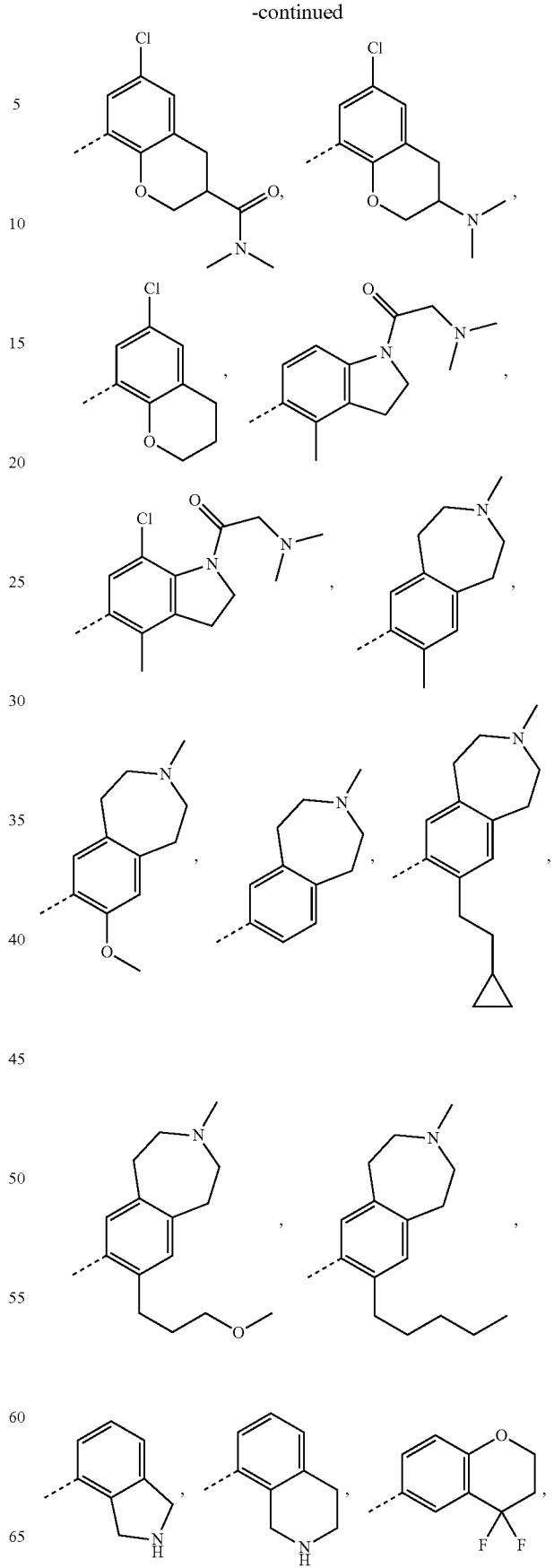

-continued

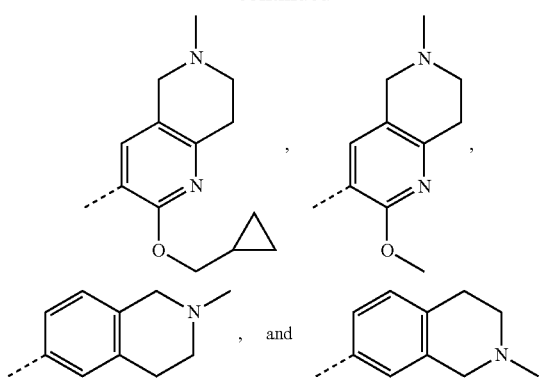

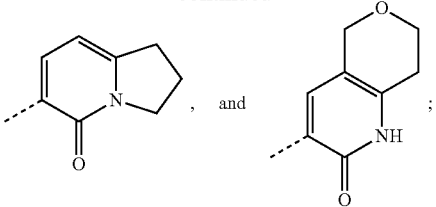

, and

In an embodiment, the present invention relates to those compounds of Formula (I) and the pharmaceutically acceptable addition salts, and the solvates thereof, or any subgroup thereof as mentioned in any of the other embodiments, wherein
R³ represents a fused bicyclic ring system selected from the following structures wherein said fused bicyclic ring system may optionally be substituted according to any one of the other embodiments.

In an embodiment, the present invention relates to those compounds of Formula (I) and the pharmaceutically acceptable addition salts, and the solvates thereof, or any subgroup thereof as mentioned in any of the other embodiments, wherein
R³ represents a fused bicyclic ring system selected from the following structures

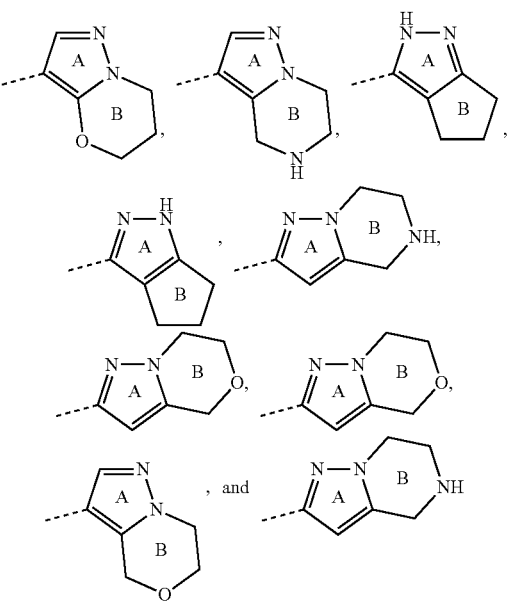

ring A may optionally be substituted with one substituent selected from the group consisting of $C_{1-4}$alkyl, —$C_{1-4}$alkyl-O—$C_{1-4}$alkyl, and $C_{1-4}$alkyl substituted with one, two or three halo atoms;
ring B may optionally be substituted on one ring carbon atom with one or two $C_{1-4}$alkyl substituents, or one ring carbon atom may optionally be substituted with oxo; and
ring B may optionally be substituted on a ring N-atom (when containing a NH group) with a substituent each independently selected from the group consisting of $C_{1-6}$alkyl; $C_{3-6}$cycloalkyl; $C_{1-4}$alkyl substituted with one, two or three halo atoms; $C_{1-4}$alkyl substituted with one, two or three —OH substituents; $C_{1-4}$alkyl substituted with one $R^{13}$; —(C=O)—$C_{1-4}$alkyl; —C(=O)NR$^{14g}$R$^{14h}$; —C(=O)—$C_{1-4}$alkyl-NR$^{14i}$R$^{14j}$;
in particular ring A may optionally be substituted with one substituent selected from the group consisting of $C_{1-4}$alkyl, and —$C_{1-4}$alkyl-O—$C_{1-4}$alkyl;
ring may optionally be substituted on one ring carbon atom with one or two $C_{1-4}$alkyl substituents, or one ring carbon atom may optionally be substituted with oxo; and ring B may optionally be substituted on a ring N-atom (when containing a NH group) with a $C_{1-6}$ alkyl substituent.

In an embodiment, the present invention relates to those compounds of Formula (I) and the pharmaceutically acceptable addition salts, and the solvates thereof, or any subgroup thereof as mentioned in any of the other embodiments, wherein
$R^3$ represents a fused bicyclic ring system selected from the following structures

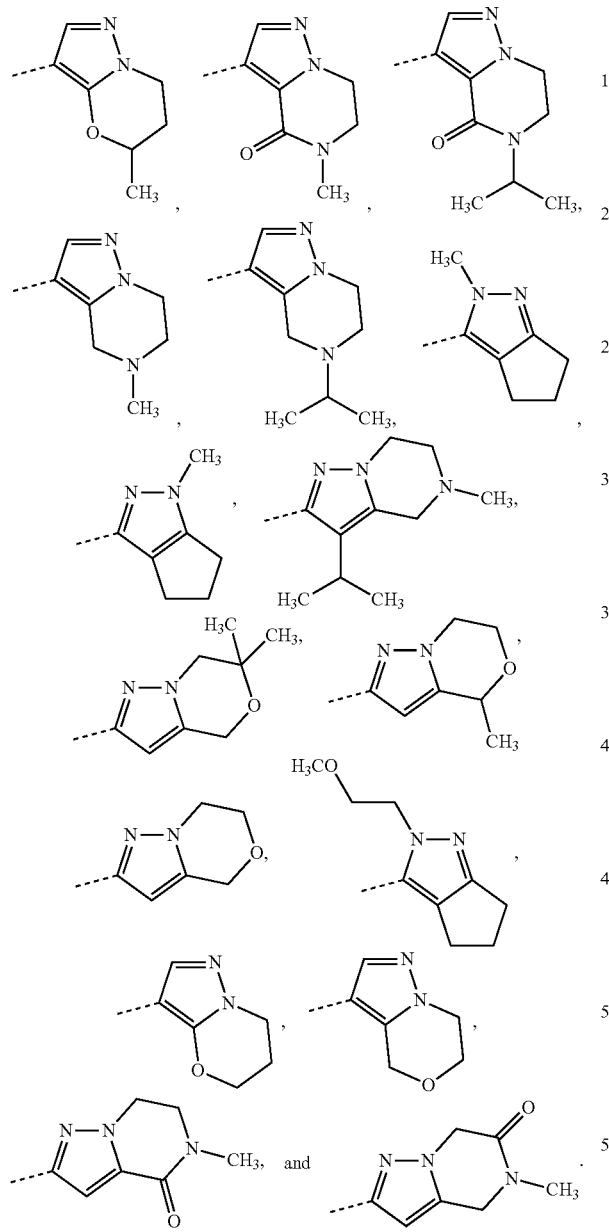

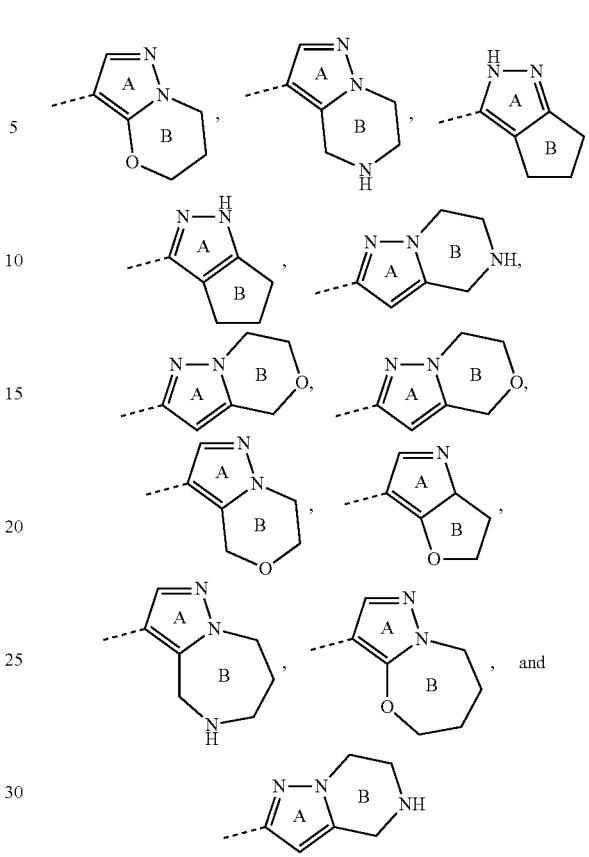

wherein said fused bicyclic ring system may optionally be substituted according to any one of the other embodiments.

In an embodiment, the present invention relates to those compounds of Formula (I) and the pharmaceutically acceptable addition salts, and the solvates thereof, or any subgroup thereof as mentioned in any of the other embodiments, wherein
$R^3$ represents a fused 9-membered bicyclic heteroaromatic ring system selected from the following structures

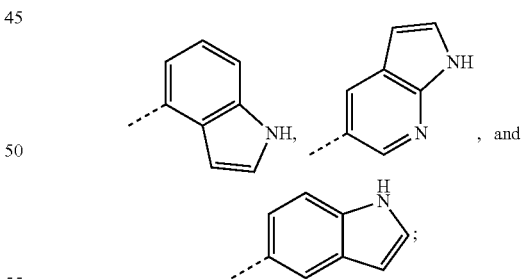

In an embodiment, the present invention relates to those compounds of Formula (I) and the pharmaceutically acceptable addition salts, and the solvates thereof, or any subgroup thereof as mentioned in any of the other embodiments, wherein
$R^3$ represents a fused bicyclic ring system selected from the following structures wherein said fused 9-membered bicyclic heteroaromatic ring system may optionally be substituted on the ring carbon atoms with in total one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —$C_{1-4}$alkyl substituted with one, two or three halo atoms; —$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms;

$C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$; and wherein said fused 9-membered bicyclic heteroaromatic ring system may optionally be substituted, where possible, on one ring N-atom with a substituent selected from the group consisting of $C_{1-6}$alkyl; $C_{3-6}$cycloalkyl; $Het^{1a}$; $R^{18}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; —(C=O)—$C_{1-4}$alkyl; —C(=O)NR$^{14g}$R$^{14h}$; —C(=O)—$C_{1-4}$ alkyl-NR$^{14i}$R$^{14j}$; —C(=O)—C(=O)NR$^{14k}$R$^{14l}$; $C_{2-6}$alkenyl; and $C_{2-6}$alkenyl substituted with one $R^{13}$;

provided that when $Het^{1a}$ or $R^{18}$ are directly attached to the N-atom of ring B, said $Het^{1a}$ or $R^{18}$ are attached to the N-atom via a ring carbon atom.

In an embodiment, the present invention relates to those compounds of Formula (I) and the pharmaceutically acceptable addition salts, and the solvates thereof, or any subgroup thereof as mentioned in any of the other embodiments, wherein $R^3$ represents a fused 9-membered bicyclic heteroaromatic ring system selected from the following structures

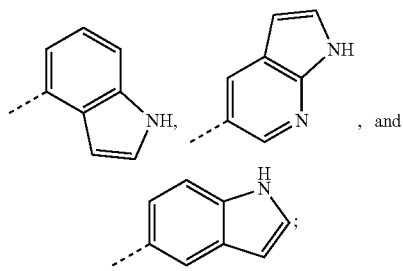

wherein said fused 9-membered bicyclic heteroaromatic ring system may optionally be substituted on the ring carbon atoms with in total one, two or three halo substituents; and wherein said fused 9-membered bicyclic heteroaromatic ring system may optionally be substituted, where possible, on one ring N-atom with a substituent selected from the group consisting of $C_{1-4}$alkyl substituted with one, two or three —OH substituents; and $C_{1-4}$alkyl substituted with one $R^{13}$.

In an embodiment, the present invention relates to those compounds of Formula (I) and the pharmaceutically acceptable addition salts, and the solvates thereof, or any subgroup thereof as mentioned in any of the other embodiments, wherein $R^3$ represents a fused 9-membered bicyclic heteroaromatic ring system selected from the following structures

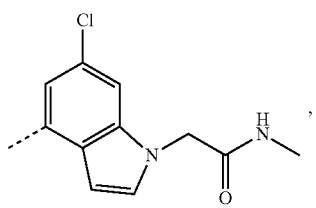

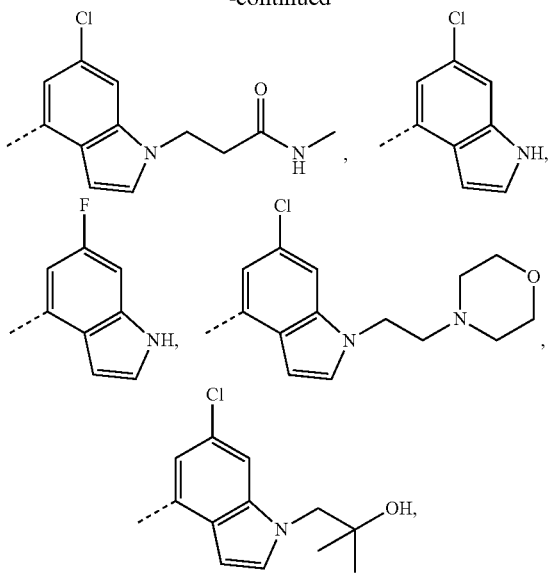

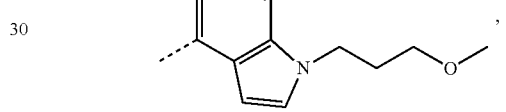

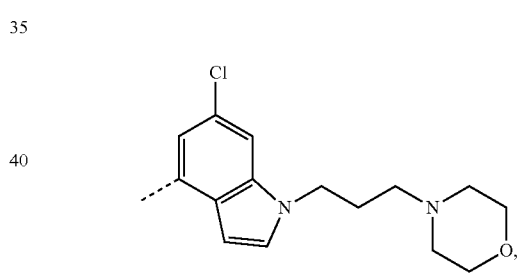

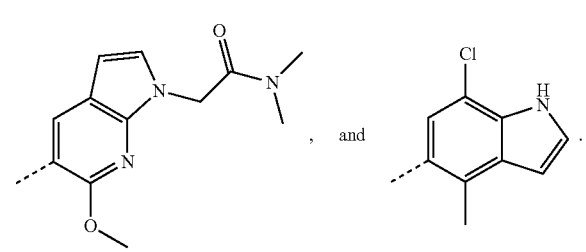

In an embodiment, the present invention relates to those compounds of Formula (I) and the pharmaceutically acceptable addition salts, and the solvates thereof, or any subgroup thereof as mentioned in any of the other embodiments, wherein Y represents $CR^4$.

In an embodiment, the present invention relates to a subgroup of Formula (I), hereby named compounds of Formula (I-x), and the pharmaceutically acceptable addition salts, and the solvates thereof:

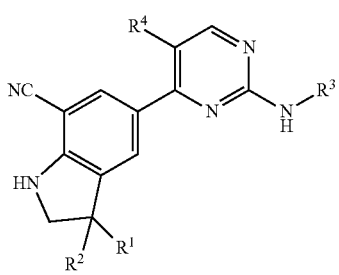

(I-x)

wherein all variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Y represents N.

In an embodiment, the present invention relates to a subgroup of Formula (I), hereby named compounds of Formula (I-y), and the pharmaceutically acceptable addition salts, and the solvates thereof:

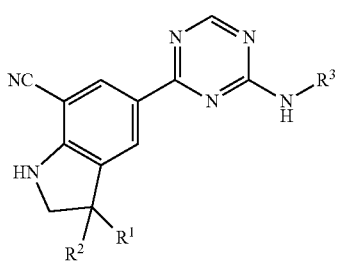

(I-y)

wherein all variables are defined according to any of the other embodiments.

In an embodiment, the present invention relates to a subgroup of Formula (I), hereby named compounds of Formula (I''), and the pharmaceutically acceptable addition salts, and the solvates thereof:

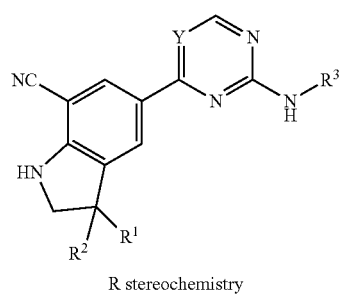

(I'')

R stereochemistry wherein all variables are defined according to any of the other embodiments.

In an embodiment the compound of Formula (I) is selected from the group consisting of compounds 21, 25, 32, 34, 35, 1b, 2b, 3b, 17b, 3c, and 8c, tautomers and stereoisomeric forms thereof, and the pharmaceutically acceptable addition salts, and the solvates thereof.

In an embodiment the compound of Formula (I) is selected from the group consisting of compounds 21, 25, 32, 34, 35, 1b, 2b, 3b, 17b, 3c, and 8c.

In an embodiment the compound of Formula (I) is selected from the group consisting of compounds 21, 25, 32, 34, and 35, tautomers and stereoisomeric forms thereof, and the pharmaceutically acceptable addition salts, and the solvates thereof.

In an embodiment the compound of Formula (I) is selected from the group consisting of compounds 21, 25, 32, 34, and 35.

In an embodiment the compound of Formula (I) is selected from the group consisting of compounds 1b, 2b, 3b, and 17b, tautomers and stereoisomeric forms thereof, and the pharmaceutically acceptable addition salts, and the solvates thereof.

In an embodiment the compound of Formula (I) is selected from the group consisting of compounds 1b, 2b, 3b, and 17b.

In an embodiment the compound of Formula (I) is selected from the group consisting of compounds 3c, and 8c, tautomers and stereoisomeric forms thereof, and the pharmaceutically acceptable addition salts, and the solvates thereof.

In an embodiment the compound of Formula (I) is selected from the group consisting of compounds 3c, and 8c.

In an embodiment the compound of Formula (I) is selected from the group consisting of any of the exemplified compounds, tautomers and stereoisomeric forms thereof, and the free bases, the pharmaceutically acceptable addition salts, and the solvates thereof.

In an embodiment, the present invention relates to a subgroup of Formula (I) as defined in the general reaction schemes.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realise that functionalization reactions illustrated in the Schemes below for compounds of Formula (I) wherein Y is $CR^4$, may also be carried out for compounds wherein Y is N. The skilled person will realise this applies, for example and without limitation, to steps 3 and 4 of scheme 2 and scheme 18.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. For example in Scheme 6, the NH moiety on the pyrimidinyl or the cyanoindoline moiety can be protected with a t-butoxycarbonyl protecting group. In general, conventional protecting groups can be used in accordance with standard practice. The protecting groups may be removed at a convenient subsequent stage using methods known from the art. This is illustrated in the specific examples.

The skilled person will realize that in the reactions described in the Schemes, it may be advisable or necessary to perform the reaction under an inert atmosphere, such as for example under N-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of formula (I).

The skilled person will realize that intermediates and final compounds shown in the schemes below may be further functionalized according to method well-known by the person skilled in the art.

It will be clear for a skilled person that in case a variable in a specific general scheme is not defined, the variable is defined according to the scope of the present invention, or as defined in any one of the other general schemes.

In general, compounds of Formula (I) wherein $R^2$ is $R^2$ being $C_{1-6}$alkyl, and wherein all the other variables are defined according to the scope of the present invention, hereby named compounds of Formula (Ia), can be prepared according to the following reaction Scheme 1. In Scheme 1, halo is defined as Cl, Br or I; and $PG^1$ represents a suitable protecting group, such as for example tert-(butoxycarbonyl). All other variables in Scheme 1 are defined according to the scope of the present invention.

For compounds wherein $R^3$ represents formula (2a-1), step 5 or 6 are preferred over step 4 in Scheme 1.

In Scheme 1, the following reaction conditions apply

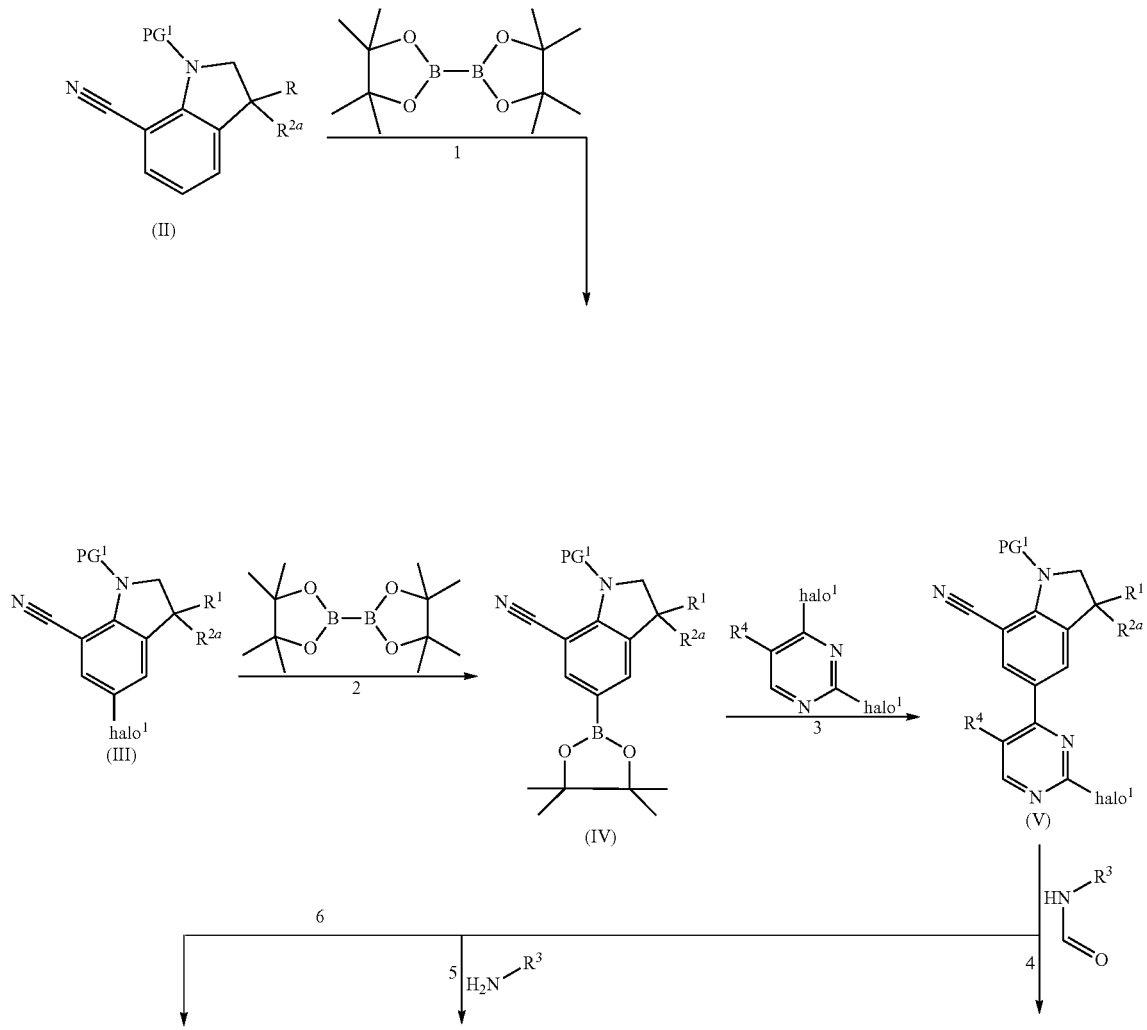

Scheme 1

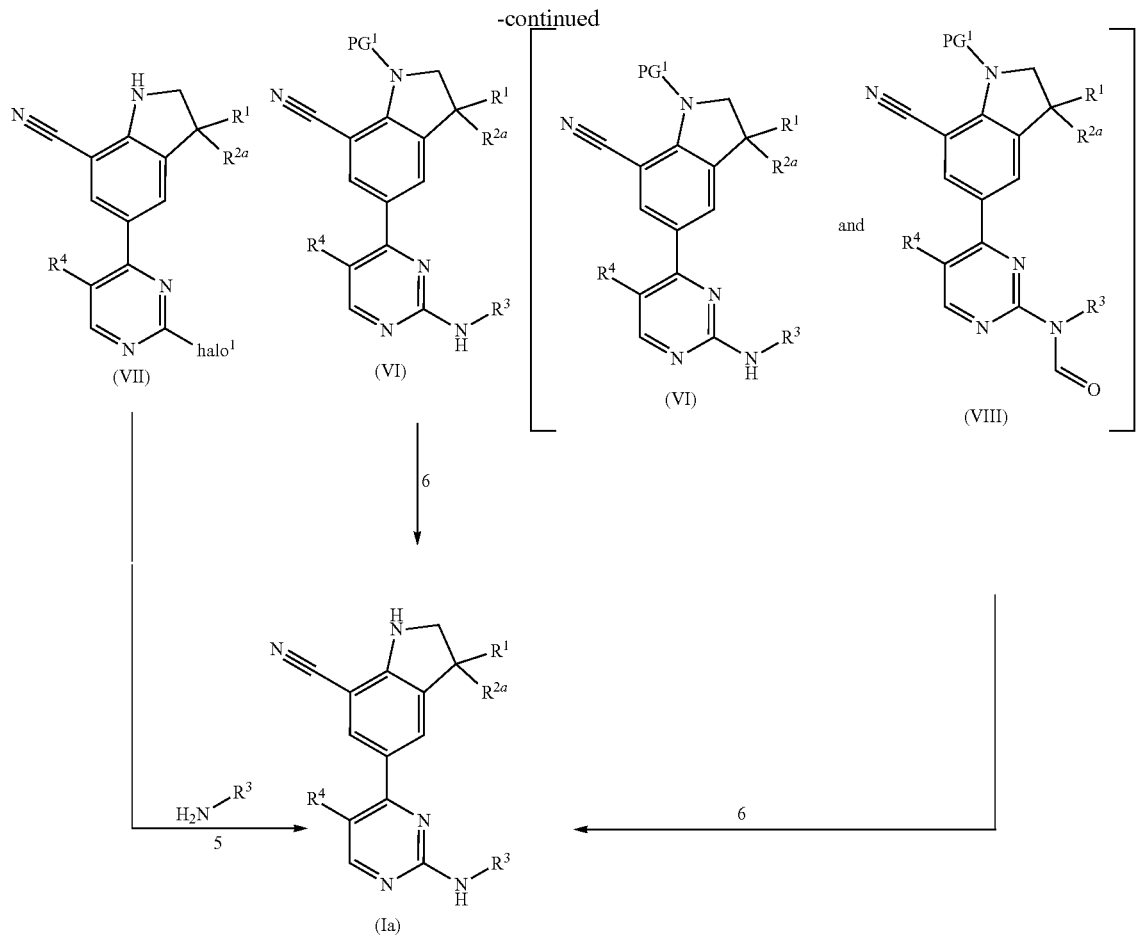

1: at a suitable temperature such as for example 80° C., in the presence of a suitable ligand such as for example 4,4'-di-tert-butyl-2,2'-dipyridyl, a suitable catalyst such as for example bis(1,5-cyclooctadiene)di-t-methoxydiiridium (I) ([Ir(OCH₃)(C₈H₁₂)]₂), and a suitable solvent such as for example heptane;

2: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;

3: at a suitable temperature such as for example 85° C., in the presence of a suitable catalyst such as for example palladium tetrakis (Pd(PPh₃)₄) or [1,1'-Bis(diphenylphosphino)ferrocene]-dichloropalladium(II).Dichloromethane (Pd(dppf)Cl₂.CH₂Cl₂), a suitable base such as for example sodium carbonate, and a suitable solvent such as for example 1,4-dioxane;

4: at a suitable temperature such as for example room temperature, in presence of a suitable base such as for example sodium hydride, and a suitable solvent such as for example dimethylformamide;

5: at a suitable temperature such as for example ranged between 60° C. and 130° C., in the presence of a suitable catalyst such as for example palladium acetate (Pd(OAc)₂) or Chloro[2-(dicyclohexylphosphino)-3,6-dimethoxy-2',4',6'-tri-i-propyl-1,1'-biphenyl][2-(2-aminoethyl)phenyl]palladium(II) (Brettphos palladacycle), a suitable ligand such as for example 2,2'-bis(diphenylphosphino)-1,1'-binaphthyl (BINAP) or 2-(Dicyclohexylphosphino)3,6-dimethoxy-2',4',6'-triisopropyl-1,1'-biphenyl (Brettphos), a suitable base such as for example cesium carbonate, and a suitable solvent such as for example 1,4-dioxane, tetrahydrofuran or, optionally under microwave irradiation;

or alternatively at a suitable temperature such as for example 95° C., in the presence of a suitable acid such as for example p-toluenesulfonic acid and a suitable solvent such as for example 1,4-dioxane;

6: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

The skilled person will understand that the reactions described in Scheme 1 will also be applicable starting from an intermediate of formula (III-a) (as described in Scheme 22).

Scheme 2

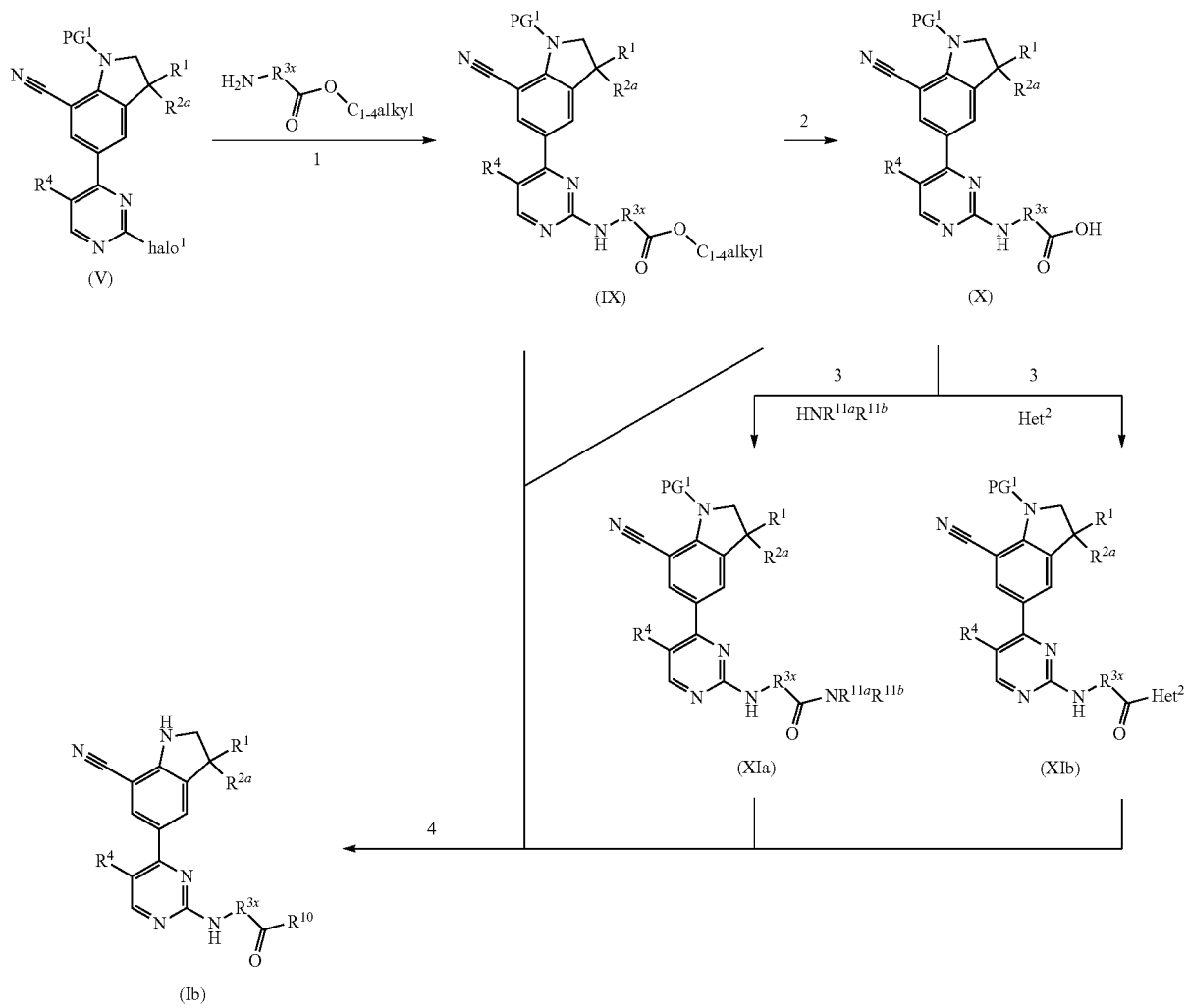

In scheme 2, R³ is limited to R³ˣ representing formula (1a-1), (1a-2) or a fused 6- to 11-membered bicyclic heteroaromatic ring system containing one or two heteroatoms each independently selected from O, S, and N.

In general, compounds of Formula (I) wherein R² is R²ᵃ being $C_{1-6}$alkyl, R³ˣ is as defined above for Scheme 2, R³ˣ is substituted with —C(=O)—R¹⁰ and additionally optionally substituted with other substituents according to the scope of the present invention, and wherein all the other variables are as defined according to the scope of the present invention, hereby named compounds of Formula (Ib), can be prepared according to the following reaction Scheme 2. In Scheme 2, halo is defined as Cl, Br or I; PG¹ represents a suitable protecting group, such as for example tert-(butoxycarbonyl). All other variables in Scheme 2 are defined according to the scope of the present invention.

In Scheme 2, the following reaction conditions apply:

1: at a suitable temperature such as for example 100° C., in the presence of a suitable catalyst such as for example palladium acetate (Pd(OAc)₂), a suitable ligand such as for example 2,2'-bis(diphenylphosphino)-1,1'-binaphthyl (BI-NAP), a suitable base such as for example cesium carbonate, and a suitable solvent such as for example 1,4-dioxane, optionally under microwave activation;

2: at a suitable temperature such as for example 70° C., in presence of a suitable base such as for example lithium hydroxide, and a suitable solvent such as for example a mixture of tetrahydrofuran and water;

3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide;

4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethylacetate, or 1,4-dioxane, and a suitable time such as for example 3 hours.

Scheme 3
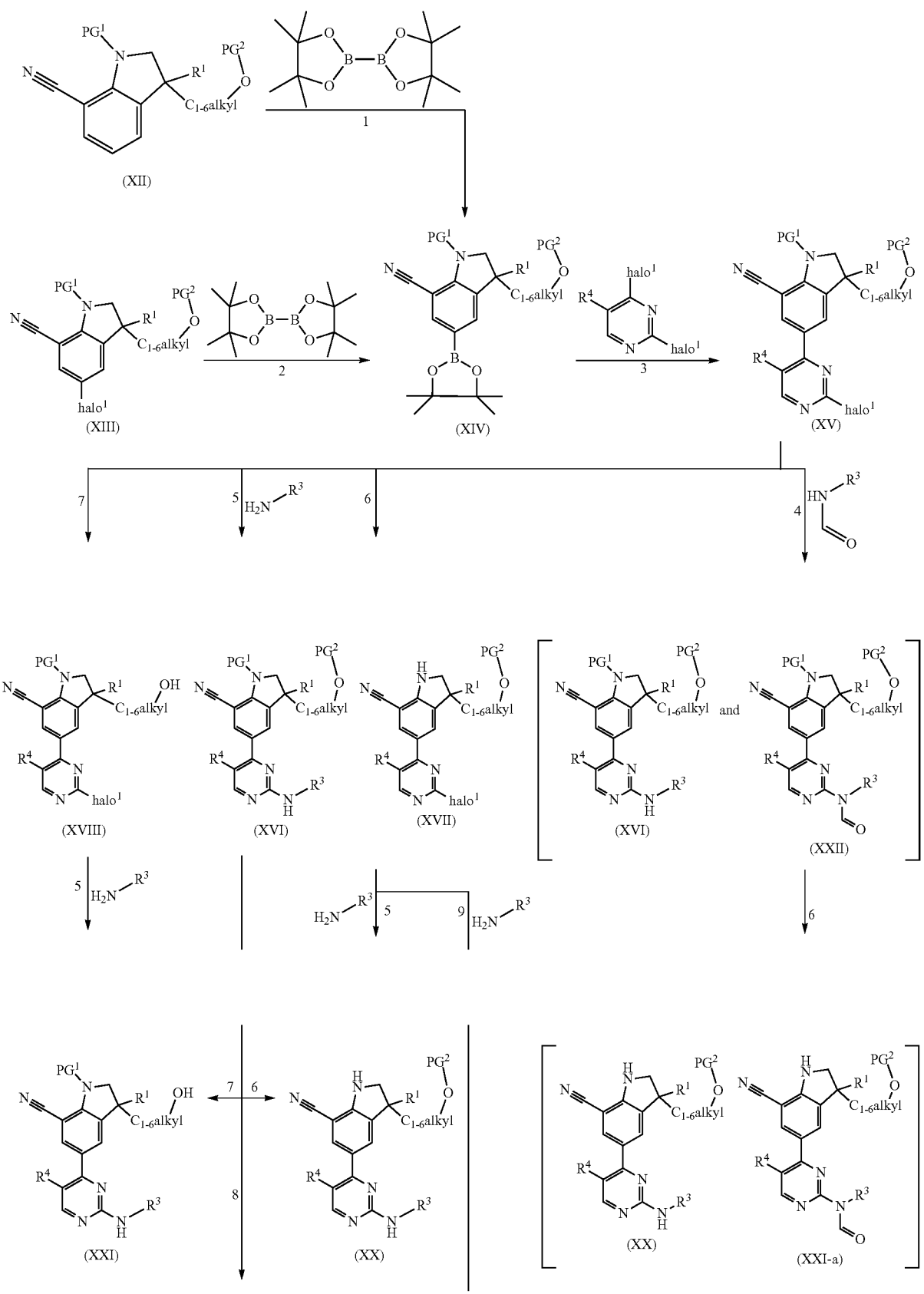

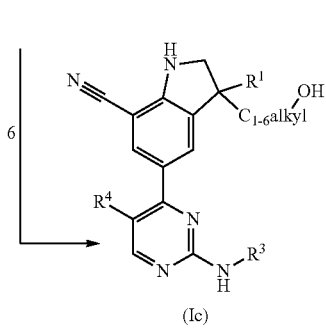
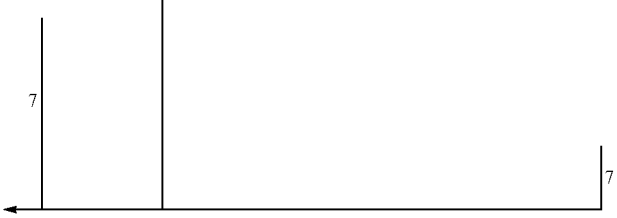

(Ic)

In general, compounds of Formula (I) wherein $R^2$ is $R^{2b}$ being $C_{1-6}$alkyl substituted with one OH, and wherein all the other variables are as defined according to the scope of the present invention, hereby named compounds of Formula (Ic), can be prepared according to the following reaction Scheme 3. In Scheme 3 halo$^1$ is defined as Cl, Br or I; PG$^1$ represents a suitable protecting group, such as for example tert-(butoxycarbonyl); and PG$^2$ represents a suitable protecting group, such as for example tert-butyl-dimethylsilyl. All other variables in Scheme 3 are defined according to the scope of the present invention.

For compounds wherein $R^3$ represents formula (2a-1), step 5, 6 or 7 are preferred over step 4 in Scheme 3. Also for compounds wherein $R^3$ represents formula (2a-1), the combination of steps 5 and 7 is preferred over step 9.

In Scheme 3, the following reaction conditions apply:

1: at a suitable temperature such as for example 80° C., in the presence of a suitable ligand such as for example 4,4'-di-tert-butyl-2,2'-dipyridyl, a suitable catalyst such as for example bis(1,5-cyclooctadiene)di-μ-methoxydiiridium (I) ([Ir(OCH$_3$)(C$_8$H$_{12}$)]$_2$), and a suitable solvent such as for example heptane;

2: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;

3: at a suitable temperature such as for example 85° C., in the presence of a suitable catalyst such as for example palladium tetrakis (Pd(PPh$_3$)$_4$), a suitable base such as for example sodium carbonate, and a suitable solvent such as for example 1,4-dioxane;

4: at a suitable temperature such as for example room temperature, in presence of a suitable base such as for example sodium hydride, and a suitable solvent such as for example dimethylformamide;

5: at a suitable temperature such as for example ranged between 80° C. and 130° C., in the presence of a suitable catalyst such as for example palladium acetate (Pd(OAc)$_2$) or Chloro[2-(dicyclohexylphosphino)-3,6-dimethoxy-2',4',6'-tri-i-propyl-1,1'-biphenyl][2-(2-aminoethyl)phenyl]palladium(II) (Brettphos palladacycle), a suitable ligand such as for example 2,2'-bis(diphenylphosphino)-1,1'-binaphthyl (BINAP), or 2-(Dicyclohexylphosphino)3,6-dimethoxy-2',4',6'-triisopropyl-1,1'-biphenyl (Brettphos), a suitable base such as for example cesium carbonate, and a suitable solvent such as for example 1,4-dioxane, tetrahydrofuran or, optionally under microwave irradiation;

6: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours;

7: at a suitable temperature such as for example room temperature, in presence of a suitable desilylating agent such as for example tetra-n-butylammonium fluoride and a suitable solvent such as for example 2-methyltetrahydrofuran or tetrahydrofuran;

8: at a suitable temperature such as for example reflux, in presence of a suitable acid such as for example aqueous hydrochloric acid with a suitable solvent such as for example dichloromethane, methanol, ethyl acetate or 1,4-dioxane, and a suitable time such as for example 6 hours;

9: at a suitable temperature such as for example 95° C., in the presence of a suitable acid such as for example p-toluenesulfonic acid and a suitable solvent such as for example 1,4-dioxane.

Scheme 4

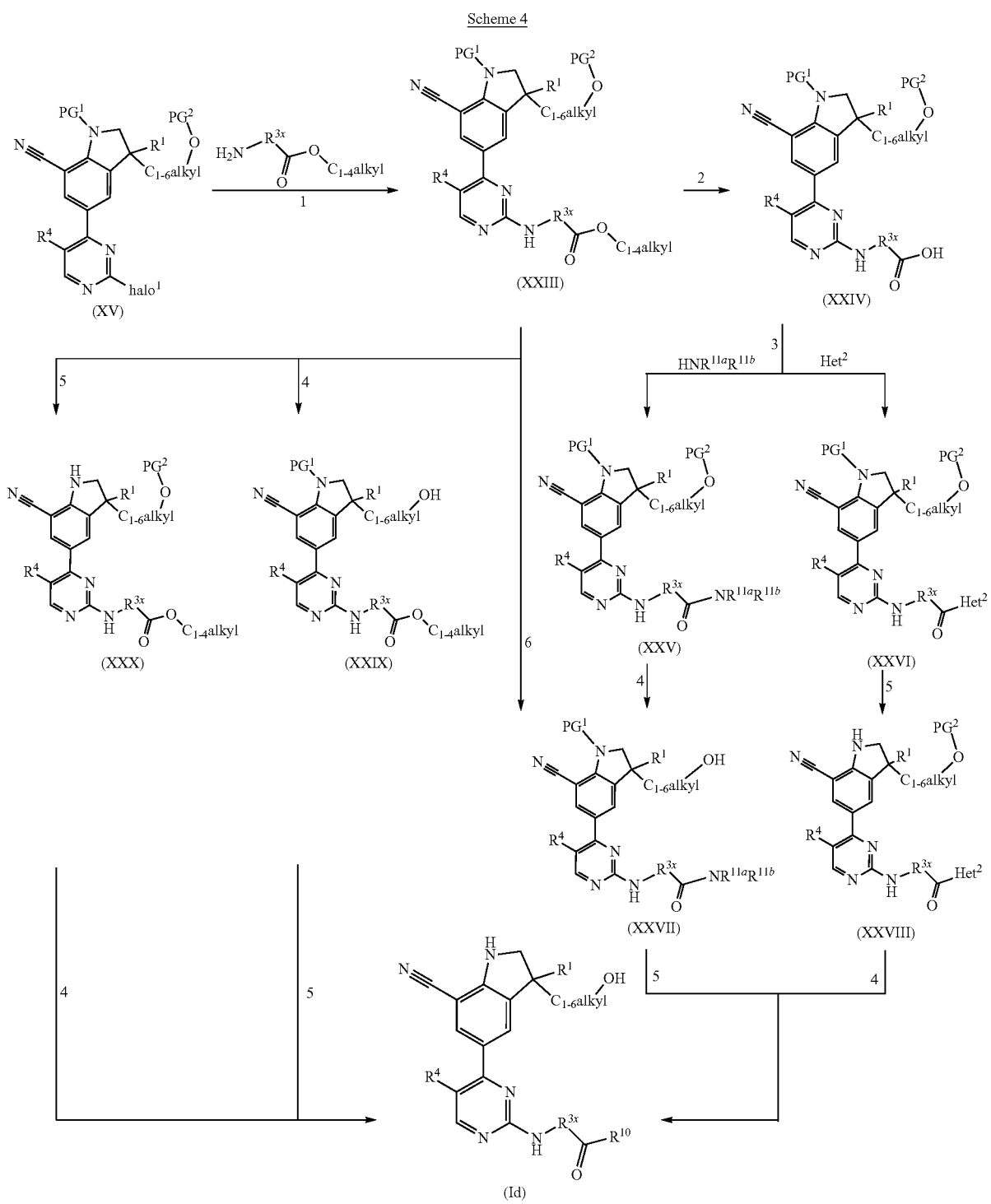

In scheme 4, $R^{3x}$ is limited to $R^{3x}$ representing formula (1a-1), (1a-2) or a fused 6- to 11-membered bicyclic heteroaromatic ring system containing one or two heteroatoms each independently selected from O, S, and N.

In general, compounds of Formula (I) wherein $R^2$ is $R^{2b}$ being $C_{1-6}$alkyl substituted with one OH, $R^{3x}$ is as defined above for Scheme 4, $R^{3x}$ is substituted with —C(=O)—$R^{10}$ on a carbon atom and additionally optionally substituted with other substituents according to the scope of the present invention, and wherein all the other variables are as defined according to the scope of the present invention, hereby named compounds of Formula (Id), can be prepared according to the following reaction Scheme 4. In Scheme 4, halo is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 4 are defined according to the scope of the present invention.

In Scheme 4, the following reaction conditions apply:

1: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BI-NAP), a suitable base such as for example cesium carbonate, and a suitable solvent such as for example 1,4-dioxane, optionally under microwave activation;

2: at a suitable temperature such as for example 70 CC, in presence of a suitable base such as for example lithium hydroxide, and a suitable solvent such as for example a mixture of tetrahydrofuran and water;

3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide;

4: at a suitable temperature such as for example room temperature, in presence of a suitable desilylating agent such as for example tetra-n-butylammonium fluoride and a suitable solvent such as for example 2-methyltetrahydrofuran or tetrahydrofuran;

5: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours;

6: at a suitable temperature such as for example reflux, in presence of a suitable acid such as for example aqueous hydrochloric acid with a suitable solvent such as for example dichloromethane, methanol, ethyl acetate or 1,4-dioxane, and a suitable time such as for example 6 hours.

In general, compounds of Formula (I) wherein $R^2$ is $R^2$ being $C_{1-6}$alkyl substituted with one Het$^3$a or —NR$^{6a}$R$^{6b}$, wherein R$^{6b}$ is R$^{6ba}$ being H, $C_{1-4}$alkyl and $C_{3-6}$cycloalkyl and wherein all the other variables are as defined according to the scope of the present invention, hereby named compounds of Formula (Ie) and Formula (If), can be prepared according to the following reaction Scheme 5. In Scheme 5 PG$^1$ represents a suitable protecting group, such as for example tert-(butoxycarbonyl). All other variables in Scheme 5 are defined according to the scope of the present invention.

In Scheme 5, the following reaction conditions apply

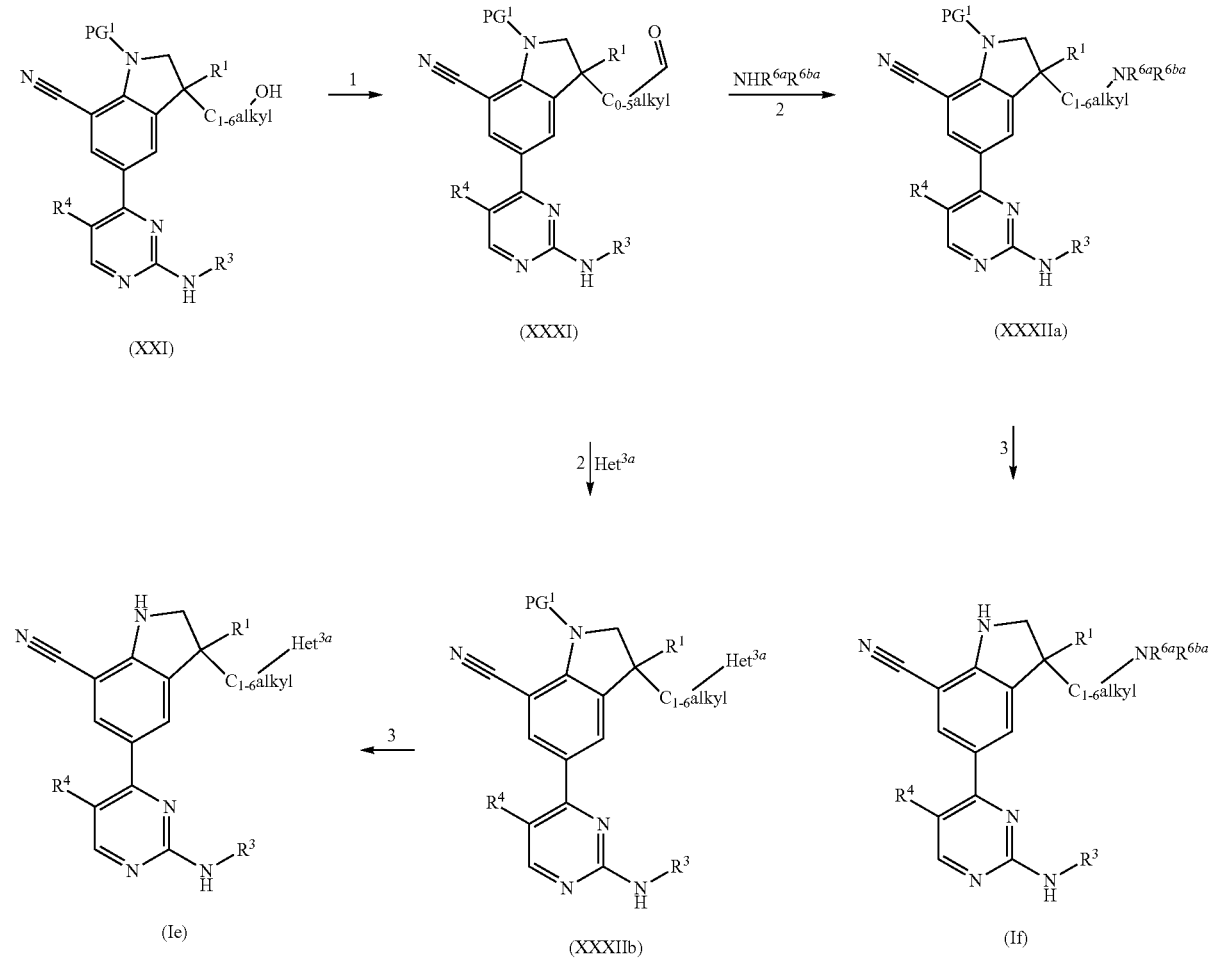

1: at a suitable temperature such as for example −78° C., in the presence of oxalyl chloride and dimethyl sulfoxide as reagents, a suitable base such as for example N,N-diisopropylethylamine, and a suitable solvent such as for example dichloromethane;

2: at a suitable temperature such as for example room temperature, in the presence of a suitable acid such as for example acetic acid, a suitable reducing agent such as for example sodium triacetoxyborohydride, and a suitable solvent such as for example dichloroethane;

3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $C_{1-6}$alkyl substituted with one $OR^7$, $R^{7a}$ being —C(=O)—$R^9$ or —(C=O)—CH(NH$_2$)—$C_{1-4}$alkyl-Ar$^1$), and wherein all the other variables are as defined according to the scope of the present invention, hereby named compounds of Formula (Ig), can be prepared according to the following reaction Scheme 6. In Scheme 6 PG$^3$ represents a suitable protecting group, such as for example a tert-(butoxycarbonyl), a tert-butyl or a benzyl. All other variables in Scheme 6 are defined according to the scope of the present invention.

In Scheme 6, the following reaction conditions apply

1: at a suitable temperature such as for example room temperature, in the presence of a suitable coupling reagent such as for example 1-[bis(dimethylamino)methylene]-1H-1,2,3-triazolo[4,5-b]pyridinium 3-oxid hexafluorophosphate (HATU), in the presence of a suitable base as for example N,N-diisopropylethylamine, and a suitable solvent such as for example a mixture of tetrahydrofuran and dimethylformamide, and optionally followed by a deprotection step using a suitable acid such as for example hydrochloric acid in a suitable solvent such as for example 1,4-dioxane;

2: at a suitable temperature such as for example 0° C. or room temperature, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $C_{1-6}$alkyl substituted with one $OR^{7b}$, $R^{7b}$ being $C_{1-4}$alkyl, and wherein all the other variables are as defined according to the scope of the present invention, hereby named compounds of Formula (Ih), can be prepared according to the following reaction Scheme 7. In Scheme 7 halo is defined as Cl, Br or I; PG$^1$ represents a suitable protecting group, such as for example tert-(butoxycarbonyl) and PG$^2$ represents a suitable protecting group, such as for example tert-butyldimethylsilyl; W represents a leaving group, such as for example a methane sulfonate or toluene sulfonate or an Scheme 6

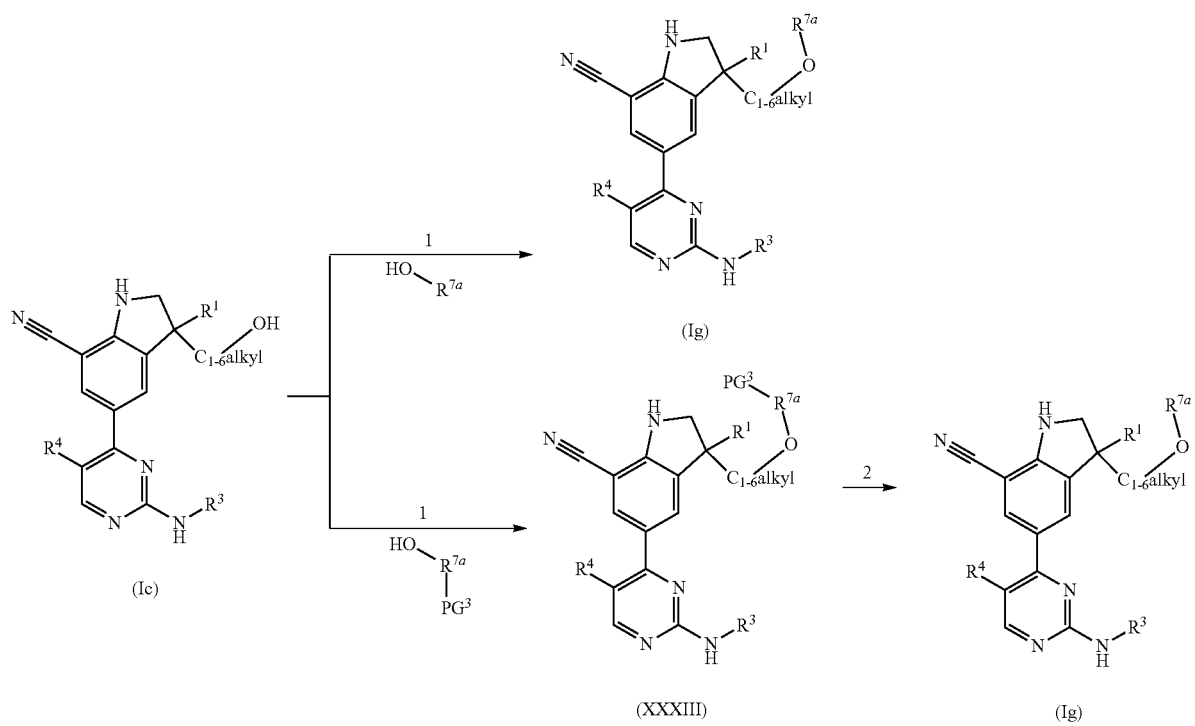

halogen (Cl, Br or I). All other variables in Scheme 7 are defined according to the scope of the present invention.

In Scheme 7, the following reaction conditions apply

Scheme 7
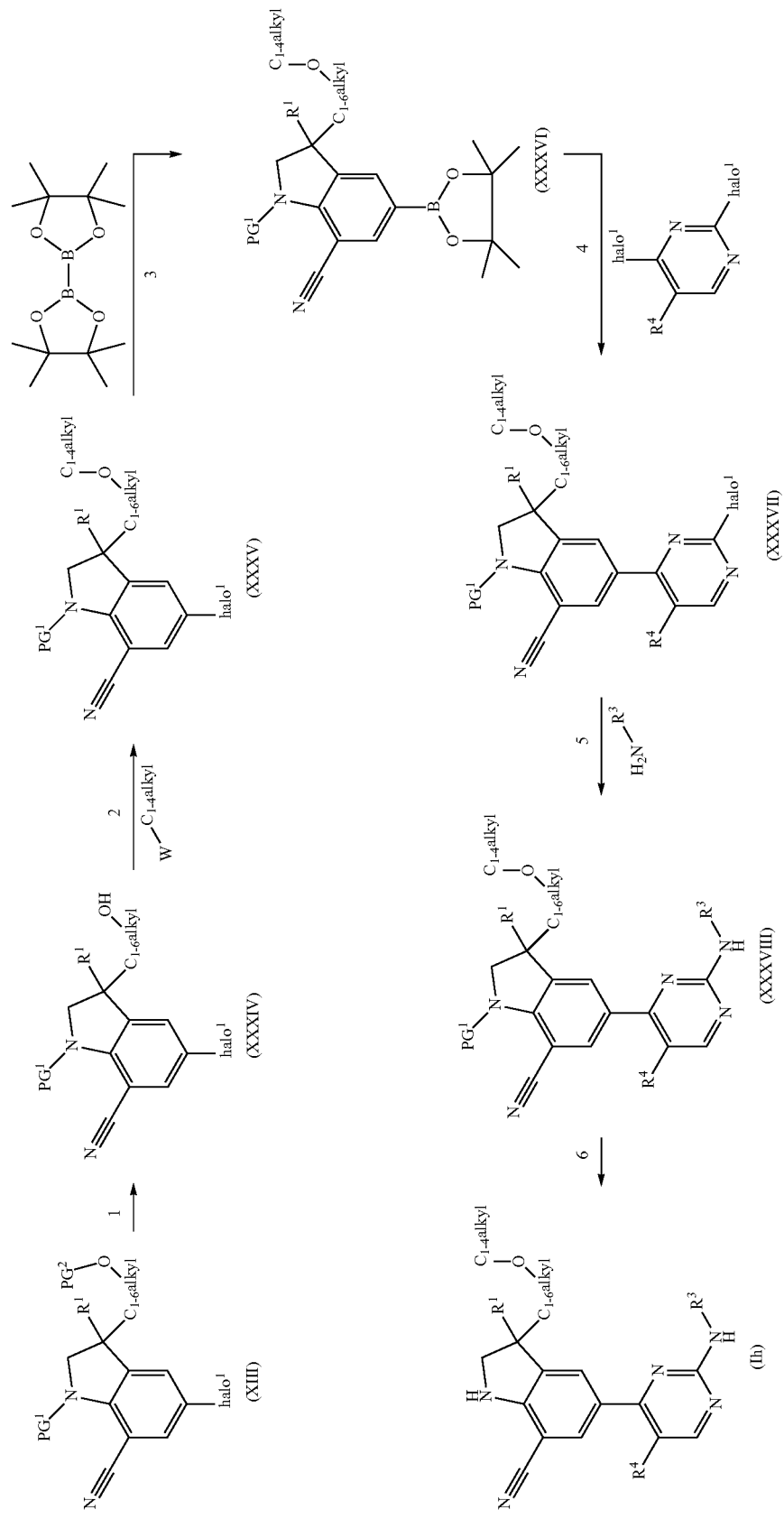

1: at a suitable temperature such as for example room temperature, in presence of a suitable desilylating agent such as for example tetra-n-butylammonium fluoride and a suitable solvent such as for example 2-methyltetrahydrofuran or tetrahydrofuran;

2: at a suitable temperature such as for example room temperature, in the presence of a suitable base as for example sodium hydride, and a suitable solvent such as for example dimethylformamide;

3: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;

4: at a suitable temperature such as for example 80° C., in the presence of a suitable catalyst such as for example palladium tetrakis ($Pd(PPh_3)_4$), a suitable base such as for example sodium carbonate, and a suitable solvent such as for example 1,4-dioxane;

5: at a suitable temperature such as for example 100° C., in the presence of a suitable catalyst such as for example palladium acetate ($Pd(OAc)_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;

6: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $C_{1-6}$alkyl substituted with one $OR^{7c}$, $R^{7c}$ being $C_{1-4}$alkyl-$NR^{8a}R^{8b}$ or $C_{1-4}$alkyl-$Het^{3b}$, and wherein all the other variables are as defined according to the scope of the present invention, hereby named compounds of Formula (Ii) and Formula (Ij), can be prepared according to the following reaction Scheme 8. In Scheme 8 $halo^1$ is defined as Cl, Br or I; $PG^1$ represents a suitable protecting group, such as for example tert-(butoxycarbonyl); $W^1$ represents a leaving group, such as for example a methane sulfonate or toluene sulfonate or an halogen (Cl, Br or I); $W^2$ represents a leaving group, such as for example a mesyl or a tosyl. All other variables in Scheme 8 are defined according to the scope of the present invention.

In Scheme 8, the following reaction conditions apply

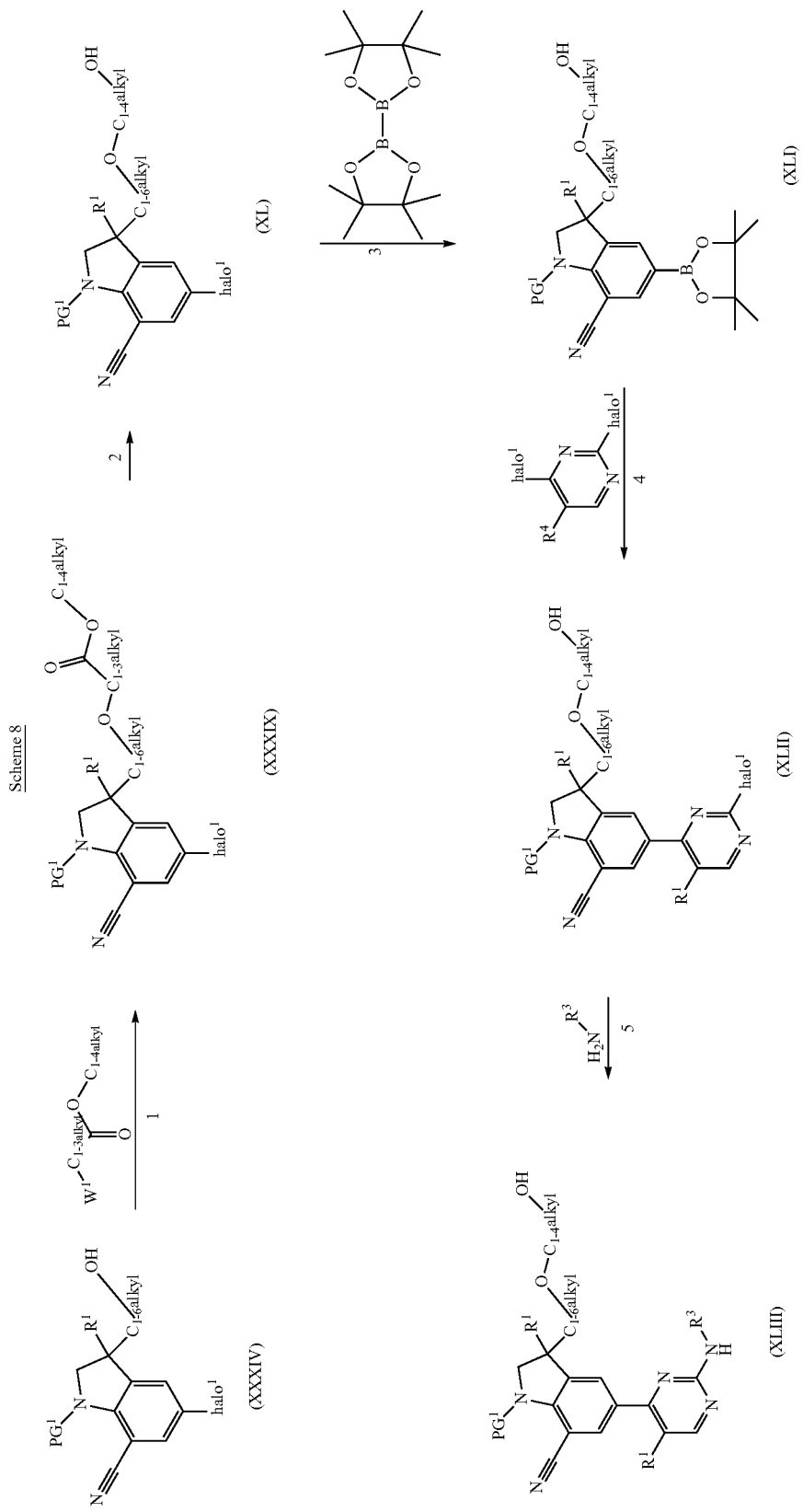

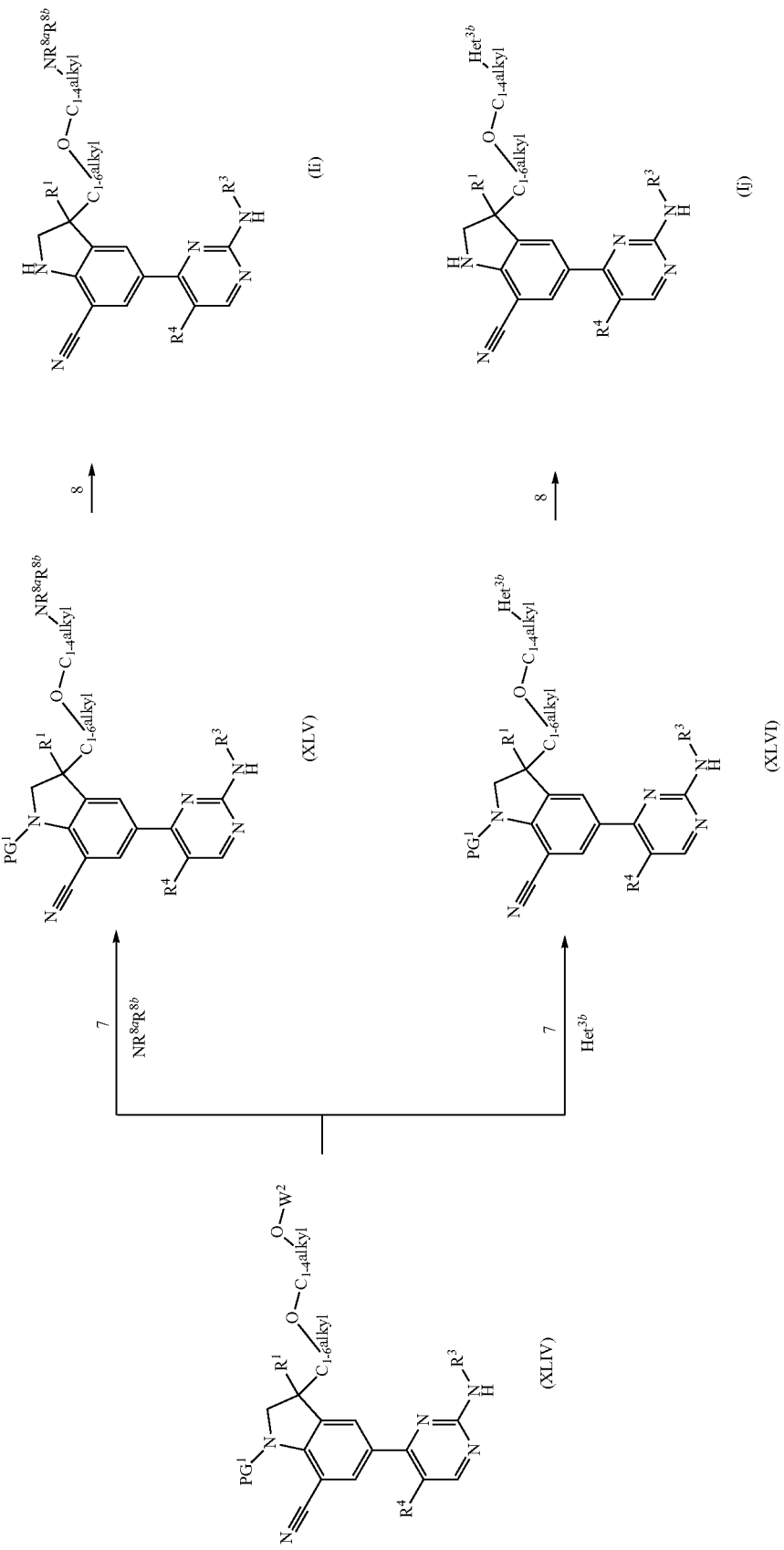

1: at a suitable temperature such as for example room temperature, in the presence of a suitable base as for example sodium hydride, and a suitable solvent such as for example dimethylformamide;

2: at a suitable temperature such as for example 55° C., in presence of reducing agent such as for example sodium borohydride and a suitable solvent such as for example a mixture of tetrahydrofuran and methanol;

3: at a suitable temperature such as for example 100° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;

4: at a suitable temperature such as for example 85° C., in the presence of a suitable catalyst such as for example palladium tetrakis (Pd(PPh$_3$)$_4$), a suitable base such as for example sodium carbonate, and a suitable solvent such as for example 1,4-dioxane;

5: at a suitable temperature such as for example 120° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;

6: at a suitable temperature such as for example 5° C., in the presence of a suitable base such as for example triethylamine, and a suitable solvent such as for example dichloromethane;

7: at a suitable temperature such as for example 80° C., and a suitable solvent such as for example acetonitrile;

8: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, intermediates of Formula (II) and (III) wherein R$^2$ is R$^2$ being C$_{1-6}$alkyl, and wherein all the other variables are as defined according to the scope of the present invention, hereby named compounds of Formula (II) and (III), can be prepared according to the following reaction Scheme 9. In Scheme 9 halo is defined as Cl, Br, I; halo$^2$ is defined as Cl, Br, I; PG$^1$ represents a suitable protecting group, such as for example tert-(butoxycarbonyl), W$^1$ represents a leaving group, such as for example a methane sulfonate or toluene sulfonate or an halogen (Cl, Br or I). All other variables in Scheme 9 are defined according to the scope of the present invention.

In Scheme 9, the following reaction conditions apply

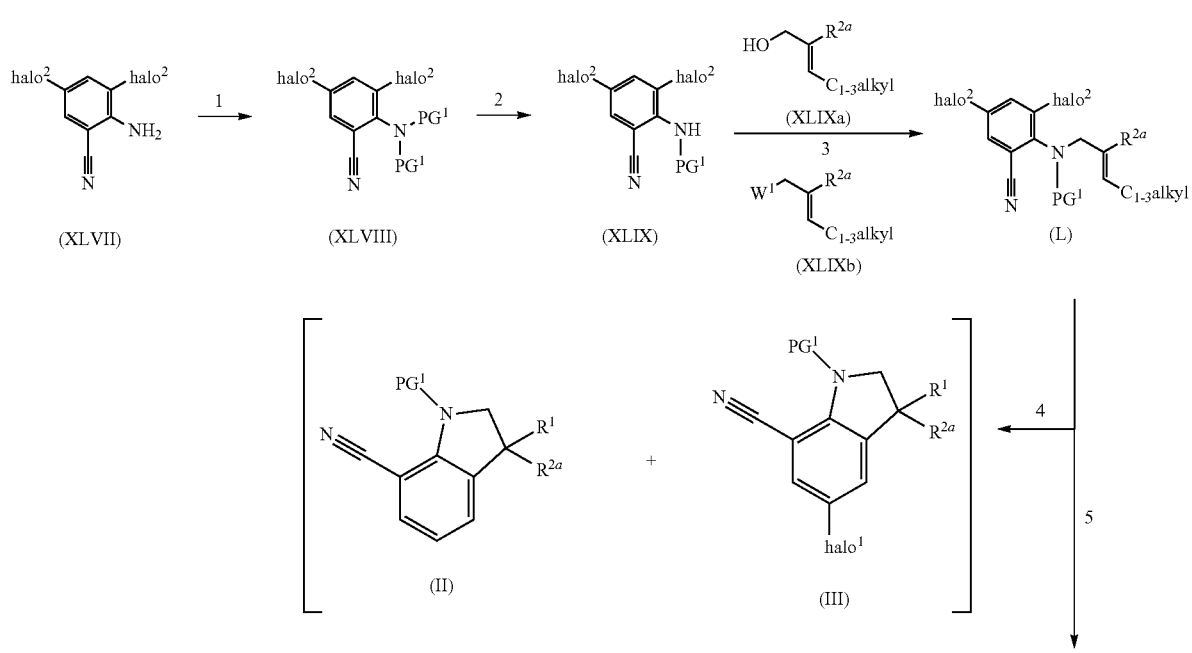

Scheme 9

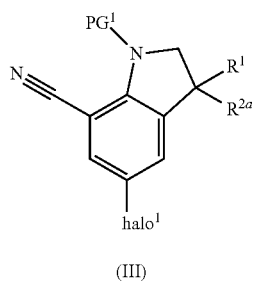

(III)

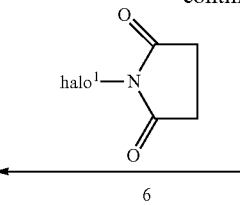

6

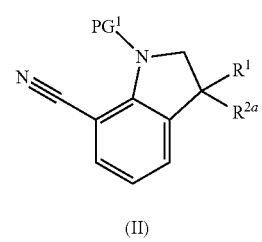

(II)

1: at a suitable temperature such as for example 45° C., in the presence of a suitable reagent such as for example di-tert-butyldicarbonate, in the presence of a suitable catalyst such as for example 4-dimethylaminopyridine (DMAP), and a suitable solvent such as for example dichloromethane;

2: at a suitable temperature such as for example 65° C. and a suitable solvent such as for example methanol;

3: in case of (XLIXa), at a suitable temperature such as for example at room temperature, in the presence of tri-n-butylphosphine and 1,1'-(azodicarbonyl)piperidine and a suitable solvent such as for example 2-methyltetrahydrofuran;

In case of (XLIXb), at a suitable temperature such as for example 80° C., in the presence of a suitable base such as for example potassium carbonate, a suitable additive such as for example sodium iodide, in a suitable solvent such as for example acetonitrile;

4: at a suitable temperature such as for example 85° C., in the presence of sodium acetate, sodium formate and tetraethylammonium chloride, a suitable catalyst such as for example palladium acetate (Pd(OAc)$_2$), and a suitable solvent such as for example dimethylformamide;

5: at a suitable temperature such as for example 60° C., in the presence of sodium acetate, sodium formate dehydrate and tetraethylammonium chloride, a suitable catalyst such as for example [1,1'-bis(diphenylphosphino) ferrocene] palladium, (II) chloride optionally with dichloromethane complex, and a suitable solvent such as for example dimethylformamide;

6: at a suitable temperature such as for example 40° C., in the presence of N-halogeno-succinimide, and a suitable solvent such as for example acetonitrile. Alternatively, in the presence of a suitable reagent such as for example 1,3-dibromo-5,5-dimethylhydantoin, in a suitable solvent such as for example acetonitrile.

In general, intermediates of Formula (XII) and (XIII) wherein $R^2$ is $R^{2b}$ being $C_{1-6}$alkyl substituted with one OH, and wherein all the other variables are as defined according to the scope of the present invention, hereby named compounds of Formula (XII) and (XIII), can be prepared according to the following reaction Scheme 10. In Scheme 10 halo$^1$ is defined as Cl, Br, I; halo$^2$ is defined as Cl, Br, I; PG$^1$ represents a suitable protecting group, such as for example tert-(butoxycarbonyl) and PG$^2$ represents a suitable protecting group, such as for example tert-butyl-dimethylsilyl; W$^1$ represents a leaving group, such as for example a methane sulfonate or toluene sulfonate or an halogen (Cl, Br or I). All other variables in Scheme 10 are defined according to the scope of the present invention.

In Scheme 10, the following reaction conditions apply

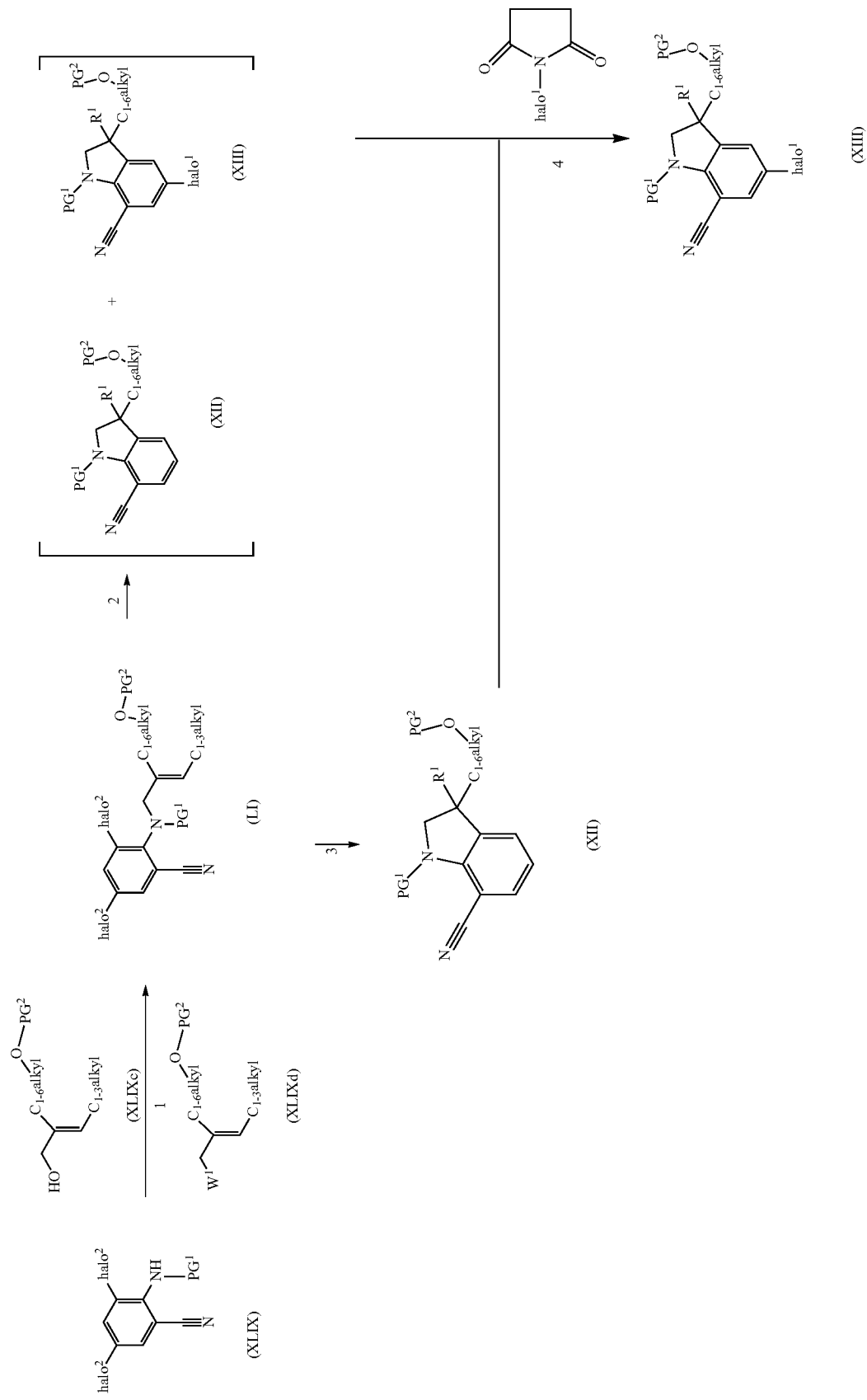

1: in case of (XLIXc), at a suitable temperature such as for example at room temperature, in the presence of tri-n-butylphosphine and 1,1'-(azodicarbonyl)piperidine and a suitable solvent such as for example 2-methyltetrahydrofuran;

In case of (XLIXb), at a suitable temperature such as for example 80° C., in the presence of a suitable base such as for example potassium carbonate, a suitable additive such as for example sodium iodide, in a suitable solvent such as for example acetonitrile;

2: at a suitable temperature such as for example 85° C., in the presence of sodium acetate, sodium formate and tetraethylammonium chloride, a suitable catalyst such as for example palladium acetate (Pd(OAc)₂), and a suitable solvent such as for example dimethylformamide;

3: at a suitable temperature such as for example 60° C., in the presence of sodium acetate, sodium formate dehydrate and tetraethylammonium chloride, a suitable catalyst such as for example [1,1'-bis(diphenylphosphino) ferrocene] palladium, (II) chloride optionally with dichloromethane complex, and a suitable solvent such as for example dimethylformamide;

4: at a suitable temperature such as for example 40° C., in the presence of N-halogeno-succinimide, and a suitable solvent such as for example acetonitrile. Alternatively, in the presence of a suitable reagent such as for example 1,3-dibromo-5,5-dimethylhydantoin, in a suitable solvent such as for example acetonitrile.

In general, compounds of Formula (I) wherein $R^2$ is as shown in the scheme 11, and wherein all the other variables are as defined according to the scope of the present invention, hereby named compounds of Formula (Ik) can be prepared according to the following reaction Scheme 11. In Scheme 11 $PG^1$ represents a suitable protecting group, such as for example tert-(butoxycarbonyl). All other variables in Scheme 11 are defined according to the scope of the present invention.

In Scheme 11, the following reaction conditions apply

Scheme 11

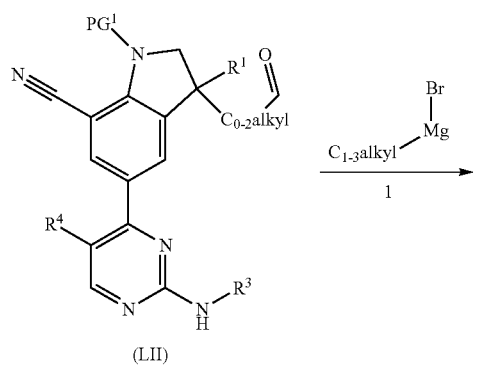

(LII)

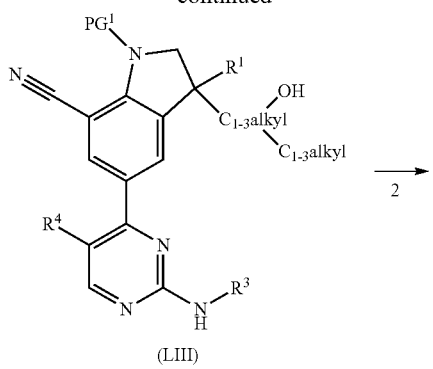

(LIII)

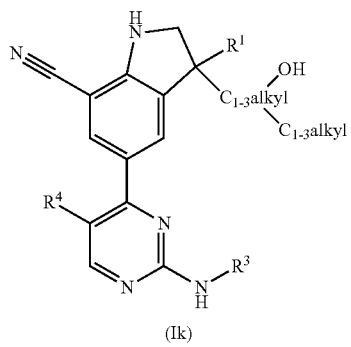

(Ik)

1: at a suitable temperature such as for example at room temperature, and a suitable solvent such as for example tetrahydrofuran;

2: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

In general, compounds of Formula (I) wherein $R^2$ is as shown in the scheme 12, and wherein all the other variables are as defined according to the scope of the present invention, hereby named compounds of Formula (II) can be prepared according to the following reaction Scheme 12. In Scheme 12 $PG^1$ represents a suitable protecting group, such as for example tert-(butoxycarbonyl). All other variables in Scheme 12 are defined according to the scope of the present invention.

In Scheme 12, the following reaction conditions apply

Scheme 12

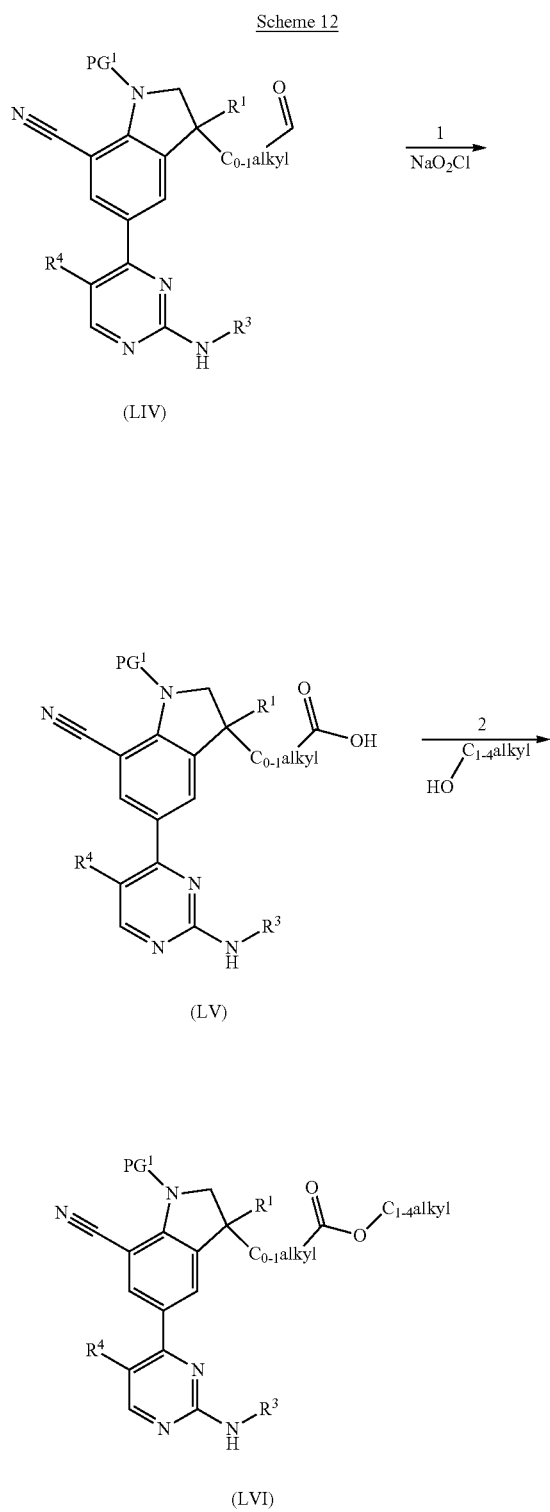

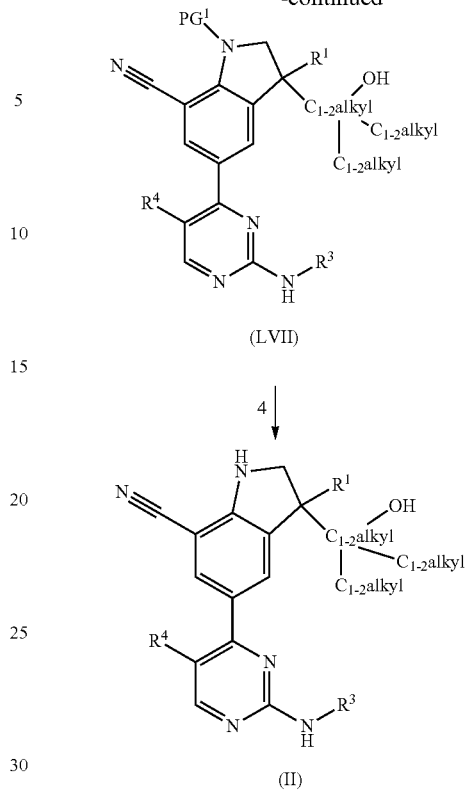

1: at a suitable temperature such as for example at room temperature, in the presence of tert-butyl alcohol, 2-methyl-2-butene, sodium dihydrogenphosphate and distilled water;

2: at a suitable temperature such as for example at room temperature, in presence of 1-[bis(dimethylamino)methylene]-1H-1,2,3-triazolo[4,5-b]pyridinium 3-oxid hexafluorophosphate (HATU) and dimethyl aminopyridine (DMAP), a suitable base such as for example DIPEA and a suitable solvent such as for example dimethylformamide;

3: at a suitable temperature such as for example at room temperature, and a suitable solvent such as for example tetrahydrofuran;

4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

In general, compounds of Formula (I) wherein $R^2$ is as shown in the scheme 13 and wherein all the other variables are as defined according to the scope of the present invention, hereby named compounds of Formula (Im) can be prepared according to the following reaction Scheme 13. In Scheme 13 $PG^1$ represents a suitable protecting group, such as for example tert-(butoxycarbonyl). All other variables in Scheme 13 are defined according to the scope of the present invention. In Scheme 13, the following reaction conditions apply:

Scheme 13

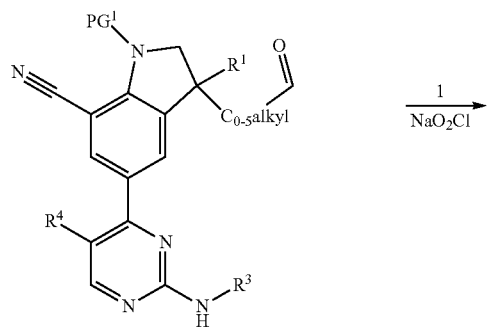

(XXXI)

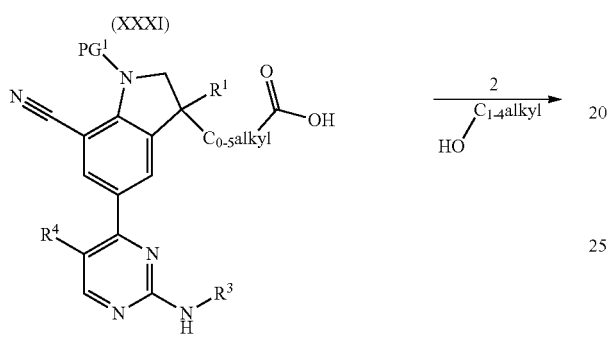

(LVIII)

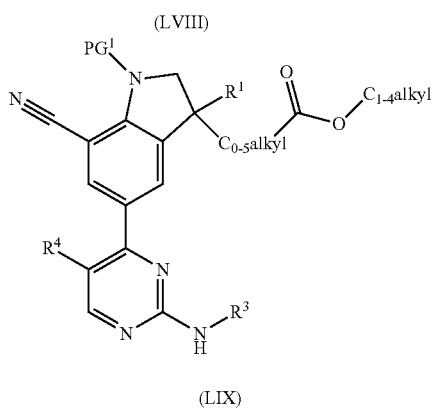

(LIX)

(LX)

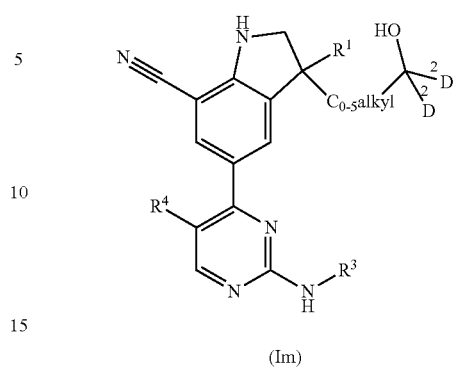

(Im)

1: at a suitable temperature such as for example at room temperature, in the presence of tert-butyl alcohol, 2-methyl-2-butene, sodium dihydrogenphosphate and distilled water;

2: at a suitable temperature such as for example at room temperature, in presence of 1-[bis(dimethylamino)methylene]-1H-1,2,3-triazolo[4,5-b]pyridinium 3-oxid hexafluorophosphate (HATU) and dimethyl aminopyridine (DMAP), a suitable base such as for example DIPEA and a suitable solvent such as for example dimethylformamide;

3: at a suitable temperature such as for example at 0° C., and a suitable solvent such as for example tetrahydrofuran; ('AlD$_4$Li' means lithium aluminum deuteride)

4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

In general, compounds of Formula (I) wherein $R^2$ is being $C_{1-6}$alkyl substituted with one Het$^3$a or —NR$^{6a}$R$^{6b}$, wherein $R^{6a}$ is being H, $R^{6b}$ is being —C(=O)—C$_{1-4}$alkyl; —C(=O)—Het$^4$; —S(=O)$_2$—C$_{1-4}$alkyl and wherein all the other variables are as defined according to the scope of the present invention, hereby named compounds of Formula (In), Formula (Io) and Formula (Ip), can be prepared according to the following reaction Scheme 14. In Scheme 14, PG$^1$ represents a suitable protecting group, such as for example tert-(butoxycarbonyl). All other variables in Scheme 14 are defined according to the scope of the present invention.

In Scheme 14, the following reaction conditions apply:

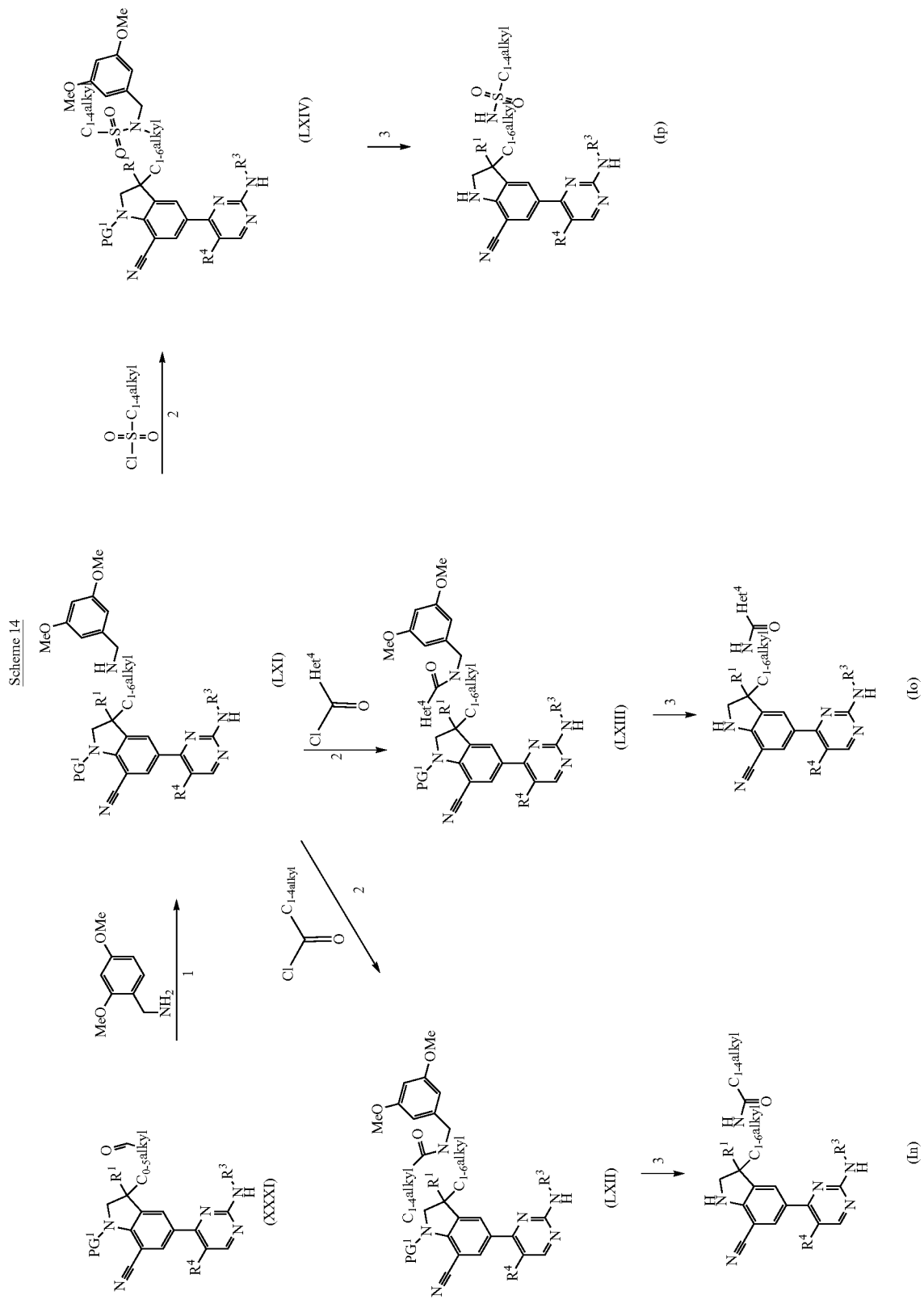

1: at a suitable temperature such as for example at room temperature, in the presence of a suitable acid such as for example acetic acid, in the presence of a suitable reducing agent such as for example sodium triacetoxyborohydride, in a suitable solvent such as for example dichloroethane;

2: at a suitable temperature such as for example at room temperature, in the presence of a suitable base such as for example triethylamine, in a suitable solvent such as for example tetrahydrofuran;

3: at a suitable temperature such as for example at room temperature, in the presence of a suitable acid such as for example trifluoroacetic acid, in a suitable solvent such as for example dichloromethane.

In general, compounds of Formula (I) wherein $R^2$ is being $C_{1-6}$alkyl substituted with one $Het^{3a}$ or —$NR^{6a}R^{6b}$, wherein $R^{6a}$ is being $C_{1-4}$alkyl, $R^{6b}$ is being —C(=O)—$C_{1-4}$alkyl; —C(=O)—$Het^4$; —S(=O)$_2$—$C_{1-4}$alkyl and wherein all the other variables are as defined according to the scope of the present invention, hereby named compounds of Formula (Iq), Formula (Ir) and Formula (Is), can be prepared according to the following reaction Scheme 15. In Scheme 15, $PG^1$ represents a suitable protecting group, such as for example tert-(butoxycarbonyl). All other variables in Scheme 5 are defined according to the scope of the present invention.

In Scheme 15, the following reaction conditions apply

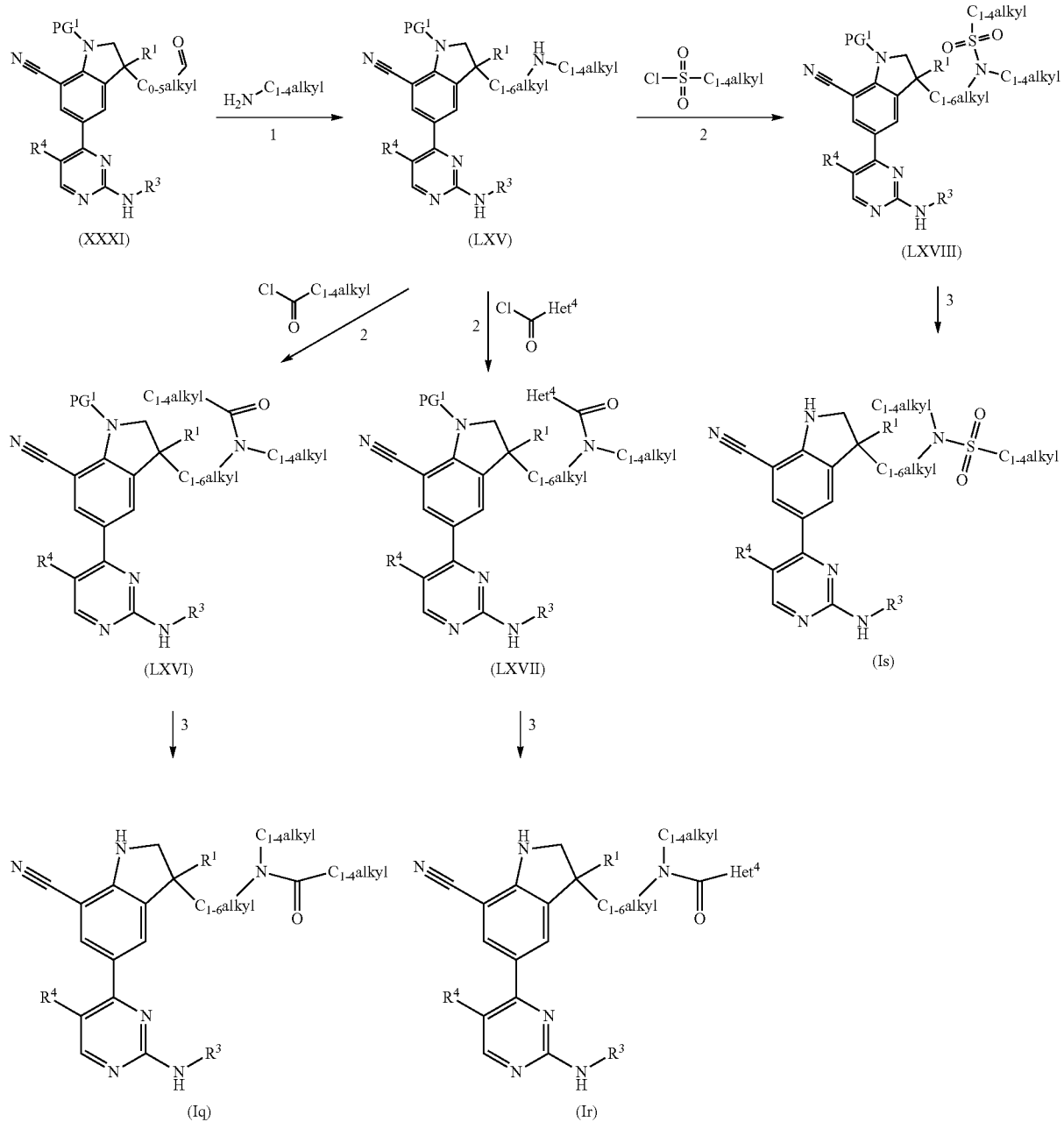

1: at a suitable temperature such as for example at room temperature, in the presence of a suitable acid such as for example acetic acid, in the presence of a suitable reducing agent such as for example sodium triacetoxyborohydride, in a suitable solvent such as for example dichloroethane;

2: at a suitable temperature such as for example at room temperature, in the presence of a suitable base such as for example triethylamine, in a suitable solvent such as for example tetrahydrofuran;

3: at a suitable temperature such as for example at room temperature, in the presence of a suitable acid such as for example trifluoroacetic acid, in a suitable solvent such as for example dichloromethane.

In general, compounds of Formula (I) wherein $R^2$ is $C_{1-6}$alkyl substituted with one $OR^{7d}$, $R^{7d}$ being —S(=O)$_2$—OH or —P(=O)—(OH)$_2$, and wherein all the other variables are as defined according to the scope of the present invention, hereby named compounds of Formula (It) and Formula (Iu), can be prepared according to the following reaction Scheme 16. All other variables in Scheme 16 are defined according to the scope of the present invention.

In Scheme 16, the following reaction conditions apply

1: at a suitable temperature such as for example at room temperature, in a suitable solvent such as for example tetrahydrofuran, in the presence of a suitable base such as for example sodium hydroxyde;

2: in the presence of a suitable reagent such as for example tetrazole, in the presence of a suitable oxidizing agent such as for example meta-chloroperbenzoic acid, in a suitable solvent such as for example acetonitrile;

3: at a suitable temperature such as for example at room temperature, in the presence of a suitable acid such as for example hydrochloric acid, in a suitable solvent such as for example acetonitrile.

In general, intermediates of Formula (XII) wherein all the variables are as defined according to the scope of the present invention or as defined before, can be prepared according to the following reaction Scheme 17. All other variables in Scheme 17 are as defined before.

Scheme 16

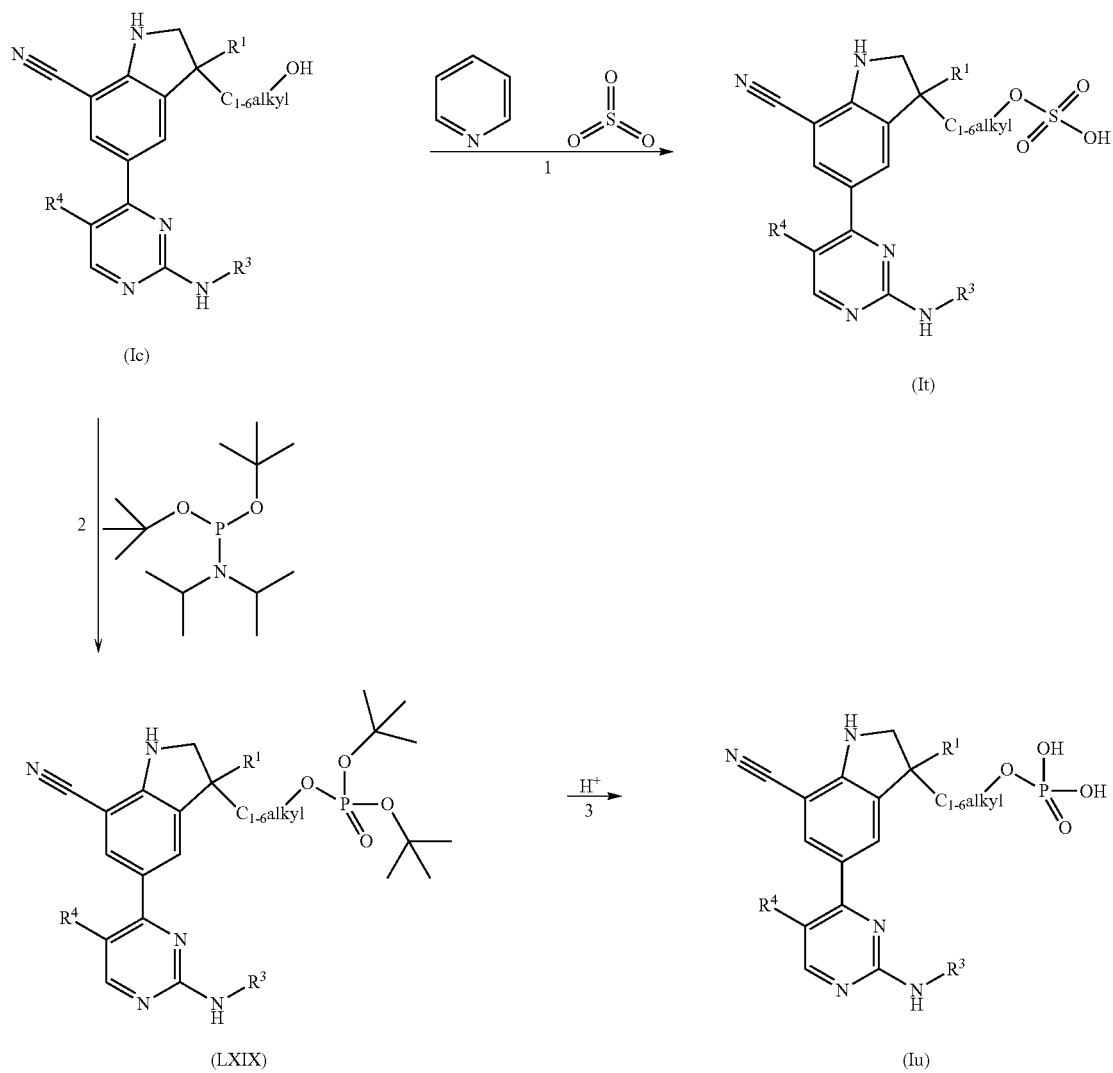

Scheme 17

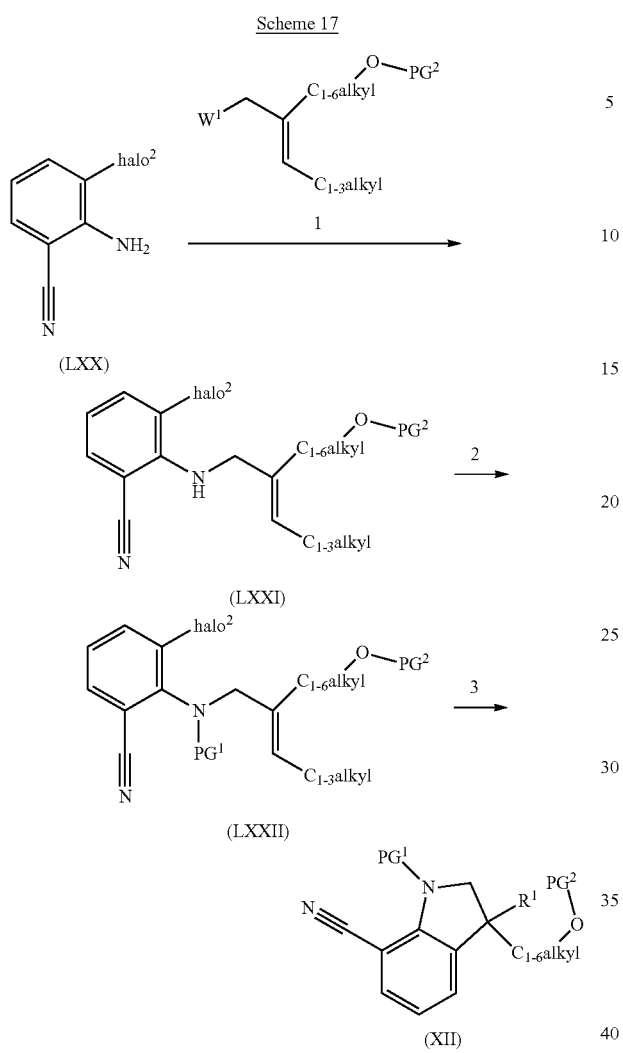

Scheme 18

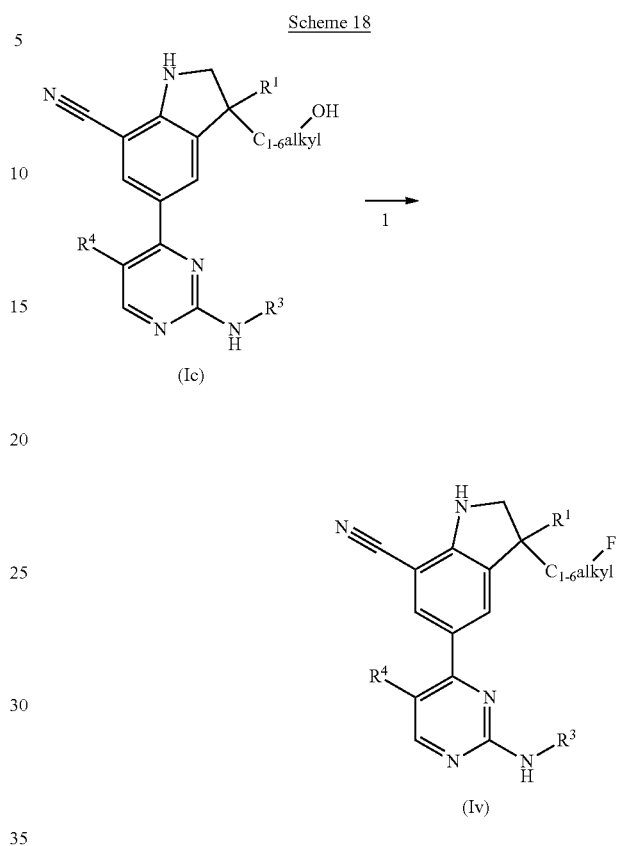

In Scheme 17, the following reaction conditions apply:

1: At a suitable temperature range between −5° C. and 5° C., in the presence of a suitable base such as for example sodium tert-butoxide in a suitable solvent such as for example tetrahydrofuran;

2: at a suitable temperature ranged between 65 and 70° C., in the presence of a suitable reagent such as for example di-tert-butyl dicarbonate, in the presence of a suitable catalyst such as for example 4-dimethylaminopyridine (DMAP), and a suitable solvent such as for example tetrahydrofuran;

3: at a suitable temperature ranged between 45 and 50° C., in the presence of sodium acetate, sodium formate dehydrate and tetraethylammonium chloride, a suitable catalyst such as for example palladium acetate or [1,1'-bis(diphenylphosphino) ferrocene] palladium, (II) chloride optionally with dichloromethane complex, and a suitable solvent such as for example dimethylformamide.

In general, compounds of Formula (I) wherein $R^2$ is $R^{2d}$ being $C_{1-6}$alkyl substituted with one fluorine, Y is $CR^4$, and wherein all the other variables are as defined according to the scope of the present invention, hereby named compounds of Formula (Iv), can be prepared according to the following reaction Scheme 18.

In Scheme 18, the following reaction conditions apply

1: in the presence of a suitable fluorinating reagent such as for example diethylaminosulfur trifluoride, a suitable solvent such as for example dichloromethane, at a suitable temperature such as for example room temperature.

In general, compounds of Formula (I) wherein $R^2$ is $R^{2b}$ being $C_{1-6}$alkyl substituted with one OH, Y is N, and wherein all the other variables are as defined according to the scope of the present invention, hereby named compounds of Formula (Iw), can be prepared according to the following reaction Scheme 19. In Scheme 19, halo is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 19 are defined according to the scope of the present invention.

In Scheme 19, the following reaction conditions apply

Scheme 19

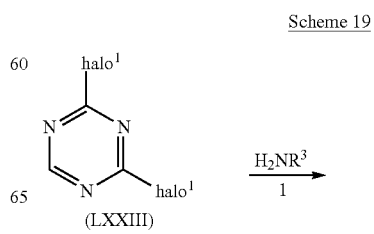

-continued

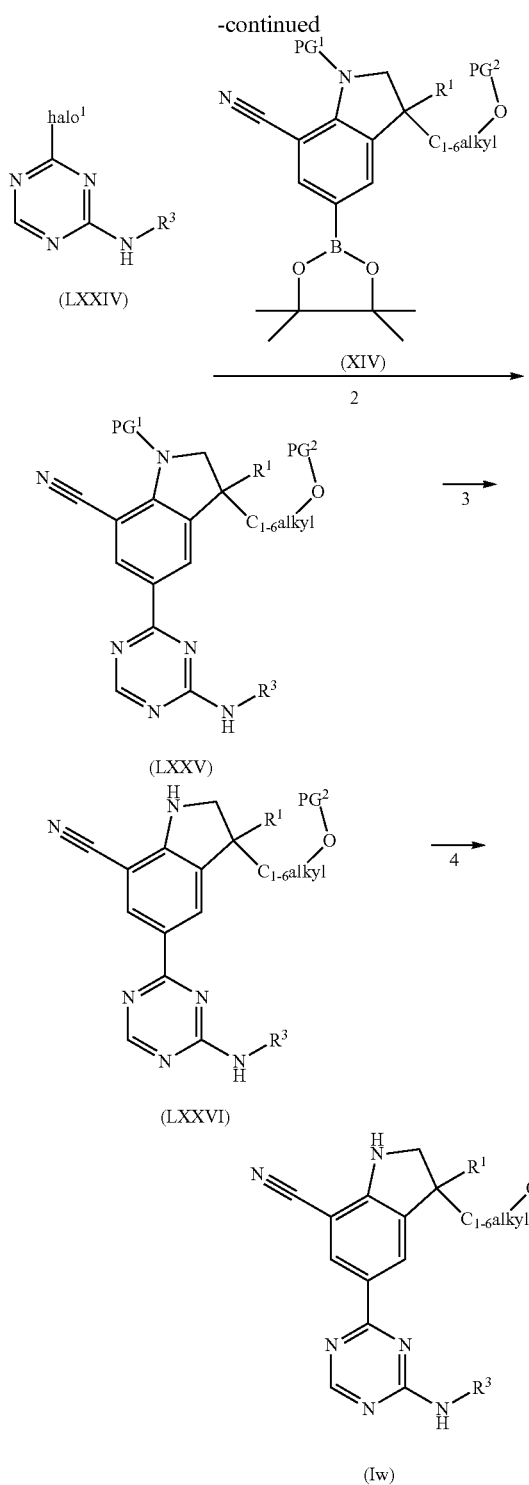

1: in the presence of a suitable base such as for example diisopropyl ethyl amine, in a suitable solvent such as for example acetonitrile;

2: in the presence of a suitable catalyst such as for example [1,1'-bis(diphenylphosphino)ferrocene] dichloropalladium (II), optionally with dichloromethane complex, a suitable base such as an aqueous solution of hydrogenocarbonate at a suitable temperature such as 80° C.;

3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours;

4: at a suitable temperature such as for example room temperature, in presence of a suitable desilylating agent such as for example tetra-n-butylammonium fluoride and a suitable solvent such as for example 2-methyltetrahydrofuran or tetrahydrofuran.

In scheme 20, $R^3$ is limited to $R^3$ representing formula (1a-1), or a fused 6- to 11-membered bicyclic heteroaromatic ring system containing one or two heteroatoms each independently selected from O, S, and N.

In general, compounds of Formula (I) wherein $R^2$ is $R^{2b}$ being $C_{1-6}$alkyl substituted with one OH, $R^{3x}$ is defined as above for scheme 20, substituted with $-C(=O)-R^{10}$ and optionally substituted with other substituents according to the scope of the present invention, Y is $CR^4$, and wherein all the other variables are as defined according to the scope of the present invention, hereby named compounds of Formula (Ida), (Idb) and (Idc) can be prepared according to the following reaction Scheme 20. In Scheme 20, halo is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 20 are defined according to the scope of the present invention.

In Scheme 20, the following reaction conditions apply

Scheme 20

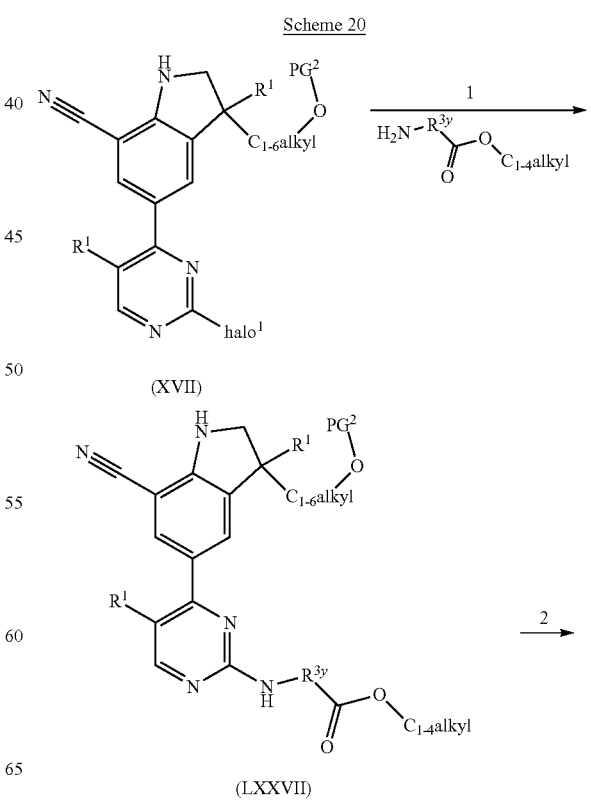

-continued

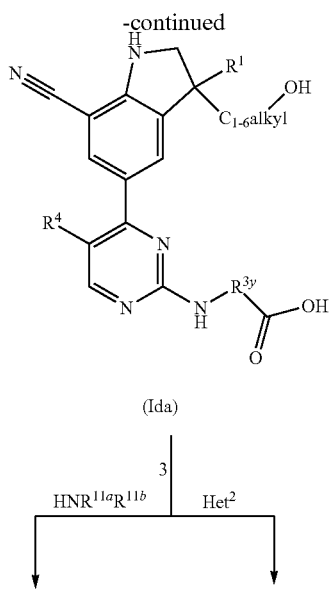

(Ida)

3 ↓   ↓ HNR¹¹ᵃR¹¹ᵇ   Het²

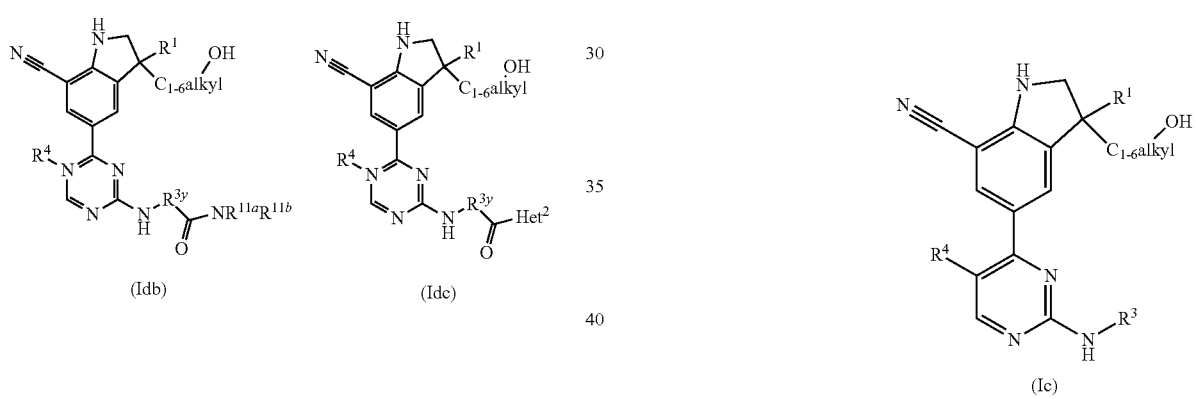

(Idb)          (Idc)

1: at a suitable temperature such as for example 120° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;

2: at a suitable temperature such as for example 60° C., in presence of a suitable base such as for example lithium hydroxide, and a suitable solvent such as for example a mixture of tetrahydrofuran and water;

3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide or dichloromethane.

In general, compounds of Formula (I) wherein R² is R²ᵇ being C$_{1-6}$alkyl substituted with one OH, Y is CR⁴, and wherein all the other variables are as defined according to the scope of the present invention, hereby named compounds of Formula (Ic), can be prepared according to the following reaction Scheme 21. All other variables in Scheme 21 are defined according to the scope of the present invention or as above.

Scheme 21

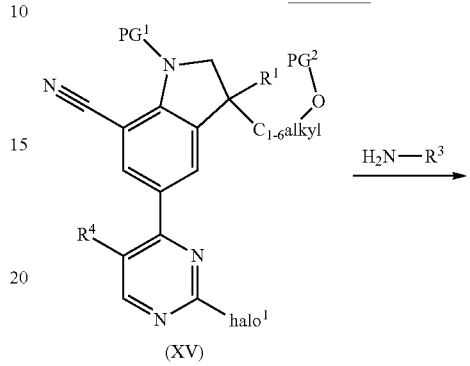

(XV)

$H_2N—R^3$ →

(Ic)

In Scheme 21, the following reaction conditions apply:

1: at a suitable temperature such as for example 90° C., in the presence of a suitable acid such as for example p-toluenesulfonic acid and a suitable solvent such as for example 1,4-dioxane.

In general, compounds of Formula (I) wherein R³ is restricted as shown below, wherein R²¹ is for example C$_{1-4}$alkyl or C$_{3-6}$cycloalkyl, and wherein all the other variables are as defined according to the scope of the present invention, hereby named compounds of Formula (Ic-a) and (Ic-b), can be prepared according to the following reaction Scheme 22. All other variables in Scheme 22 are defined according to the scope of the present invention or as above.

Scheme 22
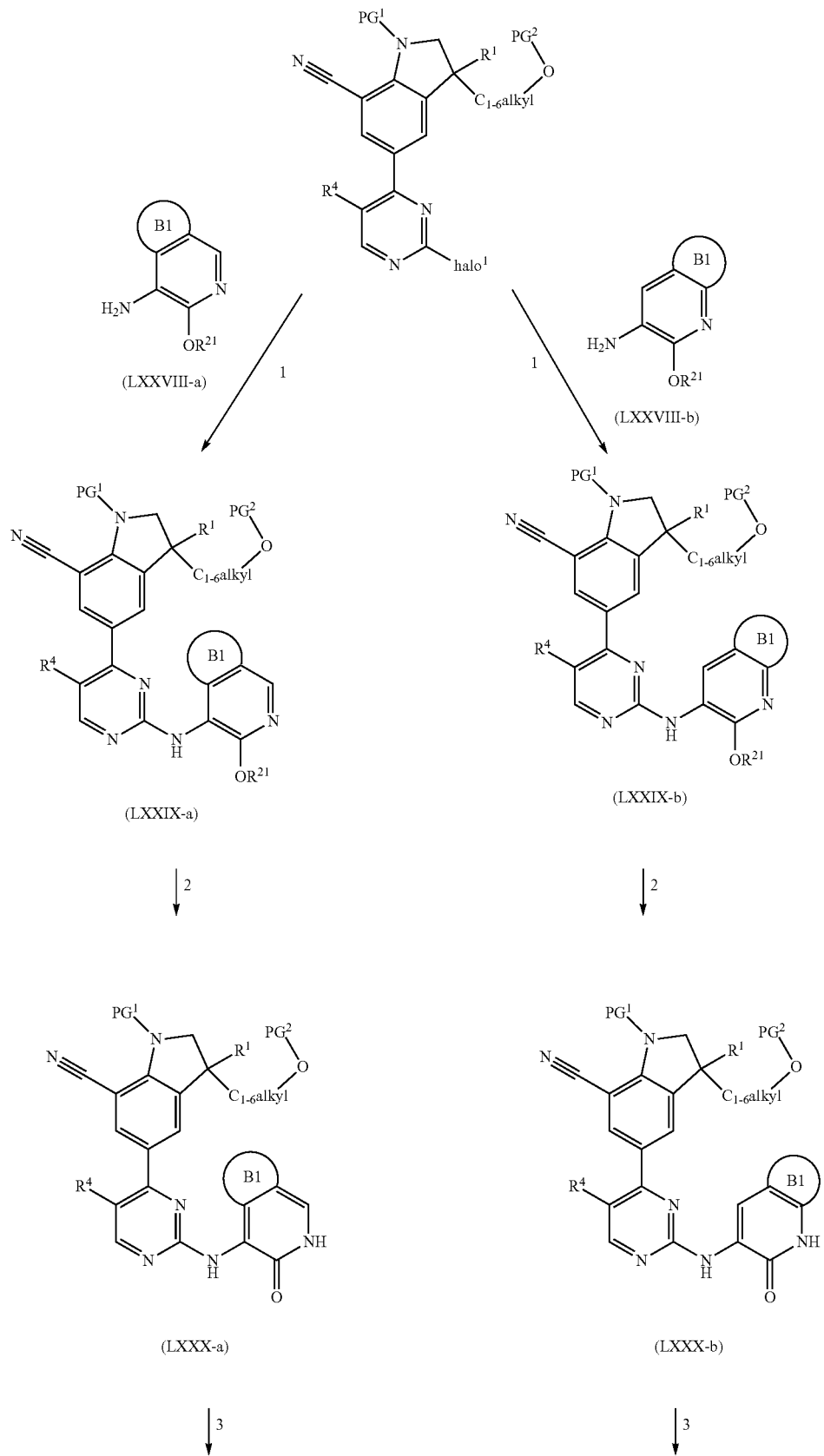

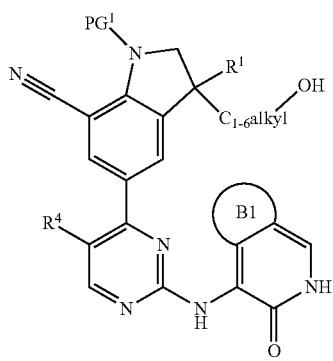

(Ic-a)

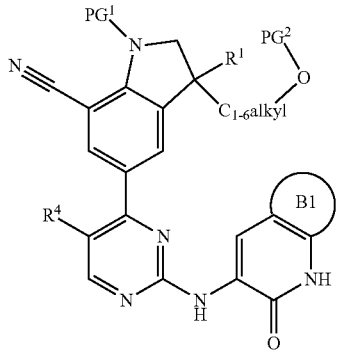

(Ic-b)

In Scheme 22, the following reaction conditions apply:

1: at a suitable temperature such as for example 85° C., in the presence of a suitable catalyst such as for example palladium acetate (Pd(OAc)$_2$), a suitable ligand such as for example 2,2'-bis(diphenylphosphino)-1,1'-binaphthyl (BI-NAP), a suitable base such as for example cesium carbonate, and a suitable solvent such as for example 1,4-dioxane, in sealed conditions;

2: at a suitable temperature such as for example 0° C. or room temperature or reflux, in presence of a suitable acid such as for example trifluoroacetic acid with a suitable solvent such as for example dichloromethane, methanol, ethyl acetate;

3: at a suitable temperature such as for example room temperature, in presence of a suitable desilylating agent such as for example tetra-n-butylammonium fluoride and a suitable solvent such as for example 2-methyltetrahydrofuran or tetrahydrofuran.

Intermediate of Formula (IIIa) wherein $R^2$ is $R^{2e}$ being $C_{1-6}$alkyl or $C_{1-6}$alkyl substituted with one, two or three Fluoro atoms, and wherein all the other variables are defined according to the scope of the present invention, can be prepared according to the following reactions. All other variables in Scheme 23 are defined according to the scope of the present invention or as defined above.

Scheme 23

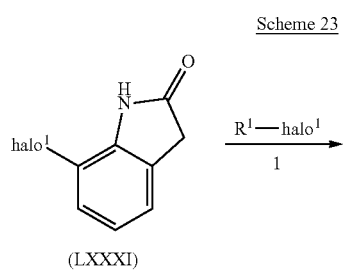

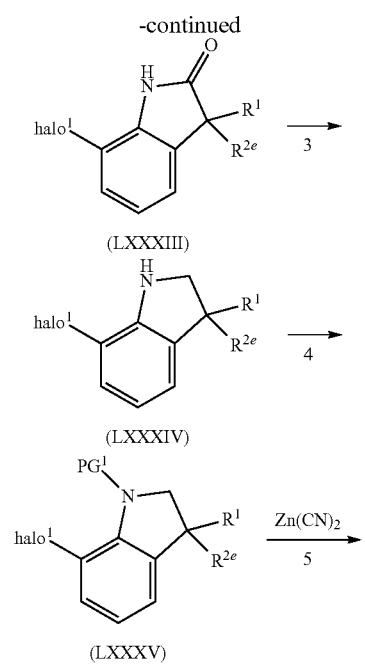

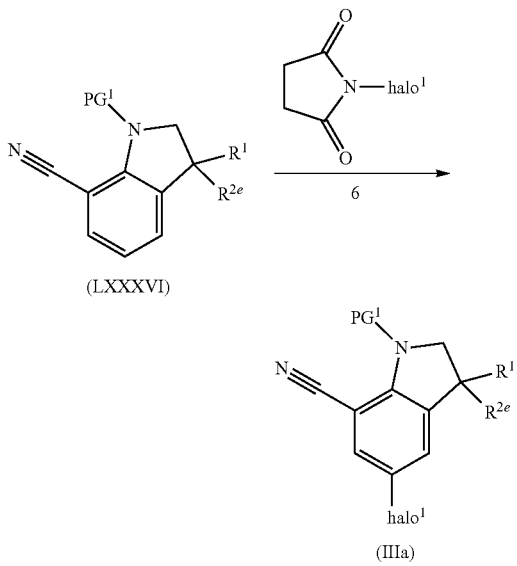

In Scheme 23, the following reaction conditions apply:

1: at a suitable temperature ranged between for example −20° C. and −78° C., in the presence of a chelating agent such as for example N,N,N',N'-tetramethylethylenediamine, a suitable deprotonating agent such as Butyl Lithium, in a suitable solvent such as for example tetrahydrofuran;

2: at a suitable temperature ranged between for example −20° C. and −78° C., in the presence of a chelating agent such as for example N,N,N',N'-tetramethylethylenediamine, a suitable deprotonating agent such as Butyl Lithium, in a suitable solvent such as for example tetrahydrofuran;

3: at a suitable temperature such as for example 70° C., in the presence of a suitable reducing agent such as for example Borane dimethyl sulfide complex, in a suitable solvent such as for example tetrahydrofuran;

4: at a suitable temperature such as for example room temperature, in the presence of a suitable reagent such as for example di-tert-butyldicarbonate, a suitable catalyst such as for example 4-dimethylaminopyridine (DMAP), a suitable base such as for example triethylamine and a suitable solvent such as for example tetrahydrofuran;

5: at a suitable temperature such as for example 100° C., in the presence of a suitable catalyst such as for example Tetrakis(triphenylphosphine)palladium(0), and a suitable solvent such as for example anhydrous dimethylformamide;

6: at a suitable temperature such as for example solvent reflux, and in a suitable solvent such as for example acetonitrile.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Pharmacology

It has been found that the compounds of the present invention inhibit NF-κB-inducing kinase (NIK—also known as MAP3K14). Some of the compounds of the present invention may undergo metabolism to a more active form in vivo (prodrugs). Therefore the compounds according to the invention and the pharmaceutical compositions comprising such compounds may be useful for treating or preventing diseases such as cancer, inflammatory disorders, metabolic disorders including obesity and diabetes, and autoimmune disorders. In particular, the compounds according to the present invention and the pharmaceutical compositions thereof may be useful in the treatment of a haematological malignancy or solid tumour. In a specific embodiment said haematological malignancy is selected from the group consisting of multiple myeloma, non-Hodgkin's lymphoma, Hodgkin lymphoma, T-cell leukaemia, mucosa-associated lymphoid tissue lymphoma, diffuse large B-cell lymphoma and mantle cell lymphoma, in a particular embodiment mantle cell lymphoma. In another specific embodiment of the present invention, the solid tumour is selected from the group consisting of pancreatic cancer, breast cancer, melanoma and non-small cell lung cancer.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma, mantle cell lymphoma), T-cell leukaemia/lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

Particular examples of cancers which may be treated (or inhibited) include B-cell malignancies, such as multiple myeloma, hodgkins lymphoma, mantle cell lymphoma, diffuse large B-cell lymphoma or chronic lymphocytic leukemia, with mutations in the non-canonical NFkB signaling pathway (eg in NIK (MAP3K14), TRAF3, TRAF2, BIRC2 or BIRC3 genes).

Hence, the invention relates to compounds of Formula (I), the tautomers and the stereoisomeric forms thereof, and the pharmaceutically acceptable addition salts, and the solvates thereof, for use as a medicament.

The invention also relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable addition salt, or a solvate thereof, or a pharmaceutical composition according to the invention, for use in the treatment, prevention, amelioration, control or reduction of the risk of disorders associated with NF-κB-inducing kinase dysfunction in a mammal, including a human, the treatment or prevention of which is affected or facilitated by inhibition of NF-κB-inducing kinase.

Also, the present invention relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament for treating, preventing, ameliorating, controlling or reducing the risk of disorders associated with NF-κB-inducing kinase dysfunction in a mammal, including a human, the treatment or prevention of which is affected or facilitated by inhibition of NF-κB-inducing kinase.

The invention also relates to a compound of Formula (I), a tautomer or a stereoisomeric form thereof, or a pharmaceutically acceptable addition salt, or a solvate thereof, for use in the treatment or prevention of any one of the diseases mentioned hereinbefore.

The invention also relates to a compound of Formula (I), a tautomer or a stereoisomeric form thereof, or a pharmaceutically acceptable addition salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable addition salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), a tautomer or a stereoisomeric form thereof, or a pharmaceutically acceptable addition salt, or a solvate thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof, or a pharmaceutically acceptable addition salt, or a solvate thereof, to warm-blooded animals, including humans.

Therefore, the invention also relates to a method for the treatment of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be from about 10 mg/kg body weight to 40 mg/kg body weight. A particular effective therapeutic daily amount might be 1 mg/kg body weight, 2 mg/kg body weight, 4 mg/kg body weight, or 8 mg/kg body weight. The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable addition salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

Therefore, an embodiment of the present invention relates to a product containing as first active ingredient a compound according to the invention and as further active ingredient one or more medicinal agent, more particularly, with one or more anticancer agent or adjuvant, as a combined preparation for simultaneous, separate or sequential use in the treatment of patients suffering from cancer.

Accordingly, for the treatment of the conditions mentioned hereinbefore, the compounds of the invention may be advantageously employed in combination with one or more other medicinal agents (also referred to as therapeutic agents), more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoiden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example pemetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacytidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, quisinostat, trichostatin A, vorinostat;

Inhibitors of the ubiquitin-proteasome pathway for example PS-341, Velcade (MLN-341) or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase;

BH3 mimetics for example ABT-199;

MEK inhibitors for example PD98059, AZD6244, CI-1040;

colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP17), e.g. abiraterone, abiraterone acetate.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m2) of body surface area, for example 50 to 400 mg/m2, particularly for cisplatin in a dosage of about 75 mg/m2 and for carboplatin in about 300 mg/m2 per course of treatment.

The taxane compound is advantageously administered in a dosage of 50 to 400 mg per square meter (mg/m2) of body surface area, for example 75 to 250 mg/m2, particularly for paclitaxel in a dosage of about 175 to 250 mg/m2 and for docetaxel in about 75 to 150 mg/m2 per course of treatment.

The camptothecin compound is advantageously administered in a dosage of 0.1 to 400 mg per square meter (mg/m2) of body surface area, for example 1 to 300 mg/m2, particularly for irinotecan in a dosage of about 100 to 350 mg/m2 and for topotecan in about 1 to 2 mg/m2 per course of treatment.

The anti-tumour podophyllotoxin derivative is advantageously administered in a dosage of 30 to 300 mg per square meter (mg/m2) of body surface area, for example 50 to 250 mg/m2, particularly for etoposide in a dosage of about 35 to 100 mg/m2 and for teniposide in about 50 to 250 mg/m2 per course of treatment.

The anti-tumour vinca alkaloid is advantageously administered in a dosage of 2 to 30 mg per square meter (mg/m2) of body surface area, particularly for vinblastine in a dosage of about 3 to 12 mg/m2, for vincristine in a dosage of about 1 to 2 mg/m2, and for vinorelbine in dosage of about 10 to 30 mg/m2 per course of treatment.

The anti-tumour nucleoside derivative is advantageously administered in a dosage of 200 to 2500 mg per square meter (mg/m2) of body surface area, for example 700 to 1500 mg/m2, particularly for 5-FU in a dosage of 200 to 500 mg/m2, for gemcitabine in a dosage of about 800 to 1200 mg/m2 and for capecitabine in about 1000 to 2500 mg/m2 per course of treatment.

The alkylating agents such as nitrogen mustard or nitrosourea is advantageously administered in a dosage of 100 to 500 mg per square meter (mg/m2) of body surface area, for example 120 to 200 mg/m2, particularly for cyclophosphamide in a dosage of about 100 to 500 mg/m2, for chlorambucil in a dosage of about 0.1 to 0.2 mg/kg, for carmustine in a dosage of about 150 to 200 mg/m2, and for lomustine in a dosage of about 100 to 150 mg/m2 per course of treatment.

The anti-tumour anthracycline derivative is advantageously administered in a dosage of 10 to 75 mg per square meter (mg/m2) of body surface area, for example 15 to 60 mg/m2, particularly for doxorubicin in a dosage of about 40 to 75 mg/m2, for daunorubicin in a dosage of about 25 to 45 mg/m2, and for idarubicin in a dosage of about 10 to 15 mg/m2 per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m2) of body surface area, or as known in the art, if different. Trastuzumab is advantageously administered in a dosage of 1 to 5 mg per square meter (mg/m2) of body surface area, particularly 2 to 4 mg/m2 per course of treatment.

These dosages may be administered for example once, twice or more per course of treatment, which may be repeated for example every 7, 14, 21 or 28 days.

The following examples further illustrate the present invention.

EXAMPLES

Several methods for preparing the compounds of this invention are illustrated in the following examples. All starting materials were obtained from commercial suppliers and used without further purification, or alternatively, can be easily prepared by a skilled person according to well-known methods.

Hereinafter, the terms: 'AcOH' or 'HOAc' means acetic acid, 'AcCl' means acetyl chloride, 'BOC' or 'Boc' means tert-butyloxycarbonyl, 'Ar' means Argon, 'Boc$_2$O' means di-tert-butyl dicarbonate, 'BrettPhos' or 'BRETTPHOS' means 2-(Dicyclohexylphosphino)-3,6-dimethoxy-2',4',6'-triisopropyl-1,1'-biphenyl, 'Brettphos Palladacycle' means Chloro[2-(dicyclohexylphosphino)-3,6-dimethoxy-2',4',6'-triisopropyl-1,1'-biphenyl][2-(2-aminoethyl)phenyl]palladium(II), 'Celite®' means diatomaceous earth, 'CV' means column volumes, 'DCE' means 1,2-dichloroethene, 'DCM' means dichloromethane, 'DiPE' means diisopropylether, 'DIBAL-H' means diisobutylaluminium hydride, 'DIPEA' means diisopropylethylamine, 'DMAP' means dimethylaminopyridine, 'DMF' means dimethylformamide, 'ee' means enantiomeric excess, 'eq.' or 'equiv.' means equivalent(s), 'Et' means ethyl, 'Me' means methyl, 'Et$_2$O' means diethyl ether, 'EtOAc' or 'AcOEt' means ethyl acetate, 'EtOH' means ethanol, 'h' means hours(s), 'HATU' means 1-[Bis(dimethylamino)methylene]-1H-1,2,3-triazolo[4,5-b]pyridinium 3-oxid hexafluorophosphate, 'HBTU' means N,N,N',N'-Tetramethyl-O-(1H-benzotriazol-1-yl)uronium hexafluorophosphate, 'HPLC' means High-performance Liquid Chromatography, 'iPrOH' or 'IPA' means isopropyl alcohol, 'LC/MS' means Liquid Chromatography/Mass Spectrometry, 'Me-THF' means 2-methyl-tetrahydrofuran, 'MeOH' means methanol, 'MgSO$_4$' means magnesium sulfate 'mn' or 'min' means minute(s), 'MsCl' means methanesulfonyl chloride, 'M.P.' or 'm.p.' means melting point, 'NaBH(OAc)$_3$' means sodium triacetoxyborohydride, 'NBS' means N-bromosuccinimide, 'NIS' means N-iodosuccinimide, 'NMR' means Nuclear Magnetic Resonance, 'OR' means optical rotation, 'Pd/C 10%' means palladium on carbon loading 10%, 'PdCl$_2$(PPh$_3$)$_2$' means Bis(triphenylphosphine)palladium chloride, 'Pd(dppf)Cl$_2$' means [1,1'-Bis(diphenylphosphino)ferrocene]-dichloropalladium (II), 'Pd(dppf)Cl$_2$.CH$_2$Cl$_2$' means [1,1'-Bis(diphenylphosphino)ferrocene]-dichloropalladium(II). dichloromethane, 'Pd(OAc)$_2$' means palladium (II) acetate, 'PtO$_2$' means platinum oxide, 'Quant.' means quantitative, 'RaNi' means Raney Nickel, 'rt' means room temperature, 'Rt' means retention time, 'SFC' means supercritical fluid chromatography, 'SOCl$_2$' means thionyl chloride, 'T' means temperature, 'TBAF' means tetrabutylammonium fluoride, 'TBD' means triazabicyclodecene, 'TBDMS' or 'SMDBT' means tert-butyldimethylsilyl, 'TEA' means triethylamine, 'TFA' means trifluoroacetic acid, 'THF' means tetrahydrofuran, 'Me-THF' means 2-methyltetrahydrofuran, 'TLC' means thin layer chromatography, 'Ti(OiPr)$_4$' means titanium isopropoxide, 'HCl' means hydrochloric acid, 'LiAlH$_4$' means lithium aluminium hydride, 'K$_2$CO$_3$' means potassium carbonate, 'NaHCO$_3$' means sodium hydrogenocarbonate, 'NaOH' means potassium hydroxide, 'CuI' means copper (I) iodide, 'H$_2$SO$_4$' means sulfuric acid, 'MeCN', 'CH$_3$CN' or 'ACN' means acetonitrile, 'iPrNH$_2$' means isopropylamine, 'v.' means volume, 'NaH' means sodium hydride, 'Na$_2$SO$_4$' means sodium sulfate, 'NaBH$_4$' means sodium borohydride, 'BH$_3$.THF' means borane.tetrahydrofuran complex, 'COMU®' means (1-Cyano-2-ethoxy-2-oxoethylidenaminooxy)dimethylamino-morpholino-carbeniun hexafluorophosphate, 'Na$_2$CO$_3$' means sodium carbonate, 'NH$_4$OH' means ammonium hydroxide, 'Cs$_2$CO$_3$' means cesium carbonate, 'Pd(PPh$_3$)$_4$' means palladium tetrakistriphenylphosphine (also tetrakis(triphenylphosphine)palladium (0)), 'NH$_4$Cl' means ammonium chloride, 'XPhos' means 2-Dicyclohexylphosphino-2',4',6'-triisopropylbiphenyl, 'Xphos palladacycle' or 'XPhos precatalyst' means (2-Dicyclohexylphosphino-2',4',6'-triisopropyl-1,1'-biphenyl)[2-(2-aminoethyl)phenyl)]palladium(II) chloride, 'BINAP', '(±)-BINAP' or 'rac-BINAP' means (±)-2,2'-Bis(diphenylphosphino)-1,1'-binaphthalene (also [1,1'-Binaphthalene]-2,2'-diylbis[diphenylphosphine] or 2,2'-bis(diphenylphosphino)-1,1'-binaphthyl), 'RuPhos Palladacycle Gen. 1' means Chloro(2-dicyclohexylphosphino-2',6'-di-i-propoxy-1,1'-biphenyl)[2-(2-aminoethylphenyl)]palladium(II), methyl-t-butylether adduct.

When a stereocenter is indicated with 'RS' this means that a racemic mixture was obtained.

For intermediates that were used in a next reaction step as a crude or as a partially purified intermediate, theoretical mol amounts are indicated in the reaction protocols described below.

It is well known to one skilled in the art that protecting groups such as TBDMS can routinely be removed with TBAF in a variety of solvents such as for example THF. Similarly, conditions for removal of BOC protecting groups are well known to one skilled in the art, commonly including for example TFA in a solvent such as for example DCM, or HCl in a solvent such as for example dioxane.

The skilled person will realize that in some cases where an organic layer was obtained at the end of an experimental protocol, it was necessary to dry the organic layer with a typical drying agent such as for example MgSO₄, or by azeotropic distillation, and to evaporate the solvent before using the product as a starting material in the next reaction step.

Preparation of the Intermediates

Example A1

Preparation of Intermediate 1

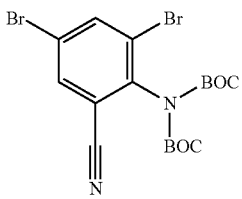 [SMILES: CC(C)(C)OC(=O)N(C(=O)OC(C)(C)C)c1c(Br)cc(Br)cc1C#N]

To a solution of 2,4-dibromo-6-cyanoaniline (200.00 g, 724.82 mmol) and DMAP (17.71 g, 144.96 mmol) in DCM (3 L), Boc₂O (474.58 g, 2.17 mol) was added and the reaction mixture was stirred at 45° C. for 4 h. The crude mixture was successively washed with saturated NaHCO₃ (2×1 L) and brine (2×1 L), dried over MgSO₄, filtered and concentrated under vacuum to give 323 g of intermediate 1 (56% yield, yellow solid, 86% purity evaluated by LC/MS). The product was used in the next step without any further purification.

Preparation of Intermediate 2

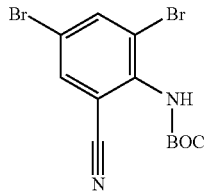

A mixture of intermediate 1 (620.00 g, 1.30 mol) and K₂CO₃ (539.02 g, 3.90 mol) in MeOH (6 L) was stirred at 65° C. for 3 h. The reaction mixture was cooled to 25° C. filtered and concentrated under vacuum. Then, the residue was dissolved in EtOAc (4 L) and the organic layer was washed with brine (2 L), dried over MgSO₄, and filtered. The filtrate was evaporated under vacuum to 1/8 solvent, filtered to collect the solid and dried under reduced pressure to give 300 g of intermediate 2 (60% yield, yellow solid). The product was used in the next step without any further purification.

Preparation of Intermediate 3

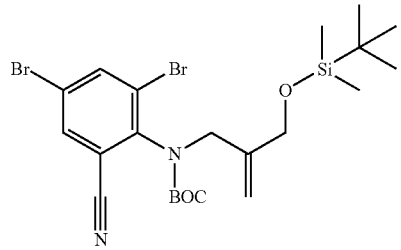 [SMILES: C=C(CO[Si](C)(C)C(C)(C)C)CN(C(=O)OC(C)(C)C)c1c(Br)cc(Br)cc1C#N]

Intermediate 2 (100.00 g, 265.93 mmol), 2-(((tert-butyl-dimethyl-silanyl)oxy)methyl)prop-2-en-1-ol (80.72 g, 398.90 mmol) and tributylphosphane (107.61 g, 531.86 mmol) were dissolved in THE (2 L) and cooled to 0° C. A solution of 1,1'-(azodicarbonyl)-dipiperidine (147.61 g, 585.05 mmol) in THE (50 mL) was added dropwise under N₂ and stirred at 0° C. for 1 h, then 25° C. for 12 h. The resulting mixture was triturated with petroleum ether (3 L), filtered and concentrated under vacuum. Then, the residue was dissolved in EtOAc (6 L), washed successively with water (2×2 L) and brine (2×2 L), dried over MgSO₄, filtered and concentrated under vacuum. Three reactions (each 100 g) were carried out in parallel. The resulting residues were purified by column chromatography on silica gel (SiO₂, mobile phase:petroleum ether/EtOAc, 10:1). The desired fractions were collected and the solvent was concentrated to dryness under vacuum to give 350 g of intermediate 3 (78% yield, yellow oil).

Preparation of Intermediate 3a

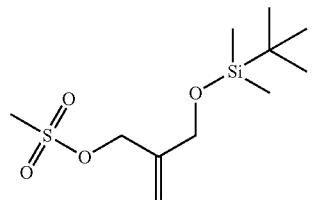 [SMILES: C=C(CO[Si](C)(C)C(C)(C)C)COS(C)(=O)=O]

Triethylamine (196.3 mL; 1.408 mol) was added to a solution of 2-(((tert-butyl-dimethyl-silanyl)oxy) methyl) prop-2-en-1-ol (114 g, 563.3 mmol) in DCM (1 L) at 0° C. Methanesulfonylchloride (56.0 mL; 704.2 mmol) was added slowly to the mixture and this mixture was stirred for 2 h at 0° C. The reaction was quenched with saturated aqueous solution of NaHCO₃ (100 ml) and extracted with DCM (500 ml*2). The organic layer was dried over MgSO₄, filtered, and concentrated under vacuum. The residue was purified by silica gel chromatography (Petroleum ether/ethyl acetate from 0/100 to 5/1) to give 50 g (32%; light yellow oil) of intermediate 3a.

Alternative Preparation of Intermediate 3a

A solution of 1,3-Hydroxy-2-methylenepropane (100 g) in dry THF (200 mL) was added dropwise at 0° C. to a suspension of sodium hydride (0.95 eq.) in dry THE (600 mL). After 30 min a solution of tert-butyldimethylsilylchloride (0.95 eq.) in dry THE (200 mL) was added dropwise to the mixture. After approximately 18 hours at 0-5° C., water (500 mL) was added slowly keeping the temperature between 0-5° C. After phase separation, the aqueous layer was back-extracted with ethyl acetate (500 mL) and the combined organic layers were washed with water (500 mL). The organic phase was concentrated to a residue which was azeotropically dried by co-evaporation with THF affording 252.7 g of the crude monoTBDMS-protected diol. A portion of the crude monoTBDMS-protected diol (152.4 g) was dissolved in dry dichloromethane (610 mL) and triethylamine (1.4 eq.) was added. The mixture was then stirred at 0° C. for 30 min and methanesulfonic anhydride (1.2 eq.) was added as a solution in dichloromethane (950 mL) and the mixture was stirred for 1 h between −5 and 5° C. An additional aliquot of methanesulfonic anhydride (0.1 eq.) and triethylamine (0.2 eq.) were added and, after 1 additional hour, water (500 mL) was added. After phase separation, the organic layer was washed twice with water (500 mL) and concentrated to a residue, which was re-diluted with THF and partially concentrated to obtain a solution of intermediate 3a (311.1 g, 57 weight % intermediate 3a in the solution).

Alternative Preparation of Intermediate 3

Intermediate 2 (140 g; 372.3 mmol) was dissolved in acetonitrile (1.3 L). Intermediate 3a (104.4 g; 372.3 mmol), potassium carbonate (128.6 g; 930.7 mmol), and sodium iodide (5.58 g; 37.2 mmol) were added. The mixture was stirred at 80° C. for 12 h, cooled and concentrated under reduced pressure. The residue was dissolved in water (1 L) and extracted with ethyl acetate (1 L×2). The combined organic phase was washed with brine (1 L), dried over $Na_2SO_4$ and filtered. The filtrate was concentrated under vacuum to give a crude product. The residue was purified by silica gel chromatography (Petroleum ether/ethyl acetate from 100/0 to 40/1) to give 180 g (86%; clear oil) of intermediate 3.

Preparation of Intermediate 4 and Intermediate 4'

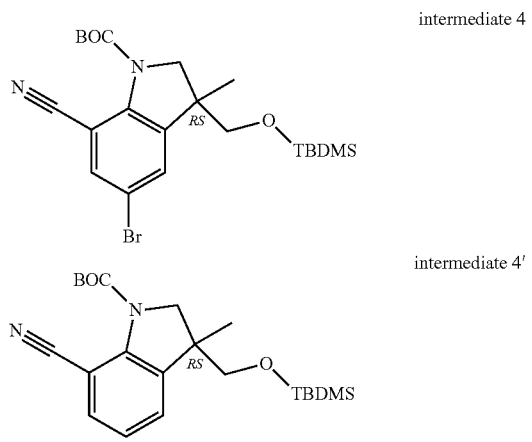

intermediate 4 intermediate 4'

A suspension of intermediate 3 (120.00 g, 214.14 mmol), sodium acetate (45.67 g, 556.76 mmol), sodium formate (37.86 g, 556.76 mmol), Pd(OAc)$_2$ (4.81 g, 21.41 mmol) and tetraethylammonium chloride (44.35 g, 267.67 mmol) in DMF (1.26 L) was degassed under vacuum, purged with Ar three times, and stirred at 85° C. for 2 h. The resulting mixture was filtered through a pad of Celite® and the solid was washed with DCM (2 L). The filtrate was concentrated under vacuum. The residue was dissolved in ethyl acetate (4 L), washed successively with water (2×2 L) and brine (2×2 L), dried over MgSO$_4$, filtered and concentrated under vacuum. Then, the residue was purified by column chromatography on silica gel (SiO$_2$, mobile phase:petroleum ether/ EtOAc, 15:1). The desired fractions were collected and the solvent was concentrated to dryness under vacuum to give a mixture of intermediates 4 and 4'. Three reactions (each on 100-120 g of intermediate 3) were carried out in parallel which gave in total 160 g of a mixture of intermediates 4 and 4' (38:62).

Alternative Preparation of Intermediate 4

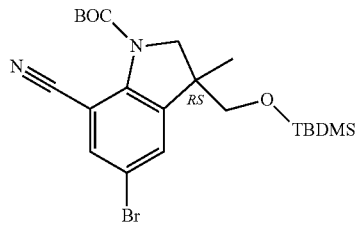

To a solution of intermediates 4 and 4' in CH$_3$CN (1.60 L), 1-bromopyrrolidine-2,5-dione (212.20 g, 1.19 mol) was added and the resulting mixture was stirred at 40° C. for 16 h. The solvent was removed by evaporation under reduced pressure. The residue was dissolved in ethyl acetate (2 L), washed successively with NaHCO$_3$ (2×1 L) and brine (2×1 L), dried over MgSO$_4$ and filtered. The filtrate was evaporated under vacuum and purified by column chromatography on silica gel (SiO$_2$, mobile phase:petroleum ether/EtOAc, 50:1). The desired fractions were collected and the solvent was concentrated to dryness under vacuum to give 110 g of intermediate 4 (56% yield, yellow oil, 97% purity evaluated by LC/MS).

Alternative Preparation a of Intermediate 4'

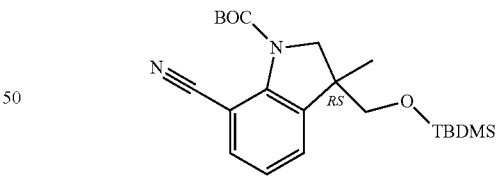

To a solution of intermediate 3 (295.00 g, 473.70 mmol), sodium acetate (101.05 g, 1.23 mol), sodium formate dihydrate (128.15 g, 1.23 mol) and [1,1'-bis(diphenylphosphino) ferrocene] palladium, (II) chloride complex with dichloromethane (19.34 g, 23.70 mmol) in DMF (2 L) was added tetra-N-butylammonium chloride (164.60 g, 592.20 mmol) under N$_2$ at rt. The reaction mixture was stirred overnight at 60° C., then, filtered through a pad of Celite® and the solid was washed with DCM (400 mL). The filtrate was concentrated under vacuum. The resulting residue was dissolved in EtOAc (4 L) and the organic layer was washed successively with water (2 L) and brine (2 L), dried over Na$_2$SO$_4$, filtered and concentrated to give the crude product as black oil. This residue was purified by column chromatography on silica gel (SiO$_2$, mobile phase:petroleum ether/EtOAc, gradient from 100:0 to 10:1). The desired fractions were collected and the solvent was concentrated to dryness under vacuum to give 155 g of intermediate 4' (70% yield, yellow oil).

Alternative Preparation B of Intermediate 4'

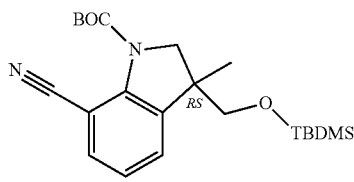

Intermediate 242 (50.0 g) was dissolved in DMF (250 mL). Sodium formate dehydrate (2.6 eq.), sodium acetate (2.6 eq.), tetraethylammonium chloride (1.25 eq.) and palladium acetate (0.05 eq.) were added. The mixture was degassed with nitrogen (3 times) and was then warmed at 45-50° C. until complete conversion (typically 24 hours monitored by HPLC). Water (350 mL) was then added followed by heptane (350 mL). The mixture was filtered and, after phase separation, the aqueous layer was extracted with heptane (350 mL). The combined organic layers were washed with water (250 mL) and then filtered on a diatomite pad (25 g; diatomaceous earth). The filtrate was concentrated to 100-150 mL, cooled to −10 to −5° C. for 2 hours and filtered to afford 37.6 g of intermediate 4'. An additional amount of intermediate 4' could be recovered by filtering the mother liquors on a silica gel pad to remove impurities, and subsequently cool down the filtrate to −10° C. to crystallize out an additional amount of intermediate 4'.

Preparation of Intermediate 4'R

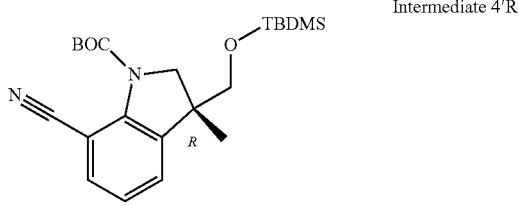

Intermediate 4'R

Intermediate 4'R was obtained from a chiral chromatography separation of intermediate 4' (column CHIRALPAK IC 5 cm*25 cm; mobile phase:hexane/EtOH:80/20; Flow rate: 60.0 mL/min; Wavelength: UV 254 nm; Temperature: 35° C.).

Preparation of Intermediate 4R and Intermediate 4S

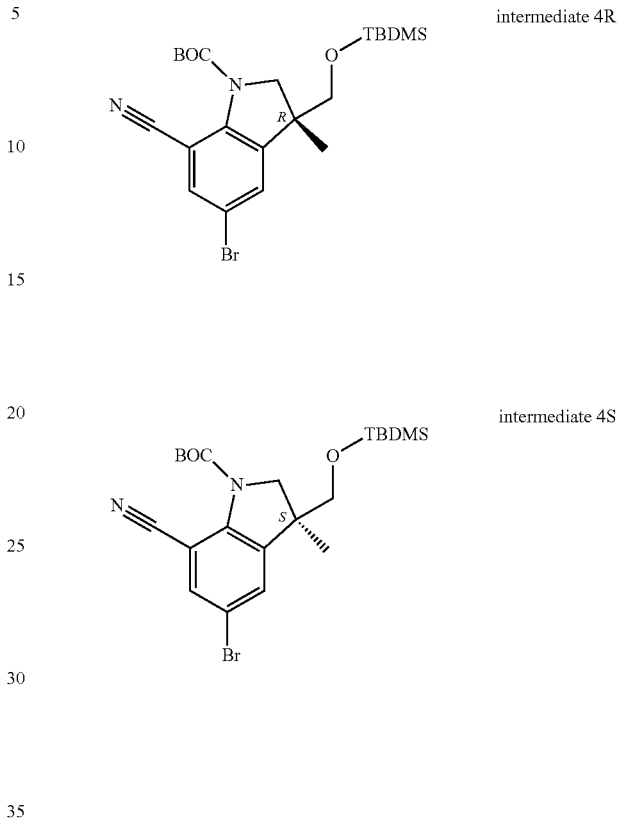

Intermediate 4 (500.00 g) was purified via Normal Phase Chiral separation (Stationary phase: Daicel Chiralpak IC 2000 gram 10 microhm, mobile phase:heptane/EtOH, Isocratic 80% heptane, 20% EtOH). The fractions containing the products were mixed and concentrated to afford 266 g of intermediate 4R (53% yield, ee>98%) and 225 g of intermediate 4S (45% yield, ee>98%).

Alternatively, intermediate 4 (10.00 g) was purified by chiral SFC (Stationary phase: CHIRALPAK IC 5 μm 250× 30 mm, mobile phase: 85% CO$_2$, 15% iPrOH). The pure fractions were collected and evaporated to dryness yielding 4.3 g of intermediate 4R (43% yield, ee=100%) and 4.5 g of intermediate 4S (45% yield, ee=100%).

Alternative Preparation of Intermediate 4R

To a solution of intermediate 4'R (10.0 g) in ACN (100 mL) 1,3-dibromo-5,5-dimethylhydantoin (0.75 eq.) was added and the mixture was stirred at 20° C. for 24-28 hours, monitoring the conversion by HPLC. After complete conversion aqueous 5% NaHCO$_3$ was added (250 mL) and the mixture was stirred for 30 minutes. Toluene (250 mL) was then added and, after 30 min stirring at room temperature, the mixture was allowed to settle and the layers were separated. The organic layer was washed twice with water (100 mL) and used directly in the next step (conversion 99.6%).

Example A2a

Preparation of Intermediate 5

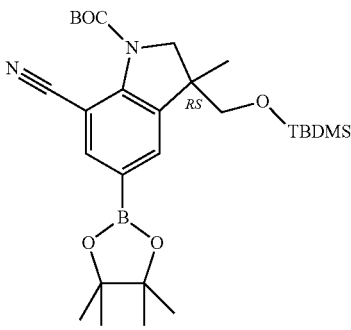

To a solution of intermediate 4 (127.00 g, 234.70 mmol) in 1,4-dioxane (1.2 L), bis(pinacolato)diboron (74.50 g, 293.40 mmol) and potassium acetate (69.11 g, 704.24 mmol) were added. Then, [1,1'-bis(diphenylphosphino) ferrocene] palladium (II) chloride (8.59 g, 11.74 mmol) was added and stirred for 4 h at 85° C. under $N_2$ atmosphere. The mixture was cooled, partitioned between EtOAc (2 L) and water (500 mL) and filtered through a pad of Celite®. The organic and aqueous layers were separated. The organic layer was washed successively with water (300 mL), brine (300 mL), dried over $Na_2SO_4$ and concentrated under vacuum. The residue was dissolved in a mixture of DCM/EtOAc (90:10, 600 mL), filtered through a plug of flash silica gel and washed with DCM/EtOAc (90:10, 3 L). The filtrate was evaporated to give 125 g of crude intermediate 5 (brown oil) which was directly engaged in the next step.

Preparation of Intermediate 5R

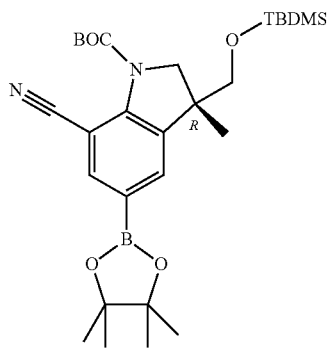

To a solution of intermediate 4R (20.00 g, 41.50 mmol) in 1,4-dioxane (200 mL), bis(pinacolato)diboron (13.20 g, 51.90 mmol) and potassium acetate (12.20 g, 124.60 mmol) were added. Then, [1,1'-bis(diphenylphosphino) ferrocene] palladium (II) chloride complex with dichloromethane (1.70 g, 2.08 mmol) was added and stirred for 4 h at 85° C. under $N_2$. The mixture was cooled, partitioned between EtOAc (200 mL) and water (100 mL), and filtered through a pad of Celite®. The organic and aqueous layers were separated. The organic layer was washed successively with water (100 mL) and brine (100 mL), dried over $Na_2SO_4$, and concentrated under vacuum. The residue was dissolved in a mixture of DCM/EtOAc (90:10, 200 mL), filtered through a plug of flash silica gel and washed with a mixture of DCM/EtOAc (90:10, 1 L). The filtrate was evaporated to give 25 g of crude intermediate 5R (brown oil) which was directly engaged in the next step.

Preparation of Intermediate 6

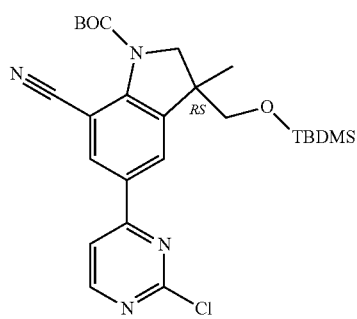

A solution of intermediate 5 (160.00 g, 302.70 mmol) in 1,4-dioxane (1.2 L) was treated with a solution of $NaHCO_3$ (76.30 g, 908.10 mmol) in water (400 mL). Then, 2,4-dichloropyrimidine (67.64 g, 545.06 mmol) and $Pd(PPh_3)_4$ (17.50 g, 15.13 mmol) were added under $N_2$. The reaction mixture was stirred at 80° C. under $N_2$. The mixture was cooled, partitioned between EtOAc (2 L) and water (800 mL), and filtered through a pad of Celite®. The organic and aqueous layers were separated. The organic layer was washed successively with water (800 mL) and brine (500 mL), dried over $Na_2SO_4$ and concentrated under vacuum. The residue was purified by flash column chromatography on silica gel ($SiO_2$, mobile phase:petroleum ether/EtOAc, gradient from 100:0 to 10:1). The desired fractions were collected and the solvent was concentrated to dryness under vacuum to give 100 g of intermediate 6 (71% yield in 2 steps, yellow solid).

Preparation of Intermediate 6R and Intermediate 6S

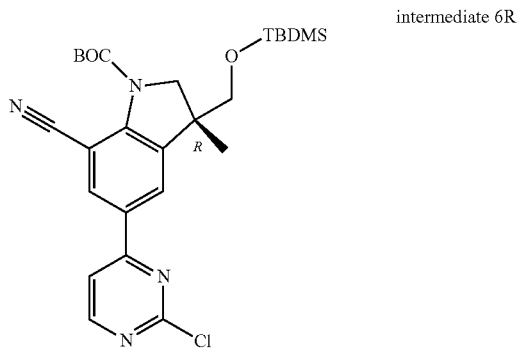

intermediate 6R intermediate 6S

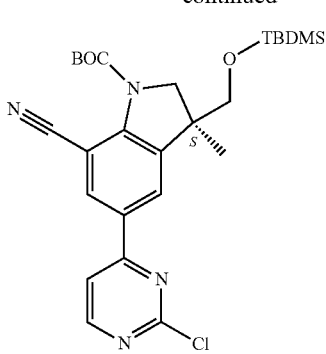

Intermediate 6 (52.00 g) was purified by chiral SFC (stationary phase: CHIRALPAK IC 5 μm 250×30 mm, mobile phase: 60% CO$_2$, 40% MeOH). The desired fractions were collected and the solvent was concentrated to dryness under vacuum to give 25 g of intermediate 6R (48% yield) and 25.1 g of intermediate 6S (48% yield).

Intermediate 6R (50.10 g) was further purified by chiral SFC (stationary phase: CHIRALPAK IA 5 μm 250*20 mm, mobile phase: 87.5% CO$_2$, 12.5% MeOH). The pure fractions were mixed and the solvent was evaporated to afford 49.10 g of intermediate 6R.

Alternative Preparation of Intermediate 6R

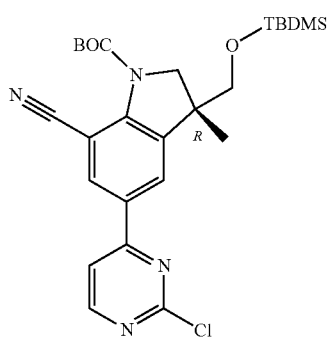

A solution of intermediate 5R (25.00 g, 41.90 mmol) in 1,4-dioxane (1.2 L) was treated with a solution of NaHCO$_3$ (10.50 g, 125.72 mmol) in water (80 mL). Then, 2,4-dichloropyrimidine (9.36 g, 62.86 mmol) and Pd(PPh$_3$)$_4$ (2.42 g, 2.09 mmol) were added under N$_2$. The reaction mixture was stirred at 80° C. under N$_2$. The mixture was cooled, partitioned between EtOAc (300 mL) and water (100 mL), and filtered through a pad of Celite®. The organic layer was washed with water (100 mL), brine (100 mL), dried over Na$_2$SO$_4$ and concentrated under vacuum. The resulting residue was combined with 3 other batches coming from reactions performed on 25 g of intermediate 5R. The residue was purified by flash column chromatography on silica gel (SiO$_2$, mobile phase:petroleum ether/EtOAc, gradient from 100:0 to 10:1). The desired fractions were collected and the solvent was concentrated to dryness under vacuum to give 63 g of intermediate 6R (70% yield over 2 steps, yellow solid).

Alternative Preparation of Intermediate 6R

To a solution of intermediate 4R (50.0 g) in toluene (400 mL) was added bis(pinacolato)diboron (1.3 eq.), potassium acetate (3.0 eq.) and Pd(dppf)Cl$_2$ (0.05 eq.). The mixture was degassed 3 times with nitrogen and heated to 90° C. for 12-14 hours. Subsequently, the mixture was cooled to room temperature and filtered on a celite pad which was washed with toluene (150 mL). The filtrate was washed with water (250 mL) and was then filtered on a silica pad (10 g) to afford a toluene solution containing 49 g of intermediate 5R. To this solution was added 2,4-dichloropyrimidine (1.5 eq.), NaHCO$_3$ (3.0 eq.), water (25 mL) and Pd(PPh$_3$)$_4$ (0.05 eq.). After degassing three times with nitrogen, the mixture was stirred at 90° C. monitoring the conversion by HPLC. After complete conversion (24-48 hours), the mixture was cooled to room temperature, filtered on a celite pad and washed with water (250 mL). To the organic layer was added silica thiol scavenging resin (10 g) and the mixture was stirred at 90° C. for 3 hours, then cooled to room temperature and filtered. The solvent was switched completely to isopropanol by repeated distillation until about 100 mL of isopropanol solution remained. The solution was warmed to 50° C. and 250 mL of methanol were added. After stirring at 50° C. for 4 hours, the mixture was cooled to 0° C. in 4 h, held at the same temperature for 16 hours and finally filtered to obtain 26 g of intermediate 6R.

Example A2b

Preparation of intermediate 158b

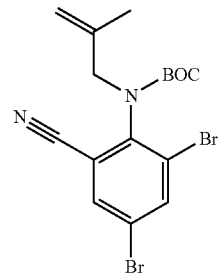 [SMILES: C=C(C)CN(C(=O)OC(C)(C)C)c1c(Br)cc(Br)cc1C#N]

A solution of intermediate 2 (10.00 g, 26.59 mmol) and 2-methyl-2-propen-1-ol (4.50 mL, 53.69 mmol) in Me-THF (200 mL) was cooled with EtOH/ice bath under N$_2$ to an internal temperature of −5° C. Tri-n-butylphosphine (13.30 mL, 53.19 mmol) was added. Then a solution of 1,1'-(azodicarbonyl)piperidine (14.80 g, 58.62 mmol) in Me-THF (120 mL) was added dropwise over 25 min. The solution was stirred for 5 min more at this temperature then the cooling bath was removed and the solution stirred at rt for 18 h. The reaction mixture was poured onto a 10% aqueous solution of K$_2$CO$_3$ and extracted with DCM. The organic layer was decanted, dried over MgSO$_4$, filtered and evaporated to dryness. The residue (20 g) was taken up with heptane and the insoluble material was removed by filtration. The filtrate was concentrated to 20 mL and purified by column chromatography on silica gel (irregular SiOH, 80 g, mobile phase:heptane/EtOAc, gradient from 100:0 to 88:12). The pure fractions were collected and evaporated to dryness to give 10.80 g of intermediate 158b (94% yield).

Preparation of Intermediate 159b and Intermediate 159b'

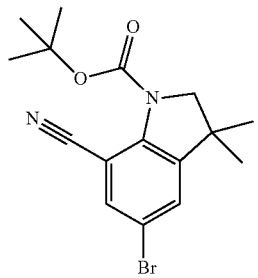
intermediate 159b

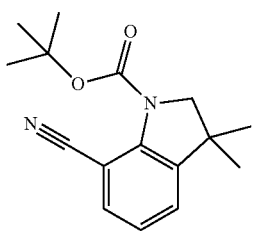
intermediate 159b'

A mixture of intermediate 158b (10.80 g, 25.11 mmol), sodium acetate (5.35 g, 65.28 mmol), sodium formate (4.44 g, 65.28 mmol) and tetraethylammonium chloride (5.20 g, 31.38 mmol) in DMF (100 mL) was de-gassed by sonication for 10 min under a stream of Ar. Pd(OAc)$_2$ (563.00 mg, 2.51 mmol) was added and the resulting orange suspension was then stirred at 85° C. (block temperature) for 4 h. The residue was diluted with EtOAc and water, then filtered through a plug of Celite®. The organic layer was decanted, washed successively with a saturated aqueous solution of NaHCO$_3$ and brine, dried over MgSO$_4$, filtered and evaporated to dryness. The residue (8.3 g, mixture of intermediates 159b and 159b') was dissolved in CH$_3$CN (230 mL) and NBS (4.47 g, 25.11 mmol) was added. The reaction mixture was heated at 55° C. (block temp) for 18 h. The reaction mixture was evaporated to dryness and the residue was taken up with heptane/DCM. The precipitate was filtered off (1 g derivative) and the filtrate (10 g) was purified by column chromatography on silica gel (irregular SiOH, 120 g, injection in DCM, mobile phase:heptane/EtOAc, gradient from 100:0 to 80:20). The pure fractions were collected and evaporated to dryness to give 4 g of intermediate 159b (45% yield).

Preparation of Intermediate 160b

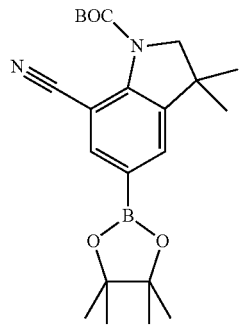 [SMILES: CC(C)(C)OC(=O)N1CC(C)(C)c2cc(B3OC(C)(C)C(C)(C)O3)cc(C#N)c21]

[1,1'-Bis(diphenylphosphino)ferrocene]dichloropalladium (II), complex with dichloromethane (243.00 mg, 0.30 mmol) was added to a solution of intermediate 159b (2.09 g, 5.95 mmol), bis(pinacolato)diboron (1.90 g, 7.44 mmol) and potassium acetate (1.75 g, 17.85 mmol) in 1,4-dioxane (45 mL) and the reaction mixture was heated for 18 h at 85° C. The reaction mixture was diluted with EtOAc and filtered through a pad of Celite®. The filtrate was washed with water, and the organic layer was decanted, dried over MgSO$_4$, filtered and evaporated to dryness. The residue was crystallized from DiPE and the precipitate was filtered and dried to give 1.85 g of intermediate 160b (78% yield).

Preparation of Intermediate 161b

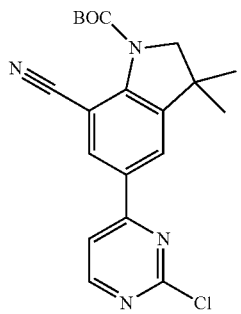 [SMILES: CC(C)(C)OC(=O)N1CC(C)(C)c2cc(-c3ccnc(Cl)n3)cc(C#N)c21]

A degassed suspension of intermediate 160b (1.12 g, 2.81 mmol), 2,4-dichloropyridine (502.00 mg, 3.37 mmol), Pd(PPh$_3$)$_4$ (162.00 mg, 0.14 mmol) and a solution of Na$_2$CO$_3$ 2M (4.20 mL, 8.14 mmol) in 1,4-dioxane (24 mL) was heated to 85° C. for 18 h. The reaction mixture was partitioned between DCM and saturated aqueous NaHCO$_3$. The organic layer was decanted, dried over MgSO$_4$, filtered and evaporated to dryness. The residue (2 g) was purified by column chromatography on silica gel (irregular SiOH, 40 g, mobile phase:heptane/EtOAc, gradient from 70:30 to 50:50). The pure fractions were collected and evaporated to dryness to give 933 mg of intermediate 161b (86% yield, 85% purity based on LC/MS).

Example A3a

Preparation of Intermediate 7

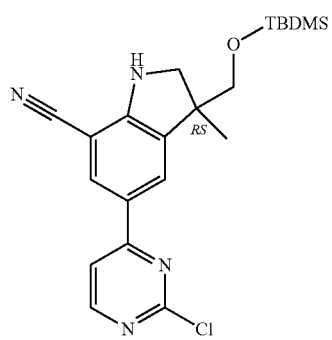

To a solution of intermediate 6 (1.50 g, 2.91 mmol) in DCM (30 mL), TFA (7 mL, 91.50 mmol) was added at 0-5° C. and the resulting mixture was stirred at 0-5° C. for 1 h, then at rt for 1 h. The crude product was poured in a mixture of crushed ice and a saturated aqueous solution of NaHCO$_3$. After extraction with DCM (twice), the organic layers were combined, washed with saturated solution of NaHCO$_3$, dried over MgSO$_4$ and concentrated under vacuum. The residue was purified by column chromatography on silica gel (Irregular SiOH, 40 µm, mobile phase: NH$_4$OH/MeOH/DCM, gradient from 0% NH$_4$OH, 0% MeOH, 100% DCM to 0.1% NH$_4$OH, 2% MeOH, 98% DCM). The desired fractions were collected and the solvent was concentrated to dryness under vacuum to give 524 mg of intermediate 7 (65% yield).

Preparation of Intermediate 7R

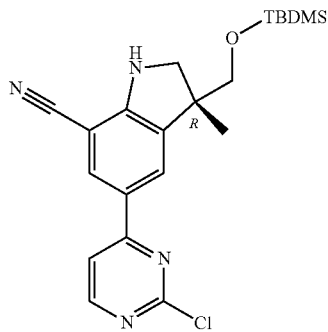

In a three neck round bottom flask, SiO$_2$ (35-70 µm) (200 g) was added to a solution of intermediate 6R (45.00 g, 87.36 mmol) in toluene (640 mL) at rt. The reaction mixture was refluxed (bath temperature 125° C.) for 6 h under mechanical agitation. Then, SiO$_2$ (35-70 µm) was filtered off, washed successively with THF and EtOAc, and the filtrate was evaporated to dryness to give 37.2 g of crude intermediate 7R which was directly engaged in the next steps.

Alternative Preparation of Intermediate 7R

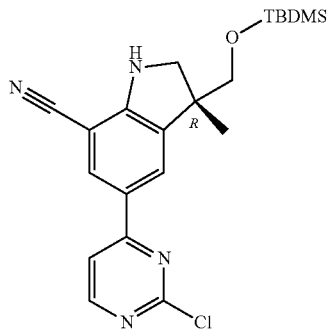

TFA (135 mL, 1.76 mol) was added dropwise at −10° C. (over 50 min) to a solution of intermediate 6R (20.00 g, 38.82 mmol) in DCM (550 mL). The reaction mixture was stirred below 0° C. for 15 min more, then poured in a mixture of crushed ice and a saturated aqueous solution of K$_2$CO$_3$. After extraction with DCM (twice), the organic layers were combined, washed with an aqueous solution of K$_2$CO$_3$, dried over MgSO$_4$ and evaporated to dryness. The residue (17.40 g) was purified by chromatography on silica gel (irregular SiOH, 80 g, mobile phase: NH$_4$OH/MeOH/DCM, gradient from 0% NH$_4$OH, 0% MeOH, 100% DCM to 0.2% NH$_4$OH, 2% MeOH, 98% DCM). The desired fractions were collected and the solvent was concentrated to dryness under vacuum to give 12.1 g of intermediate 7R (75% yield).

Example A3b

Preparation of Intermediate 10b

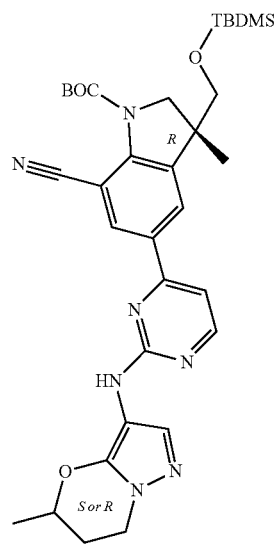

Intermediate 6R (224.83 mg, 0.44 mmol), intermediate 9b (117.00 mg, 0.764 mmol), Pd(OAc)$_2$ (9.80 mg, 43.65 µmol), BINAP (27.18 mg, 43.65 µmol) and Cs$_2$CO$_3$ (426.61 mg, 1.31 mmol) in 1,4-dioxane (7.19 mL) in a sealed tube were stirred at 120° C. using one single mode microwave (Biotage Initiator EXP 60®) with a power output ranging from 0 to 400 W for 30 min. The reaction mixture was poured into water and DCM. The mixture was filtered over Celite®, decanted and the organic layer was dried over MgSO$_4$, filtered and evaporated under vacuum. The residue was purified by silica gel chromatography (Irregular SiOH 40 µm 80 g, mobile phase gradient: from 100% DCM to 96% DCM, 4% MeOH, 0.5% NH$_4$OH). The pure fractions were combined and the solvent was evaporated to give 170 mg of intermediate 10b (62% yield).

Preparation of Intermediate 12b

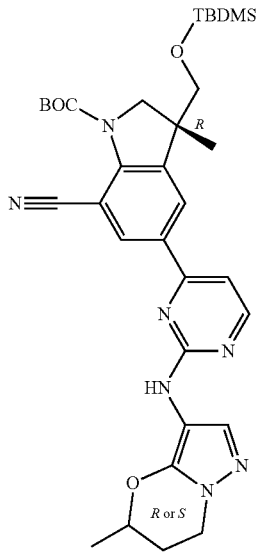

Intermediate 6R (224.83 mg, 0.446 mmol), intermediate 9a (117.00 mg, 0.76 mmol), Pd(OAc)$_2$ (9.80 mg, 43.65 μmol), BINAP (27.18 mg, 43.65 μmol) and Cs$_2$CO$_3$ (426.61 mg, 1.31 mmol) in 1,4-dioxane (7.19 mL) in a sealed tube were stirred at 120° C. using one single mode microwave (Biotage Initiator EXP 60®) with a power output ranging from 0 to 400 W for 30 min. The reaction mixture was poured into water and DCM. The mixture was filtered over Celite®, decanted and the organic layer was dried over MgSO$_4$, filtered and evaporated under vacuum. The residue was purified by silica gel chromatography (Irregular SiOH 40 μm 40 g, mobile phase gradient: from 100% DCM to 96% DCM, 4% MeOH, 0.5% NH$_4$OH). The pure fractions were combined and the solvent was evaporated to give 300 mg of intermediate 12b (quant. yield).

Preparation of Intermediate 16b

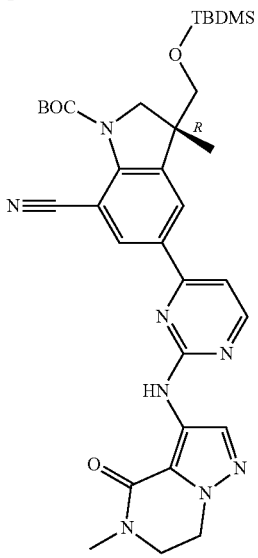

A mixture of intermediate 6R (600.00 mg, 1.17 mmol), intermediate 15b (0.25 g, 1.50 mmol), Cs$_2$CO$_3$ (0.90 g, 2.76 mmol), Pd(OAc)$_2$ (0.022 g, 0.10 mmol) and BINAP (0.059 g, 0.10 mmol) in 1,4-dioxane (14.00 mL) was stirred in a sealed tube at 120° C. using one single mode microwave (Anton Paar monowave 300®) with a power output ranging from 0 to 850 W for 30 min. The reaction was cooled down to room temperature. Water was added and the mixture was extracted twice with DCM. The organic layers were combined, dried over Na$_2$SO$_4$, filtered and the solvent was evaporated until dryness. The crude residue was purified by silica gel chromatography (Irregular SiOH 40 μm, 80 g, mobile phase gradient: from 69% Heptane, 29% EtOAc, 2% MeOH (+10% NH$_4$OH) to 40% Heptane, 52% EtOAc, 8% MeOH (+10% NH$_4$OH)). The pure fractions were collected and the solvent was evaporated to dryness to give 580 mg of intermediate 16b (77% yield).

The intermediates in the table below were prepared by using an analogous method as described for the preparation of intermediate 10b, starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 22b | ![structure] | 410 | 69 |

From intermediates 6b and 18b

-continued
| Intermediate number | Structure | Mass (mg) | Yield (%) |
|---|---|---|---|
| Intermediate 56b | 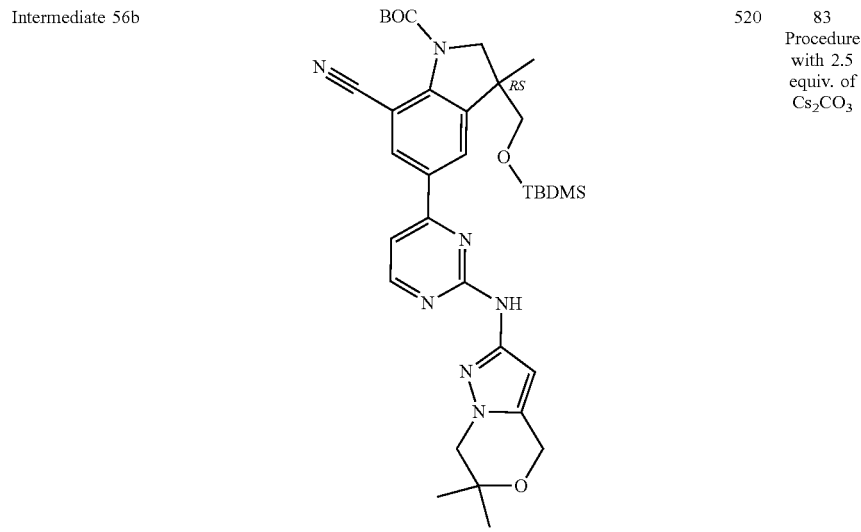 From intermediates 6b and 55b | 520 | 83 Procedure with 2.5 equiv. of $Cs_2CO_3$ |
| Intermediates 59b | 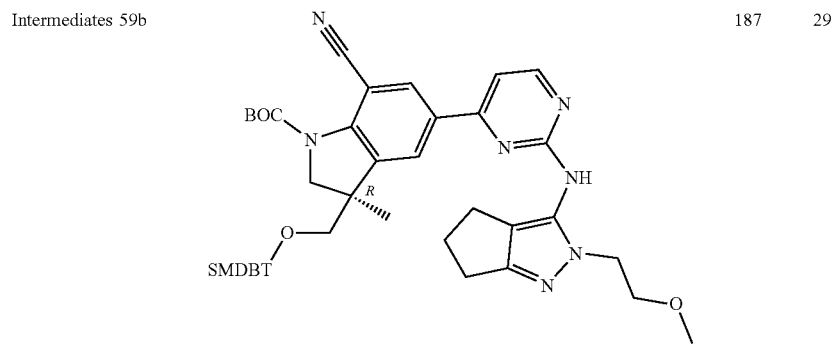 From intermediate 6R and a mixture of intermediates 58b and 58b' (86/14) | 187 | 29 |
| Intermediate 73b | 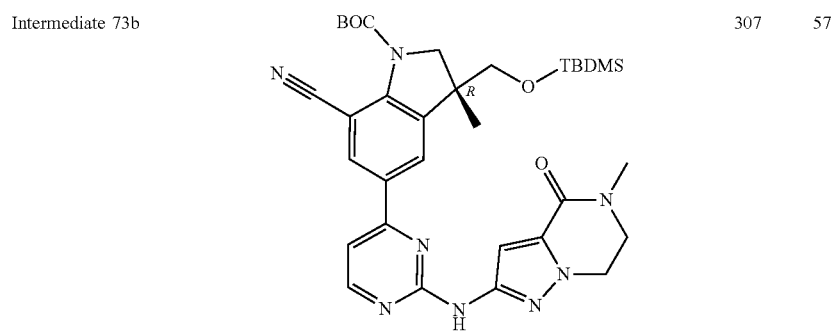 From intermediates 6R and 72b | 307 | 57 |

-continued

| Intermediate number | Structure | Mass (mg) | Yield (%) |
|---|---|---|---|
| Intermediate 78b | From intermediates 6R and 77b | 650 | 78 Procedure with dioxane/DMF: 11/1 |
| Intermediate 87b | From intermediates 6R and 86b | 430 | 85 |
| Intermediate 92b | From intermediates 6R and 91b | 627 | 93 Procedure with 2.5 equiv. of $Cs_2CO_3$ |

-continued

| Intermediate number | Structure | Mass (mg) | Yield (%) |
|---|---|---|---|
| Intermediate 99b | From intermediates 6R and 98b | 400 | 73 |
| Intermediate 104b | From intermediates 6R and 103b | 1000 | quant Procedure with 3 equiv. of Cs₂CO₃ |
| Intermediate 109b (methyl groups are cis in bicyclic pyrazole) | methyl groups CIS: mixture of (R,S) and (S,R)  From intermediates 6 and 108b | 530 | 94 Procedure with 3 equiv. of Cs₂CO₃ |

-continued

| Intermediate number | Structure | Mass (mg) | Yield (%) |
|---|---|---|---|
| Intermediate 113b (methyl groups are trans in bicyclic pyrazole) | 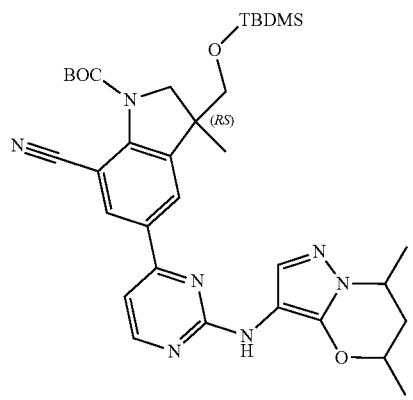 methyl groups TRANS: mixture of (S,S) and (R,R) From intermediates 6 and 112b | 194 | 85 Procedure with 3 equiv. of Cs$_2$CO$_3$ |
| Intermediate 127b | 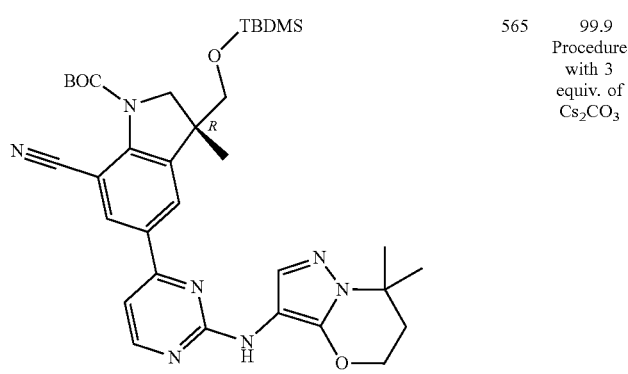 From intermediates 6R and 126b | 565 | 99.9 Procedure with 3 equiv. of Cs$_2$CO$_3$ |
| Intermediate 131b | 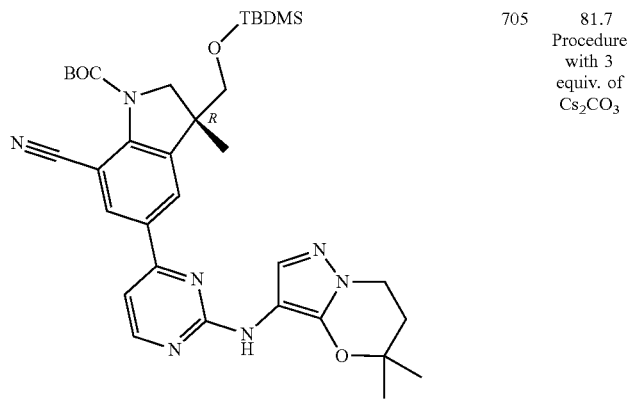 From intermediates 6R and 130b | 705 | 81.7 Procedure with 3 equiv. of Cs$_2$CO$_3$ |

-continued
| Intermediate number | Structure | Mass (mg) | Yield (%) |
|---|---|---|---|
| Intermediate 135b | 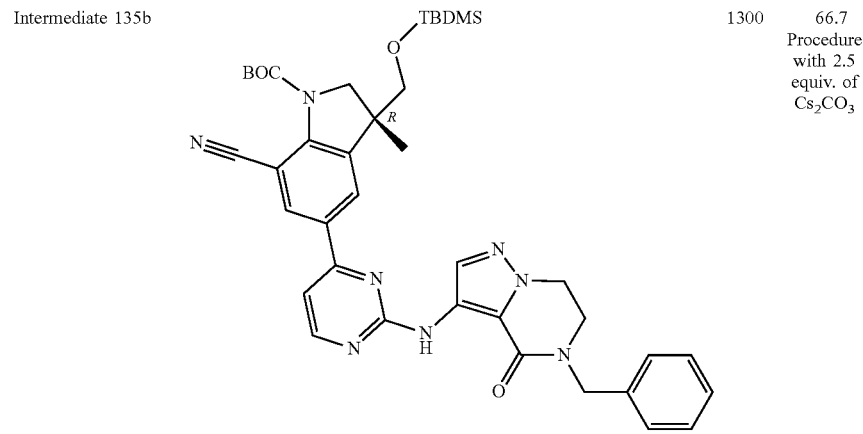<br>From intermediates 6R and 134b | 1300 | 66.7 Procedure with 2.5 equiv. of $Cs_2CO_3$ |
| Intermediate 139b | 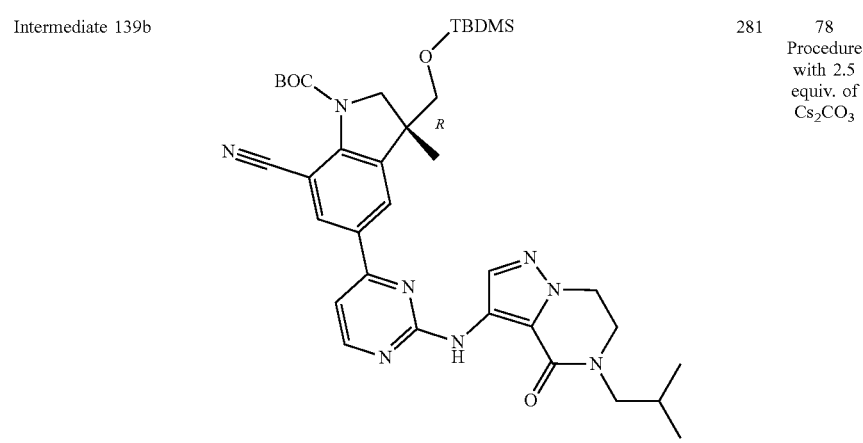<br>From intermediates 6R and 138b | 281 | 78 Procedure with 2.5 equiv. of $Cs_2CO_3$ |
| Intermediate 143b | 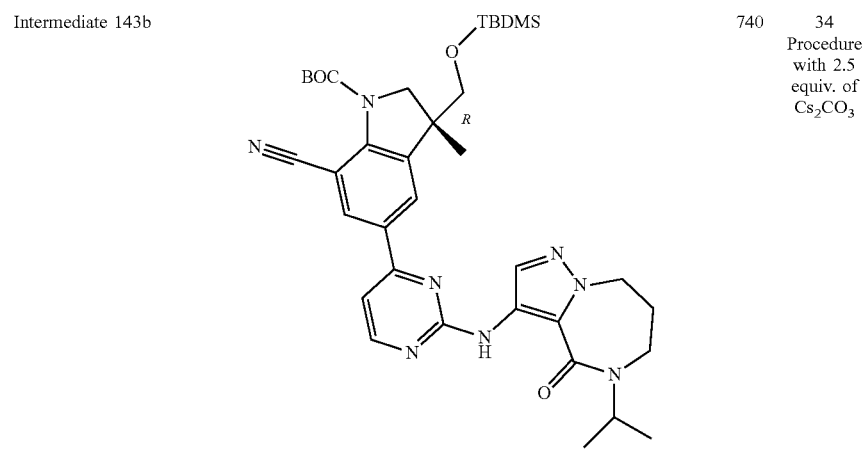<br>From intermediates 6R and 142b | 740 | 34 Procedure with 2.5 equiv. of $Cs_2CO_3$ |

| Intermediate number | Structure | Mass (mg) | Yield (%) |
|---|---|---|---|
| Intermediate 150b Isomer separation performed via chiral SFC (Stationary phase: Chiralpak AS-H 5 μm 250*20 mm, Mobile phase: 90% CO₂, 10% EtOH) | (structure) From intermediates 6R and 149b | 180 | 16 Procedure with 3 equiv. of Cs₂CO₃ |
| Intermediate 152b Isomer separation performed via chiral SFC (Stationary phase: Chiralpak AS-H 5 μm 250*20 mm, Mobile phase: 90% CO₂, 10% EtOH) | (structure) From intermediates 6R and 149b | 180 | 16 Procedure with 3 equiv. of Cs₂CO₃ |

Preparation of Intermediate 47b

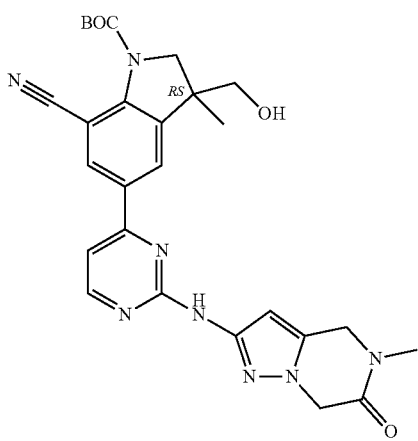

A mixture of intermediate 46b (180 mg, 0.45 mmol), intermediate 45b (82.08 mg, 0.494 mmol) and Cs₂CO₃ (365.75 mg, 1.123 mmol) in 1,4-dioxane (4 mL) was purged with nitrogen. A catalytic amount of Pd(OAc)₂ (8.065 mg, 35.922 μmol) and BINAP (22.37 mg, 35.922 μmol) were then added. The reaction mixture was purged with nitrogen and stirred at 95° C. for 2 hours. Water and DCM were added. The organic layer was separated, dried over MgSO₄, filtered and evaporated. The residue (210 mg) was purified by silica gel chromatography (Irregular SiOH 40 μm 40 g, mobile phase from 100% DCM to 95% DCM, 5% MeOH, 0.5% NH₄OH. The pure fractions were combined and the solvent was evaporated to give 87 mg of intermediate 47b (37%).

The intermediates in the table below were prepared by using an analogous method as described for the preparation of intermediate 47b, starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 32b | From intermediates 6 and 31b | 160 | 43 Procedure with 2.5 equiv. of Cs$_2$CO$_3$ and R-BINAP |
| Intermediate 39b | From intermediates 6 and 38b | 120 63% purity based on LC/MS | 63 Procedure with 1.5 equiv. of Cs$_2$CO$_3$ and R-BINAP |
| Intermediate 51b | From intermediates 6 and 50b | 140 | 23 Procedure with 2.5 equiv. of Cs$_2$CO$_3$ |

-continued

| Intermediate number | Structure | Mass (mg) | Yield (%) |
|---|---|---|---|
| Intermediate 67b | 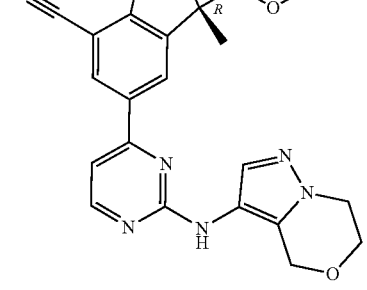<br>From intermediates 6R and 66b | 570 Yellow foam | Quant. Procedure with 2 equiv. of Cs$_2$CO$_3$ |
| Intermediate 82b | 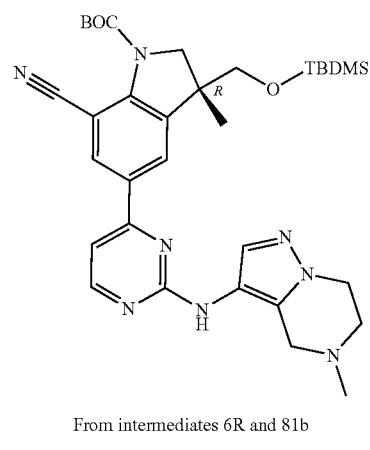<br>From intermediates 6R and 81b | 300 | 25 Procedure with 2.5 equiv. of Cs$_2$CO$_3$ at 120° C. |
| Intermediate 120<br>Isomer separation performed via achiral SFC (Stationary phase: CHIRALPAK IC 5 μm 250 × 30 mm, Mobile phase: 50% CO$_2$, 50% EtOH (0.3% $^i$PrNH$_2$)) | 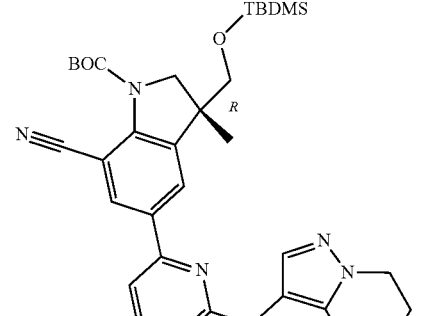<br>From intermediates 6R and 119b | 244 | 16 Procedure at 120° C.; sealed tube; 4 hrs; with 3 equiv. of Cs$_2$CO$_3$ |

-continued

| Intermediate number | Structure | Mass (mg) | Yield (%) |
|---|---|---|---|
| Intermediate 121b Isomer separation performed via achiral SFC (Stationary phase: CHIRALPAK IC 5 µm 250 × 30 mm, Mobile phase: 50% CO$_2$, 50% EtOH (0.3% $^i$PrNH$_2$)) | 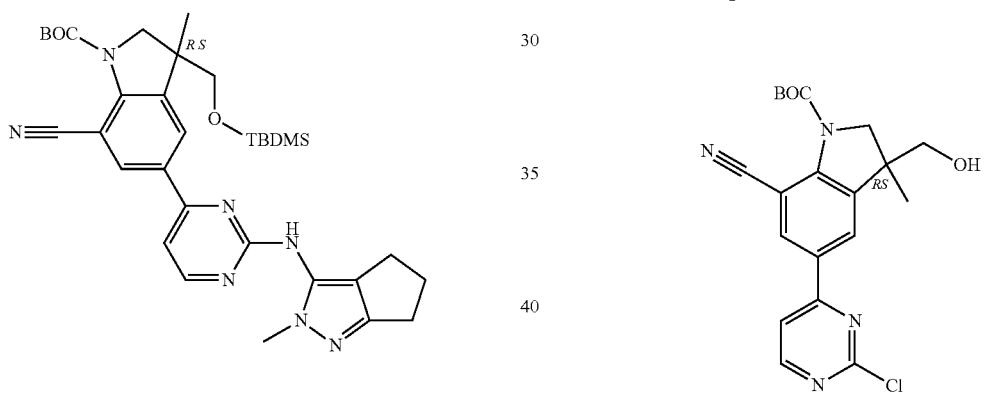<br>From intermediates 6R and 119b | 210 | 14 Procedure at 120° C.; sealed tube; 4 hrs; with 3 equiv. of Cs$_2$CO$_3$ |

Preparation of Intermediate 20b

Intermediate 6 (500.00 mg, 0.97 mmol), intermediate 19b (266.31 mg, 1.94 mmol), Brettphos Palladacycle (77.54 mg, 97.06 µmol), Brettphos (52.10 mg, 97.06 µmol) and Cs$_2$CO$_3$ (0.95 g, 2.91 mmol) in THF (15.80 mL) in a sealed tube were stirred at 140° C. for 7 hours. The reaction mixture was poured into water and DCM, filtered over Celite® and decanted. The organic layer was separated, dried over MgSO$_4$, filtered and evaporated. The residue was purified by silica gel chromatography (Irregular SiOH 40 µm, mobile phase: 97% DCM, 3% MeOH, 0.1% NH$_4$OH). The pure fractions were combined and the solvent was evaporated. The crude residue was purified by silica gel chromatography (Irregular SiOH 40 µm, mobile phase: 60% Heptane, 5% MeOH (+10% NH$_4$OH), 35% EtOAc) to give 145 mg of intermediate 20b (24% yield).

Example A4a

Preparation of Intermediate 8

A solution of intermediate 6 (500.00 mg, 0.97 mmol) in THF (5.71 mL) was treated with TBAF (1M in THF) (1.16 mL, 1.16 mmol) and stirred at rt for 12 h. The reaction mixture was poured in EtOAc. The organic layers were washed with water and brine, dried over MgSO$_4$ and evaporated in vacuo. The residue (483 mg) was purified by column chromatography on silica gel (Irregular SiOH, 40 µm, 40 g, mobile phase: DCM/MeOH/NH$_4$OH, gradient from 100% DCM to 98% DCM, 2% MeOH, 0.2% NH$_4$OH). The pure fractions were combined and the solvent was evaporated to give 358 mg of intermediate 8 (92% yield).

Example A4b

Preparation of Intermediate 11b

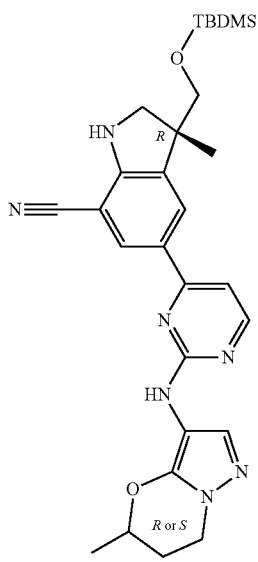

SiO$_2$ (35-70 µm) (1.00 g) was added to a solution of intermediate 10b (170.00 mg, 0.27 mmol) in toluene (8.58 mL) at rt. The reaction mixture was stirred at reflux for 4 hours. After cooling down to rt, SiO$_2$ was filtered off, washed with DCM/MeOH (80/20) and the filtrate was evaporated to give 140 mg of intermediate 11b (98% yield).

Preparation of Intermediate 13b

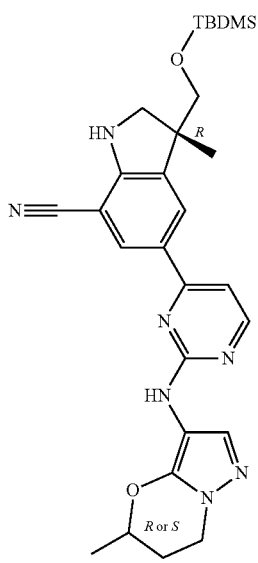

SiO$_2$ (35-70 µm) (1.40 g) was added to a solution of intermediate 12b (300.00 mg, 0.48 mmol) in toluene (8.58 mL) at rt. The reaction mixture was stirred at reflux for 4 hours. After cooling down to rt, SiO$_2$ was filtered off, washed with DCM/MeOH (80/20) and the filtrate was evaporated to give 252 mg of intermediate 13b (quantitative yield).

Preparation of Intermediate 17b

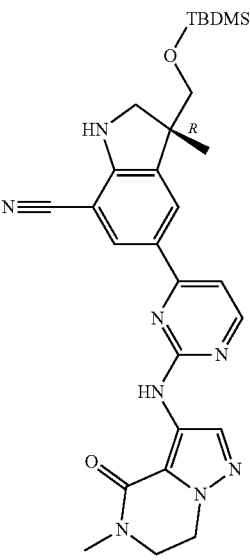

A mixture of intermediate 16b (0.58 g, 0.90 mmol) and SiO$_2$ (35-70 µm) (700.00 mg) in toluene (8 mL) was stirred at 120° C. for 4 hours. Another amount of SiO$_2$ (35-70 µm) (0.55 g) was added and the reaction mixture was stirred at 120° C. for 2 hours. The hot mixture was filtered, washed with a solution of EtOAc/MeOH (80/20) (twice) then with a solution of DCM/MeOH (80/20) (twice) and the solvent was evaporated until dryness. The crude residue was purified by silica gel chromatography (Irregular SiOH 15-40 µm, 40 g, mobile phase gradient: from 98% DCM, 2% MeOH (+10% NH$_4$OH) to 92% DCM, 8% MeOH (+10% NH$_4$OH)). The pure fractions were collected and the solvent was evaporated until dryness to give 311 mg of intermediate 17b (64% yield).

The intermediates in the table below were prepared by using an analogous method as described for the preparation of intermediate 11b, starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 74b | 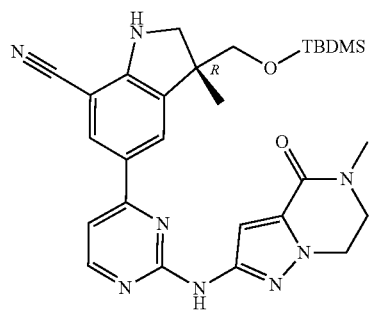<br>From intermediate 73b | 154 | 59 |
| Intermediate 79b | 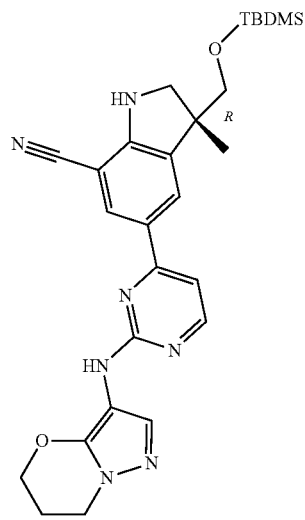<br>From intermediate 78b | 543 | Quant. |
| Intermediate 83b | 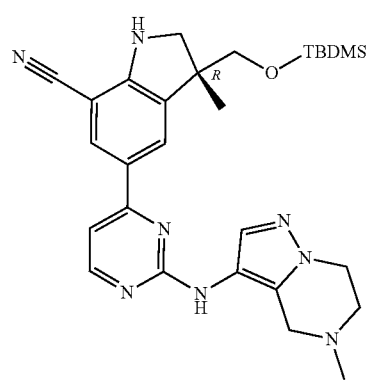<br>From intermediate 82b | 78 | 31 |

-continued
| Intermediate number | Structure | Mass (mg) | Yield (%) |
|---|---|---|---|
| Intermediate 88b | 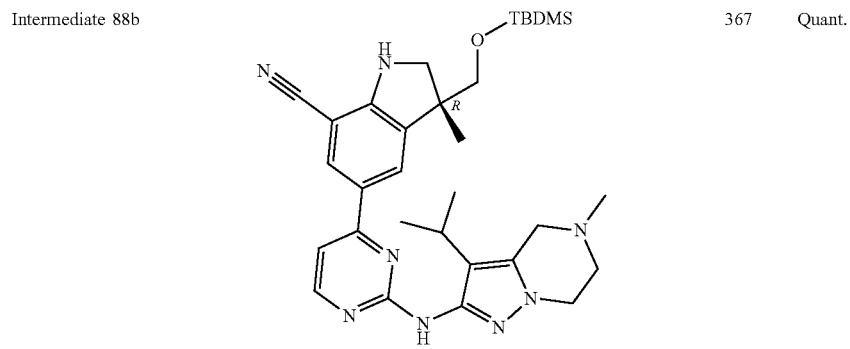 From intermediate 87b | 367 | Quant. |
| Intermediate 93b | 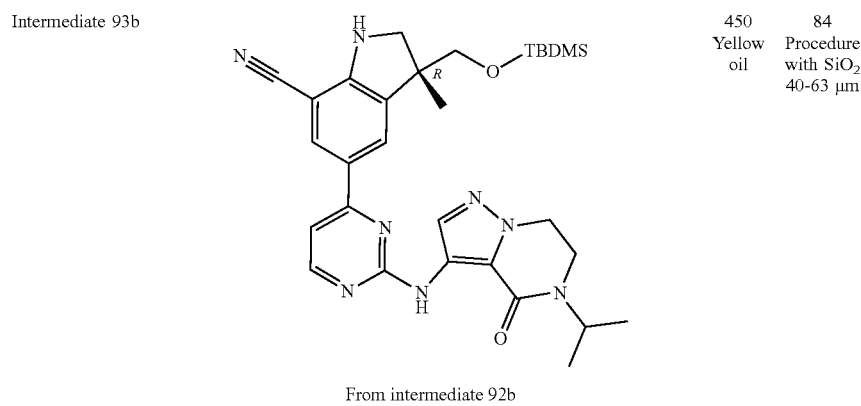 From intermediate 92b | 450 Yellow oil | 84 Procedure with SiO$_2$ 40-63 μm |
| Intermediate 100b | 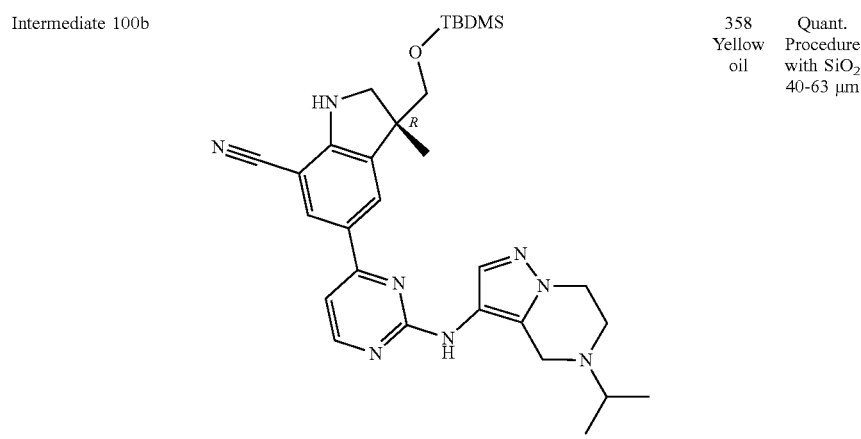 From intermediate 99b | 358 Yellow oil | Quant. Procedure with SiO$_2$ 40-63 μm |

-continued
| Intermediate number | Structure | Mass (mg) | Yield (%) |
|---|---|---|---|
| Intermediate 105b | 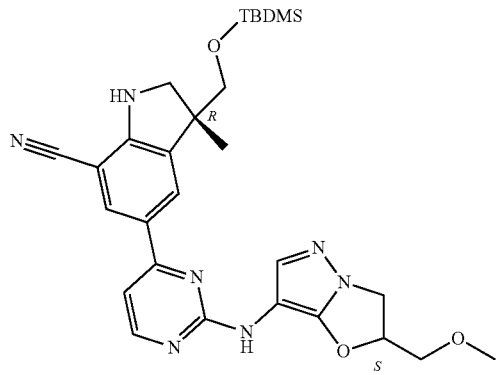<br>From intermediate 104b | 760 | 90 |
| Intermediate 110b (methyl groups cis in bicyclic pyrazole) | 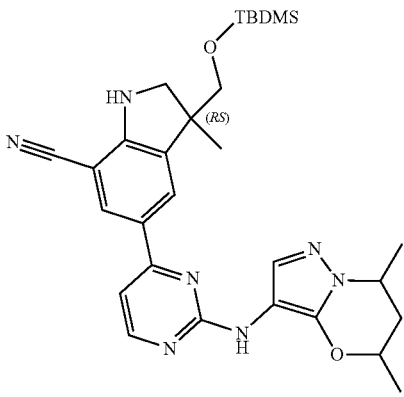<br>methyl groups CIS:<br>mixture of (R,S) and (S,R)<br>From intermediate 109b | 437 | 98 |
| Intermediate 114b (methyl groups trans in bicyclic pyrazole) | 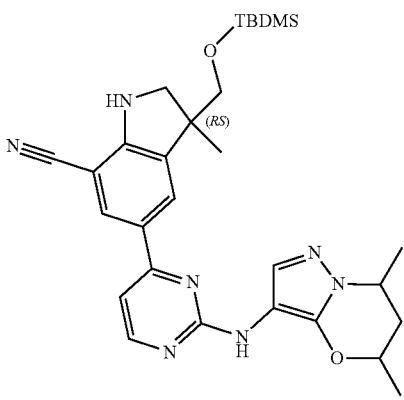<br>methyl groups TRANS:<br>mixture of (S,S) and (R,R)<br>From intermediate 113b | 194 | Quant |

-continued
| Intermediate number | Structure | Mass (mg) | Yield (%) |
|---|---|---|---|
| Intermediate 122b | 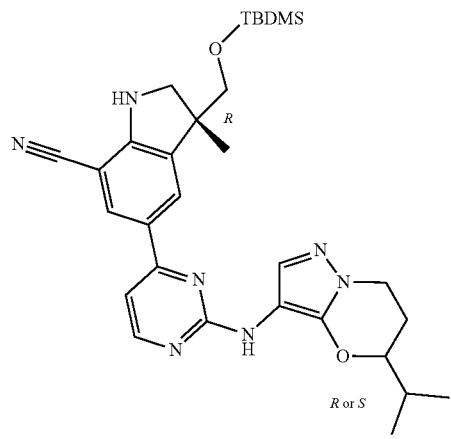<br>From intermediate 120b | 205 | Quant. |
| Intermediate 123b | 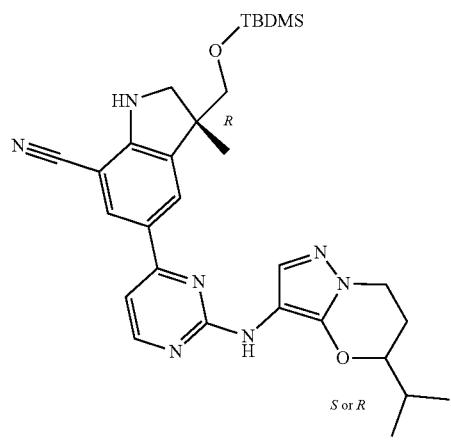<br>From intermediate 121b | 178 | Quant. |
| Intermediate 128b | 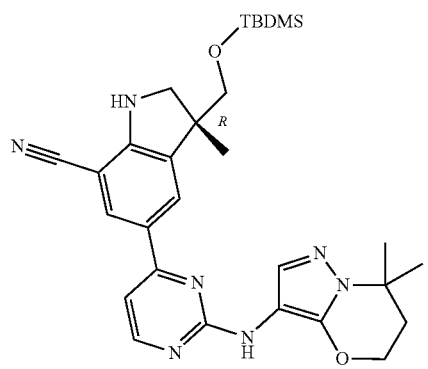<br>From intermediate 127b | 435 | 91 |

| Intermediate number | Structure | Mass (mg) | Yield (%) |
|---|---|---|---|
| Intermediate 132b | 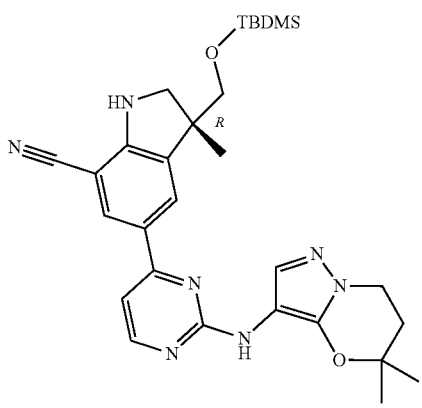 From intermediate 131b | 595 | 99.9 |
| Intermediate 136b | 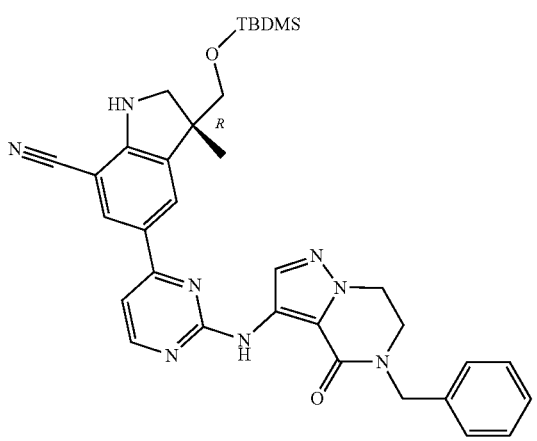 From intermediate 135b | 1470 | Quant (used directly in next step) |
| Intermediate 140b | 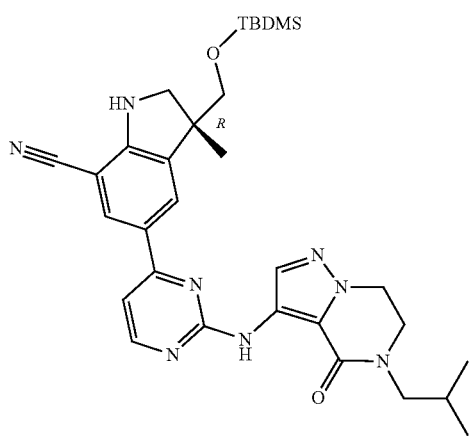 From intermediate 139b | 146 | Quant (used directly in next step) |

-continued
| Intermediate number | Structure | Mass (mg) | Yield (%) |
|---|---|---|---|
| Intermediate 144b | 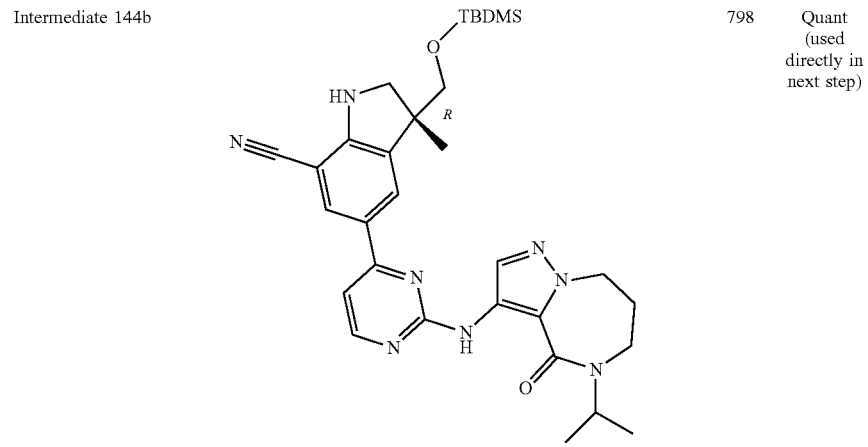<br>From intermediate 143b | 798 | Quant (used directly in next step) |
| Intermediate 151b | 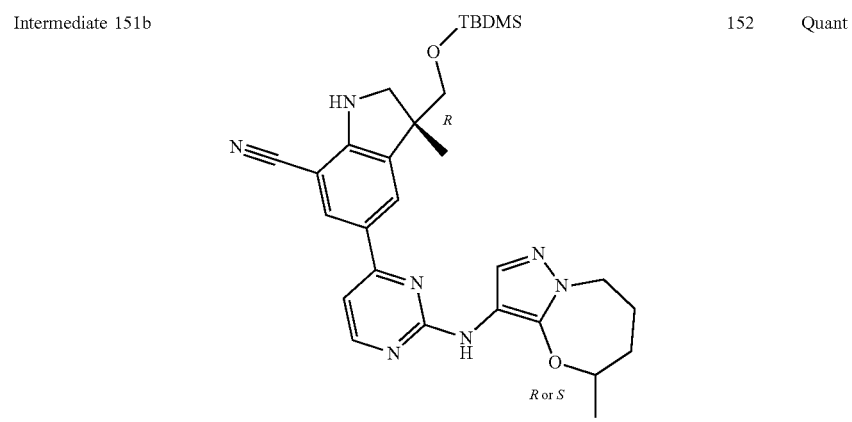<br>From intermediate 150b | 152 | Quant |
| Intermediate 153b | 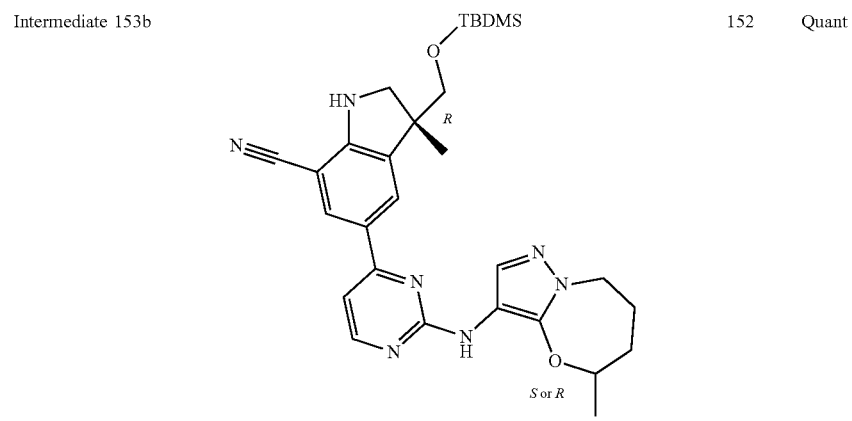<br>From intermediate 152b | 152 | Quant |

| Intermediate number | Structure | Mass (mg) | Yield (%) |
|---|---|---|---|
| Intermediate 154b | (structure shown) From intermediate 6R | 3450 | 83 18 hrs at 125° C. under mechanical agitation |

Preparation of Intermediate 21b

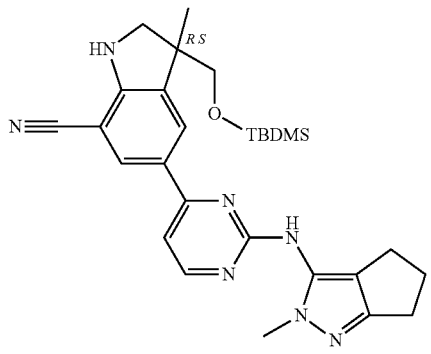

A solution of intermediate 20b (145.00 mg, 0.24 mmol) and TFA (0.36 mL) in DCM (1.49 mL) was stirred at 0° C. for 30 minutes. The reaction mixture was poured into a mixture of ice, water and NH$_4$OH. The mixture was extracted with EtOAc, dried over MgSO$_4$, filtered and evaporated to give 122 mg of intermediate 21b (quantitative yield) which was used in the next step without any further purification.

The intermediates in the table below were prepared by using an analogous method as described for the preparation of intermediate 21b, starting from the respective starting materials. Minor deviations to the referenced method are indicated as additional information in the column 'Yield (%)'.

| Intermediate number | Structure | Mass (μg) | Yield (%) |
|---|---|---|---|
| Intermediate 23b | (structure shown) From intermediate 22b | 344 | Quant. |

-continued
| Intermediate number | Structure | Mass (μg) | Yield (%) |
|---|---|---|---|
| Intermediate 52b | 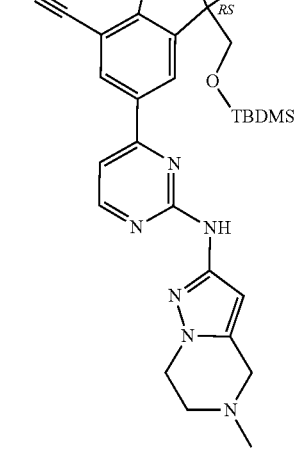<br>From intermediate 51b | 84 | 49<br>Procedure with TFA/DCM: 1/6, v/v |
| Intermediate 57b | 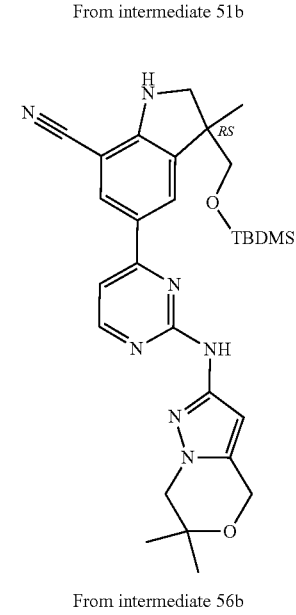<br>From intermediate 56b | 240 | 55<br>Procedure with TFA/DCM: 1/6, v/v |
| Intermediate 60b | 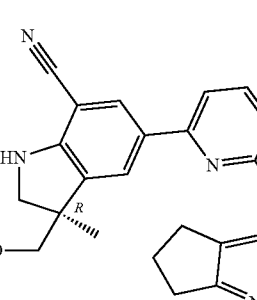<br>From intermediate 59b | 172 | 97<br>Procedure with TFA/DCM: 1/10, v/v |

| Intermediate number | Structure | Mass (μg) | Yield (%) |
|---|---|---|---|
| Intermediate 68b | 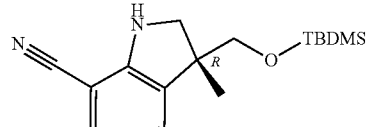<br>From intermediate 67b | 420 Yellow foam | 93 Procedure with TFA/DCM: 1/12, v/v |

Preparation of Intermediate 157b

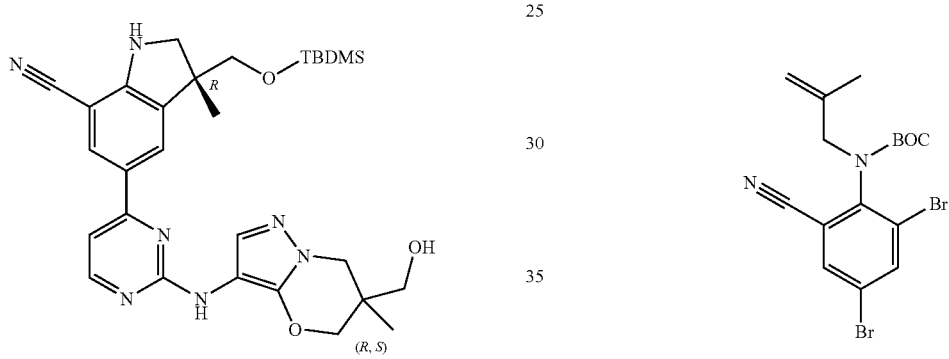

A mixture of intermediate 156b (0.300 g; 1.64 mmol), intermediate 154b (0.500 g; 1.21 mmol), Pd(OAc)₂ (0.024 g; 0.11 mmol), BINAP (0.066 g; 0.11 mmol) and Cs₂CO₃ (0.780 g; 2.39 mmol) in 1,4-dioxane (15.00 mL) was stirred in a sealed tube at 120° C. using one single mode microwave (Antoon Parr Monowave300) with a power output ranging from 0 to 850 W for 30 min. (fixed hold time). The reaction mixture was cooled to room temperature. Water was added and the mixture was extracted twice with DCM. The organic layer was decanted and the solvent was evaporated until dryness. The resultant crude material was purified by preparative LC (Irregular SiOH 15-40 μm 80 g GraceResolv®, mobile phase Gradient from: 99% DCM, 1% MeOH, 0.1% NH₄OH to 93% DCM, 7% MeOH, 0.7% NH₄OH). The pure fractions were collected and the solvent was evaporated until dryness to give 286 mg (42%) of intermediate 157b.

Example A5a

Preparation of Intermediate 9

A solution of intermediate 2 (10.00 g, 26.59 mmol) and 2-methyl-2-propen-1-ol (4.50 mL, 53.69 mmol) in Me-THF (200 mL) was cooled with EtOH/ice bath under N₂ to an internal temperature of −5° C. Tri-n-butylphosphine (13.30 mL, 53.19 mmol) was added. Then, a solution of 1,1'-(azodicarbonyl)piperidine (14.80 g, 58.62 mmol) in Me-THF (120 mL) was added dropwise over 25 min and the solution was stirred for 5 min more at this temperature. The cooling bath was removed and the solution was stirred at rt for 18 h. The reaction mixture was poured onto a 10% aqueous solution of K₂CO₃ and extracted with DCM. The organic layer was decanted, dried over MgSO₄, filtered and evaporated to dryness. The residue (20 g) was taken up with heptane and the insoluble material was removed by filtration. The filtrate was concentrated to 20 mL and purified by column chromatography on silica gel (irregular SiOH, 80 g, mobile phase:heptane/EtOAc, gradient from 100:0 to 88:12). The pure fractions were collected and evaporated to dryness to give 10.80 g of intermediate 9 (94% yield).

Preparation of Intermediate 10 and Intermediate 10'

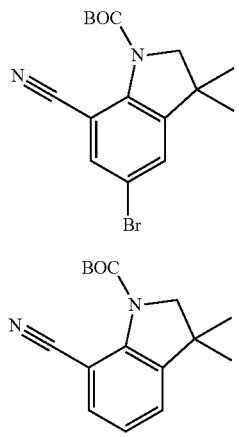

intermediate 10 intermediate 10'

A mixture of intermediate 9 (10.80 g, 25.11 mmol), sodium acetate (5.35 g, 65.28 mmol), sodium formate (4.44 g, 65.28 mmol) and tetraethylammonium chloride (5.20 g, 31.38 mmol) in DMF (100 mL) was degassed by sonication for 10 min under a stream of Ar. Pd(OAc)$_2$ (563.00 mg, 2.51 mmol) was added and the resulting orange suspension was stirred at 85° C. for 4 h. The residue was diluted with EtOAc and water, then filtered through a pad of Celite®. The organic layer was decanted, washed successively with a saturated aqueous solution of NaHCO$_3$ and brine, dried over MgSO$_4$, filtered and evaporated to dryness. The resulting residue (8.3 g) was dissolved in CH$_3$CN (230 mL) and NBS (4.47 g, 25.11 mmol) was added. The reaction mixture was heated at 55° C. for 18 h. The reaction mixture was evaporated to dryness and the residue was taken up with heptane/DCM. The precipitate was filtered off and the filtrate (10 g) was purified by silica gel chromatography (irregular SiOH, 120 g, injection in DCM, mobile phase:heptane/EtOAc, gradient from 100:0 to 80:20). The pure fractions were collected and evaporated to dryness to give 4 g of intermediate 10 (45% yield).

Preparation of intermediate 11

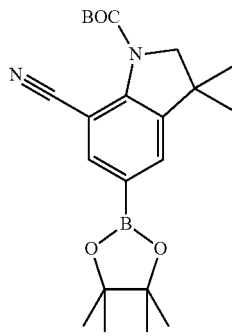 [SMILES: CC(C)(C)OC(=O)N1CC(C)(C)c2cc(B3OC(C)(C)C(C)(C)O3)cc(C#N)c21]

[1,1'-Bis(diphenylphosphino)ferrocene]dichloropalladium (II), complex with dichloromethane (243.00 mg, 0.30 mmol) was added to a solution of intermediate 10 (2.09 g, 5.95 mmol), bis(pinacolato)diboron (1.90 g, 7.44 mmol) and potassium acetate (1.75 g, 17.85 mmol) in 1,4-dioxane (45 mL) and the reaction mixture was heated for 18 h at 85° C. The reaction mixture was diluted with EtOAc and filtered through a pad of Celite®. The filtrate was washed with water, and the organic layer was decanted, dried over MgSO$_4$, filtered and evaporated to dryness. The residue was crystallized from DiPE and the precipitate was filtered and dried to give 1.85 g of intermediate 11 (78% yield).

Preparation of Intermediate 12

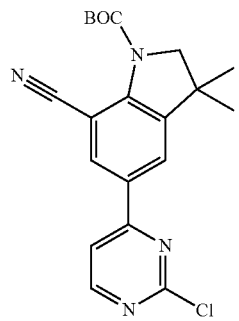 [SMILES: CC(C)(C)OC(=O)N1CC(C)(C)c2cc(-c3ccnc(Cl)n3)cc(C#N)c21]

A degassed suspension of intermediate 11 (1.12 g, 2.81 mmol), 2,4-dichloropyridine (502.00 mg, 3.37 mmol), Pd(PPh$_3$)$_4$ (162.00 mg, 0.14 mmol) and a 2M solution of Na$_2$CO$_3$ (4.20 mL, 8.14 mmol) in 1,4-dioxane (24 mL) was heated to 85° C. for 18 h. The reaction mixture was partitioned between DCM and saturated aqueous NaHCO$_3$. The organic layer was decanted, dried over MgSO$_4$, filtered and evaporated to dryness. The residue (2 g) was purified by column chromatography on silica gel (irregular SiOH, 40 g, mobile phase:heptane/EtOAc, gradient from 70:30 to 50:50). The pure fractions were collected and evaporated to dryness to give 933 mg of intermediate 12 (86% yield, 85% purity based on LC/MS).

Example A5b

Preparation of Intermediate 33b

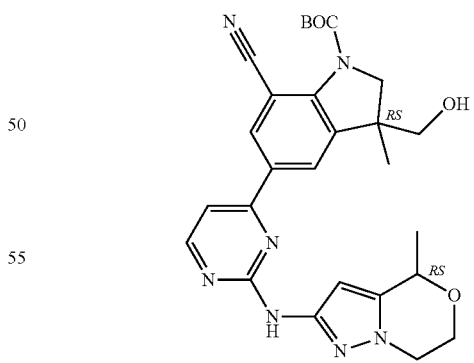

TBAF (1M in THF) (0.28 mL, 0.28 mmol) was added to a solution of intermediate 32b (180.00 mg, 0.14 mmol) in THF (1 mL). The mixture was stirred at rt for 17 h. The reaction mixture was poured into EtOAc (5 mL) and water (5 mL) was added. The layers were separated and the aqueous layer was extracted with EtOAc (2×20 mL). The organic layers were combined, dried over Na$_2$SO$_4$, filtered and evaporated under vacuo to give 100 mg of intermediate 33b (61% yield; mixture of 4 diastereoisomers) which was used in the next step without any further purification.

The intermediates in the table below were prepared by using an analogous method as described for the preparation of intermediate 33b starting from the respective starting materials. Minor deviations to the referenced method are indicated as additional information in the column 'Yield (%)'.

| Intermediate number | Structure | Mass (mg) | Yield (%) |
|---|---|---|---|
| Intermediate 40b | 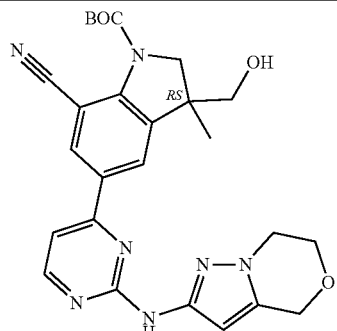<br>From intermediate 39b | 180 | 50<br>30% purity based on LC/MS<br>Procedure with 1.2 equiv. of TBAF |
| Intermediate 46b | 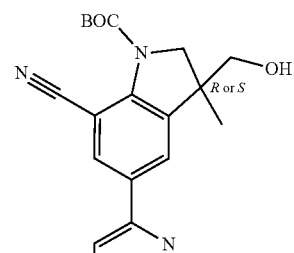<br>From intermediate 6 | 2100 | 90<br>Procedure with 1.2 equiv. of TBAF |

Example A6a

Preparation of Intermediate 13

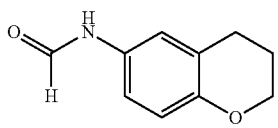 [SMILES: O=CNc1ccc2c(c1)CCCO2]

Phenyl formate (405.00 L, 3.71 mmol) was added dropwise to a stirred solution of 3.4-dihydro-2H-1-benzopyran-6-amine (369.00 mg, 2.47 mmol) in DCM (7.2 mL) at rt. After addition, the reaction mixture was stirred at room temperature for 18 h. The solution was purified by silica gel chromatography (Irregular SiOH 40 μm, mobile phase gradient: from 10000 DCM, 0% MeOH, 0.1% NH₄OH to 94% DCM, 6% MeOH, 0.1% NH₄OH). The pure fractions were combined and the solvent was evaporated under vacuum to give 445 mg of intermediate 13 (quant. yield).

Preparation of Intermediate 14

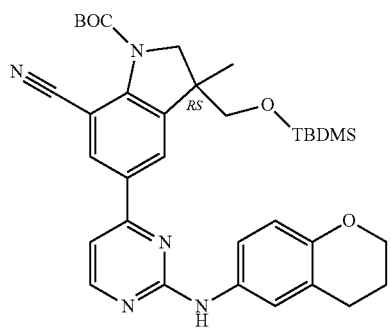

NaH (60% dispersion in mineral oil) (81.53 mg, 2.04 mmol) was added portionwise to a stirred solution of intermediate 13 (120.40 mg, 0.68 mmol) in DMF (6.6 mL) under N₂ atmosphere at rt. The mixture was stirred at rt for 20 min. This suspension was added to a solution of intermediate 6 (280.00 mg, 0.54 mmol) in DMF (3.30 mL). The mixture was stirred at rt for 1.5 h. The reaction mixture was poured onto ice and 10% NH₄Cl aqueous solution, stirred for 30 min and the precipitate was filtered off and dried under vacuum. The precipitate was purified by chromatography on silical gel (Irregular SiOH, 40 μm, mobile phase: 70% Heptane, 30% EtOAc). The pure fractions were combined and the solvent was evaporated to dryness under vacuum to give 129 mg of intermediate 14 (38% yield).

Example A6b

Preparation of Intermediate 7b

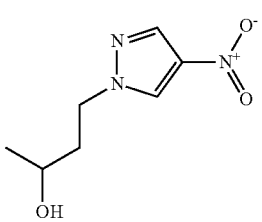

In a sealed tube, 4-nitro-1H-pyrazole (3.31 g, 29.25 mmol) and methyl vinyl ketone (4.10 g, 58.495 mmol) in EtOH (34.16 mL) were stirred at 140° C. for 12 h. NaBH₄ (2.21 g, 58.50 mmol) was added dropwise to the previous solution at rt. The reaction mixture was stirred for 1 hour and poured into ice and water. The solution was acidified with 3N aqueous solution of HCl and the aqueous layer was extracted twice with DCM. The combined organic layers were combined, dried over MgSO₄, filtered and evaporated. The crude residue was purified via silica gel chromatography (Stationary phase: irregular SiOH 15-40 μm, 120 g, mobile phase gradient: from 100% DCM to 95% DCM, 5% MeOH (2% NH₄OH)) to give 4.7 g of intermediate 7b (87% yield).

Preparation of Intermediate 8b

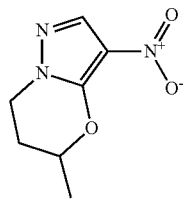

Lithium bis(trimethylsilyl)amide (1M in THF) (12.31 mL, 12.31 mmol) was added dropwise to a stirred solution of intermediate 7b (950.00 mg, 5.13 mmol) in THE (15.39 mL) at −70° C. under nitrogen. The reactive mixture was stirred at −70° C. for 2 hours and hexachloroethane (1.46 g, 6.16 mmol) in THE (3.08 mL) was added dropwise. The reactive mixture was allowed to stir at rt for 20 h. Water and NH$_4$Cl were added and the solution was extracted with DCM. The organic layer was dried over MgSO$_4$, filtered and evaporated. The crude residue was purified via silica gel chromatography (Stationary phase: irregular SiOH 15-40 μm, 24 g, mobile phase: 100% DCM) to give 363 mg of intermediate 8b (39% yield).

The intermediates in the table below were prepared by using an analogous method as described for the preparation of intermediate 8b, starting from the respective starting materials.

| Intermediate number | Structure | Mass (mg) | Yield (%) |
|---|---|---|---|
| Intermediate 76b | 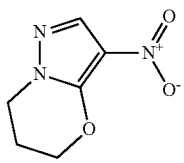 From intermediate 75b | 737 | 50 |
| Intermediate 102b | 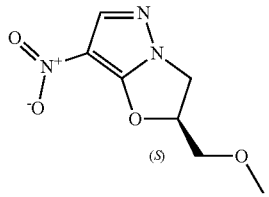 From intermediate 101b | 540 | 32 |
| Intermediate 107b (cis) isolation via achiral SFC (Stationary phase: DIETHYLAMINO-PROPYL 5 μm 150 × 21.2 mm, Mobile phase: 97.5% CO$_2$, 2.5% MeOH) | 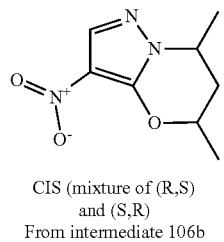 CIS (mixture of (R,S) and (S,R)) From intermediate 106b | 610 | 37 |
| Intermediate 111b (trans) isolation via achiral SFC (Stationary phase: DIETHYLAMINO-PROPYL 5 μm 150 × 21.2 mm, Mobile phase: 97.5% CO$_2$, 2.5% MeOH) | TRANS (mixture of (R,R) and (S,S)) From intermediate 106b | 120 | 7 |
| Intermediate 118b | (RS) From intermediate 117b | 1000 | 72 |
| Intermediate 125b Isolation via preparative LC (Stationary phase: irregular SiOH 15-40 μm 40 g Grace, Mobile phase: gradient from 80% heptane, 20% AcOEt to 50% heptane, 50% AcOEt) | From intermediate 124b + 124b' | 294 | 50 |
| Intermediate 129b Isolation via preparative LC (Stationary phase: irregular SiOH 15-40 μm 40 g Grace, Mobile phase: gradient from 80% heptane, 20% AcOEt to 50% heptane, 50% AcOEt) | From intermediate 124b + 124b' | 115 | 19 |
| Intermediate 148b | (RS) From intermediate 147b | 590 | 60 |

Example A6c

Preparation of Intermediate 15c

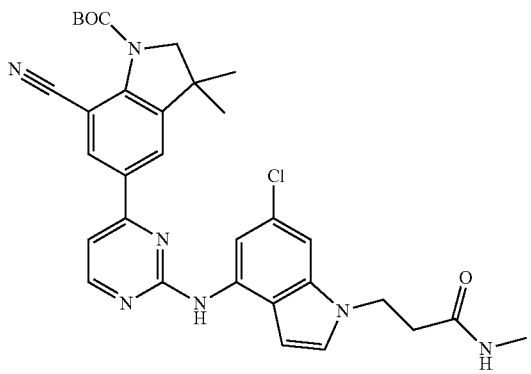 [SMILES: CNC(=O)CCn1ccc2c(Nc3nccc(-c4cc(C#N)c5c(c4)C(C)(C)CN5C(=O)OC(C)(C)C)n3)cc(Cl)cc21]

A degassed suspension of intermediate 12 (100.00 mg, 0.26 mmol), intermediate 14 (81.81 mg, 0.29 mmol based on 88% purity determined by LC/MS), Pd(OAc)$_2$ (5.84 mg, 0.026 mmol), BINAP (16.19 mg, 0.026 mmol) and Cs$_2$CO$_3$ (254.14 mg, 0.70 mmol) in 1,4-dioxane (3 mL) was heated to 85° C. for 30 min. The reaction mixture was partitioned between DCM and water. The organic layer was decanted, dried over MgSO$_4$, filtered and evaporated to dryness to give 156 mg of intermediate 15c (quantitative yield, brown oil) which was directly engaged in the next step without any further purification.

Preparation of Intermediate 21c

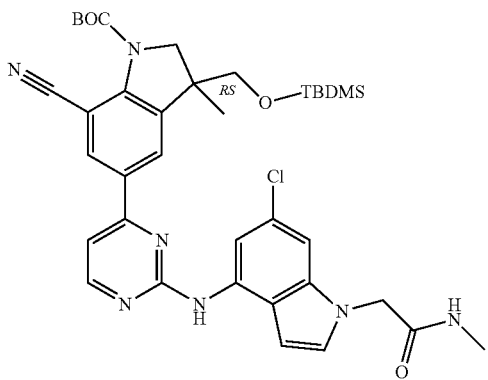

To a solution of intermediate 6 (0.66 g, 1.28 mmol), intermediate 20c (0.34 g, 1.41 mmol), Pd(OAc)$_2$ (0.029 g, 0.128 mmol) and Cs$_2$CO$_3$ (1.25 g, 3.84 mmol) in 1,4-dioxane (24 mL) was added BINAP (79.80 mg, 0.128 mmol) and the reaction mixture was heated for 3 h at 95° C. The reaction mixture was then diluted with ethyl acetate and washed with water and brine. The organic layer was dried with sodium sulfate and concentrated under vacuo. The residue was purified by chromatography over silica gel (15-40 µm, 40 g, eluent: DCM/MeOH: 100/0 to 99/1). The pure fractions were combined and the solvent was evaporated to give 817 mg of intermediate 21c (89% yield).

Preparation of Intermediate 35c

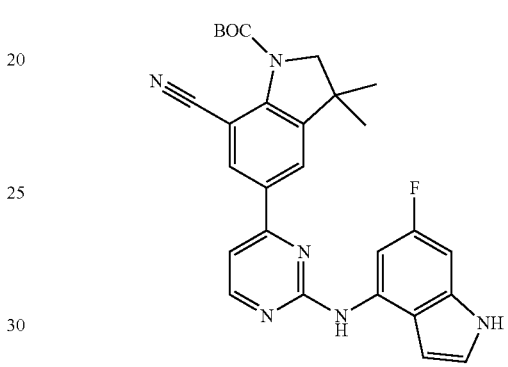

To a solution of intermediate 12 (233.00 mg, 0.61 mmol), intermediate 34c (100.00 mg, 0.67 mmol), Pd(OAc)$_2$ (137.00 mg, 0.061 mmol) and Cs$_2$CO$_3$ (592.00 mg, 1.82 mmol) in 1,4-dioxane (5 mL) was added BINAP (38.00 mg, 0.061 mmol) and the reaction mixture was heated for 3 h at 95° C. The reaction mixture was then diluted with ethyl acetate and washed with water and brine. The organic layer was dried with sodium sulfate and concentrated in vacuo to give 397 mg of intermediate 35c (quant. yield, 7600 purity based on LC/MS, dark black foam) which was used in the next step without any further purification.

The intermediates in the table below were prepared by using an analogous method starting from the respective starting materials. Minor deviations to the referenced method are indicated as additional information in the column 'Yield (%)'.

| Intermediate number | Structure | Mass (mg) | Yield (%) |
|---|---|---|---|
| Intermediate 18c | From intermediate 12 and 17c | 153 (79% purity based on LC/MS) brown oil | Quant. with T = 85° C. for 30 mn |
| Intermediate 25c | From intermediate 7 and intermediate 24c | 70 (90%) purity based on LC/MS yellow solid | 34 |
| Intermediate 28c | From intermediate 7 and intermediate 27c | 465 (85% purity based on LC/MS) yellow solid | 96 Heat time: 1h00 |

-continued
| Intermediate number | Structure | Mass (mg) | Yield (%) |
|---|---|---|---|
| Intermediate 31c | 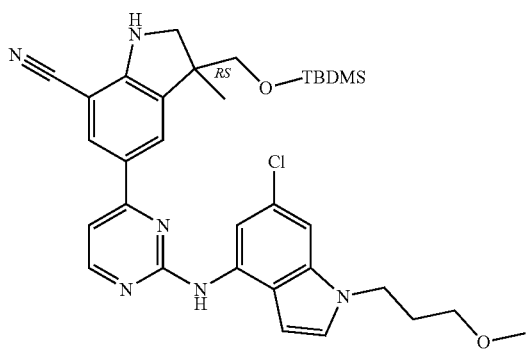   From intermediate 7 and intermediate 30c | 470 brown residue | 51 Heat time: 1h00 |
| Intermediate 33c | 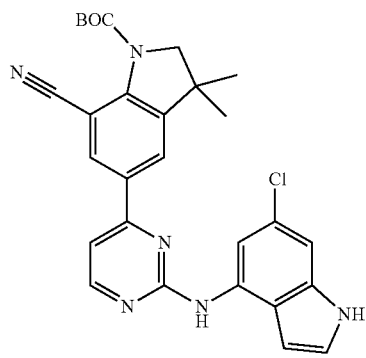   From intermediate 12 and 32c | 384 (73%) purity based on LC/MS) dark black foam | Quant. |
| Intermediate 40c | 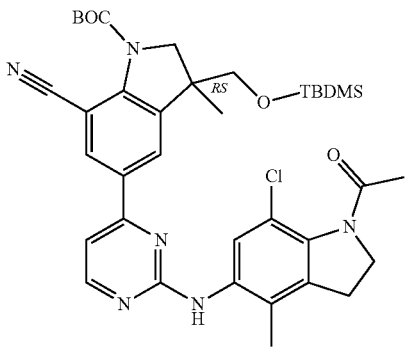   From intermediate 6 and 39c | 1250 (76% purity) brown foam | Quantitative |

-continued

| Intermediate number | Structure | Mass (mg) | Yield (%) |
|---|---|---|---|
| Intermediate 45c | 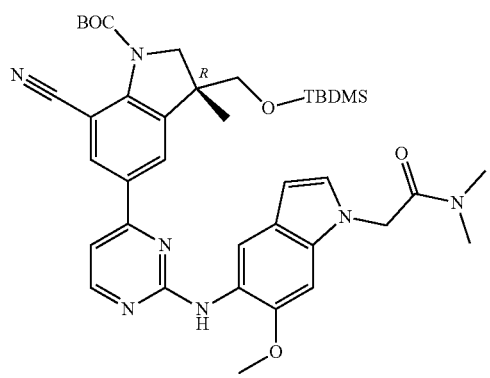<br>From intermediate 6R and intermediate 44c | 690 (95% purity based on ¹H NMR) white solid | 80 Procedure with T = 100° C. and 2.0 equiv. of Cs₂CO₃ |
| Intermediate 47c | 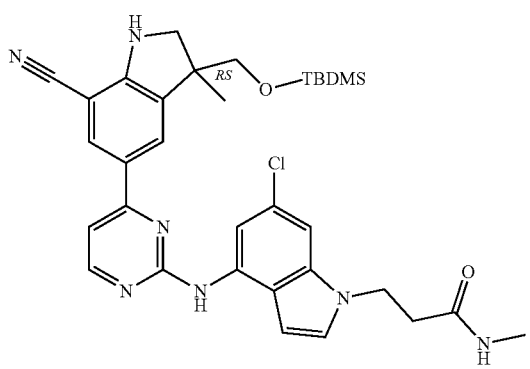<br>From intermediate 7 and 14c | 510 (55% purity based on ¹H NMR) | 44 |
| Intermediate 50c | 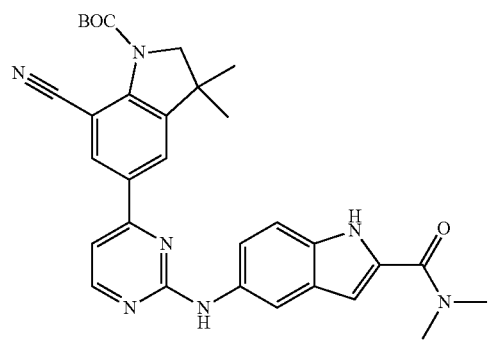<br>From intermediate 12 and 49c | 200 | 3 Based on a purity of 21% evaluated by LC/MS Procedure with 2.5 equiv. of of Cs₂CO₃ |

| Intermediate number | Structure | Mass (mg) | Yield (%) |
|---|---|---|---|
| Intermediate 53c | From intermediate 6 and 52c | 440 | 69 Procedure with 2.5 equiv. of $Cs_2CO_3$ |
| Intermediate 57c | From intermediate 6R and 56c | 250 | 77 Procedure with 2 equiv. of $Cs_2CO_3$ and T = 100° C. |

Example A7a

Preparation of Intermediate 16

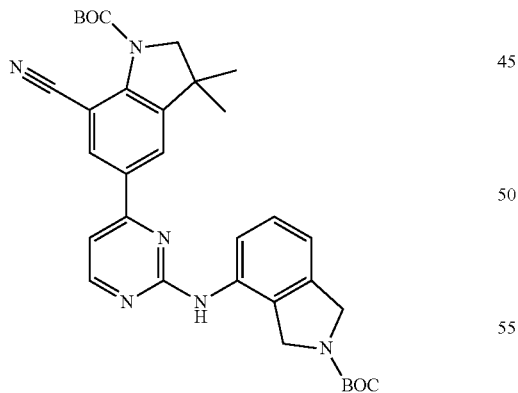

In a sealed tube, BINAP (40.45 mg, 0.07 mmol) was added to a solution of intermediate 12 (250.00 mg, 0.65 mmol), tert-butyl 4-aminoisoindoline-2-carboxylate (228.29 mg, 0.97 mmol), Pd(OAc)$_2$ (14.58 mg, 0.065 mmol) and Cs$_2$CO$_3$ (635.94 mg, 1.95 mmol) in 1,4-dioxane (12.5 mL) and the reaction mixture was heated at 110° C. using one single mode microwave (Biotage® Initiator EXP 60) with a power output ranging from 0 to 400 W for 20 min. The reaction mixture was cooled to rt, diluted with DCM and poured onto water. The organic layer was decanted, dried over MgSO$_4$, filtered and evaporated to dryness. The residue was purified by chromatography over silica gel (Irregular SiOH, 40 g, mobile phase gradient: from 0% NH$_4$OH, 0% MeOH, 100% DCM to 0.5% NH$_4$OH, 5% MeOH, 95% DCM). The pure fractions were collected and evaporated to dryness to give 378 mg of intermediate 16 (quant. yield).

Preparation of Intermediate 148

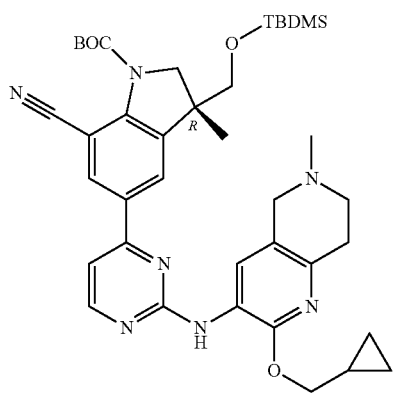

In a sealed tube, intermediate 6R (291.04 mg, 0.57 mmol), intermediate 147 (145.00 mg, 0.62 mmol), Pd(OAc)₂ (12.68 mg, 56.50 µmol), BINAP (35.18 mg, 56.50 µmol) and Cs₂CO₃ (0.46 g, 1.41 mmol) in 1,4-dioxane (9.31 mL) were stirred at 120° C. using one single mode microwave (Biotage® Initiator EXP 60) with a power output ranging from 0 to 400 W for 30 min. The mixture in a sealed tube was then stirred at 125° C. using one single mode microwave (Biotage® Initiator EXP 60) with a power output ranging from 0 to 400 W for 45 min. The reaction mixture was poured onto water and DCM. The mixture was filtered over celite, decanted and the organic layer was dried over MgSO₄, filtered and evaporated under vacuum. The residue was purified by chromatography on silical gel (Irregular SiOH 40 µm, 40 g, mobile phase gradient: from 100% DCM to 95% DCM, 5% MeOH, 0.5% NH₄OH). The pure fractions were combined and the solvent was evaporated to give 85 mg of intermediate 148 (21% yield).

Preparation of Intermediate 194

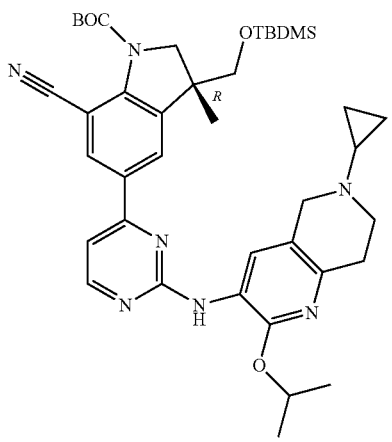

Intermediate 6R (132.5 mg, 0.257 mmol), intermediate 193 (70 mg, 0.283 mmol), Pd(OAc)₂ (5.78 mg, 25.73 µmol), BINAP (16 mg, 25.73 µmol) and Cs₂CO₃ (209 mg, 0.64 mmol) in 1,4-dioxane (4.24 mL, 49.72 mmol) in a sealed tube were stirred at 120° C. using one single mode microwave (Anton Paar) with a power output ranging from 0 to 900 W for 30 min. The reaction mixture was poured onto water and DCM. The mixture was filtered over a pad of Celite®, decanted and the organic layer was dried over MgSO₄, filtered and evaporated. The residue (203 mg) was purified by silica gel chromatography (Irregular SiOH 40 µm 24 g; Mobile phase from 100% DCM to 95% DCM, 5% MeOH, 0.5% NH₄OH. The fractions containing the product were combined and the solvent was evaporated to give 130 mg (70%) of intermediate 194.

Preparation of Intermediate 198

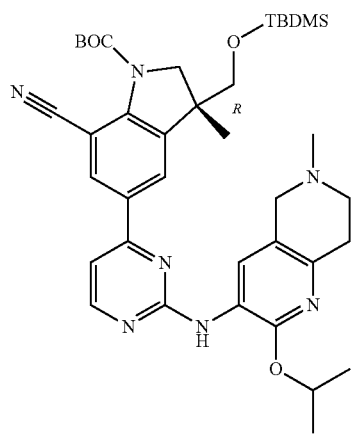

Intermediate 198 was prepared using a similar protocole that the one used for the preparation of intermediate 148 starting from intermediate 6R and intermediate 197 (900 mg; 83%).

Preparation of Intermediate 202

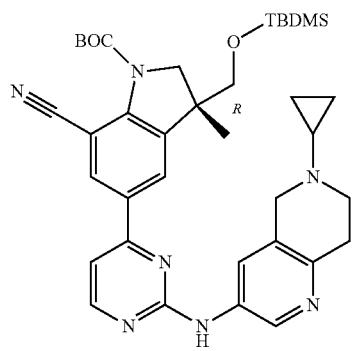

Intermediate 202 was prepared using a similar protocole that the one used for the preparation of intermediate 194 starting from intermediate 6R and intermediate 201 (130 mg; 43%).

Preparation of Intermediate 206

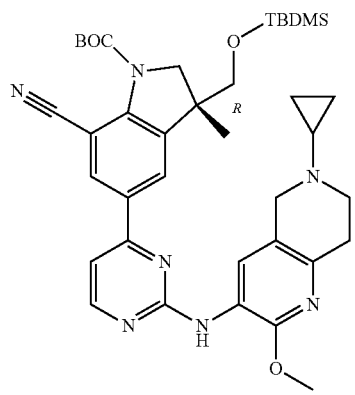

Intermediate 206 was prepared using a similar protocole that the one used for the preparation of intermediate 194 starting from intermediate 6R and intermediate 205 (93 mg; 49%).

Example A7b

Preparation of Intermediate 14b

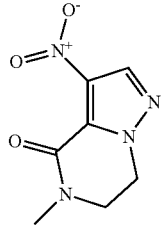

2-(methylamino)ethanol (2.00 g, 26.63 mmol) and 4-nitro-1H-pyrazole-3-carboxylic acid (3.54 g, 22.52 mmol) in toluene (24.44 mL) were stirred at 15° C. $SOCl_2$ (4.52 mL, 62.28 mmol) was slowly added followed by DMF (171.44 µL, 2.21 mmol). The reaction mixture was stirred at 55° C. for 10 minutes then 70° C. for 18 h. Solvents were evaporated. The residue was taken up into DMF (20.62 mL) and TEA (16.66 mL) was added slowly. The reaction mixture was stirred at rt for 12 h. Water was added and the mixture was extracted twice with EtOAc, dried over $MgSO_4$, filtered and evaporated. The crude residue was purified via silica gel chromatography (Stationary phase: irregular SiOH 15-40 µm, 80 g, mobile phase gradient: from 100% DCM to 97% DCM, 3% MeOH (+10% $NH_4OH$)) to give 1.96 g of intermediate 14b (38% yield).

The intermediates in the table below were prepared by using an analogous method as described for the preparation of intermediate 14b, starting from the respective starting materials.

| Intermediate number | Structure | Mass (mg) | Yield (%) |
|---|---|---|---|
| Intermediate 48b | <br>From 2-(methylamino)ethanol and 3-nitro-1H-pyrazole-5-carboxylic acid | 743 | 50 |

Preparation of Intermediate 37b

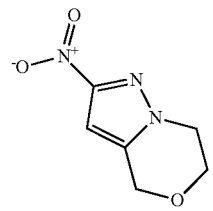

$K_2CO_3$ (579.60 mg, 4.20 mmol) was added into a mixture of intermediate 36b (500.00 mg, 1.60 mmol) in $CH_3CN$ (3 mL) and the resulting solution was stirred at 80° C. for 8 h. The mixture was filtered and evaporated under vacuo to give 400 mg of intermediate 37b (66% yield, 45% purity based on LC/MS) which was used in the next step without further purification.

Preparation of Intermediate 44b

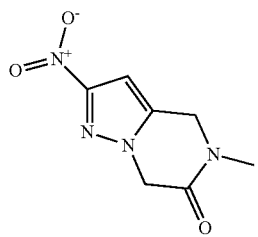

Intermediate 43b (3.60 g, 7.58 mmol) and methylamine (2M in THF) (37.9 mL, 75.8 mmol) in a sealed tube were stirred at 75° C. for 12 h. The reaction mixture was evaporated. The residue was taken up into water, extracted with DCM and evaporated. The residue was purified by silica gel chromatography (Irregular SiOH 40 µm, mobile phase gradient: from 0% $NH_4OH$, 100% DCM, 0% MeOH to 0.1% $NH_4OH$, 97% DCM, 3% MeOH). The pure fractions were combined and the solvent was evaporated. The crude residue was taken up into $Et_2O$. The solid was filtered and dried under vacuo to give 420 mg of intermediate 44b (28% yield).

Preparation of Intermediate 54b

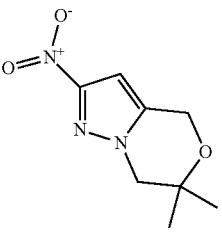

Intermediate 53b (2.15 g, 9.99 mmol) in $H_2SO_4$ (14.00 mL, 262.64 mmol) was stirred at 45° C. for 16 hours. The reaction mixture was cooled down to room temperature and was poured onto a mixture of ice/water and basified with $K_2CO_3$ powder. This mixture was extracted with DCM. The organic layer was decanted, dried over MgSO$_4$, filtered and the solvent was evaporated until dryness to give 1.12 g of intermediate 54b (57% yield).

Preparation of Intermediate 97b

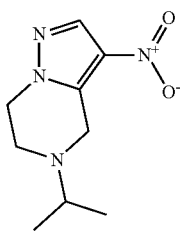

Intermediate 96b (1.30 g, 3.96 mmol), 2-aminopropane (2.02 mL, 23.77 mmol) and TEA (1.10 mL, 7.92 mmol) in DCM (20.3 mL) were stirred at 60° C. for 6 hours. Solvent was evaporated and the crude residue was purified by silica gel chromatography (solid deposit) (Irregular SiOH 40 μm 40 g, mobile phase gradient: from 80% Heptane, 20% EtOAc to 50% Heptane, 50% EtOAc). The pure fractions were combined and the solvent was evaporated under vacuo to give 640 mg of intermediate 97b (77% yield).

Example A7c

Preparation of Intermediate 41c

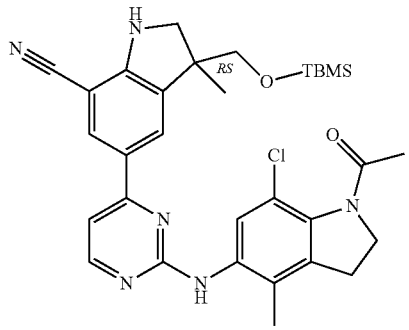

A solution of intermediate 40c (1.25 g, 1.35 mmol based on 76%) in a mixture of TFA (1 mL) and DCM (7 mL) was stirred at rt for 1 h. The mixture was basified with saturated aqueous NaHCO$_3$ solution. An extraction was performed with DCM. The organic layer was washed with brine, dried over MgSO$_4$, evaporated and purified by column chromatography on silica gel (irregular SiOH 15-40 μm, 120 g, liquid injection with DCM, mobile phase:heptane/EtOAc, gradient from 100:0 to 0:100 in 15 CV). The product containing fractions were combined and concentrated under vacuum to give 521 mg of intermediate 41c (64% yield, off-white solid).

The intermediate in the table below was prepared by using an analogous method starting from the respective starting materials. Minor deviations to the referenced method are indicated as additional information in the column 'Yield (%)'.

| Intermediate number | Structure | Mass (mg) | Yield (%) |
|---|---|---|---|
| Intermediate 46c | ![structure] From intermediate 45c | 390 yellow foam | 66 Procedure with DCM/TFA (11:1, v/v) |

| Intermediate number | Structure | Mass (mg) | Yield (%) |
|---|---|---|---|
| Intermediate 54c | From intermediate 53c | 321 | Quant. Procedure with DCM/TFA (3:1, v/v) |
| Intermediate 58c | From intermediate 57c | 96 | 50 Procedure with DCM/TFA (11:1, v/v) and reaction time: 30 mn |

Example A8a

Preparation of Intermediate 21

In a sealed tube, a mixture of intermediate 6 (500.00 mg, 0.97 mmol), intermediate 20 (188.19 mg, 1.07 mmol) and Cs$_2$CO$_3$ (948.75 mg, 2.91 mmol) in dry 1,4-dioxane (10 mL) was purged with N$_2$. Then Pd(OAc)$_2$ (21.79 mg, 97.10 μmol) and BINAP (60.44 mg, 97.10 μmol) were added. The mixture was purged with N$_2$ and stirred at 95° C. for 17 h. The reaction mixture was diluted with EtOAc and water, and the layers were separated. The organic layer was washed with brine, dried over MgSO$_4$, filtered and evaporated under reduced pressure to give 635 mg of intermediate 21 (quant. yield) which was directly engaged in the next step without further purification.

Preparation of Intermediate 105

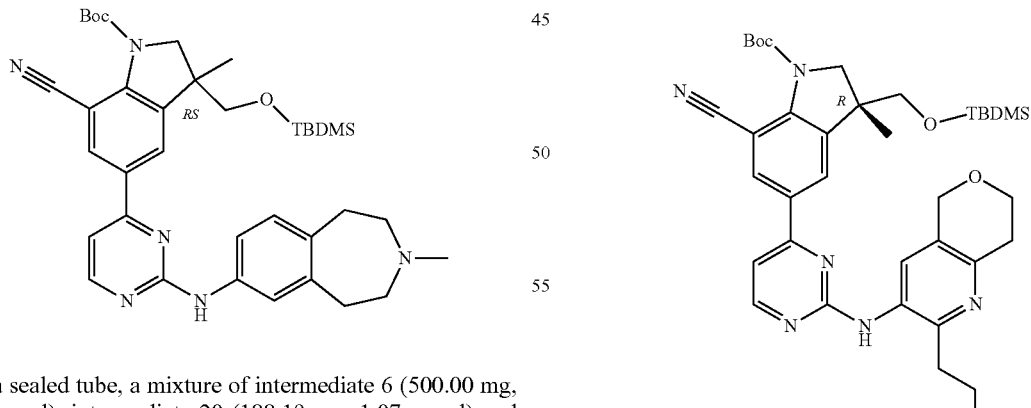

In a sealed tube, a mixture of intermediate 6R (475.61 mg, 0.79 mmol), intermediate 104 (260.00 mg, 1.19 mmol) and Cs$_2$CO$_3$ (1.03 g, 3.18 mmol) in dry 1,4-dioxane (20.2 mL) was purged with N$_2$. Then Pd(OAc)$_2$ (17.83 mg, 0.079 mmol) and BINAP (49.44 mg, 0.079 mmol) were added. The mixture was purged with N₂ and stirred at 90° C. for 16 h. The reaction mixture was diluted with EtOAc and water. The layers were separated and the aqueous layer was extracted with EtOAc (twice). The combined organic layers were dried over MgSO₄, filtered and the solvent was removed under reduced pressure. The crude residue was purified by chromatography on silica gel (irregular SiOH, 15-40 μm, 24 g, dry loading on celite, mobile phase gradient: from heptane/EtOAc 95/5 to 60/40) to give 450 mg of intermediate 105 (81% yield, yellow residue).

The intermediates in the table below were prepared by using an analogous method starting from the respective starting materials. The most relevant minor deviations to the reference method are indicated as additional information in the column 'Yield (%)'.

| Intermediate number | Structure | Mass (mg) | Yield (%) |
|---|---|---|---|
| Intermediate 26 | From intermediate 6 and intermediate 25 | 688 | Quant. brown solid |
| Intermediate 36 | From intermediate 12 and 2-Boc-8-amino-3,4-dihydroisoquinoline | 142 | 57 |
| Intermediate 39 | From intermediate 6 and intermediate 38 | 139 | 22 Procdure with 2.5 equiv. of Cs₂CO₃ |

-continued
| Intermediate number | Structure | Mass (mg) | Yield (%) |
|---|---|---|---|
| Intermediate 46 | 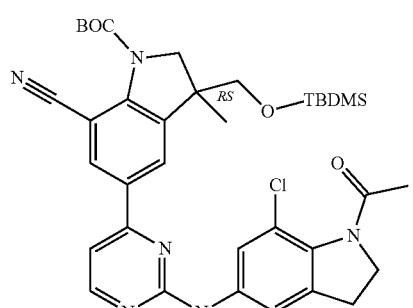 From intermediate 6 and intermediate 45 | 1250 (76% purity based on LC/MS) brown foam | Quant. |
| Intermediate 51 | From intermediate 7 and intermedate 50 | 486 brown solid | 59 |
| Intermediate 58 | From intermediate 6R and intermediate 57 | 440 yellow oil | Quant. |

-continued
| Intermediate number | Structure | Mass (mg) | Yield (%) |
|---|---|---|---|
| Intermediate 61 | 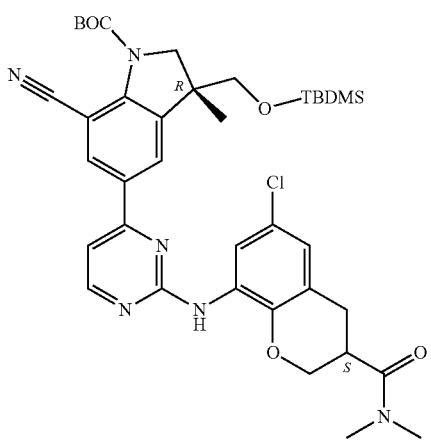 From intermediate 6R and intermediate 60 | 530 yellow oil | Quant. |
| Intermediate 65 | 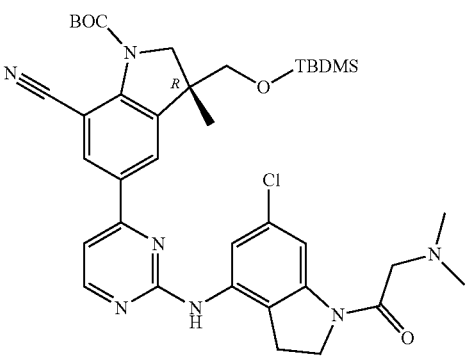 From intermediate 6R and intermediate 64 | 214 yellow solid | 60 |
| Intermediate 70 | 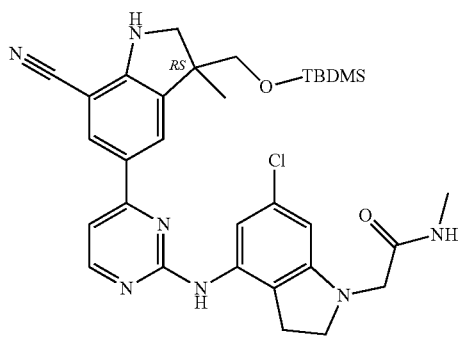 From intermediate 7 and intermediate 69 | 254 orange solid | 77 |

-continued
| Intermediate number | Structure | Mass (mg) | Yield (%) |
|---|---|---|---|
| Intermediate 75 | 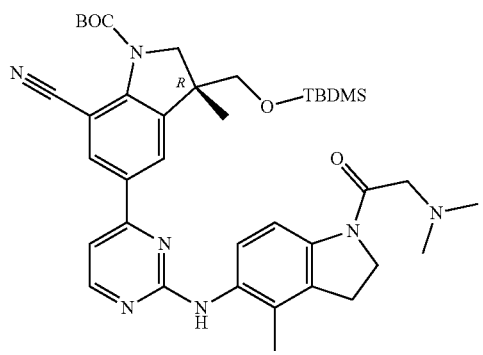<br>From intermediate 6R and intermediate 74 | 365 | Quant. (74% purity based on LC/MS brown solid) |
| Intermediate 81 | 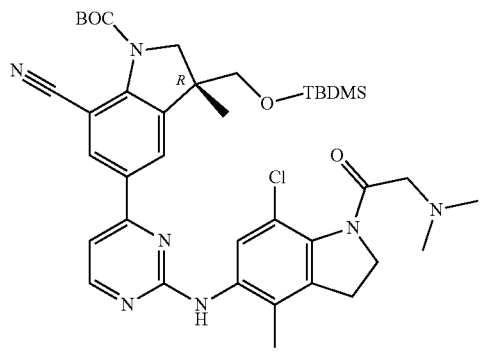<br>From intermediate 6R and intermediate 80 | 756 | Quant. (67% purity based on LC/MS brown foam) |
| Intermediate 86 | 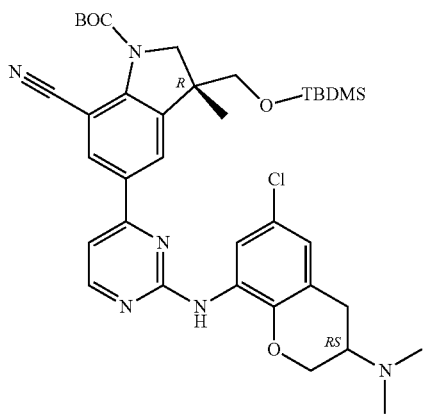<br>From intermediate 6R and intermediate 85 | 860 yellow oil | Quant. |

-continued

| Intermediate number | Structure | Mass (mg) | Yield (%) |
|---|---|---|---|
| Intermediate 92 | From intermediate 6R and intermediate 91 | 260 brown oil | 88 |
| Intermediate 98 | From intermediate 6R and intermediate 97 | 1040 brown oil | 82 With T = 90° C. |
| Intermediate 107 | From intermediate 6R and intermediate 103 | 270 yellow oil | 62 With T = 90° C. Procedure with 4 equiv. of Cs$_2$CO$_3$ |

| Intermediate number | Structure | Mass (mg) | Yield (%) |
|---|---|---|---|
| Intermediate 130 | 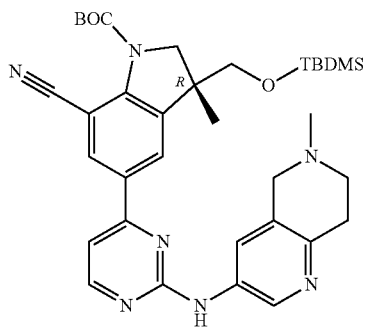  From intermediate 6R and intermediate 129 | 620 beige foam | Quant. With T = 90° C. Procedure with 2.5 equiv. of Cs$_2$CO$_3$ |
| Mixture of intermediate 123c and 123' | 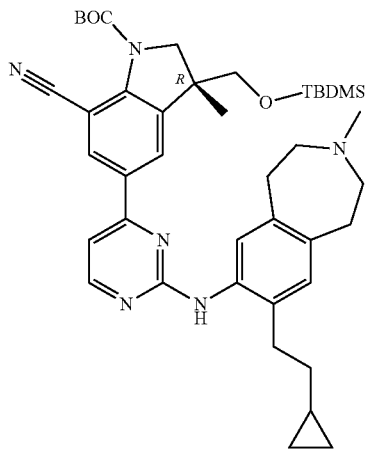  From intermediate 6R and intermediate 122  +  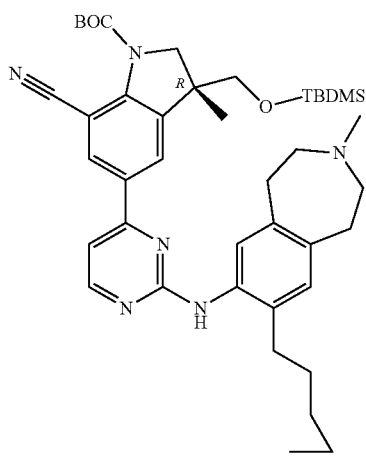  From intermediate 6R and intermediate 122' | 1530 yellow solid  130 yellow solid | Quant. With T = 90° C. Procedure with 4 equiv. of Cs$_2$CO$_3$  9 |

-continued
| Intermediate number | Structure | Mass (mg) | Yield (%) |
|---|---|---|---|
| Intermediate 151 | 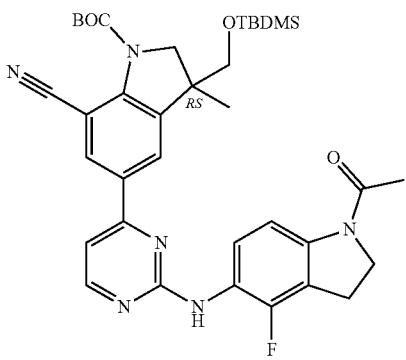<br>From intermediate 6 and intermediate 150 | 800 | 85<br>With T = 80° C. |
| Intermediate 156 | 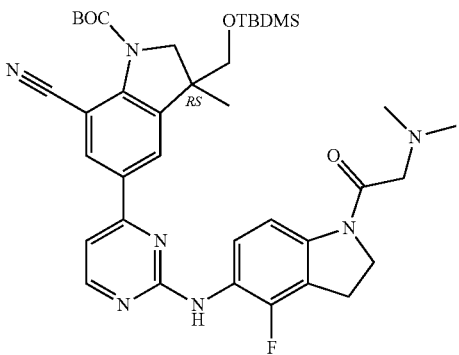<br>From intermediate 6 and intermediate 155 | 500 | 38 |
| Intermediate 159 | 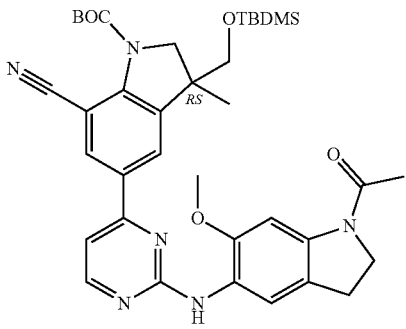<br>From intermediate 6 and intermediate 158 | 480 | 58<br>Procedure with 2.5 equiv. of Cs$_2$CO$_3$ |
| Intermediate 164 | 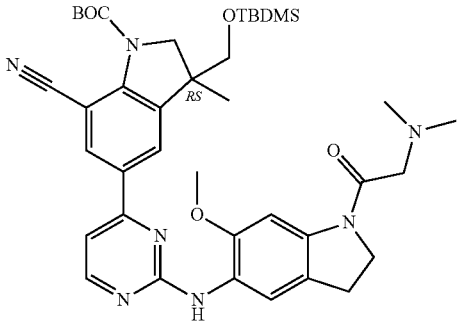<br>From intermediate 6 and intermediate 163 | 300 | 41<br>With T = 80° C. |

-continued

| Intermediate number | Structure | Mass (mg) | Yield (%) |
|---|---|---|---|
| Intermediate 166 | From intermediate 6 and 5-chloro-2,3-dihydro-7-benzofuranamine | 130 | 51 Based on a purity of 48% evaluated by LC/MS Procedure with 1.5 equiv. of $Cs_2CO_3$ |
| Intermediate 170 | From intermediate 6 and intermediate 169 | 200 | 66 With T = 80° C. |
| Intermediate 173 | From intermediate 12 and intermediate 172 | 500 | 22% based on a purity of 59% evaluated by LC/MS Procedure with 2.5 equiv. of $Cs_2CO_3$ |
| Intermediate 178 | From intermediate 6R and intermediate 177 | 290 | 92 Procedure with 2.5 equiv. of $Cs_2CO_3$ |

| Intermediate number | Structure | Mass (mg) | Yield (%) |
|---|---|---|---|
| Intermediate 180 | 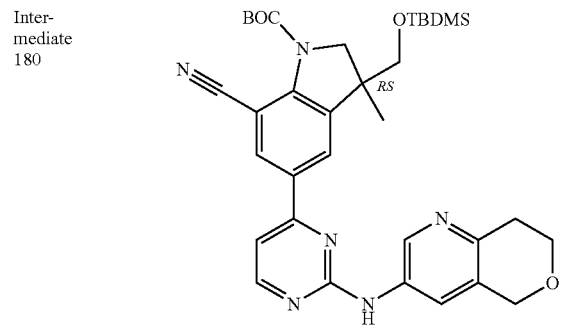  From intermediate 6 and intermediate 102 | 978 | Quant. Based on a purity of 74% evaluated by LC/MS |
| Intermediate 183 | 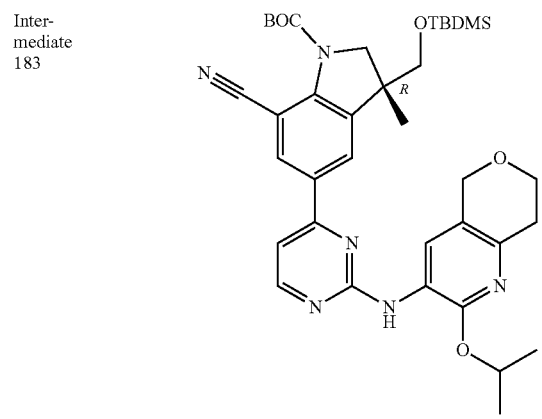  From intermediate 6R and intermediate 182 | 160 | 67% 78% of purity based on LC/MS Procedure with 2 equiv. of $Cs_2CO_3$ and T = 120° C. |
| Intermediate 186 | 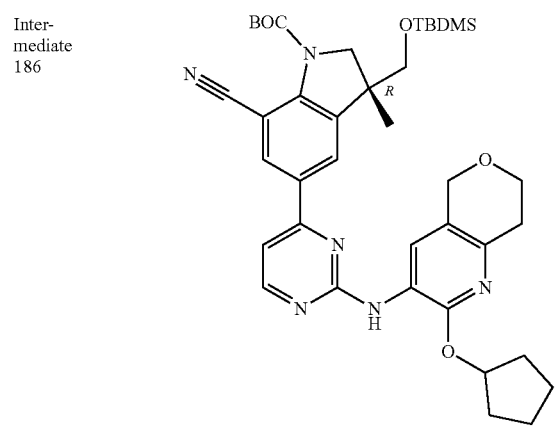  From intermediate 6R and intermediate 185 | 190 | 68 Procedure with 2 equiv. of $Cs_2CO_3$ and T = 120° C. |

-continued

| Intermediate number | Structure | Mass (mg) | Yield (%) |
|---|---|---|---|
| Intermediate 210 | 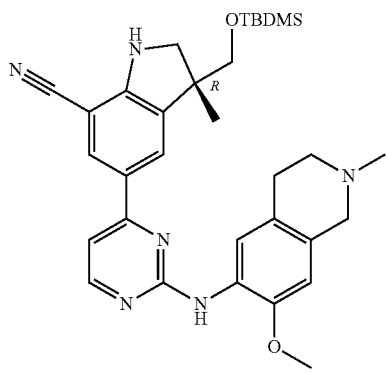<br>From intermediate 7R and intermediate 209 | 81 | 33<br>Procedure with 2 equiv. of Cs$_2$CO$_3$ and T = 120° C. |
| Intermediate 212 | 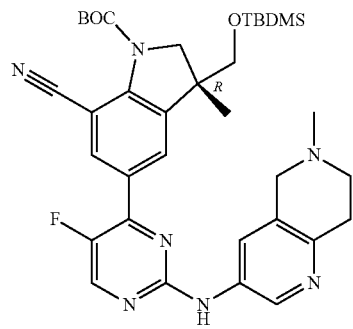<br>From intermediate 211 and intermediate 129 | 160 | 86<br>Procedure with 2 equiv. of Cs$_2$CO$_3$ and T = 120° C. |
| Intermediate 228 | 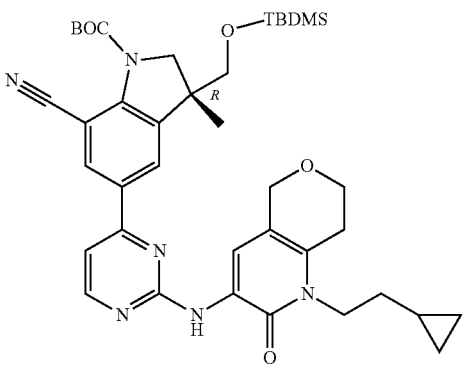<br>From intermediate 6R and intermediate 227 | 236 | 54<br>Procedure with 2 equiv. of Cs$_2$CO$_3$ and T = 100° C. |

-continued

| Intermediate number | Structure | Mass (mg) | Yield (%) |
|---|---|---|---|
| Intermediate 233 | [structure: BOC-N indoline with CN, RS methyl, OTBDMS, linked via pyrimidine-NH to dihydroquinolinone with OMe]<br>From intermediate 6 and intermediate 232 | 980 | 86<br>Based on a purity of 86% evaluated by LC/Ms Procedure with 2.5 equiv. of $Cs_2CO_3$ |
| Intermediate 240 | [structure: NH-indoline with CN, R methyl, OTBDMS, linked via pyrimidine-NH to tetrahydroisoquinoline bearing ethyl and N-CH(CH_3)CH_2OH]<br>From intermediate 7R and intermediate 239 | 39 | 19<br>Procedure with 2 equiv. of $Cs_2CO_3$ and T = 120° C. |

Example A8b

Preparation of Intermediate 8b' and intermediate 8b"

intermediate 8b'

[structure: pyrazole fused oxazine with $NO_2$, R or S]

R or S intermediate 8b"

[structure: pyrazole fused oxazine with $NO_2$, S or R]

S or R

Intermediate 8b (363 mg) was purified via chiral SFC (Stationary phase: Whelk O1 (S,S) 5 μm 250*21.1 mm, mobile phase: 85% $CO_2$, 15% iPrOH). Pure fractions were collected and evaporated to give 140 mg of intermediate 8b' (39% yield) and 145 mg of intermediate 8b" (40% yield).

Example A8c

Preparation of Intermediate 22c

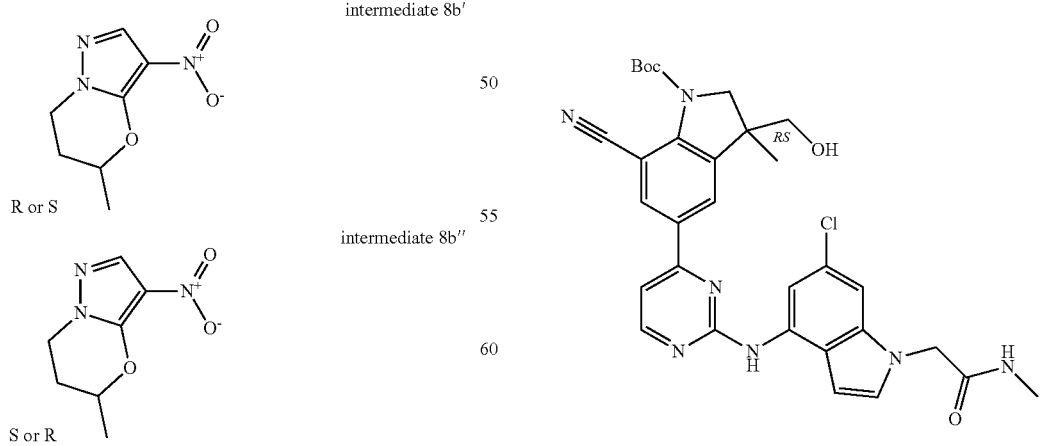

A solution of intermediate 21c (266.00 mg, 0.26 mmol based on 70% purity determined by LC/MS) and TBAF (1M in THF) (0.26 mL, 0.26 mmol) in THF (3 mL) was stirred at rt for 0.5 h. The reaction mixture was diluted with EtOAc and washed with water. The organic layer was dried with Na$_2$SO$_4$ and concentrated under vacuum to give 240 mg of intermediate 22c (99% yield, 65% purity based on LC/MS, dark oil) which was directly engaged in the next step without further purification.

The intermediate in the table below was prepared by using an analogous method starting from the respective starting materials. Minor deviations to the referenced method are indicated as additional information in the column 'Yield (%)'.

| Intermediate number | Structure | Mass (mg) | Yield (%) |
|---|---|---|---|
| Intermediate 42c | 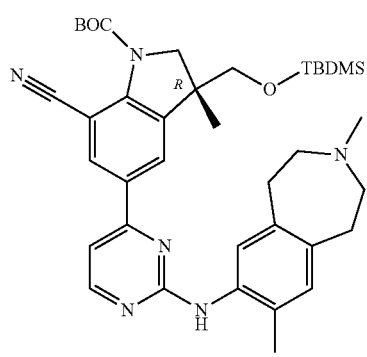<br>From intermediate 41c | 299 Off-white solid | 71 Procedure with Me-THF as solvent and 1.16 equiv. of TBAF |

Example A9a

Preparation of Intermediate 111

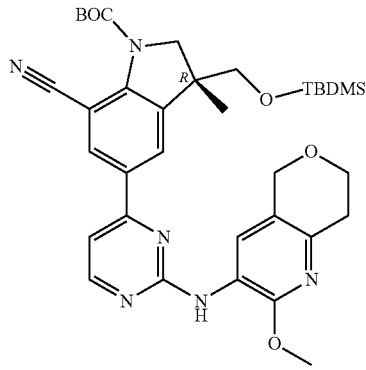

In a sealed tube, a mixture of intermediate 6R (400.00 mg, 0.77 mmol), intermediate 110 (265.97 mg, 1.40 mmol), Pd(OAc)$_2$ (17.43 mg, 77.65 µmol), BINAP (48.35 mg, 77.65 µmol) and Cs$_2$CO$_3$ (632.50 mg, 1.94 mmol) was purged with N$_2$ (three times). Dry Me-TH (8 mL) was added and the reaction mixture was degassed under N$_2$ for 5 min and then heated at 90° C. for 18 h. The reaction mixture was concentrated under vacuum and purified by silica gel chromatography (Irregular SiOH 15-40 µm, 40 g, dry loading on celite, mobile phase gradient: from DCM/MeOH (+5% aq. NH$_3$) 100/0 to 85/15). The pure fractions were collected and evaporated under vacuum to give 371 mg of intermediate 111 (71% yield, orange powder).

Preparation of Intermediate 118

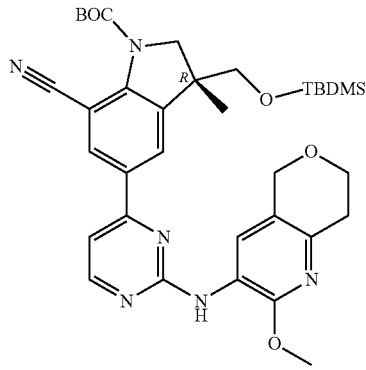

In a sealed tube, a solution of intermediate 6R (500.00 mg, 0.97 mmol), intermediate 117 (279.86 mg, 1.55 mmol) and Cs$_2$CO$_3$ (790.63 mg, 2.43 mmol) in dry Me-TH (9.70 mL) was purged with N$_2$. Pd(OAc)$_2$ (21.79 mg, 97.06 µmol) and BINAP (60.44 mg, 97.06 µmol) were added and the mixture was purged with N$_2$ and heated at 85° C. for 3 h. After cooling down to rt, the crude was filtered on a pad of Celite®. The cake was washed with EtOAc and the filtrate was evaporated in vacuo. The crude residue was purified by silica gel chromatography (Irregular SiOH, 15-40 µm, 50 g, liquid loading (DCM), mobile phase gradient: from Heptane 95%, EtOAc/MeOH (9:1) 5% to Heptane 70%, EtOAc/MeOH (9:1) 30%) to give 692 mg of intermediate 118 (88% yield, 81% purity based on 1H NMR, pale brown solid).

Preparation of Intermediate 139

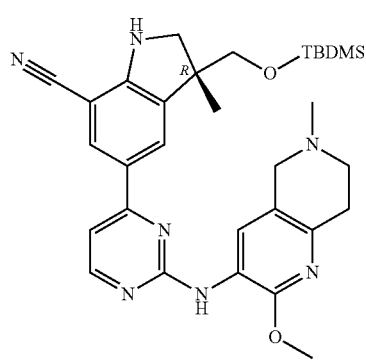

In a sealed tube, a suspension of intermediate 7R (300.00 mg, 0.68 mmol based on 94% purity determined by LC/MS), intermediate 138 (196.97 mg, 1.02 mmol), Pd(OAc)$_2$ (15.26 mg, 0.068 mmol), BINAP (42.31 mg, 0.068 mmol) and Cs$_2$CO$_3$ (664.18 mg, 2.04 mmol) was purged with N$_2$. Me-TH (6 mL) was added and the mixture was purged with N$_2$ and stirred at 85° C. overnight. The mixture was filtered on a pad of Celite®. The cake was washed with EtOAc and the filtrate was evaporated in vacuo. The crude residue was purified by silica gel chromatography (irregular SiOH, 15-40 µm, 40 g, liquid loading (DCM), mobile phase gradient: from Heptane 75%, EtOAc/MeOH (9:1) 25% to Heptane 20%, EtOAc/MeOH (9:1) 80%) to give 340 mg of intermediate 139 (88% yield, 89% purity based on LC/MS, beige foam).

Preparation of Intermediate 145

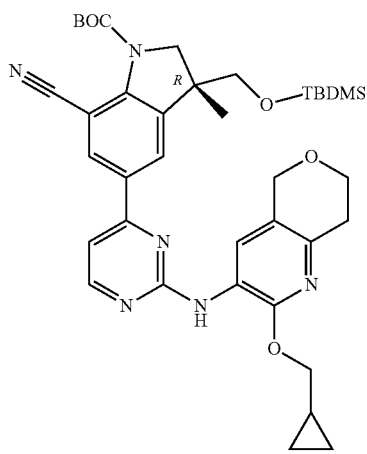

In a sealed tube, a solution of intermediate 6R (300.00 mg, 0.58 mmol), intermediate 144 (205.25 mg, 0.93 mmol) and Cs$_2$CO$_3$ (474.37 mg, 1.46 mmol) in dry Me-TH (5.80 mL) was purged with N$_2$. Pd(OAc)$_2$ (13.08 mg, 58.24 μmol) and BINAP (36.26 mg, 58.24 μmol) were added and the mixture was purged with N$_2$ and heated at 85° C. for 3 h. After cooling down to rt, the crude was filtered on a pad of Celite®. The cake was washed with EtOAc and the filtrate was evaporated in vacuo. The crude residue was purified by silica gel chromatography (Irregular SiOH, 15-40 μm, 24 g, liquid loading (DCM), mobile phase gradient: from heptane 95%, EtOAc/MeOH (9:1) 5% to heptane 70%, EtOAc/MeOH (9:1) 30%) to give 348 mg of intermediate 145 (59% yield, 69% purity based on 1H NMR, yellow oil) which was used in the next step without further purification.

The intermediates in the table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
| --- | --- | --- | --- |
| Intermediate 115 | From intermediate 6R and intermediate 114 | 416 yellow powder | 78 With T = 90° C. |
| Intermediate 126 | From intermediate 6R and intermediate 125 | 607 (81% purity based on LC/MS pale brown solid) | 79 |

-continued

| Intermediate number | Structure | Mass (mg) | Yield (%) |
|---|---|---|---|
| Intermediate 133 | 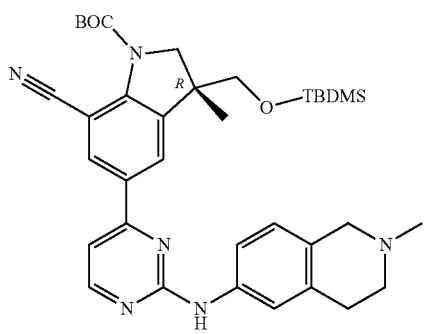<br>From intermediate 6R and intermediate 132 | 680 yellow oil | 89 With T = 90° C. Procedure with 4 equiv. of Cs₂CO₃ |
| Intermediate 135 | 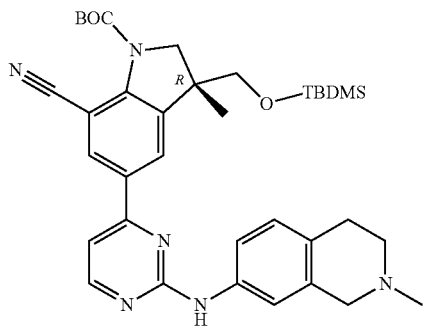<br>From intermediate 6R and 2-methyl-1,2,3,4-tetrahydroisoquinolin-7-amine | 348 yellow solid | 58 With T = 90° C. Procedure with 4 equiv. of Cs₂CO₃ |
| Intermediate 142 | 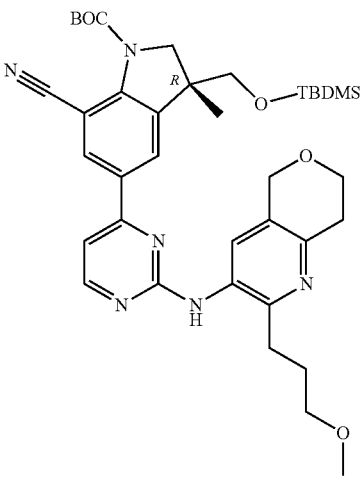<br>From intermediate 6R and intermediate 141 | 333 | 82 With T = 85° C. |

Example A9b

Preparation of Compound 9a

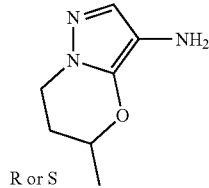

R or S

A mixture of intermediate 8b' (140.00 mg, 0.76 mmol) in MeOH (8.54 mL) was hydrogenated at room temperature at atmospheric pressure for 12 h with Pd/C (10% wt) (18.04 mg, 16.95 µmol) as catalyst. The catalyst was filtered over a pad of Celite® which was washed with DCM and MeOH. The filtrate was evaporated to afford 117 mg of intermediate 9a (quantitative yield) which was used directly in the next reaction step.

Preparation of Intermediate 9b

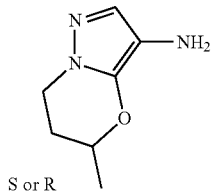

S or R

A mixture of intermediate 8b" (140.00 mg, 0.76 mmol) in MeOH (8.54 mL) was hydrogenated at room temperature at atmospheric pressure for 12 h with Pd/C (10% wt) (18.04 mg, 16.95 µmol) as catalyst. The catalyst was filtered over a pad of Celite® which was washed with DCM and MeOH. The filtrate was evaporated to afford 117 mg of intermediate 9b (quantitative yield) which was used directly in the next reaction step.

Preparation of Intermediate 15b

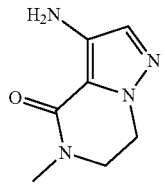

Intermediate 14b (1.16 g, 5.91 mmol) in MeOH (23.96 mL) was hydrogenated at rt with Pd/C (10% wt.) (167.74 mg, 0.16 mmol) as a catalyst under atmospheric pressure for 12 hours. The catalyst was filtered o a pad of Celite® and the filtrate was evaporated under reduced pressure to give 983 mg of intermediate 15b (quantitative yield).

Preparation of Intermediate 25b

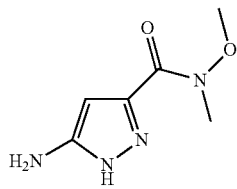

A mixture of intermediate 24b (6.20 g, 30.98 mmol) in MeOH (250 mL) and THE (250 mL) was hydrogenated (1 bar) at rt with Pd/C (10% wt) (220 mg) as a catalyst for 12 h. The catalyst was filtered off and the filtrate was concentrated under reduce pressure to give 4.7 g of intermediate 25b (89% yield) which was used in the next step without any further purification.

The intermediates in the table below were prepared by using an analogous method as described for the preparation of intermediate 9a, starting from the respective starting materials. Minor deviations to the referenced method are indicated as additional information in the column 'Yield (%)'.

| Intermediate number | Structure | Mass (mg) | Yield (%) |
|---|---|---|---|
| Intermediate 38b | From intermediate 37b | 60 88% purity based on LC/MS | 36 Procedure with MeOH as solvent |
| Intermediate 45b | From intermediate 44b | 331 | 93 Procedure with MeOH/EtOAc, 1:1 as solvent |

-continued

| Intermediate number | Structure | Mass (mg) | Yield (%) |
|---|---|---|---|
| Intermediate 50b | From intermediate 49b | 576 | Quantitative<br>Procedure with MeOH as solvent |
| Intermediate 55b | From intermediate 54b | 930 | 98<br>Procedure with MeOH/EtOAc, 1:1 as solvent |
| Intermediate 72b | From intermediate 71b | 153 | 38<br>Procedure with MeOH as solvent |
| Intermediate 77b | From intermediate 76b | 329 | Quantitative<br>Procedure with MeOH as solvent |
| Intermediate 81b | From intermediate 80b | 320 | 87<br>Procedure with MeOH as solvent |
| Intermediate 91b | From intermediate 90b | 238 | Quantitative<br>With MeOH as solvent |

-continued

| Intermediate number | Structure | Mass (mg) | Yield (%) |
|---|---|---|---|
| Intermediate 98b | From intermediate 97b | 225 | 42<br>Procedure with MeOH as solvent |
| Intermediate 103b | From intermediate 102b | 420 | 92<br>Procedure with EtOAc as solvent |
| Intermediate 108b (cis) | CIS: mixture of (R,S) and (S,R)<br>From intermediate 107b | 305 | Quant<br>Procedure with MeOH as solvent |
| Intermediate 112b (trans) | TRANS: mixture of (R,R) and (S,S)<br>From intermediate 111b | 101 | 99<br>Procedure with MeOH as solvent |
| Intermediate 119b | From intermediate 118b | 705 | 86<br>Procedure with EtOAc as solvent at 5 bars for 48 hrs |
| Intermediate 126b | From intermediate 125b | 305 | 99.9<br>Procedure with $^i$PrOH; THF as solvent |

-continued

| Intermediate number | Structure | Mass (mg) | Yield (%) |
|---|---|---|---|
| Intermediate 130b | [structure: pyrazolo-oxazine with H₂N and gem-dimethyl]<br>From intermediate 129b | 382 | Quant<br>Procedure with ⁱPrOH; THF as solvent |
| Intermediate 134b | [structure: aminopyrazolo-pyrazinone with N-benzyl]<br>From intermediate 133b | 738 | Quant<br>Procedure for 2 hrs, with EtOH; Me-THF as solvent |
| Intermediate 138b | [structure: aminopyrazolo-pyrazinone with N-isobutyl]<br>From intermediate 137b | 120 | 27<br>Procedure for 2 hrs, with EtOH; Me-THF as solvent |
| Intermediate 142b | [structure: aminopyrazolo-diazepinone with N-isopropyl]<br>From intermediate 141b | 758 | Quant<br>Procedure for 2 hrs at 3 bars, with EtOH; Me-THF as solvent |
| Intermediate 149b | [structure: aminopyrazolo-oxazepine with methyl (RS)]<br>From intermediate 148b | 500 | Quant<br>Procedure with ⁱPrOH; THF as solvent |
| Intermediate 156b | [structure: aminopyrazolo-oxazine with CH₂OH and methyl (RS)]<br>From intermediate 155b | 313 | Quant<br>Procedure for 5 hrs, with ⁱPrOH; THF as solvent |

Preparation of Intermediate 66b

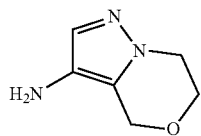

A mixture of intermediate 65b (750.00 mg, 4.43 mmol), iron powder (1.24 g, 22.17 mmol) and NH$_4$Cl (0.95 g, 18 mmol) in EtOH (26 mL) and water (26 mL) was heated at 80° C. for 2 h. The reaction mixture was cooled down to room temperature, diluted with DCM and filtered through a pad of celite. The solution was washed twice with a 10% aqueous solution of K$_2$CO$_3$. The organic layer was dried over MgSO$_4$, filtered and evaporated to dryness yielding to 386 mg of a first batch of crude intermediate 66b which was combined with 106 mg of another batch of crude intermediate 66v. The resulting residue was purified by silica gel chromatography (irregular silica, 15-40 μm, 40 g, liquid loading (DCM), mobile phase gradient: from 100% DCM, 0% MeOH/aq. NH$_3$ (9:1) to 95% DCM, 5% MeOH/aq. NH$_3$ (9:1), in 10 CV). The fractions containing the product were combined and evaporated to give 209 mg of intermediate 66b (23% yield, yellow brown solid).

Example A9c

Preparation of Intermediate 13c

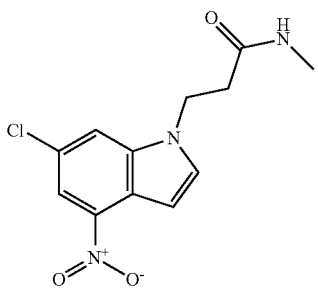 [SMILES: CNC(=O)CCn1ccc2c([N+](=O)[O-])cc(Cl)cc21]

To a solution of 6-chloro-4-nitro-1H-indole (500.00 mg, 2.54 mmol) and Cs$_2$CO$_3$ (1.24 g, 3.81 mmol) in DMF (5 mL) was added 3-chloro-N-methylpropanamide (464.00 mg, 3.81 mmol) under N$_2$ and the reaction mixture was stirred at 90° C. for 0.5 h. The reaction mixture was then partitioned between EtOAc and water. The organic layer was washed with brine, dried over Na$_2$SO$_4$ and concentrated to dryness under vacuum. The residue was triturated with cyclohexane and the solid was collected by filtration and dried under vacuum to give 687 mg of crude intermediate 13c (96% yield) which was used in the next step without any further purification.

Preparation of Intermediate 19c

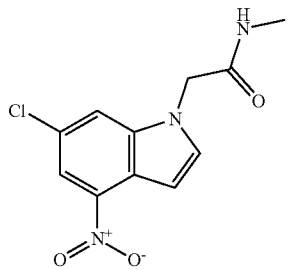 [SMILES: CNC(=O)Cn1ccc2c([N+](=O)[O-])cc(Cl)cc21]

To a solution of 6-chloro-4-nitro-1H-indole (500.00 mg, 2.54 mmol) and Cs$_2$CO$_3$ (1.24 g, 3.82 mmol) in DMF (5 mL) was added 2-chloro-N-methyl-acetamide (410.00 mg, 3.82 mmol) under nitrogen and the reaction mixture was stirred at 90° C. for 0.5 h. The reaction mixture was then partitioned between ethyl acetate and water, and layers were separated. The organic layer was washed with brine, dried over sodium sulfate and concentrated in vacuo. The yellow solid residue was triturated with cyclohexane and the solid was collected by filtration and dried in vacuo to give 541 mg of intermediate 19c (79% yield, yellow solid) which was used in the next step without any further purification.

The intermediates in the table below were prepared by using an analogous method starting from the respective starting materials. Minor deviations to the referenced method are indicated as additional information in the column 'Yield (%)'.

| Intermediate number | Structure | Mass (mg) | Yield (%) |
|---|---|---|---|
| Intermediate 16c | ![structure] From 6-chloro-4-nitro-1H-indole and 1-chloro-2-methyl-propan-2-ol | 1860 brown solid | 68 Procedure with 1.8 equiv. of Cs$_2$CO$_3$ |

-continued

| Intermediate number | Structure | Mass (mg) | Yield (%) |
|---|---|---|---|
| Intermediate 23c | 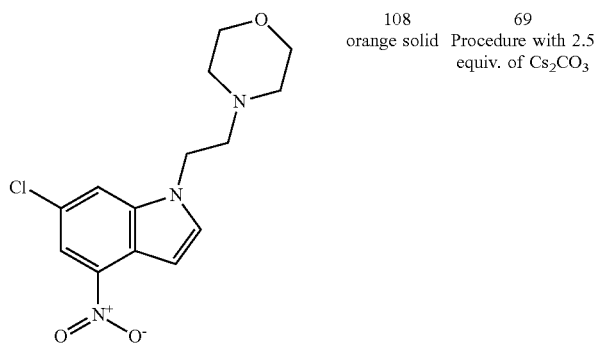 From 6-chloro-4-nitro-1H-indole and 4-(2-chloroethyl)morpholine hydrochloride | 108 orange solid | 69 Procedure with 2.5 equiv. of $Cs_2CO_3$ |
| Intermediate 26c | 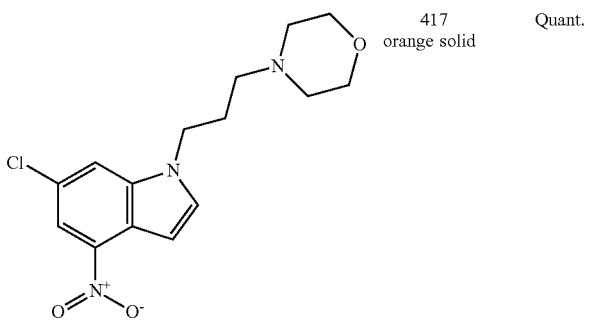 From 6-chloro-4-nitro-1H-indole and 4-(3-chloropropyl)morpholine | 417 orange solid | Quant. |
| Intermediate 29c | 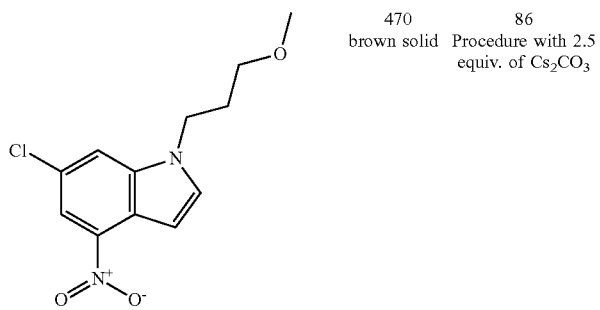 From 6-chloro-4-nitro-1H-indole and 1-chloro-3-methoxy-propane | 470 brown solid | 86 Procedure with 2.5 equiv. of $Cs_2CO_3$ |

Example A10a

Preparation of Intermediate 33 and Intermediate 34

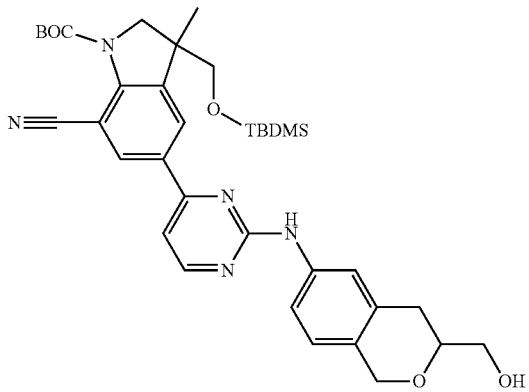

intermediate 33: mixture of two diastereoisomers with unknown configuration (DIA A)
intermediate 34: mixture of two diastereoisomers with unknown configuration (DIA B)

In a sealed tube, a mixture of intermediate 6 (547.86 mg, 1.12 mmol), intermediate 31 (400.00 mg, 2.23 mmol), $Cs_2CO_3$ (1.09 g, 3.35 mmol), chloro[2-(dicyclohexylphosphino)-3,6-dimethoxy-2',4',6'-triisopropyl-1,1'-biphenyl][2-(2-aminoethyl)phenyl] palladium (II) (89.14 mg, 111.59 µmol) and BRETTPHOS (59.90 mg, 111.59 µmol) in THF (18 mL) was stirred at 140° C. using one single mode microwave (Biotage® Initiator EXP 60) with a power output ranging from 0 to 400 W for 2 h. The reaction mixture was poured onto water and DCM. The mixture was filtered over Celite®, decanted and the organic layer was dried over $MgSO_4$, filtered and evaporated under vacuum. The residue was purified by chromatography on silical gel (Irregular SiOH 40 µm, mobile phase: 97% DCM, 3% MeOH, 0.1% $NH_4OH$). The pure fractions were combined and the solvent was evaporated under vacuum. Another purification was performed via silica gel chromatography (Irregular bare silica 40 g, mobile phase: 60% Heptane, 5% MeOH (+10% $NH_4OH$), 35% EtOAc). The pure fractions were combined and the solvent was evaporated under vacuum to give 350 mg of a mixture of 4 diastereoisomers (48% yield) which was further purified by achiral SFC (Stationary phase: Chiralcel OD-H 5 µm 250*4.6 mm, mobile phase: 65% $CO_2$, 35% MeOH (0.3% $iPrNH_2$)). The desired fractions were collected and the solvent was concentrated to dryness under vacuum to give 131 mg of intermediate 33 (37% yield, eluted in the first position from the column) and 146 mg of intermediate 34 (42% yield, eluted in the second position from the column).

Example A10b

Preparation of Intermediate 18b

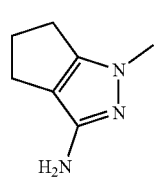

And Intermediate 19b

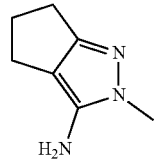

Cyclopentanone-2-carbonitrile (4.00 g, 36.65 mmol), methylhydrazine (2.12 mL, 40.32 mmol) and TEA (7.07 mL, 50.89 mmol) in toluene (26.76 mL) were heated to 120° C. for 16 hours. The reaction was cooled down to room temperature and the solvent was evaporated. The residue was taken up into $Et_2O$, filtered and dried under vacuo. The filtrate was evaporated and the crude residue was purified via silica gel chromatography (Stationary phase: Irregular SiOH 20-45 µm, 450 g, mobile phase gradient: from 44% Heptane, 6% MeOH (+10% $NH_4OH$), 50% EtOAc to 42% Heptane, 8% MeOH (+10% $NH_4OH$), 50% EtOAc). The pure fractions were collected and evaporated to give 205 mg of intermediate 18b (4% yield) and 545 mg of intermediate 19b (11% yield).

Preparation of Intermediate 30b

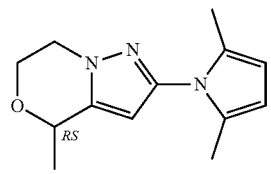 [SMILES: Cc1ccc(C)n1-c1cc2n(n1)CCOC2C]

To a solution of intermediate 29b (2.60 g, 8.33 mmol) in $CH_3CN$ (100 mL) was added $K_2CO_3$ (2.30 g, 16.67 mmol) and the mixture was refluxed for 5 h. The reaction mixture was then cooled and filtered. The filtrate was concentrated under reduced pressure. The residue was purified by silica gel chromatography (petroleum ether/EtOAc, 5/1) to give 683 mg of intermediate 30b (71% yield, yellow oil).

Preparation of Intermediate 58b and Intermediate 58b'

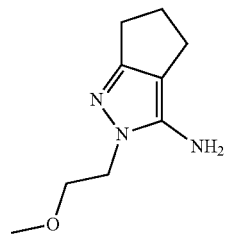

intermediate 58b

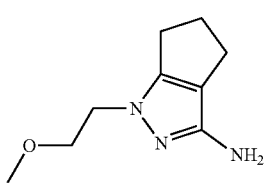

intermediate 58b'

A mixture of 2-oxocyclopentanecarbonitrile (1.00 g, 9.16 mmol) and 2-methoxyethylhydrazine hydrochloride (1.50 g, 11.85 mmol) in EtOH (10.00 mL) was stirred at 90° C. for 5 hours. The reaction was cooled down to room temperature and the solvent was evaporated until dryness. The crude residue was purified by silica gel chromatography (Irregular SiOH 40 μm, 40 g, mobile phase gradient: from 99% DCM, 1% MeOH (+10% NH$_4$OH) to 93% DCM, 7% MeOH (+10% NH$_4$OH)). The pure fractions were collected and the solvent was evaporated until dryness to give 570 mg of intermediate 58b and intermediate 58b' mixture (86/14 evaluated by LC/MS).

Example A10c

Preparation of Intermediate 14c

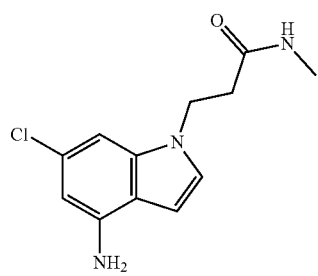 [SMILES: CNC(=O)CCn1ccc2c(N)cc(Cl)cc21]

A suspension of intermediate 13c (687.00 mg, 2.43 mmol), ammonium chloride (521.53 mg, 9.75 mmol) and iron powder (680.81 mg, 12.19 mmol) in EtOH (10 mL) and water (10 mL) was heated at 75° C. for 2 h. The reaction mixture was filtered through Celite® and the filtrate was concentrated to dryness under vacuum. The residue was partitioned between EtOAc and water. The organic layer was dried with Na$_2$SO$_4$ and concentrated under vacuum to give 437 mg of crude intermediate 14c (63%, 88% purity based on LC/MS, dark foam) which was directly engaged in the next step.

Preparation of Intermediate 20c

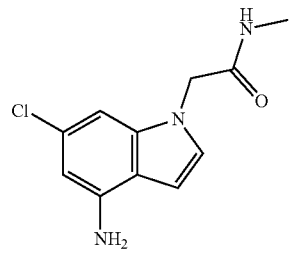 [SMILES: CNC(=O)Cn1ccc2c(N)cc(Cl)cc21]

A suspension of intermediate 19c (541.00 mg, 2.02 mmol), ammonium chloride (432.00 mg, 8.08 mmol) and iron powder (564 mg, 10.11 mmol) in EtOH (10 mL) and water (10 mL) was heated at 75° C. for 1 h. The reaction mixture was filtered through Celite® and the filtrate was concentrated in vacuo. The residue was partitioned between ethyl acetate and water. Layers were separated and the organic layer was dried over sodium sulfate, filtered and concentrated in vacuo to give 476 mg of intermediate 20c (quant. yield) which was used in the next step without any further purification.

Preparation of Intermediate 34c

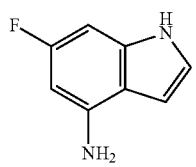 [SMILES: Nc1cc(F)cc2[nH]ccc12]

A suspension of 6-fluoro-4-nitro-1H-indole (1.00 g, 5.55 mmol), ammonium chloride (1.19 g, 22.21 mmol) and iron powder (1.55 g, 27.76 mmol) in EtOH (16 mL) and water (16 mL) was heated at 75° C. for 1 h. The reaction mixture was filtered through Celite® and the filtrate was concentrated in vacuo. The residue was partitioned between ethyl acetate and water. Layers were separated and the organic layer was dried over sodium sulfate and concentrated in vacuo to give 842 mg of intermediate 34c (quant. yield, purple solid) which was used in the next step without any further purifications.

The intermediates in the table below were prepared by using an analogous method starting from the respective starting materials. Minor deviations to the referenced method are indicated as additional information in the column 'Yield (%)'.

| Intermediate number | Structure | Mass (mg) | Yield (%) |
|---|---|---|---|
| Intermediate 17c | 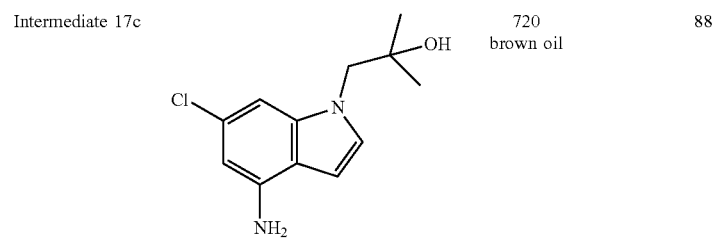<br>From intermediate 16c | 720<br>brown oil | 88 |
| Intermediate 24c | 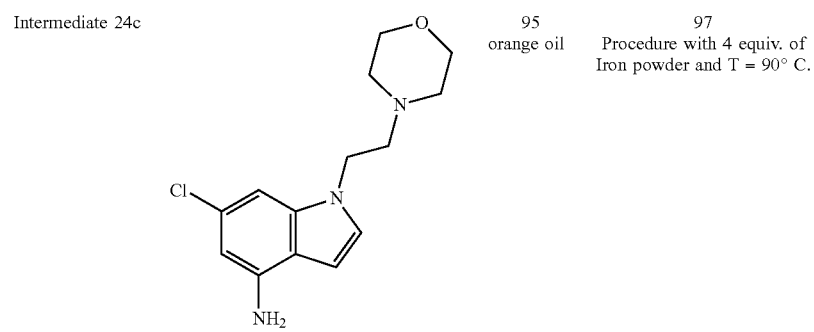<br>From intermediate 23c | 95<br>orange oil | 97<br>Procedure with 4 equiv. of Iron powder and T = 90° C. |
| Intermediate 30c | 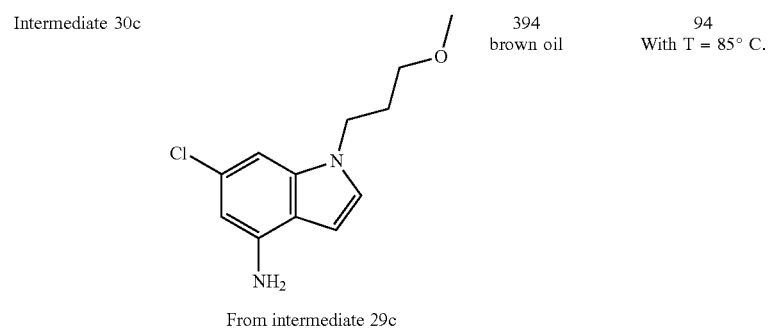<br>From intermediate 29c | 394<br>brown oil | 94<br>With T = 85° C. |
| Intermediate 32c | 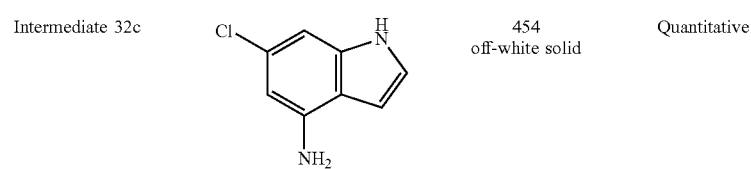<br>From 6-chloro-4-nitro-1H-indole | 454<br>off-white solid | Quantitative |

273
Alternative Preparation of Intermediate 14c

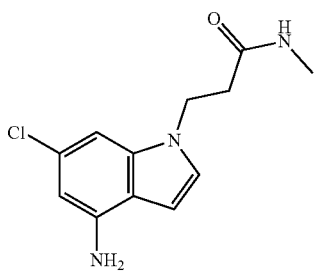 [SMILES: CNC(=O)CCn1ccc2c(N)cc(Cl)cc21]

A mixture of intermediate 13c (410.00 mg, 1.45 mmol) in titanium trichloride (18.7 mL, 21.8 mmol) and THF (40 mL) was stirred at rt for 2 h. The mixture was mixed with another reaction performed on 180 mg of intermediate 13c, diluted with water, basified by addition of $K_2CO_3$ powder at 0° C. and then, diluted with EtOAc. The organic layer was separated, dried over $MgSO_4$, filtered and evaporated under vacuum. The crude product was purified by silica gel chromatography (irregular SiOH 15-40 µm, 24 g, liquid injection with DCM, mobile phase gradient: from DCM/MeOH 100/0 to 80/20). The product containing fractions were combined and concentrated under vacuum to give 280 mg of intermediate 14c (53% yield based on 590 mg of intermediate 13, yellow residue).

The intermediates in the table below were prepared by using an analogous method starting from the respective starting materials. Minor deviations to the referenced method are indicated as additional information in the column 'Yield (%)'.

| Intermediate number | Structure | Mass (mg) | Yield (%) |
|---|---|---|---|
| Intermediate 30c | From intermediate 29c | 400 brown solid | 90 Procedure with 20 equiv. of $TiCl_3$ |
| Intermediate 32c | From 6-chloro-4-nitro-1H-indole | 118 brown oil | Quant. Procedure with 20 equiv. of $TiCl_3$ |

274
Preparation of Intermediate 27c

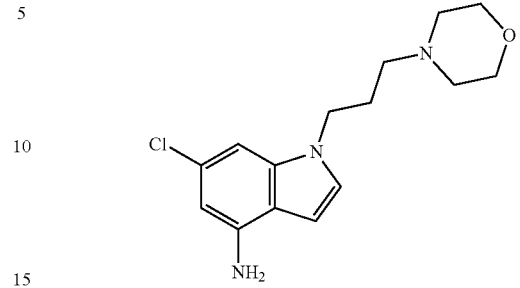

In a sealed tube, a mixture of intermediate 26c (639.68 mg, 1.97 mmol) and iron powder (441.34 mg, 7.90 mmol) in 10% aqueous $NH_4Cl$ solution (6.2 mL), EtOH (11.3 mL) and EtOAc (27.8 mL) was stirred at 90° C. for 18 h. Further Iron powder (441.34 mg, 7.90 mmol) was added and the mixture was stirred at 90° C. for 4 h. The mixture was filtered over a pad of Celite® and was washed with EtOAc. The organic layer was washed with a saturated aqueous solution of $NaHCO_3$ and brine, dried over $MgSO_4$, filtered and the solvent was removed under reduced pressure to give 460 mg of intermediate 27c (79%, orange oil) which was directly engaged in the next step.

Example A11a

Preparation of Intermediate 15

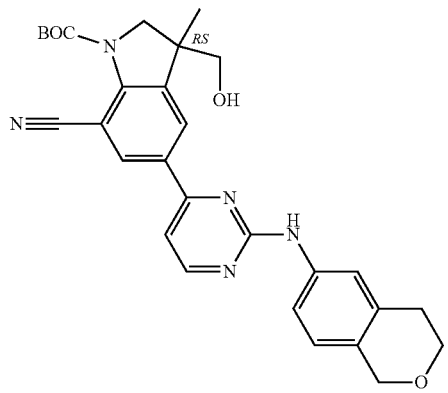 [SMILES: CC(C)(C)OC(=O)N1CC(C)(CO)c2cc(-c3ccnc(Nc4ccc5c(c4)CCOC5)n3)cc(C#N)c21]

A mixture of intermediate 14 (175.00 mg, 0.28 mmol) and TBAF (1M in THF) (0.56 mL, 0.56 mmol) in THF (2.4 mL) was stirred at rt for 48 h. The reaction mixture was diluted with EtOAc and water. The layers were separated and the organic layer was dried over $MgSO_4$, filtered and the solvent was removed under reduced pressure.

The residue was taken up into $Et_2O$, filtered and dried under vacuum to give 126 mg of intermediate 15 (88% yield) which was directly engaged in the next step without further purification.

The intermediates in the table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 22 | (structure from intermediate 21) | 524 Brown solid | Quant. Procedure with 2.2 equiv. of TBAF |
| Intermediate 27 | (structure from intermediate 26) | 201 brown oil | 32 Procedure with 2.2 equiv. of TBAF |
| Intermediate 40 | (structure from intermediate 39) | 77 | 67 Procedure with 1.2 equiv. of TBAF |

-continued
| Intermediate number | Structure | Mass (mg) | Yield (%) |
|---|---|---|---|
| Intermediate 99 | 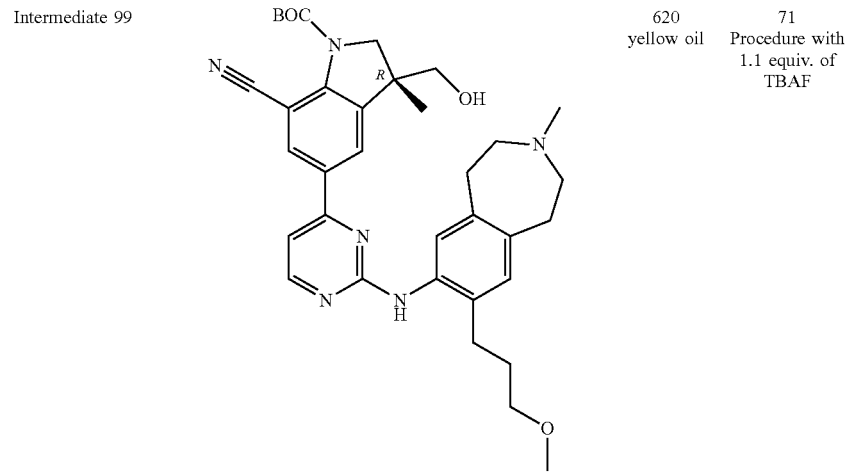<br>From intermediate 98 | 620 yellow oil | 71<br>Procedure with 1.1 equiv. of TBAF |
| Intermediate 157 | 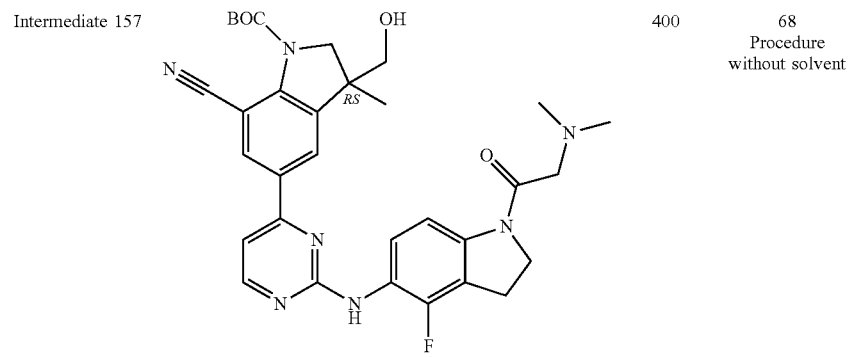<br>From intermediate 156 | 400 | 68<br>Procedure without solvent |
| Intermediate 167 | 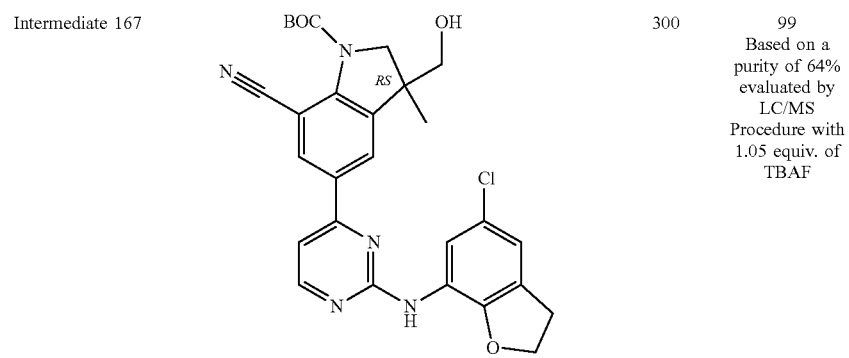<br>From intermediate 166 | 300 | 99<br>Based on a purity of 64% evaluated by LC/MS<br>Procedure with 1.05 equiv. of TBAF |

-continued

| Intermediate number | Structure | Mass (mg) | Yield (%) |
|---|---|---|---|
| Intermediate 181 | 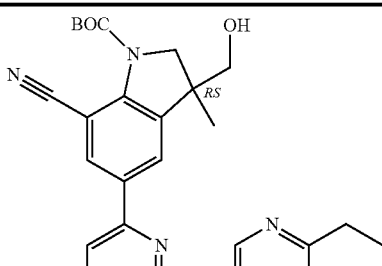<br>From intermediate 180 | 500 | Quant. Procedure with 1.1 equiv. of TBAF |

Preparation of Intermediate 234

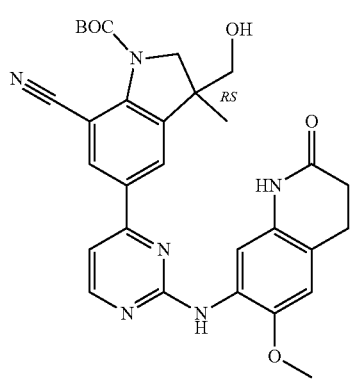 [SMILES: COc1cc2c(cc1Nc1nccc(-c3cc(C#N)c4c(c3)C(C)(CO)CN4C(=O)OC(C)(C)C)n1)NC(=O)CC2]

Intermediate 233 (400 mg; 0.517 mmol, 86% of purity based on LC/MS) was stirred in TBAF (0.925 mL; 0.925 mmol; 1M in THF) at room temperature. The reaction was concentrated and the resulting crude residue (300 mg) was washed with water. The mixture was filtered to give 200 mg (66%) of intermediate 234 as a yellow solid.

Example A11b

Preparation of Intermediate 24b

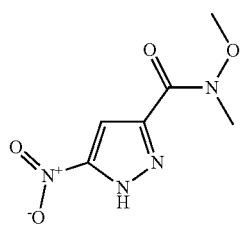

5-nitro-3-pyrazolecarboxylic acid (5.00 g, 31.83 mmol) was suspended in dichloroethane (130 mL) under $N_2$. $SOCl_2$ (7 mL, 96.38 mmol) and DMF (1 mL) were then added and the mixture was refluxed overnight. The precipitate was collected by filtration and suspended in DCM (82.5 mL). N,O-dimethylhydroxylamine hydrochloride (3.74 g, 38.34 mmol) and TEA (13.35 mL, 95.99 mmol) were added and the mixture was stirred at rt overnight. The mixture was poured into water (100 mL) and extracted with DCM (3×60 mL) and DCM/MeOH (9/1, 60 mL). The organic layers were combined, dried over $Na_2SO_4$, filtered and concentrated in vacuo to give 6.2 g of intermediate 24b (97% yield).

Preparation of Intermediate 34b

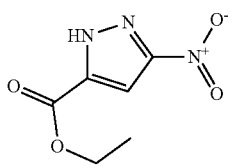

To a solution of 5-nitro-3-pyrazolecarboxylic acid (4.00 g, 25.46 mmol) in EtOH (80 mL) was added $SOCl_2$ (25 mL) and the mixture was stirred at 70° C. overnight. The mixture was evaporated under vacuo and the residue was added into water (20 mL). The mixture was extracted with EtOAc (3×50 mL). The combined organic layers were dried over $Na_2SO_4$, filtered and evaporated under reduced pressure to give 4 g of intermediate 34b (68% yield, 80% purity based on LC/MS) which was used in the next step without any further purification.

The intermediates in the table below were prepared by using an analogous method as reported for the preparation of intermediate 34b, starting from the respective starting materials.

| Intermediate number | Structure | Mass (mg) | Yield (%) |
|---|---|---|---|
| Intermediate 69b | 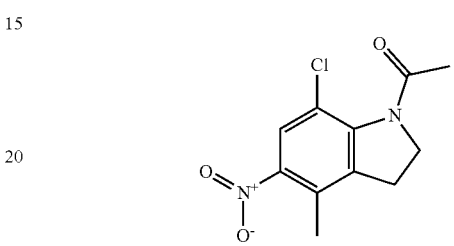<br>From 5-nitro-3-pyrazolecarboxylic acid and MeOH | 1600 | Quant. |
| Intermediate 89b | 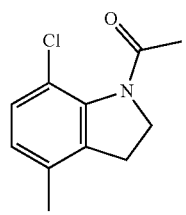<br>From 4-nitro-3-pyrazolecarboxylic acid and MeOH | 9500 | 87 |

Example A11c

Preparation of Intermediate 36c

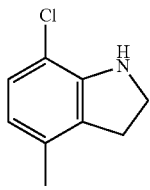

Sodium cyanoborohydride (759.86 mg, 12.1 mmol) was added slowly to a solution of 7-chloro-4-methyl-1H-indole (1.00 g, 6.04 mmol) in AcOH (10 mL). The mixture was stirred at rt for 3 h. The mixture was poured into a mixture of ice and 3M aqueous NaOH solution. An extraction was performed with EtOAc. The organic layer was washed with brine, dried over MgSO$_4$ and concentrated under reduced pressure to give 1.15 g of intermediate 36c (quant. yield, 88% purity, orange oil) which was directly engaged in the next step.

Preparation of Intermediate 37c

A mixture of intermediate 36c (1.15 g, 6.04 mmol based on 88% purity), acetyl chloride (0.64 mL, 9.06 mmol) and triethylamine (1.34 mL, 9.66 mmol) in DCM (20 mL) was stirred under N$_2$ at rt for 6 h. An extraction was performed with DCM and brine. The organic layer was dried over MgSO$_4$, evaporated and purified by silica gel chromatography (irregular SiOH 15-40 μm, 40 g, liquid injection with DCM, mobile phase gradient: from DCM/MeOH 100/0 to 95/05 in 10 CV). The fractions containing the product were combined and concentrated under vacuum to give 1.13 g of intermediate 37c (89%, light yellow solid).

Preparation of Intermediate 38c

A mixture of intermediate 37c (1.13 g, 5.39 mmol) and NaNO$_3$ (503.87 mg, 5.93 mmol) in TFA (20 mL) was stirred at rt for 18 h. The mixture was poured in a mixture of ice and aqueous NaHCO$_3$ and the product was extracted with EtOAc. The organic layer was washed with brine, dried over MgSO$_4$, evaporated and purified by silica gel chromatography (irregular SiOH 15-40 μm, 120 g, liquid injection with DCM, mobile phase gradient: from DCM/MeOH 100/0 to 95/05 in 10 CV). The fractions containing the product were combined and concentrated under vacuum to give 1.01 g of intermediate 38c (73%, brown solid).

Preparation of Intermediate 39c

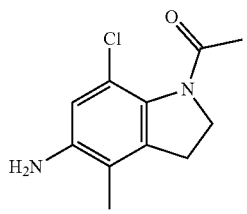

A mixture of intermediate 38c (1.00 g, 3.93 mmol), Zinc (2.57 g, 39.27 mmol) and AcOH (42.25 mL, 39.27 mmol) in MeOH (25 mL) was stirred at rt for 2.5 h. The mixture was filtered over a pad of Celite® and an extraction was performed with EtOAc. The organic layer was washed with HCl 1N. The aqueous layer was basified with NaOH 1N and extracted with EtOAc (twice). The organic layers were combined, washed with brine, dried over MgSO$_4$ and evaporated to dryness to give 550 mg of intermediate 39c (62%, light brown foam) which was directly engaged in the next step.

Example A12a

Preparation of Intermediate 35 (Mixture of 2 Diastereoisomers with Unknown Configuration (DIA A))

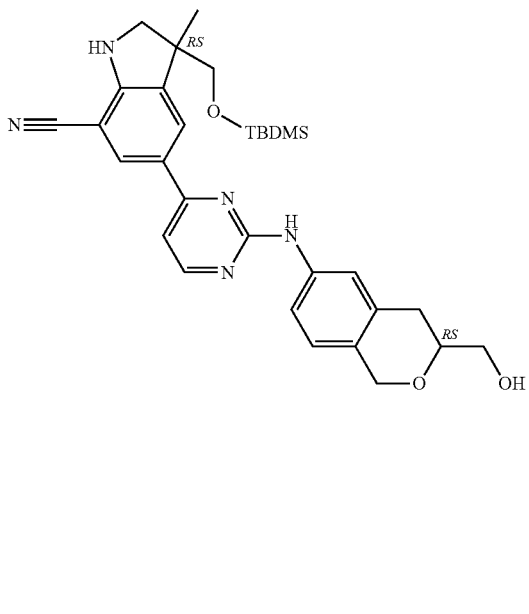

A solution of intermediate 33 (131.00 mg, 0.20 mmol) in a mixture of TFA (305.00 µL) and DCM (1.3 mL) was stirred at 0° C. for 30 min. The reaction mixture was poured onto ice, water and NH₄OH. The mixture was extracted with EtOAc and the organic layer was dried over MgSO₄, filtered and concentrated under vacuum to give 70 mg of intermediate 35 (72% yield) which was directly engaged in the next step without further purification.

Preparation of Intermediate 106

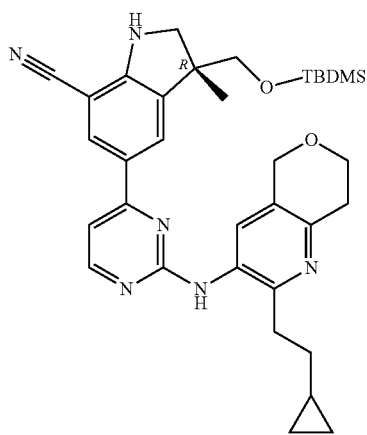

To a solution of intermediate 105 (450.00 mg, 0.65 mmol) in DCM (15 mL) was added TFA (1.46 mL, 19.0 mmol) and the mixture was stirred at rt for 20 min. The mixture was poured into a saturated solution of NaHCO₃ solution and stirred for 10 min. The layers were separated and the aqueous layer was extracted with DCM (twice). The combined organic layers were dried over MgSO₄, filtered and evaporated in vacuo. The crude residue was purified by silica gel chromatography (irregular SiOH, 15-40 µm, 24 g, liquid injection (DCM), mobile phase gradient: from CH₂Cl₂/MeOH 100/0 to 95/5) to give 260 mg of intermediate 106 (67% yield, yellow solid).

Preparation of Intermediate 119

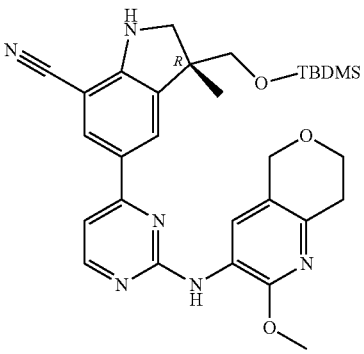

TFA (3.26 mL, 42.54 mmol) was added to a solution of intermediate 118 (692.00 mg, 0.85 mmol, 81% purity based on 1H NMR) in dry DCM (12 mL) at 0° C. The solution was allowed to warm to rt and stirred for 1 h. The solution was quickly poured into a saturated aqueous solution of NaHCO₃ and DCM was added. The layers were separated and the organic layer was dried over MgSO₄, filtered and evaporated in vacuo. The crude residue was purified by silica gel chromatography (Irregular SiOH 15-40 µm, 24 g, liquid loading (DCM), mobile phase gradient: from heptane 90%, EtOAc 10% to heptane 70%, EtOAc 30%) to give 338 mg of intermediate 119 (59% yield, 83% purity based on 1H NMR, yellow oil).

The intermediates in the table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 41 (Mixture of 2 diastereoisomers with unknown configuration (DIA B)) | From intermediate 34 | 124 | Quantitative |
| Intermediate 47 | From intermediate 46 | 521 Off-white solid | 64 Procedure with DCM/TFA (8:1, eq./eq.) |
| Intermediate 59 | From intermediate 58 | 379 brown solid | Quant. Procedure with DCM/TFA (3:1, eq./eq.) |

-continued

| Intermediate number | Structure | Mass (mg) | Yield (%) |
|---|---|---|---|
| Intermediate 62 | From intermediate 61 | 250 yellow solid | 68 Procedure with DCM/TFA (3:1, eq./eq.) |
| Intermediate 66 | From intermediate 65 | 137 yellow oil | 74 Procedure with DCM/TFA (6:1, eq./eq.) |
| Intermediate 76 | From intermediate 75 | 94 White solid | 40 Procedure with DCM/TFA (7:1, eq./eq.) |
| Intermediate 82 | From intermediate 81 | 219 orange solid | 50 Procedure with DCM/TFA (8:1, eq./eq.) |

-continued

| Intermediate number | Structure | Mass (mg) | Yield (%) |
|---|---|---|---|
| Intermediate 87 | From intermediate 86 | 570 Yellow oil | 77 Procedure with DCM/TFA (3:1, eq./eq.) |
| Intermediate 93 | From intermediate 92 | 135 Yellow oil | 60 |
| Intermediate 108 | From intermediate 107 | 160 Yellow residue | 69 Procedure with DCM/TFA (12:1, eq./eq.) |

-continued
| Intermediate number | Structure | Mass (mg) | Yield (%) | |
|---|---|---|---|---|
| Intermediate 112 | 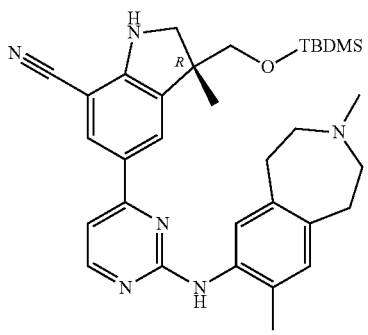<br>From intermediate 111 | 241<br>Yellow solid | 79 | Procedure with DCM/TFA (12:1, eq./eq.) |
| Intermediate 116 | 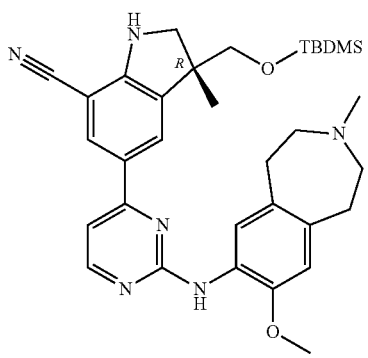<br>From intermediate 115 | 306<br>Yellow solid | 90 | Procedure with DCM/TFA (12:1, eq./eq.) |
| Mixture of intermediate 124 and 124' | 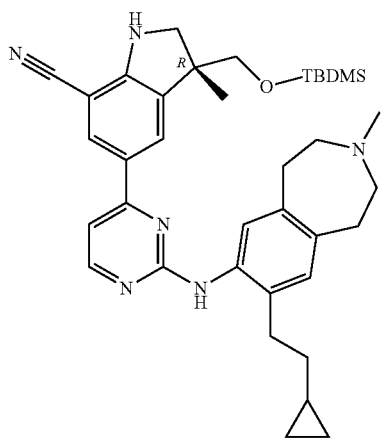<br>From intermediate 123 | 840<br>yellow solid | 64 | Procedure with DCM/TFA (10:1 eq./eq.) |
+

-continued

| Intermediate number | Structure | Mass (mg) | Yield (%) |
|---|---|---|---|
| | From intermediate 123' | | |
| Intermediate 127 | From intermediate 126 | 378 (75% purity based on LC/MS) Off-white solid | 68 |
| Intermediate 131 | From intermediate 130 | 523 Orange foam | Quant. Procedure with DCM/TFA (8:1, eq./eq.) |
| Intermediate 134 | From intermediate 133 | 310 Yellow solid | 54 Procedure with DCM/TFA (6:1, eq./eq.) |

-continued

| Intermediate number | Structure | Mass (mg) | Yield (%) |
|---|---|---|---|
| Intermediate 136 | From intermediate 135 | 235 | 81 Procedure with DCM/TFA (6:1, eq./eq.) |
| Intermediate 152 | From intermediate 135 | 700 | Quant. |
| Intermediate 160 | From intermediate 159 | 538 | Quant. Procedure with DCM/TFA (2:1, v./v.) |
| Intermediate 165 | From intermediate 164 | 260 | Quant. Procedure with DCM/TFA (4:1, v./v.) |

-continued
| Intermediate number | Structure | Mass (mg) | Yield (%) |
|---|---|---|---|
| Intermediate 178 | 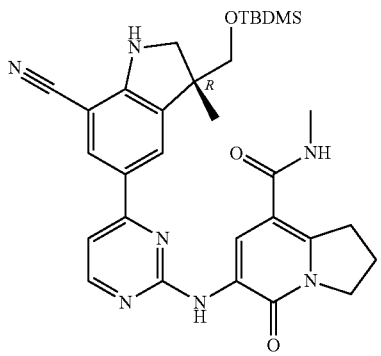 From intermediate 178 | 192 | 79 Procedure with DCM/TFA (10:1, v./v.) |
| Intermediate 188 | 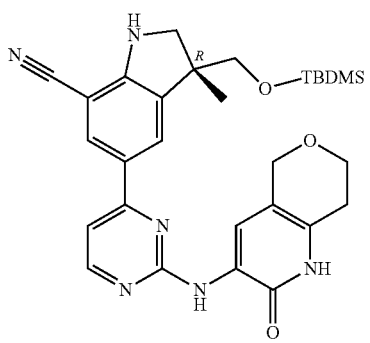 From intermediate 145 | 177 | 66 Procedure with DCM/TFA (3:1, v./v.) |
| Intermediate 216 | 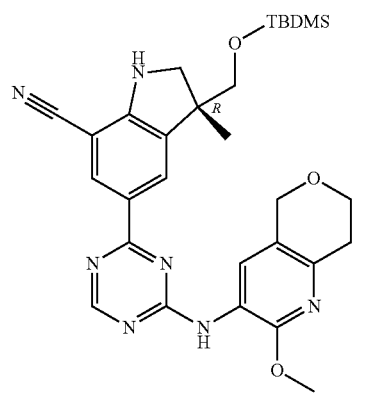 From intermediate 215 | 350 | 58 50% of purity evaluated by LC/MS Procedure with DCM/TFA (4:1, v./v.) |

Example A12b

Preparation of Intermediate 26b

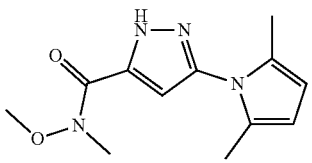 [SMILES: CON(C)C(=O)c1cc(-n2c(C)ccc2C)n[nH]1]

Intermediate 25b (4.40 g, 25.86 mmol) and 2,5-hexanedione (3.25 g, 28.43 mmol) were dissolved in acetic acid (30 mL) and toluene (90 mL). The mixture was refluxed for 2 h, then washed with water and DCM and layers were separated. The organic phase was dried over Na$_2$SO$_4$, filtered and concentrated under vacuo. The crude residue was purified by silica gel chromatography (elution: petroleum ether/EtOAc, 5/1). The desired fractions were collected and concentrated under vacuum to give 4.8 g of intermediate 26b (75% yield).

Preparation of Intermediate 27b

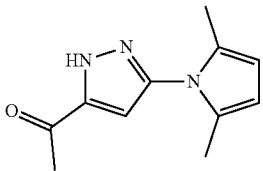

Intermediate 26b (4.80 g, 19.33 mmol) was dissolved in THF (140 mL) under N$_2$. Methylmagnesium bromide (3M in Et$_2$O) (16 mL, 48 mmol) was added dropwise at 0° C. and the resulting mixture was stirred at room temperature for 4 h. The mixture was quenched with an aqueous NH$_4$Cl solution (25 mL) and extracted with EtOAc (2×100 mL). The organic layer was dried over Na$_2$SO$_4$, filtered and concentrated. The residue was purified by silica gel chromatography (elution: petroleum ether/EtOAc, 4/1) to give 3.6 g of intermediate 27b (92% yield).

Preparation of Intermediate 28b

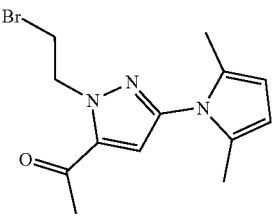 [SMILES: CC(=O)c1cc(-n2c(C)ccc2C)nn1CCBr]

Intermediate 27b (2.00 g, 9.84 mmol) was dissolved in CH$_3$CN (50 mL). 1,2-dibromoethane (7.4 g, 39.39 mmol) and K$_2$CO$_3$ (2.72 g, 19.71 mmol) were added and the mixture was refluxed for 2 h. The mixture was cooled to room temperature and filtered. The filtrate was concentrated and the crude residue was purified by silica gel chromatography (elution: Petroleum ether/EtOAc, 5/1). The desired fractions were collected and concentrated to give 2.8 g of intermediate 28b (92% yield).

The intermediates in the table below were prepared by using an analogous method as described in the preparation of intermediate 28b, starting from the respective starting materials. The most relevant minor deviations to the referenced method are indicated as additional information in the column 'Yield (%)'.

| Intermediate number | Structure | Mass (mg) | Yield (%) |
| --- | --- | --- | --- |
| Intermediate 35b | ![structure] From intermediate 34b and 1,2-dibromoethane | 500 90% purity based on LC/MS | 14 Procedure with acetone as solvent |

-continued

| Intermediate number | Structure | Mass (mg) | Yield (%) |
|---|---|---|---|
| Intermediate 42b | (structure) From intermediate 41b and tert-butyl bromoacetate | 1970 | 44 Procedure with 2.2 equiv. of K$_2$CO$_3$ and DMF as solvent |
| Intermediate 53b | (structure) From intermediate 41b and 2,2-dimethyloxirane | 2150 | 89 Procedure with 2.2 equiv. of K$_2$CO$_3$ and DMF as solvent |
| Intermediate 75b | (structure) From 4-nitro-1H-pyrazole and 3-bromo-1-propanol | 2200 | 58 Procedure with 2.4 equiv. of K$_2$CO$_3$ |
| Intermediate 94b | (structure) From intermediate 89b and 1,2-dibromoethane | 2310 | 18 Procedure with 5 equiv. of K$_2$CO$_3$ and acetone as solvent |

Example A12c

Preparation of Intermediate 43c

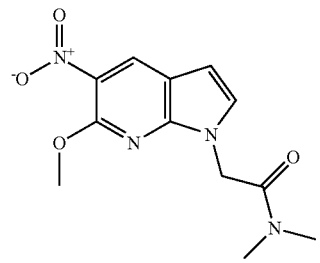

To a solution of 6-methoxy-5-nitro-1H-pyrrolo[2,3-b]pyridine (412.00 mg, 2.13 mmol) in dry DMF (10 mL) was added NaH (60% dispersion in mineral oil) (93.84 mg, 2.35 mmol) and the mixture was stirred at rt for 10 min. Then, 2-chloro-N,N-dimethylacetamide (241 µL, 2.35 mmol) was added and the reaction mixture was stirred at rt for 18 h. Celite® was added and a dry load was prepared under vacuum. The resulting crude product was purified by silica gel chromatography (regular SiOH 30 µm, 40 g, dry load with Celite®, mobile phase gradient: from DCM/MeOH 100/0 to 98/02 in 10 CV). The fractions containing the product were combined and concentrated under vacuum to give 530 mg of intermediate 43c (89% yield, yellow solid).

Preparation of Intermediate 44c

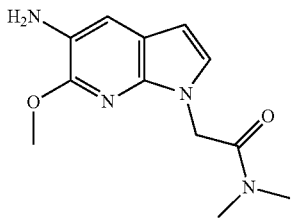 [SMILES: COc1nc2c(ccn2CC(=O)N(C)C)cc1N]

A suspension of intermediate 43c (530.00 mg, 1.91 mmol) and Pd/C (10%) (0.10 g, 0.09 mmol) in Me-THF (30 mL) and EtOH (40 mL) was stirred in the dark at rt for 20 h under $H_2$ atmosphere (1 bar). The mixture was then diluted with DCM, filtered over Celite® and the filtrate was evaporated to dryness under vacuum to give 490 mg of intermediate 44c (quant. yield, greenish residue) which was used as it in the next step.

Example A13a

Preparation of Intermediate 143

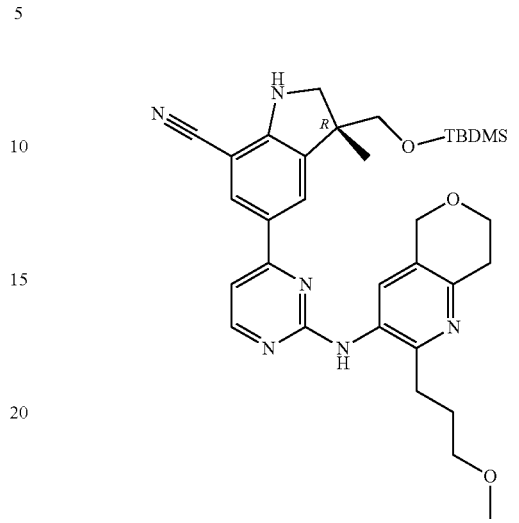

$SiO_2$ (40-63 µm) (1.57 g) was added to a solution of intermediate 142 (313.00 mg, 0.45 mmol) in toluene (4 mL) and the mixture was refluxed for 2 h. After cooling down to rt, the mixture was diluted with EtOAc and filtered on a glass frit. The filtrate was evaporated under vacuum to give 287 mg of intermediate 143 (quant. yield, yellow oil) which was directly engaged in the next step without further purification.

Preparation of Intermediate 146

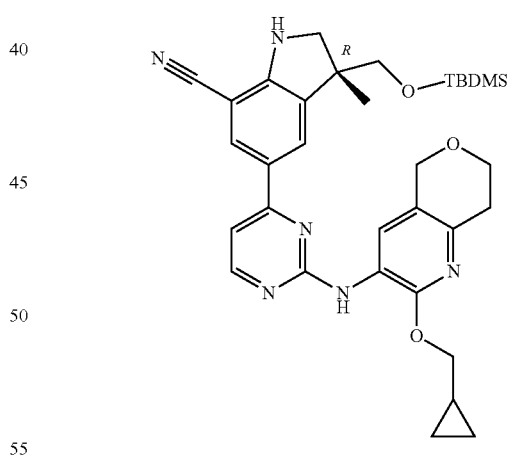

$SiO_2$ (1.74 g, 5 equiv. wt) was added to a solution of intermediate 145 (348.00 mg, 0.34 mmol, 69% of purity based on 1H NMR) in toluene (3 mL) and the mixture was refluxed for 2 h. After cooling down to rt, the mixture was diluted with EtOAc and filtered on a glass frit. The filtrate was evaporated in vacuo. The crude residue was purified by silica gel chromatography (Irregular SiOH 15-40 µm, 12 g, liquid loading (DCM), mobile phase gradient: from heptane 95%, EtOAc/MeOH (9:1) 5% to heptane 70%, EtOAc/MeOH (9:1) 30%) to give 255 mg of intermediate 146 (86% yield, 69% purity based on 1H NMR, yellow oil).

Preparation of Intermediate 149

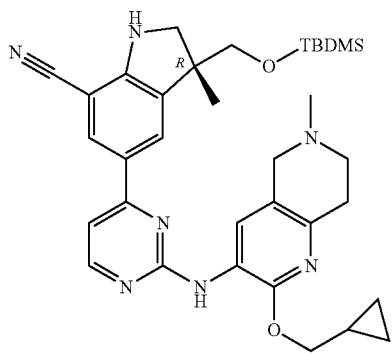

SiO$_2$ (40-63 μm) (0.43 g) was added to a solution of intermediate 148 (85.00 mg, 0.12 mmol) in toluene (1.04 mL) and the mixture was refluxed for 2 h. After cooling down to rt, the mixture was diluted with DCM and MeOH and filtered on a glass frit. The filtrate was evaporated in vacuo to give 65 mg of intermediate 149 (89% yield, yellow oil) which was used in the next step without further purification.

Preparation of Intermediate 184

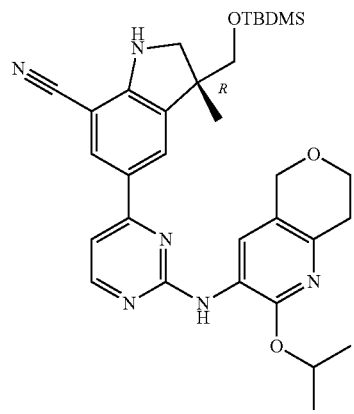

SiO$_2$ was added to a solution of intermediate 183 (160 mg; 0.233 mmol) in toluene (2.3 mL). The mixture was heated to 90° C. for two days. The mixture was filtered and washed with ethyl acetate. The filtrate was evaporated and the crude was purified by silica gel chromatography (Eluent:Heptane-EtOAc: 8/2). The fractions containing the product were mixed and concentrated to give 136 mg (99%) of intermediate 184.

Preparation of Intermediate 187

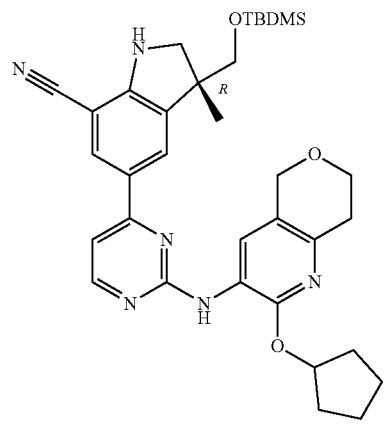

Intermediate 187 was prepared accordingly to intermediate 184 starting from intermediate 186 (152 mg; 93%).

Preparation of Intermediate 195

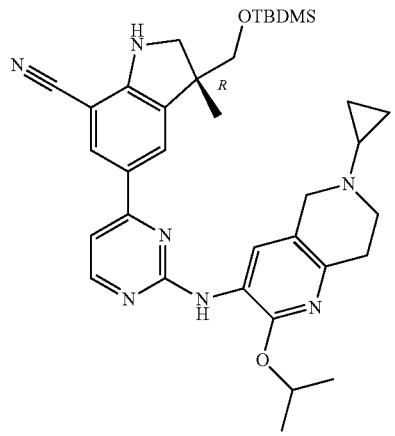

Intermediate 195 was prepared accordingly to intermediate 143 starting from intermediate 194 (120 mg).

Preparation of Intermediate 199

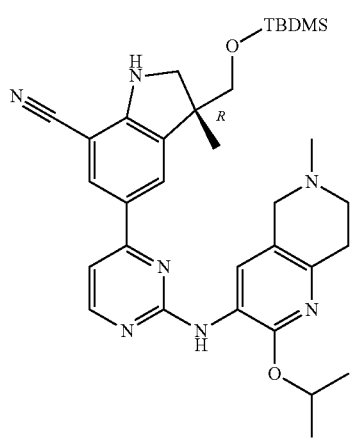

Intermediate 199 was prepared accordingly to intermediate 143 starting from intermediate 198 (664 mg; 81%).

Preparation of Intermediate 203

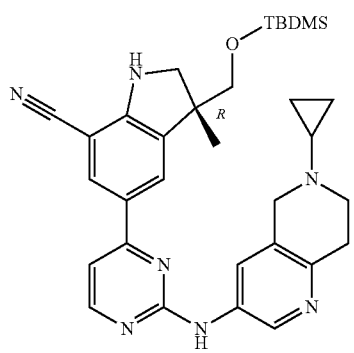

Intermediate 203 was prepared accordingly to intermediate 143 starting from intermediate 202 (110 mg; 99%).

Preparation of Intermediate 207

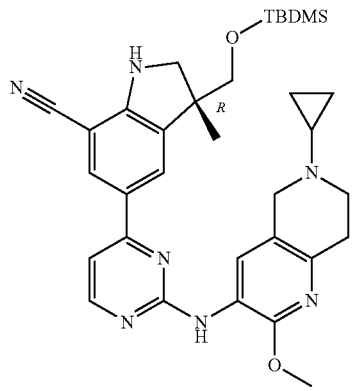

Intermediate 207 was prepared accordingly to intermediate 143 starting from intermediate 206 (120 mg, purity 68% based evaluated by LC/MS).

Preparation of Intermediate 213

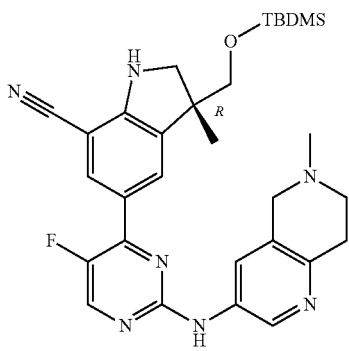

Intermediate 213 was prepared accordingly to intermediate 143 starting from intermediate 212 (130 mg, 95%).

Preparation of Intermediate 229

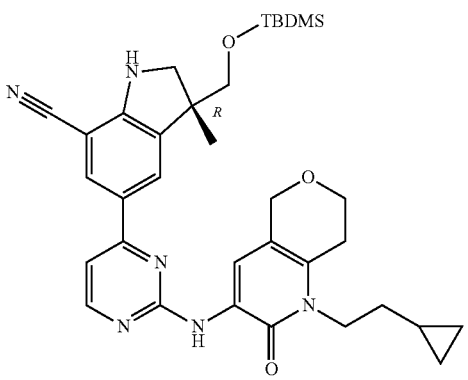

Intermediate 229 was prepared accordingly to intermediate 184 starting from intermediate 228 (135 mg; 96%).

Example A13b

Preparation of intermediate 70b

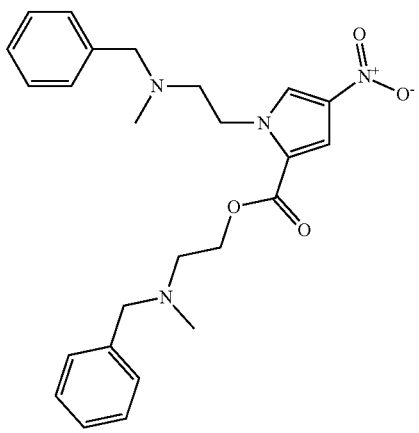 [SMILES: CN(CCOC(=O)c1cc([N+](=O)[O-])cn1CCN(C)Cc1ccccc1)Cc1ccccc1]

Cyanomethylenetributylphosphorane (2.91 mL, 11.10 mmol) was added to a stirred solution of intermediate 69b (950.00 mg, 5.55 mmol) and N-benzyl-N-methylethanolamine (1.36 mL, 8.33 mmol) in toluene (24.78 mL) at rt. The reaction mixture was stirred at rt for 9 h. Solvent was evaporated and the crude residue was purified via silica gel chromatography (Stationary phase: irregular SiOH 15-40 μm, 80 g, mobile phase gradient: from 80% Heptane, 20% EtOAc to 50% Heptane, 50% EtOAc) to give 1.3 g of intermediate 70b (52% yield).

Preparation of Intermediate 90b

The reaction was performed twice the same quantities of intermediate 89b (0.5 g, 2.922 mmol):

Cyanomethylenetributylphosphorane (1.41 mL, 5.38 mmol) was added to a solution of intermediate 89b (0.5 g, 2.92 mmol) and 2-(isopropylamino)ethanol (468.63 μL, 4.075 mmol) in toluene (14 mL) in a sealed tube were stirred at 110° C. using one single mode microwave (Masterwave BTR Anton Paar®) with a power output ranging from 0 to 1700 W for 30 min. The reaction mixtures were diluted with EtOAc, mixed and washed with a 10% aqueous solution of $K_2CO_3$, water and a solution of saturated NaCl. The layers were separated and the organic layer was dried over $MgSO_4$, filtered and the solvent was removed under reduced pressure.

The crude (3.8 g) was purified by silica gel chromatography (Irregular SiOH 40 μm 80 g; Mobile phase 100% DCM to 97% DCM, 3% MeOH, 0.3% $NH_4OH$. The pure fractions were combined and the solvent was evaporated to give 458 mg of an intermediate fraction which was purified again by silica gel chromatography (Irregular SiOH 40 μm 40 g; Mobile phase from 80% Heptane, 20% AcOEt to 40% Heptane, 50% AcOEt, 10% MeOH, 0.1% $NH_4OH$. The pure fractions were combined and the solvent was evaporated to give 249 mg (19%) of intermediate 90b.

Preparation of Intermediate 71b

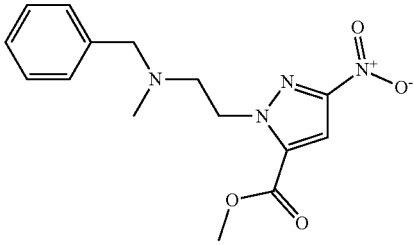 [SMILES: COC(=O)c1cc([N+](=O)[O-])nn1CCN(C)Cc1ccccc1]

A mixture of intermediate 70b (1.10 g, 2.44 mmol) in MeOH (7.37 mL) was stirred at 100° C. in a sealed tube using one single mode microwave (Anton Paar monowave 300®) with a power output ranging from 0 to 850 W for 10 min. The solution was evaporated under reduced pressure to give 775 mg of intermediate 71b (quant. yield) which was used in the next step without further purification.

Example A13c

Preparation of Intermediate 48c

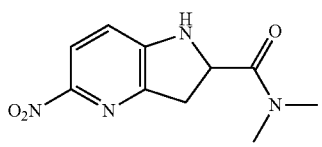 [SMILES: CN(C)C(=O)C1Cc2nc([N+](=O)[O-])ccc2N1]

A mixture of 5-nitro-indoline-2-carboxylic acid (1.8 g; 8.65 mmol), dimethylamine hydrochloride (1.41 g; 17.30 mmol), Propylphosphonic acid anhydride (13.8 g; 21.62 mmol; 50% in EtOAc and TEA (5 mL; 34.6 mmol) in DCM (100 mL) was stirred at room temperature overnight. The mixture was poured into water and extracted with DCM (50 mL*3). The organic layers were combined and washed with brine (30 mL), dried over $Na_2SO_4$, filtered and concentrated. The intermediate product was washed with EtOH and dried under vacuo to give 1.8 g (88%) of intermediate 171c as a yellow solid.

Preparation of Intermediate 49c

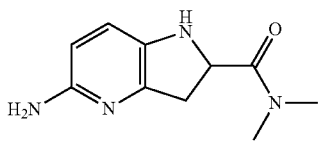

A mixture of intermediate 48c (1.8 g; 7.65 mmol) in EtOH (100 mL) was hydrogenated at room temperature (atmospheric pressure) with Pd/C 10% as a catalyst under 1 atmosphere of hydrogen. After overnight stirring, the reaction mixture was filtered and the solvent was removed to give 1.3 g (83%) of intermediate 49c as a brown sticky oil.

It was directly used for next step.

Example A14a

Preparation of Intermediate 17

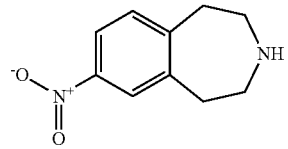

In a round bottom flask, potassium nitrate (3.60 g, 35.66 mmol) was added portionwise at 5° C. to a solution of 2,3,4,5-tetrahydro-1H-3-benzazepine (5.00 g, 33.96 mmol) in $H_2SO_4$ (34 mL). The reaction mixture was stirred for 10 min. Then, the reaction mixture was poured into ice water and carefully basified with solid $K_2CO_3$. The aqueous layer was extracted with EtOAc, dried over $MgSO_4$, filtered and evaporated to dryness to give 4.65 g of intermediate 17 (71% yield, brown oil) which was directly engaged in the next step without further purification.

Example A14b

Preparation of Intermediate 29b

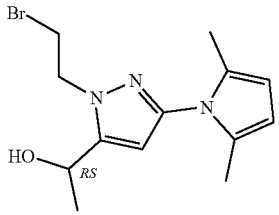 [SMILES: Cc1ccc(C)n1-c1cc(C(C)O)n(CCBr)n1]

To a solution of intermediate 28b (2.80 g, 9.03 mmol) in MeOH (50 mL) was added $NaBH_4$. The reaction mixture was stirred at room temperature for 2 h. The mixture was quenched with water, extracted with DCM. The organic phase was washed with brine, dried over $Na_2SO_4$, filtered and concentrated in vacuo to give 2.6 g of intermediate 29b (92% yield) which was used in the next step without any further purification.

The intermediate in the table below was prepared by using an analogous method as described for the preparation of intermediate 29b, starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 36b | 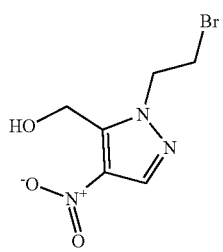<br>From intermediate 35b | 500<br>80% purity based on LC/MS | 94<br>Procedure with EtOH as solvent |

Preparation of Intermediate 95b

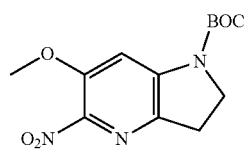

Diisobutylaluminium hydride in DCM (1M) (5.92 mL, 33.23 mmol) was added dropwise to a dry solution of intermediate 94b (2.31 g, 8.31 mmol) in DCM (22.35 mL) at rt under nitrogen (syringe pump, 20 mL/h). The reaction mixture was stirred at rt for 4 h. Additional diisobutylaluminium hydride in DCM (5.922 mL, 0.798 g/mL, 33.23 mmol) was added dropwise (syringe pump, 20 mL/h) and the resulting solution was stirred at rt for 16 h. The reactive mixture was poured onto ice and water. The mixture was acidified with a 3N aqueous solution of HCl, extracted twice with DCM, filtered over Celite® and the layers were separated. The organic layer was dried over $MgSO_4$, filtered and evaporated. The crude residue was purified by silica gel chromatography (Irregular SiOH 40 µm, 80 g, mobile phase gradient: from 80% Heptane, 20% EtOAc to 50% Heptane, 50% EtOAc). The pure fractions were combined and the solvent was evaporated to give 1.04 g of intermediate 95b (50% yield).

Example A14c

Preparation of Intermediate 51c

To a stirred solution of 6-(methoxy)-5-nitro-2,3-dihydro-1-H-indole (300 mg; 1.33 mmol) in DCM (5 mL) was added trimethylamine (463 µL; 3.32 mmol), di-tert-butyldicarbonate (319 mg; 1.46 mmol) and 4-dimethylaminopyridine (16 mg; 0.13 mmol). The reaction mixture was stirred at room temperature overnight. Then, the mixture was stirred for 12 hrs at 40° C. Water (10 mL) was added and the mixture was extracted with DCM (3*20 mL). The combined organic layers were washed brine and dried over Na₂SO₄ and the solvent was removed under vacuum. The resulting residue (500 mg) was purified by flash column chromatography over silica gel (eluent: petroleum ether/ethyl acetate from 100/0 to 60/40). The desired fractions were collected and the solvent was concentrated to dryness under vacuum to give 340 mg (87%) of intermediate 51c.

Preparation of Intermediate 52c

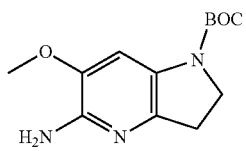

A mixture of intermediate 51c (340 mg; 1.15 mmol) in MeOH (5 mL) and EtOAc (5 mL) was hydrogenated overnight at room temperature (25 psi of hydrogen) with Pd/C 10% as catalyst. The catalyst was filtered off and the filtrate was evaporated under reduced pressure to afford 240 mg (79%) of intermediate 52c.

Example A15a

Preparation of Intermediate 24

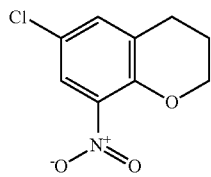

Sodium nitrite (479.00 mg, 6.95 mmol) was added to a solution of intermediate 23 (1.00 g, 5.94 mmol) in TFA (36 mL) and the mixture was stirred at rt for 4 h. The reaction mixture was diluted with EtOAc and a 10% aqueous solution of Na₂CO₃. The layers were separated and the organic layer was dried over MgSO₄, filtered and the solvent was removed under reduced pressure. The crude residue was purified by silica gel chromatography (irregular SiOH 15-40 µm, 40 g, dry loading on celite, mobile phase gradient: from heptane/EtOAc 100/0 to 40/60) to give 340 mg of intermediate 24 (27% yield, off-white solid).

The intermediate in the table below was prepared by using an analogous method starting from the respective starting materials.

| Intermediate number | Structure | Mass (mg) | Yield (%) |
|---|---|---|---|
| Intermediate 54 | 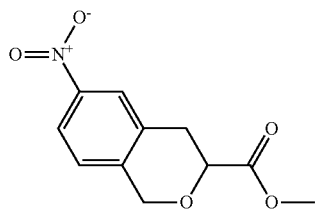 [SMILES: COC(=O)C1Cc2cc([N+](=O)[O-])ccc2CO1]<br>From intermediate 53 | 732 | 56 |

Example A15a

Preparation of Intermediate 29

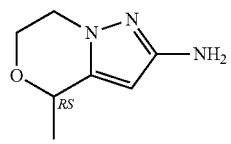

To fuming nitric acid (19.48 mL, 426.61 mmol) previously cooled between −40 and −50° C. was added dropwise intermediate 28 (4.10 g, 21.33 mmol) in AcOH (8.2 mL, 143.24 mmol). The reaction mixture was stirred between −40 and −50° C. for 40 min, poured onto ice and extracted with DCM. The organic layer was dried over MgSO₄, filtered and evaporated under vacuum. The residue was purified by silica gel chromatography (spherical SiOH 30 µm, mobile phase: DCM 100%). The pure fractions were combined and the solvent was removed in vacuo to give 5.2 g of intermediate 29 (quant. yield).

Example A15b

Preparation of Intermediate 31b

To a solution of intermediate 30b (913.00 mg, 3.95 mmol) in EtOH (3 mL) was added a mixture of KOH (664.00 mg, 11.86 mmol) and hydroxylamine hydrochloride (1.65 g, 23.71 mmol) in H₂O (6 mL) and EtOH (6 mL). The resulting mixture was refluxed overnight. The solution was concentrated under reduced pressure and the crude residue was dissolved in EtOAc (10 mL), washed with water and brine, dried over Na₂SO₄, filtered and concentrated in vacuo. The crude residue was purified by silica gel chromatography (eluent: 100% EtOAc) to give 200 mg of intermediate 31b (33% yield).

Example A15c

Preparation of Intermediate 55c

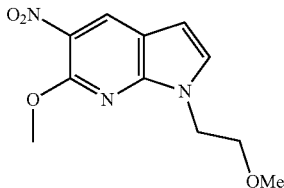 [SMILES: COCCn1ccc2cc([N+](=O)[O-])c(OC)nc21]

To a solution of 6-methoxy-5-nitro-7-azaindole (144 mg; 0.745 mmol) in dry DMF (4 mL) was added sodium hydride (33 mg; 0.82 mmol; 60% dispersion in oil) and the mixture was stirred at room temperature for 30 min. Then 2-bromoethylmethyl ether (77 µL; 0.82 mmol) was added, and the reaction mixture was stirred at room temperature for 16 h, then evaporated, taken up with a mixture of DCM/MeOH (3:1) and combined 2 other reactions respectively performed on 10 mg and 50 mg of 6-methoxy-5-nitro-7-azaindole. Celite was added and a dry load was prepared under vacuum. The resulting residue was purified by silica gel chromatography (regular silica 30 µm, 25 g, dry load (Celite), mobile phase gradient: from heptane 100% to heptane 70%, EtOAc/MeOH (90:10) 30% in 10 CV) to afford, after evaporation in vacuo, 190 mg (71%, combined yield) of intermediate 55c as an orange oil.

Preparation of Intermediate 56c

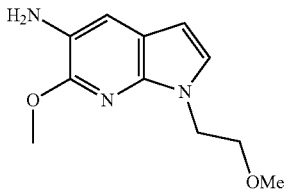

Intermediate 56c was prepared accordingly to intermediate 49c starting from intermediate 55c (110 mg; 67%).

Example A16a

Preparation of Intermediate 44

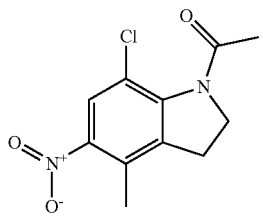 [SMILES: CC(=O)N1CCc2c(C)c([N+](=O)[O-])cc(Cl)c21]

A mixture of intermediate 43 (1.13 g, 5.39 mmol) and sodium nitrate (503.87 mg, 5.93 mmol) in TFA (20 mL) was stirred at rt for 18 h. The mixture was poured into a mixture of ice and aqueous NaHCO$_3$ and extracted with EtOAc. The organic layer was washed with brine, dried over MgSO$_4$, filtered and evaporated under reduced pressure. The crude residue was purified by silica gel chromatography (irregular SiOH 15-40 µm, 120 g, liquid injection with DCM, mobile phase gradient: DCM/MeOH from 100:0 to 95:05 in 10 CV). The pure fractions were combined and the solvent was removed in vacuo to give 1.01 g of intermediate 44 (74% yield, brown solid).

The intermediates in the table below were prepared by using an analogous method starting from the respective starting materials.

| Intermediate number | Structure | Mass (mg) | Yield (%) |
|---|---|---|---|
| Intermediate 73 | ![](From intermediate 72) | 180 Yellow solid | 19 |
| Intermediate 79 | ![](From intermediate 78) | 378 Yellow solid | 72 |
| Intermediate 84 | ![](From intermediate 83) | 470 Brown oil | 79 |

Example A16b

Preparation of Intermediate 41b

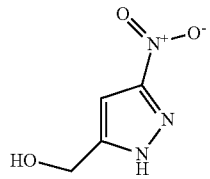

BH$_3$.THF (1M) (166.46 mL, 166.46 mmol) was added dropwise to a stirred solution of 3-nitro-1H-pyrazol-5-carboxylic acid (8.70 g, 55.38 mmol) in THF (131 mL) at 0° C. under nitrogen. The reaction mixture was stirred at rt for 16 h. HCl (2M in H$_2$O) (43.5 mL, 87 mmol) was added and the reaction mixture was stirred at reflux for 1 h. The reaction mixture was cooled down to rt and concentrated under reduce pressure to a volume of approximately 30 mL. The aqueous layer was extracted 3 times with EtOAc, dried over MgSO₄, filtered and evaporated under vacuo to give 8 g of intermediate 41b (quantitative yield) which was used in the next step without any further purification.

The intermediates in the table below were prepared by using an analogous method as reported for the preparation of intermediate 41b, starting from the respective starting materials. The most important minor deviations to the referenced method are indicated as additional information in the column 'Yield (%)'.

| Intermediate number | Structure | Mass (mg) | Yield (%) |
|---|---|---|---|
| Intermediate 49b | From intermediate 48b | 690 | Quant. Procedure with 2 equivalent of BH₃•THF |
| Intermediate 80b | From intermediate 14b | 439 | 16 Procedure with 2 equivalent of BH₃•THF |

Example A17a

Preparation of Intermediate 18:0

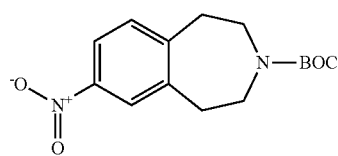

Boc₂ (2.00 g, 9.16 mmol) was added portionwise to a solution of intermediate 17 (880.00 mg, 4.58 mmol) in CH₃CN (30 mL) and the reaction mixture was stirred at rt for 15 h. The reactive mixture was poured into H₂O and extracted with EtOAc. The organic layer was dried over MgSO₄, filtered and evaporated to dryness. The residue was purified by silical gel chromatography (irregular SiOH 35-40 μm, 40 g, mobile phase gradient: from 100% heptane, 0% EtOAc to 60% heptane, 40% EtOAc). The pure fractions were collected and evaporated to dryness to give 1.07 g of intermediate 18 (80% yield).

Alternative Preparation of Intermediate 18

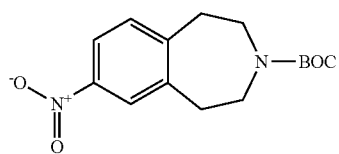

To a solution of intermediate 17 (5.28 g, 27.46 mmol) in TEA (8.77 mL, 63.15 mmol) and DCM (274 mL) were added at rt Boc₂O (14.98 g, 68.64 mmol) and DMAP (0.67 g, 5.49 mmol). The reaction mixture was stirred at rt for 13 h. The solvent was evaporated in vacuo and the crude residue was dissolved in EtOAc and washed with sat. NaHCO₃ solution and brine. The organic layer was dried over MgSO₄, filtered and concentrated under vacuo. The crude product was purified by silical gel chromatography (SiO₂, mobile phase gradient: 95% hexane, 5% EtOAc to 50% hexane, 50% EtOAc). The pure fractions were collected and evaporated to dryness to give 7.3 g of intermediate 18 (91% yield).

Preparation of Intermediate 49

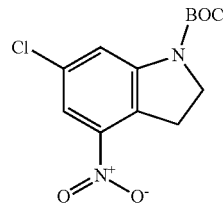 [SMILES: CC(C)(C)OC(=O)N1CCc2c1cc(Cl)cc2[N+](=O)[O-]]

Boc₂O (356.04 mg, 1.63 mmol) was added to a solution of intermediate 48 (270.00 mg, 1.36 mol) in THE (11 mL) and the solution was stirred at rt for 3 days. DMAP (16.61 mg, 0.14 mmol) and additional Boc₂O (356.04 mg, 1.63 mmol) were added and the mixture was stirred at 60° C. in a sealed tube for 3 h. The reaction mixture was cooled to rt and was diluted with EtOAc and water. The organic layer was dried over MgSO₄, filtered and the solvent was removed under reduced pressure to give 400 mg of intermediate 49 (98% yield, yellow solid) which was directly engaged in the next step without further purification.

Example A17b

Preparation of Intermediate 43b

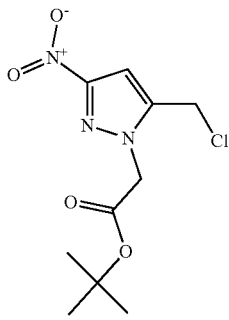 [SMILES: CC(C)(C)OC(=O)Cn1nc([N+](=O)[O-])cc1CCl]

MsCl (1.17 mL, 15.16 mmol) was added dropwise to a stirred solution of intermediate 42b (1.95 g, 7.58 mmol) and TEA (1.58 mL, 11.37 mmol) in DCM (34.8 mL) at rt. The reaction mixture was stirred at rt for 2 h. MsCl (1.17 mL, 15.16 mmol) was added dropwise and the reaction mixture was stirred at rt for 24 hours. Water was added and the residue was extracted with DCM, dried over $MgSO_4$, filtered and evaporated under vacuum to give 3.6 g of intermediate 43b (quant. yield) which was used in the next step without any further purification.

The intermediate in the table below was prepared by using an analogous method as reported for the preparation of intermediate 43b, starting from the respective starting materials. The most important minor deviations to the referenced method are indicated as additional information in the column 'Yield (%)'.

| Intermediate number | Structure | Mass (mg) | Yield (%) |
|---|---|---|---|
| Intermediate 96b | From intermediate 95b | 1310 | Quantitative. Procedure with 3 equiv. of MsCl and 3 equiv. of TEA |

Example A18a

Preparation of Intermediate 19:

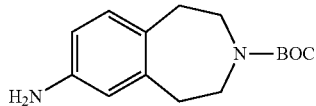

Intermediate 18 (7.30 g, 24.97 mmol) was dissolved in MeOH (300 mL) and the solution was purged using vacuum and nitrogen. Pd/C (10 wt. %, 1.00 g, 1.00 mmol) was added and the reaction mixture was purged with hydrogen and stirred at rt under an atmosphere of hydrogen (1 bar) for 15 h. The reaction mixture was filtered through Celite® and washed with MeOH. The filtrate was concentrated to dryness and the residue was purified by silica gel chromatography (mobile phase: $DCM/MeOH/NH_3$). The pure fractions were collected and evaporated to dryness to give 6.6 g of intermediate 19 (quant. yield).

Preparation of Intermediate 101

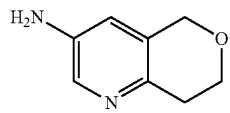

Intermediate 100 (1.30 g, 7.22 mmol) was dissolved in MeOH (77 mL) and the solution was degassed by $N_2$ bubbling. Pd/C (10% wt, 767.89 mg, 0.72 mmol) was added and the mixture was hydrogenated under an atmosphere of $H_2$ (1 bar) at rt for 16 h. The reaction mixture was filtered on a pad of Celite® and the solvent was removed under reduced pressure to give 1.03 g of intermediate 101 (95% yield, brown solid) which was used in the next step without further purification.

The intermediate in the table below was prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermdiate 30 | From intermediate 29 | 1060 | 23 |
| Intermediate 158 | From Indoline,1-acetyl-6-methoxy | 320 | 96 Procedure with MeOH/ EtOAc: 1/1 as solvent |
| Intermediate 163 | From intermediate 162 | 850 | Quant. Procedure with EtOH as solvent |
| Intermediate 169 | From intermediate 168 | 350 | 55 Based on a purity of 80% evaluated by LC/MS Procedure with EtOH as solvent |
| Intermediate 172 | From intermediate 171 | 1300 | 83 Procedure with EtOH as solvent |

Preparation of Intermediate 25

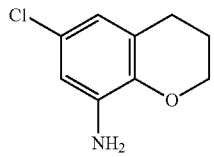 [SMILES: Nc1cc(Cl)cc2c1OCCC2]

Zinc (10.41 mg, 0.16 mmol) was added to a solution of intermediate 24 (340.00 mg, 1.59 mmol) in AcOH (25 mL) and the mixture was stirred at rt for 20 h. The solvent was removed under reduced pressure. The residue was taken up with EtOAc and was basified with an aqueous saturated solution of $NaHCO_3$. The layers were separated and the organic layer was dried over $MgSO_4$, filtered and the solvent was removed under reduced pressure to give 250 mg of intermediate 25 (86% yield, brown oil).

Preparation of Intermediate 38

A solution of intermediate 37 (0.78 g, 3.62 mmol) in MeOH (29.37 mL, 725.05 mmol) was hydrogenated at rt with RaNi (0.79 g, 13.54 mmol) under 3 bars pressure for 12 h. The catalyst was filtered over a pad of Celite® and the filtrate was evaporated to dryness. The residue was purified by silica gel chromatography (Irregular SiOH 40 μm, mobile phase: 100% DCM). The pure fractions were evaporated to give 515 mg of intermediate 38 (77% yield).

Preparation of Intermediate 45

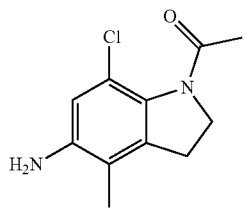

A mixture of intermediate 44 (1.00 g, 3.93 mmol), Zinc (2.57 g, 39.26 mmol) and AcOH (42.25 mL, 39.26 mmol) in MeOH (25 mL) was stirred at rt for 2.5 h. The mixture was filtered over a pad Celite®. Then, an extraction was performed with EtOAc and HCl 1N. The aqueous layer was basified with NaOH 1N and extracted with EtOAc (twice). The organic layers were washed with brine, dried with $MgSO_4$, filtered and evaporated under vacuum to give 550 mg of intermediate 45 (62% yield, light brown foam) which was directly engaged in the next step without any further purification.

The intermediates in the table below were prepared by using an analogous method starting from the respective starting materials.

| Intermediate number | Structure | Mass (mg) | Yield (%) |
|---|---|---|---|
| Intermediate 74 | From intermediate 73 | 116 Orange solid | 73 |
| Intermediate 80 | From intermediate 79 | 271 (90% purity based on LC/MS) orange solid | 63 |

Preparation of Intermediate 50

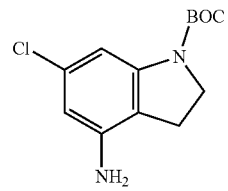 [SMILES: CC(C)(C)OC(=O)N1CCc2c(N)cc(Cl)cc21]

In a sealed tube, a suspension of intermediate 49 (390.00 mg, 1.31 mmol), $NH_4Cl$ (279.33 mg, 5.22 mmol) and iron powder (364.54 mg, 6.53 mmol) in EtOH (7 mL) and water (7 mL) was stirred at 85° C. for 2 h. The reaction mixture was diluted with EtOAc and water and, the layers were separated. The organic layer was dried over $MgSO_4$, filtered and the solvent was removed under reduced pressure to give 390 mg of intermediate 50 (90% yield, 83% purity based on 1H NMR, yellow oil) which was directly engaged in the next step without further purification.

The intermediates in the table below were prepared by using an analogous method starting from the respective starting materials.

| Intermediate number | Structure | Mass (mg) | Yield (%) |
|---|---|---|---|
| Intermediate 57 | 6-chloro-8-amino chroman-3-(R)-carboxylic acid N,N-dimethylamide<br>From intermediate 55 | 222<br>Colorless oil | Quant. |
| Intermediate 60 | 6-chloro-8-amino chroman-3-(S)-carboxylic acid N,N-dimethylamide<br>From intermediate 56 | 230<br>Colorless oil | 99 |
| Intermediate 64 | 1-(6-chloro-4-amino-2,3-dihydro-1H-indol-1-yl)-2-(dimethylamino)ethan-1-one<br>From intermediate 63 | 152 | 70 |
| Intermediate 69 | 2-(6-chloro-4-amino-2,3-dihydro-1H-indol-1-yl)-N-methylacetamide<br>From intermediate 68 | 192<br>brown oil | 58 |
| Intermediate 85 | 6-chloro-8-amino-3-(RS)-(dimethylamino)chroman<br>From intermediate 84 | 320<br>brown oil | 77 |

| Intermediate number | Structure | Mass (mg) | Yield (%) |
|---|---|---|---|
| Intermediate 91 | ![structure]<br>From intermediate 90 | 129 | 43 |
| Intermediate 155 | ![structure]<br>From intermediate 154 | 350 | 63<br>Procedure in an open vessel with MeOH as solvent |
| Intermediate 232 | ![structure]<br>From intermediate 231 | 600 | 63<br>in an open vessel with MeOH as solvent |

Preparation of Intermediate 129

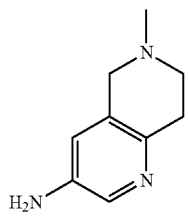

To a solution of intermediate 128 (1.50 g, 7.76 mmol) in EtOH (35 mL) and Me-THF (35 mL) was added Pd/C (10 wt. %) (826.24 mg, 0.77 mmol) and the mixture was stirred under H$_2$ atmosphere for 2 h. The mixture was filtered over a pad of Celite® and the cake was washed with EtOH. The filtrate was evaporated in vacuo to give 1.33 g of intermediate 129 which crystallized upon standing (quant. yield, 95% purity based on 1H NMR, yellow oil).

Example A18b

Preparation of Intermediate 61b

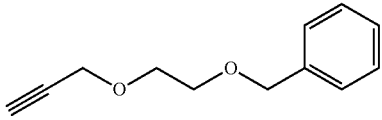

In a 500 mL triple-neck flask under N$_2$, NaH (95%) (7.91 g, 313 mmol) was suspended at 0° C. in dry Me-THF (200 mL). 2-benzyloxyethanol (31.75 g, 209 mmol) was added dropwise at 0-5° C. over 30 min, and the mixture was stirred at rt for 30 min. Propargyl bromide (80% in toluene) (45.35 mL, 417 mmol) was then added dropwise at 0-5° C. over 30 min and the mixture was allowed to reached rt, then refluxed (oil bath temperature: 85° C.) for 16 h and cooled down to rt. A 10% aqueous solution of NH$_4$Cl (~100 mL) was added dropwise to the reaction mixture at 0-5° C. over 30 min under stirring, and the resulting mixture was extracted with EtOAc (5×200 mL), dried over MgSO$_4$, filtered and evaporated in vacuo. The crude residue was then suspended in 500 mL of a mixture heptane/EtOAc (9:1). Irregular silica was added and the suspension was stirred for 30 min, then filtered. The plug of silica was washed with heptane/EtOAc (9:1, 3×500 mL). The solvent was evaporated to give 38.6 g of intermediate 61b (97% yield, clear yellow oil).

Preparation of Intermediate 62b

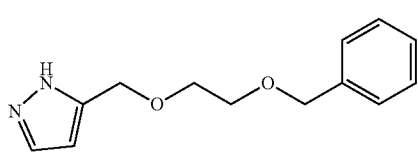 [SMILES: c1ccc(COCCOCc2ccn[nH]2)cc1]

In a 300 mL-sealed tube, intermediate 61b (32.32 g, 170 mmol) and (trimethylsilyl)diazomethane (2M in hexane) (87.50 mL, 175 mmol) were mixed and the tube was sealed and stirred at 135° C. for 20 h. After cooling down to rt, the mixture was evaporated under vacuum to give 51 g of intermediate 62b (quant. yield, yellow-brown oil) which was used in the next step without any further purification.

Preparation of Intermediate 63b

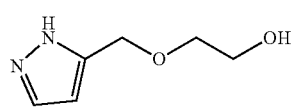

In a 1 L autoclave, Pd(OH)$_2$ on carbon (9.25 g, 6.6 mmol) was added to a solution of intermediate 62b (51.00 g, 0.22 mol) in EtOH (400 mL). The mixture was hydrogenated during 18 h at 100° C. under 10 bar. The mixture was cooled down to rt and filtered with DCM and EtOH on Celite®. The solvents were evaporated under vacuum and the resulting residue was dried under vacuum to give 25.7 g of intermediate 63b (82% yield, colorless oil).

Preparation of Intermediate 64b

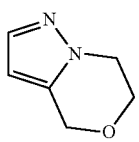

To a mixture of intermediate 63b (3.27 g, 23.0 mmol) in dry DCM (on amylene, EtOH free) (490 mL) was added cyanomethylenetributylphosphorane (7.23 mL, 28 mmol). The mixture was then stirred for 60 hours at 40° C. The solvent was evaporated and the mixture was purified via silica gel chromatography (Stationary phase: irregular bare silica 150 g, mobile phase: 30% heptane, 70% EtOAc) to afford, after evaporation, 1.57 g of intermediate 64b (55% yield, clear brown oil).

Preparation of Intermediate 65b

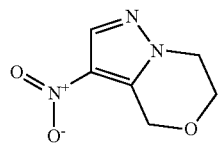 [SMILES: O=[N+]([O-])c1cnn2c1COCC2]

Intermediate 64b (1.57 g, 12.6 mmol) was dissolved in sulfuric acid (98%) (20 mL) and the reaction mixture was cooled to 0° C. A mixture of nitric acid (63%) (10.4 mL) in sulfuric acid (98%) (12 mL) was added dropwise and the reaction mixture was stirred at room temperature for 3.5 hours. The reaction was then poured into ice/water and extracted with DCM (5×200 mL). The combined organic layers were washed with a saturated solution of NaHCO$_3$ (twice), dried over MgSO$_4$, filtered, and evaporated in vacuo to give 1.4 g of intermediate 65b (65% yield, off-white solid).

Example A19a

Preparation of Intermediate 20

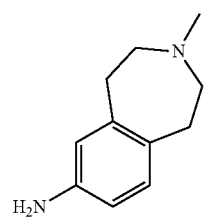

In a Schlenk flask, LiAlH$_4$ (4.34 g, 114.35 mmol) was added to a solution of intermediate 19 (5.00 g, 19.1 mmol) in dry THE (400 mL). The reaction mixture was heated at 60° C. for 6 h, then quenched with addition of water (4.34 mL, very slow addition), 3N solution of NaOH (4.34 mL) and water (13 mL). The mixture was stirred at rt for 5 min, diluted with EtOAc and water. The layers were separated and the organic layer was dried over MgSO$_4$, filtered and the solvent was removed under reduced pressure to give 3.43 g of intermediate 20 (quant. yield, orange oil).

The intermediates in the table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 97 | 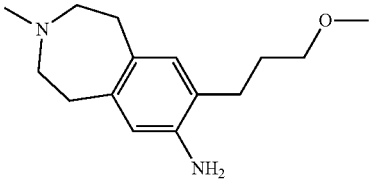<br>From intermediate 96 | 450<br>Yellow oil | Quant. |
| Intermediate 110 | 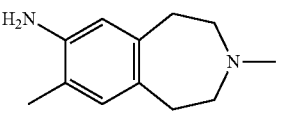<br>From intermediate 109 | 346<br>Yellow solid | 74 |
| Intermediate 114 | 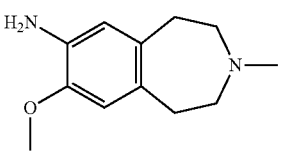<br>From intermediate 113 | 278<br>Yellow oil | 72 |
| Mixture of intermediate 122 and intermediate 122' | 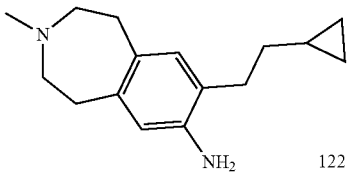 [SMILES: CN1CCc2cc(N)c(CCC3CC3)cc2CC1]<br>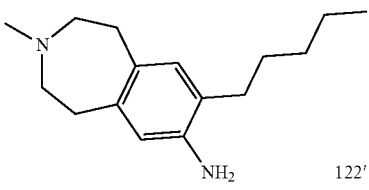<br>From a mixture of intermediate 121 and 121' | 917<br>Yellow oil<br>122/122': 76/24 based on 1H NMR | 91 |
| Intermediate 132 | 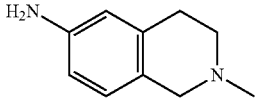<br>From 6-amino-2-N-Boc-1,2,3,4-tetrahydro-isoquinoline | 320<br>beige solid | 98<br>Procedure with Me-THF as solvent and 3 equiv. of LiAlH$_4$ |

Example A19b

Preparation of Intermediate 84b

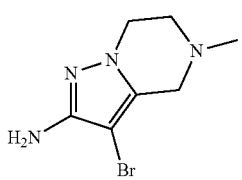

NBS (1.93 g, 10.81 mmol) was added portionwise to a solution of intermediate 50b (1.50 g, 9.86 mmol) in DCM (85.22 mL). The reaction mixture was stirred at room temperature for 12 hours. The reaction mixture was poured onto ice and water and basified with K$_2$CO$_3$ powder. The mixture was extracted with DCM, dried over MgSO$_4$, filtered and evaporated under vacuum to give 2.15 g of intermediate 84b (94% yield).

Preparation of Intermediate 85b

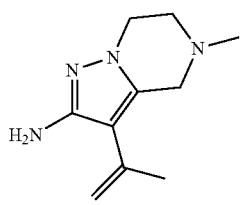

Intermediate 84b (600.00 mg, 2.60 mmol), 2-isopropenyl-4,4,5,5-tetramethyl-1,3,2-dioxaborolane (683.24 µL, 3.635 mmol), XPhos precatalyst (153.21 mg, 0.20 mmol) and potassium phosphate (0.5 M aqueous solution) (10.39 mL, 5.19 mmol) in THF (5.28 mL) were stirred in a sealed tube at 130° C. using one single mode microwave (Biotage Initiator EXP 60) with a power output ranging from 0 to 400 W for 15 min. Water was added and the reaction mixture was filtered over a pad of Celite® which was washed with DCM. The filtrate was decanted and The organic layer was separated, dried over MgSO₄, filtered and evaporated. The residue was purified by silica gel chromatography (Stationary phase: Irregular SiOH 40 g, mobile phase gradient: from 100% DCM to 94% DCM, 6% MeOH (2% NH₄OH)). The pure fractions were combined and the solvent was evaporated to give 220 mg of intermediate 85b (44% yield).

Preparation of Intermediate 86b

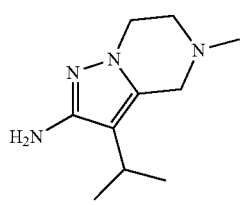

Intermediate 85b (220.00 mg, 1.14 mmol) in MeOH (15.87 mL) and EtOAc (9.1 mL) was hydrogenated at room temperature with Pd/C (10%) (31.74 mg, 0.030 mmol) as a catalyst in a pressure vessel reactor (3 bars) for 12 h. The catalyst was filtered off on a pad of celite and the solvent was evaporated to give 220 mg of intermediate 86b (quant. yield).

Example A20a

Preparation of Intermediate 23

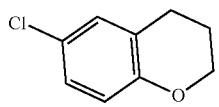 [SMILES: Clc1ccc2c(c1)CCCO2]

To a solution of 6-chlorochroman-4-one (3.00 g, 16.43 mmol) in AcOH (105 mL), degassed with N₂ bubbling, was added Pd/C (10 wt. %, 1.75 g, 1.64 mmol) and the mixture was hydrogenated under an atmosphere of H₂ (1 bar) at rt for 16 h. The mixture was filtered over a pad of Celite® and the solvent was removed under reduced pressure. The residue was coevaporated with toluene (twice) to give 2.87 g of intermediate 23 (quant. yield, off-white solid).

Example A20b

Preparation of Intermediate 101b

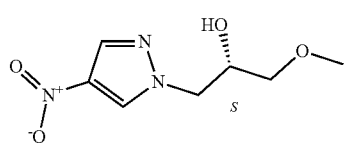

In a sealed tube, 4-nitro-1H-pyrazole (1.5 g, 13.265 mmol), (S)-glycidyl methyl ether (1.753 g, 19.898 mmol) and K₂CO₃ (2.75 g, 19.898 mmol) in DMF (14.38 mL) were stirred at 130° C. using one single mode microwave (Masterwave BTR Anton Paar) with a power output ranging from 0 to 1700 W for 5 min. [fixed hold time].

The reaction mixture was poured into water, acidified with 3N HCl (aq), extracted twice with EtOAc and the combined organic layers were washed with water, dried over MgSO₄, filtered and concentrated in vacuo. The residue was purified by normal phase flash chromatography (Irregular SiOH 40 µm 40 g GraceResolv®). Mobile phase gradient from 80% heptane, 20% EtOAc to 60% heptane, 40% EtOAc. The pure fractions were combined and the solvent was evaporated in vacuo to afford the product (1.7 g, yield 63.7%).

Example A21a

Preparation of Intermediate 42

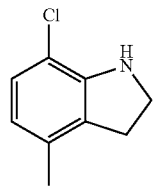

Sodium cyanoborohydride (758.86 mg, 12.08 mmol) was added slowly to a solution of 7-chloro-4-methyl-1H-indole (1.00 g, 6.04 mmol) in AcOH (10 mL). The mixture was stirred at rt for 3 h. The mixture was poured in ice and aqueous NaOH 3M. An extraction was performed with EtOAc. The organic layer was washed with brine, dried over MgSO₄, filtered and evaporated to give 1.15 g of intermediate 42 (quant. yield, 88% purity based on 1H NMR, orange oil) which was directly engaged in the next step without any further purification.

The intermediate in the table below was prepared by using an analogous method starting from the respective starting materials.

| Intermediate number | Structure | Mass (mg) | Yield (%) |
| --- | --- | --- | --- |
| Intermediate 71 | ![structure] From 4-methylindole | 912 Colorless oil | 90 |

Preparation of Intermediate 48

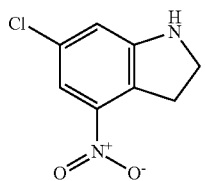 [SMILES: O=[N+]([O-])c1cc(Cl)cc2c1CCN2]

In a sealed tube, a mixture of 6-chloro-4-nitro-indoline (1.00 g, 5.09 mmol) and triethylsilane (2.11 mL, 13.22 mmol) in TFA (16 mL) was stirred at 60° C. for 2 h. The reaction mixture was diluted with EtOAc and was treated with an aqueous saturated solution of NaHCO$_3$. The layers were separated and the organic layer was dried over MgSO$_4$, filtered and the solvent was removed under reduced pressure. The crude residue was purified by silica gel chromatography (irregular SiOH 15-40 μm, 40 g, dry loading on celite, mobile phase gradient: from Heptane/EtOAc 100/0 to 60/40) to give 650 mg of intermediate 48 (64% yield, red solid).

The intermediate in the table below was prepared by using an analogous method starting from the respective starting materials.

| Intermediate number | Structure | Mass (mg) | Yield (%) |
|---|---|---|---|
| Intermediate 68 | 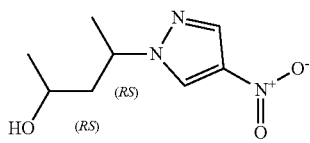<br>From intermediate 67 | Yellow solid | Quant. |

Example A21b

Preparation of Intermediate 106b

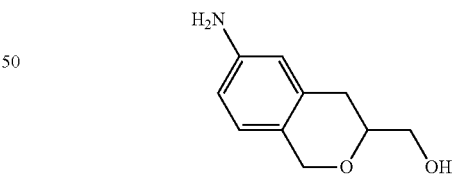

In a sealed tube, 4-nitro-1H-pyrazole (3.898 g, 34.475 mmol) and 3-penten-2-one (6.729 mL, 0.862 g/mL, 68.951 mmol) in EtOH (40.26 mL) were stirred at 140° C. for 4 hours. After cooling down to rt, sodium borohydride (2.609 g, 68.951 mmol) was added portionwise. The reaction mixture was stirred at rt overnight. The reaction mixture was poured onto ice water, acidified with 3N HCl(aq), extracted with DCM twice, dried over MgSO$_4$, filtered and concentrated in vacuo. The crude material was purified via preparative LC (Stationary phase: irregular SiOH 15-40 μm 80 g Grace, Mobile phase: gradient from 80% heptane, 20% EtOAc to 40% heptane, 60% EtOAc, 10% MeOH (2% NH$_4$OH)) to afford intermediate 106b (5.3 g, yield 77.2%)

Example A22a

Preparation of Intermediate 28

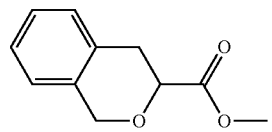

In a sealed tube, a mixture of DL-Phenyllactic acid (5.00 g, 30.09 mmol) and paraformaldehyde (903.44 mg, 30.09 mmol) in trifluoroacetic acid (17.5 mL) were purged by N$_2$. The reaction mixture was stirred at 150° C. using one single mode microwave (Biotage® Initiator EXP 60) with a power output ranging from 0 to 400 W for 5 min. The reaction mixture was evaporated and dissolved in MeOH (62.5 mL) and a catalytic amount of H$_2$SO$_4$ (80.19 μL, 1.50 mmol). The reaction mixture was refluxed for 4 h. The reaction mixture was diluted with DCM and washed with sat. NaHCO$_3$. The organic layer was dried over MgSO$_4$, filtered and evaporated to dryness. A purification was performed via silica gel chromatography (Irregular SiOH 20-45 μm, 80 g, mobile phase gradient: from 90% Heptane, 10% EtOAc to 70% Heptane, 30% EtOAc) to give 5.2 g of intermediate 28 (90% yield).

Preparation of Intermediate 31

LiAlH$_4$ (2.4 M in THF) (2.54 mL, 6.11 mmol) was added dropwise to a stirred solution of intermediate 30 (530.00 mg, 2.56 mmol) in THF (16.6 mL) at −40° C. under nitrogen. The reaction mixture was stirred at −40° C. for 45 min. Water was carefully added. The reaction mixture was stirred at rt for 15 min and filtered over a pad of Celite®. The Celite® was washed with DCM. The organic layer was separated, dried over MgSO$_4$, filtered and evaporated to give 470 mg of intermediate 31 (quantitative yield).

Example A22b

Preparation of Intermediate 115b

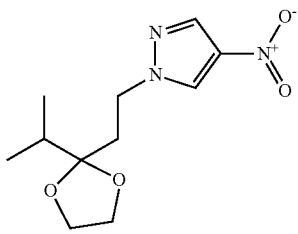 [SMILES: CC(C)C1(CCn2cc([N+](=O)[O-])cn2)OCCO1]

In a sealed tube, (cyanomethylene)tributylphosphorane (CMBP) (5.141 mL, 0.92 g/mL, 19.596 mmol) was added to a solution of 4-nitro-1H-pyrazole (1.153 g, 10.195 mmol) and 2-(2-isopropyl-1,3-dioxolan-2-yl)ethanol (2.45 g, 15.292 mmol) in toluene (45.352 mL). The mixture was heated at 60° C. for 12 hours. The solvent was evaporated. The residue was purified by preparative LC (Irregular SiOH 20-45 m 120 g GraceResolv®, mobile phase Gradient from 100% DCM to 99% DCM, 1% MeOH (2% NH$_4$OH))

The pure fractions were combined and the solvent was concentrated in vacuo to afford intermediate 115b (2.6 g, yield 99.9%).

Preparation of Intermediate 116b

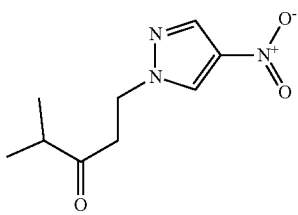

Intermediate 115b (2.6 g, 10.185 mmol) in HCl (1M in H$_2$O) (40.741 mL, 1 M, 40.741 mmol) and ACN (49.553 mL) was stirred at rt for 12 hours. Water was added. The reaction mixture was extracted twice with DCM, dried over MgSO$_4$, filtered and concentrated in vacuo to afford intermediate 116b (2.15 g, yield 99.9%).

Preparation of Intermediate 117b

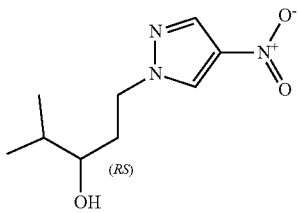

Sodium borohydride (752.279 mg, 19.884 mmol) was added to intermediate 116b (2.1 g, 9.942 mmol) in EtOH (17.416 mL) at rt. The reaction mixture was stirred for 3 hours, poured out onto ice and water and made acidic with 3N HCl(aq). The aqueous layer was extracted twice with DCM, dried over MgSO$_4$, filtered and concentrated in vacuo. A purification was performed via preparative LC (Stationary phase: irregular SiOH 15-40 µm 80 g GRACE, Mobile phase: 100% DCM) to afford intermediate 117b (1.53 g, yield 72.2%).

Example A23a

Preparation of Intermediate 37

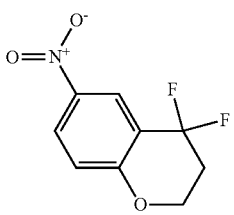 [SMILES: O=[N+]([O-])c1ccc2c(c1)C(F)(F)CCO2]

To a solution of 6-nitrochroman-4-one (2.00 g, 10.35 mmol) in DCM (1.99 mL) was added at rt (diethylamino) sulfur trifluoride (2.5 mL). The mixture was stirred at 60° C. for 7 h. The reaction mixture was carefully quenched with MeOH. The solvents were evaporated under vacuum and the residue was purified by silica gel chromatography (Irregular SiOH 40 µm, mobile phase 100% DCM) to give 680 mg of intermediate 37 (31% yield).

Example A23b

Preparation of Intermediate 124b and 124b'

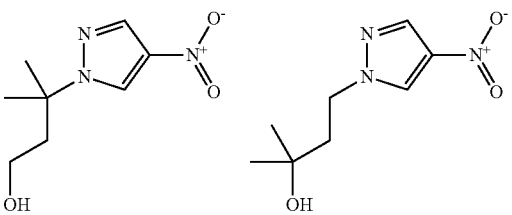

In a sealed tube, (cyanomethylene)tributylphosphorane (CMBP) (15.608 mL, 0.92 g/mL, 59.496 mmol) was added dropwise to a solution of 4-nitro-1H-pyrazole (3.5 g, 30.953 mmol) and 3-methyl-1,3-butanediol (4.836 g, 46.429 mmol) in toluene (137.696 mL). The mixture was heated at 60° C. for 12 hours. The solvent was evaporated. The residue was purified by preparative LC (Irregular SiOH 20-45 m 220 g GraceResolv®, mobile phase Gradient from 90% heptane, 10% AcOEt to 40% heptane, 60% AcOEt)

The pure fractions were combined and the solvent was evaporated to afford a residue (3.3 g, yield 53.5%). The residue was purified by preparative LC (Irregular SiOH 20-45 µm 80 g GraceResolv®, mobile phase Gradient from 100% DCM to 97% DCM, 3% MeOH (2% NH$_{40}$1H)). The pure fractions were combined and the solvent was evaporated to afford a 55/45 mixture of intermediate 124b and 124b' (620 mg, yield 10%).

Example A24a

Preparation of Intermediate 43

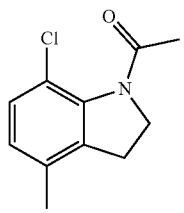

A mixture of intermediate 42 (1.15 g, 6.04 mmol based on 88% purity based on 1H NMR), acetyl chloride (0.64 mL, 9.06 mmol) and TEA (1.34 mL, 9.66 mmol) in DCM (20 mL) was stirred under $N_2$ at rt for 6 h. An extraction was performed with DCM and brine. The organic layer was dried over $MgSO_4$, filtered and evaporated under reduced pressure. The crude residue was purified by silica gel chromatography (irregular SiOH 15-40 µm, 40 g, liquid injection with DCM, mobile phase gradient: DCM/MeOH from 100:0 to 95:05 in 10 CV) to give 1.13 g of intermediate 43 (89% yield, light yellow solid).

The intermediate in the table below was prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 78 | 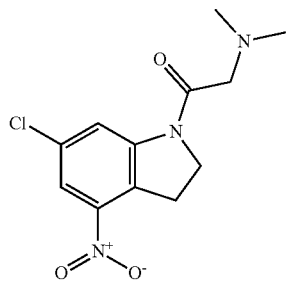 [SMILES: CN(C)CC(=O)N1CCc2c1cc(Cl)cc2[N+](=O)[O-]]<br>From intermediate 42 and dimethylaminoacetyl chloride hydrochloride | 442<br>Brown oil | 41<br>Procedure with DCM/TEA (10:1, eq/eq) |

Preparation of Intermediate 63

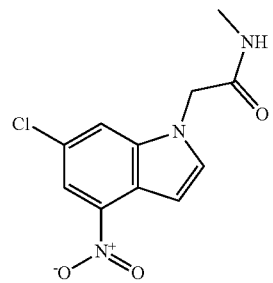

Bromoacetyl bromide (264 µL, 3.02 mmol) was added to a stirred suspension of intermediate 48 (500 mg, 2.52 mmol) and triethylamine (770 µL, 5.54 mmol) in dry DCM (6.7 mL) at 0° C. under $N_2$. The mixture was stirred at 0° C. under $N_2$ for 17 h. Then, dimethylamine (1.9 mL, 3.78 mmol) was added to the mixture under $N_2$. The reaction mixture was stirred at 0° C. under $N_2$ and allowed to warm to room temperature for 20 h. The reaction mixture was diluted with EtOAc and water and the layers were separated. The organic layer was dried over $MgSO_4$, filtered off and evaporated under reduced pressure to give 572 mg of a brown oil. This residue was purified by silica gel chromatography (irregular SiOH 15-40 µm, 30 g, dry loading on celite, mobile phase gradient: from DCM 100% to DCM 90%, MeOH 10%) to give 243 mg of intermediate 63 (34%).

Preparation of Intermediate 67

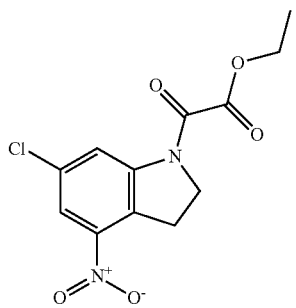 [SMILES: CCOC(=O)C(=O)N1CCc2c1cc(Cl)cc2[N+](=O)[O-]]

In a sealed tube, intermediate 77 (287.19 mg, 2.67 mmol) was added to a solution of 6-chloro-4-nitroindole (350.00 mg, 1.78 mmol) and $Cs_2CO_3$ (870.11 mg, 2.67 mmol) in dry DMF (3.5 mL) under $N_2$. The mixture was stirred at 90° C. for 17 h. The reaction mixture was diluted with EtOAc and water and the layers were separated. The organic layer was washed with brine, dried over $MgSO_4$ and filtered. The solvent was removed under reduced pressure to give 378 mg of intermediate 67 (79% yield, brown solid) which was directly engaged in the next step without further purification.

Preparation of Intermediate 88

A solution of intermediate 48 (510.00 mg, 2.57 mmol) and DIPEA (1.33 mL, 7.70 mmol) in dry DCM (8 mL) was cooled in an ice bath. Then, ethyl oxalyl chloride (345 µL, 3.08 mmol) was added dropwise. The reaction was stirred and allowed to warm to room temperature for 17 h. The reaction mixture was diluted with EtOAc and washed with water, a saturated aqueous solution of $NaHCO_3$ and brine. The organic layer was dried over $MgSO_4$, filtered and the solvent was removed under reduced pressure to give 752 mg of intermediate 88 (98% yield, brown residue) which was directly engaged in the next step without further purification.

Example A24b

Preparation of Intermediate 133b

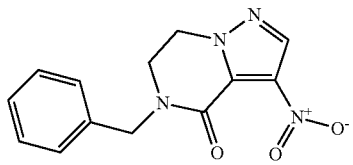 [SMILES: O=C1c2c([N+](=O)[O-])cnn2CCN1Cc1ccccc1]

N-Benzylethanolamine (2.147 mL, 1.06 g/mL, 15.052 mmol) and 4-nitro-1H-pyrazole-3-carboxylic acid (2 g, 12.732 mmol) in toluene (13.814 mL) were stirred at 15° C. SOCl$_2$ (2.554 mL, 1.64 g/mL, 35.206 mmol) was slowly added followed by DMF (96.907 µL, 0.944 g/mL, 1.252 mmol). The reaction mixture was stirred at 55° C. for 10 minutes then 70° C. for 18 h. The reaction was allowed to cool to room temperature and then the solvents were evaporated in vacuo. The residue was taken up into DMF (11.655 mL) and triethylamine (9.415 mL, 0.728 g/mL, 67.732 mmol) was added slowly. The reaction mixture was stirred at rt for 12 h. Water was added. The mixture was extracted twice with EtOAc, dried over MgSO$_4$, filtered and concentrated in vacuo to give 4.4 g of crude material. A purification was performed via preparative LC (Stationary phase: irregular SiOH 15-40 µm 120 g Grace, Mobile phase: gradient from 100% DCM to 97% DCM, 3% MeOH, 0.3% NH$_4$OH) to give 1.7 g of intermediate 133b (410%).

The intermediates in the table below were prepared by using an analogous method as described for the preparation of intermediate 133b, starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 137b | 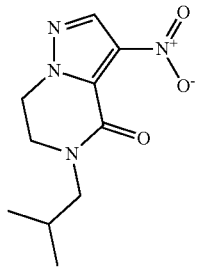<br>From 4-nitro-1H-pyrazole-3-carboxylic acid and 2-(Isobutylamino)ethanol Hydrochloride | 500 | 44 |
| Intermediate 141b | 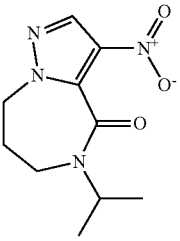<br>From 4-nitro-1H-pyrazole-3-carboxylic acid and 3-(Isopropylamino)propanol | 850 | 9 |

Example A25a

Preparation of Intermediate 52

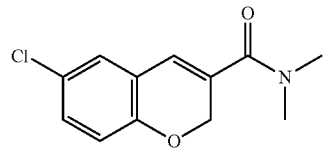 [SMILES: CN(C)C(=O)C1=Cc2cc(Cl)ccc2OC1]

To a solution of 6-chloro-2H-chromene-3-carboxylic acid (1.00 g, 4.75 mmol) in dry DMF (50 mL) were added DIPEA (2.07 mL, 11.87 mmol) and HBTU (1.80 g, 4.75 mmol). The mixture was stirred at rt for 15 min and dimethylamine (2.0 M in THF) (3.56 mL, 7.12 mmol) was added. The mixture was stirred at rt for 16 h and evaporated in vacuo. The residue was taken-up in EtOAc and a mixture of a saturated aqueous solution of NaHCO$_3$ and water (50:50) was added. The aqueous layer was separated and extracted with EtOAc (three times). The combined organic layers were washed with a saturated aqueous solution of NaCl (three times), dried over MgSO$_4$, filtered off and evaporated in vacuo to give 1.45 g of intermediate 52 (quantitative yield, brown oil) which was directly engaged in the next step without further purification.

Preparation of Intermediate 72

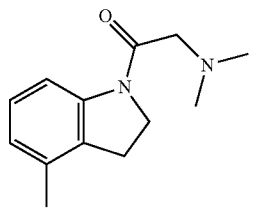 [SMILES: Cc1cccc2c1CCN2C(=O)CN(C)C]

A solution of intermediate 71 (912.00 mg, 6.85 mmol), HATU (3.12 g, 8.22 mmol), DIPEA (2.37 mL, 13.7 mmol) and N,N-dimethylglycine hydrochloride (955.74 mg, 6.85 mmol) in dry DMF (80 mL) was stirred for 3 h at rt under nitrogen. The mixture was evaporated to dryness and extracted with EtOAc and aqueous NaOH 1N. The organic layer was washed with brine, dried over MgSO₄, filtered and evaporated. Another extraction was performed using DCM and water. The organic layer was washed with brine, dried over MgSO₄, filtered, evaporated and purified by silica gel chromatography (irregular SiOH 15-40 μm, 80 g, liquid injection with DCM, mobile phase gradient: DCM/MeOH from 100:0 to 95:05 in 10 CV) to give 0.9 g of intermediate 72 (60% yield, white solid).

Example A25b

Preparation of Intermediate 145b

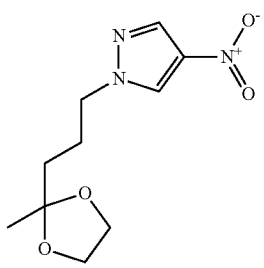 [SMILES: CC1(CCCn2cc([N+](=O)[O-])cn2)OCCO1]

5-Chloro-2-pentanone ethylene ketal (8.014 mL, 1.09 g/mL, 53.062 mmol) was added to a suspension of 4-nitro-1H-pyrazole (4 g, 35.375 mmol) and K₂CO₃ (7.333 g, 53.062 mmol) in DMF (40.198 mL) at rt. The reaction mixture was stirred at 50° C. for 3 h.

The reaction mixture was partitioned between water and DCM. The aqueous layer was extracted with DCM. The combined organic layers were dried over MgSO₄, filtered and concentrated in vacuo. A purification was performed via preparative LC (Stationary phase: irregular SiOH 15-40 μm 80 g Grace, Mobile phase: gradient from 80% heptane, 20% EtOAc to 60% heptane, 40% EtOAc) to afford intermediate 145b (5.1 g, yield 59.8%)

Preparation of Intermediate 146b

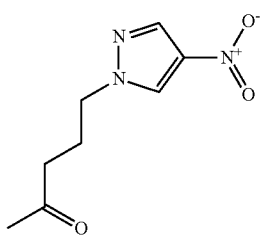

HCl(aq) 3M (1.326 mL, 3 M, 3.979 mmol) was added to intermediate 145b (240 mg, 0.995 mmol) in ACN (4.84 mL) and distilled water (2.65 mL) and the reaction mixture stirred at rt for 12 hours. Water was added. The reaction mixture was extracted twice with DCM, dried over MgSO₄, filtered and concentrated in vacuo to afford intermediate 146b (230 mg, yield 117%) which was used directly in the next step.

Preparation of Intermediate 147b

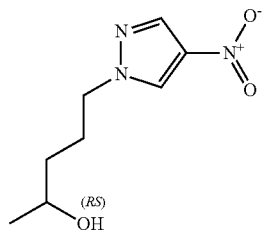

Sodium borohydride (1496.468 mg, 39.555 mmol) was added to intermediate 146b (3.9 g, 19.778 mmol) in EtOH (34.644 mL) at rt. The reaction mixture was stirred for 5 hours, poured out onto ice and water and made acidic with 3N HCl(aq). The aqueous layer was extracted twice with DCM, dried over MgSO₄, filtered and concentrated in vacuo. A purification was performed via preparative LC (Stationary phase: irregular SiOH 15-40 μm 80 g GRACE, Mobile phase: gradient from 100% DCM to 98% DCM, 2% MeOH (2% NH₄OH)) to afford intermediate 147b (3360 mg, yield 85.3%).

Example A26a

Preparation of Intermediate 53

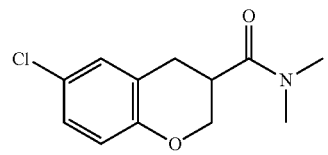 [SMILES: CN(C)C(=O)C1COc2ccc(Cl)cc2C1]

To a solution of intermediate 52 (2.08 g, 8.75 mmol) in MeOH (103 mL) degassed with N₂ was added PtO₂ (198.72 mg, 0.87 mmol) and the mixture was hydrogenated under an atmosphere of H₂ (1 bar) at rt for 16 h. The mixture was filtered over a pad of Celite® and the solvent was removed under reduced pressure. The crude residue was purified by silica gel chromatography (irregular SiOH 15-40 μm, 120 g, dry loading on celite, mobile phase gradient: from Heptane/EtOAc 80/20 to 20/80) to give 1.28 g of intermediate 53 (61% yield, colourless oil).

Preparation of Intermediate 55 and intermediate 56 intermediate 55

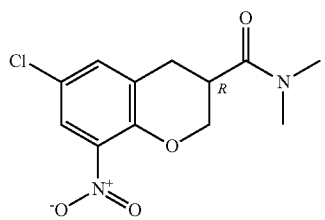

343

-continued intermediate 56

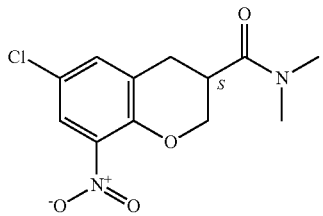

Intermediate 54 (732.00 mg) was purified by chiral SFC (Chiralcel OD-H 5 μm 250*30 mm, mobile phase: 85% $CO_2$, 15% EtOH). The desired fractions were collected and the solvent was concentrated to dryness under vacuum to give 250 mg of intermediate 55 as a white solid (34%) and 260 mg of intermediate 56 as a white solid (36%).

Example A26b

Preparation of Intermediate 155b

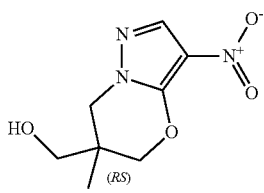

At 0° C. under $N_2$, NaH (60% dispersion in mineral oil) (440 mg, 11.00 mmol) was added portionwise to a solution of 3-methyl-3-oxetanemethanol (1.10 mL, 11.03 mmol) in methyl-THF (40 mL). The reaction mixture was stirred at 0° C. for 15 minutes. The reaction mixture was cooled to −78° C., and a solution of 1,4-dinitro-1H-pyrazole (2.60 g; 16.45 mmol) in methyl-THF (5.00 mL) was added dropwise. The reaction was diluted with Methyl-THF (15.00 mL) and stirred at −78° C. for 45 minutes. The reaction was quenched with water/ice and acidified with 3N HCl (aq), before being extracted with EtOAc. The organic layer was decanted and the solvent was evaporated until dryness. The product was taken up in DCM, triturated and the precipitate was filtered, dried under vacuum to give 0.46 g of intermediate 155b (20%). The material was used directly in the next step.

Example A27a

Preparation of Intermediate 77

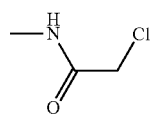

In a sealed tube, under $N_2$, methylamine (13 mL, 26.0 mmol) was added dropwise to a solution of chloroacetyl chloride (1 mL, 12.6 mmol) in dry DCM (20 mL) at 0° C. and the mixture was allowed to warm to rt and was stirred at this temperature for 16 h. The reaction mixture was diluted with $CH_2Cl_2$ and water. The layers were separated

344 and the organic layer was washed with a saturated aqueous solution of $NaHCO_3$. The organic layer was dried over $MgSO_4$, filtered and the solvent was removed under reduced pressure to give 993 mg of intermediate 77 (73% yield, colorless oil) which was directly engaged in the next step without further purification.

Example A27b

Preparation of Intermediate 162b

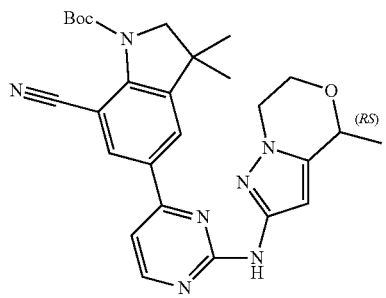 [SMILES: CC1OCCn2nc(Nc3nccc(-c4cc(C#N)c5c(c4)C(C)(C)CN5C(=O)OC(C)(C)C)n3)cc21]

To a mixture of intermediate 31b (100 mg, 0.564 mmol), intermediate 161b (238.66 mg, 0.62 mmol) and $Cs_2CO_3$ (459.2, 1.409 mmol) in 1,4-dioxane (5 ml) was added $Pd(OAc)_2$ (12.657 mg, 0.0564 mmol) and BINAP (35.103 mg, 0.0564 mmol). The mixture was stirred for 2 hrs at 95° C. The mixture was filtered and evaporated in vacuo to give a crude product. This residue was purified by flash column chromatography over silica gel (eluent: petroleum ether/ethyl acetate=1:1). The desired fractions were collected and the solvent was concentrated to dryness under vacuum to give the product intermediate 162b as a yellow solid (200 mg, 34.7%).

Example A28

Preparation of Intermediate 83

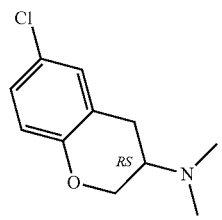

In a sealed tube, a mixture of 6-chlorochroman-3-one (350.00 mg, 1.92 mmol), dimethylamine (2.88 mL, 5.75 mmol) and $Ti(OiPr)_4$ (1.70 mL, 5.75 mmol) in Me-THF (18 mL) in presence of activated molecular sieve 4 Å was stirred at 60° C. for 3 h. $NaBH(OAc)_3$ (2.03 g, 9.58 mmol) and HOAc (3.28 mL) were added and the mixture was stirred at rt for 20 h. The reaction mixture was diluted with EtOAc and water. The layers were separated and the organic layer was washed with brine, dried over $MgSO_4$, filtered and the solvent was removed under reduced pressure. The crude residue was purified by silica gel chromatography (irregular SiOH 15-40 μm, 24 g, dry loading on celite, mobile phase gradient: from heptane/EtOAc 100/0 to 40/60) to give 265 mg of intermediate 83 (65% yield, brown oil).

Example A29

Preparation of Intermediate 89

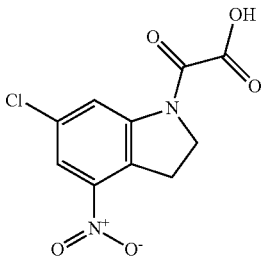 [SMILES: O=C(O)C(=O)N1CCc2c1cc(Cl)cc2[N+](=O)[O-]]

A mixture of intermediate 88 (514.00 mg, 1.72 mmol) and LiOH monohydrate (108.32 mg, 2.58 mmol) in Me-THF (12 mL) and distilled water (5 mL) was stirred at room temperature for 2 h. The reaction mixture was diluted with water and washed (twice) with DCM. The aqueous layer was acidified with 3N HCl and extracted with DCM (three times). The combined organic layers were dried over $MgSO_4$, filtered and evaporated under reduced pressure to give 198 mg of intermediate 89 (43% yield, brown oil) which was directly engaged in the next step without any further purification.

Preparation of Intermediate 90

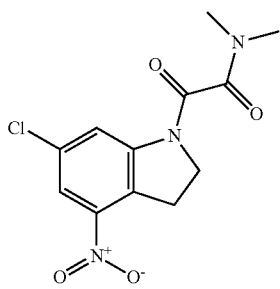 [SMILES: CN(C)C(=O)C(=O)N1CCc2c1cc(Cl)cc2[N+](=O)[O-]]

In a sealed glassware, Triazabicyclo[4.4.0]dec-5-ene (23.78 mg, 167.40 µmol) and dimethylamine (0.50 mL, 1.00 mmol) were added to a stirred solution of intermediate 88 (100.00 mg, 0.33 mmol) in dry toluene (6.5 mL) at room temperature. The mixture was stirred at 50° C. for 17 h. The reaction mixture was diluted with EtOAc and water and the layers were separated. The organic layer was dried over $MgSO_4$, filtered and the solvent was removed under reduced pressure to give 77 mg of intermediate 90 (77% yield, brown oil) which was directly engaged in the next step without any further purification.

Alternative Preparation of Intermediate 90

In a sealed tube, intermediate 89 (198.00 mg, 0.73 mmol) and dimethylamine (438.98 µL, 0.88 mmol) were diluted in DMF (8.5 mL). Then, HATU (612.02 mg, 1.61 mmol) and DIPEA (319.46 µL, 1.83 mmol) were added and the mixture was stirred at 70° C. for 17 h. The reaction mixture was diluted with EtOAc and water and an extraction was performed (three times). The organic layer was washed with brine, dried over $MgSO_4$ and filtered. The solvent was removed under reduced pressure to give 354 mg of intermediate 90 (quant. yield, brown residue) which was directly engaged in the next step without any further purification.

Example A30

Preparation of Intermediate 94

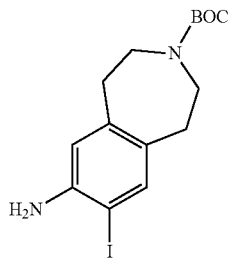 [SMILES: CC(C)(C)OC(=O)N1CCc2cc(N)c(I)cc2CC1]

N-iodosuccinimide (4.72 g, 20.96 mmol) in MeCN (80 mL) was added via a dropping funnel to a solution of intermediate 19 (5.00 g, 19.1 mmol) in MeCN (170 mL) at 0° C. over 30 min and the mixture was stirred from 0° C. to room temperature for 16 h. The reaction mixture was diluted with EtOAc and water. The layers were separated and the aqueous layer was extracted with EtOAc. The combined organic layers were dried over $MgSO_4$, filtered and the solvent was removed under reduced pressure. The crude residue was purified by silica gel chromatography (irregular SiOH 15-40 µm, 220 g, dry loading on celite, mobile phase gradient: from Heptane/EtOAc 90/10 to 60/40) to give 6.00 g of intermediate 94 (82% yield, yellow solid).

Preparation of Intermediate 95

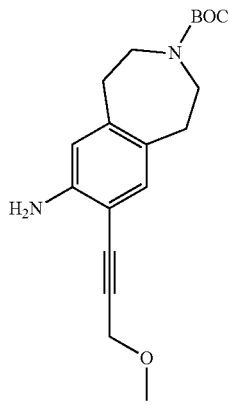 [SMILES: COCC#Cc1cc2c(cc1N)CCN(C(=O)OC(C)(C)C)CC2]

In a Schlenk flask, a mixture of intermediate 94 (1.00 g, 2.58 mmol), methyl propargyl ether (218.00 µL, 2.58 mmol) and TEA (1.79 mL, 12.9 mmol) in dry Me-TH (13 mL) was purged with $N_2$. Then, $PdCl_2(PPh_3)_2$ (90.40 mg, 0.13 mmol) and copper(I) iodide (49.05 mg, 0.26 mmol) were added. The mixture was purged with $N_2$ and stirred at rt for 16 h. The mixture was then diluted with EtOAc and an aqueous saturated solution of $NaHCO_3$. The layers were separated and the aqueous layer was extracted with EtOAc (once). Organic layer was dried over MgSO$_4$, filtered and the solvent was removed under reduced pressure. The crude residue was purified by silica gel chromatography (irregular SiOH 15-40 μm, 40 g, dry load on celite, mobile phase gradient: from DCM/MeOH 100/0 to 95/5) to give 1.6 g of intermediate 95 (94% yield, yellow oil).

The intermediate in the table below was prepared by using an analogous method starting from the respective starting materials.

| Intermediate number | Structure | Mass (mg) | Yield (%) |
|---|---|---|---|
| Intermediate 120 | 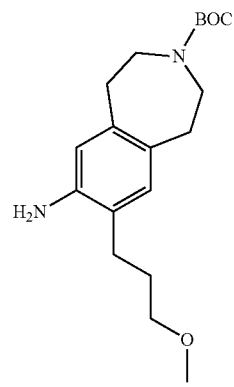 [SMILES: COCCCc1cc2c(cc1N)CCN(C(=O)OC(C)(C)C)CC2]<br>From intermediate 94 and cyclopropylacetylene | 1560<br>Brown oil | 88 |

Preparation of Intermediate 103

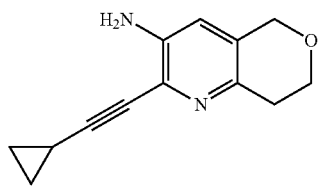 [SMILES: Nc1cc2c(nc1C#CC1CC1)CCOC2]

In a sealed tube, a mixture of intermediate 102 (0.89 g, 3.89 mmol), ethynylcyclopropane (0.51 g, 7.77 mmol) and TEA (2.70 mL, 19.4 mmol) in dry DMF (19 mL) was purged with N$_2$. PdCl$_2$(PPh$_3$)$_2$ (136.35 mg, 0.19 mmol) and CuI (73.99 mg, 0.39 mmol) were added. The mixture was purged with N$_2$ and stirred at 60° C. for 1 h. The reaction mixture was diluted with EtOAc and treated with an aqueous saturated solution of NaHCO$_3$. The organic layer was washed with brine (twice), dried over MgSO$_4$, filtered and the solvent was removed under reduced pressure. The crude residue was purified by silica gel chromatography (irregular SiOH 15-40 μm, 24 g, dry load on celite, mobile phase gradient: from Heptane/EtOAc 90/10 to 30/70) to give 740 mg of intermediate 103 (89% yield, yellow solid).

Preparation of Intermediate 140

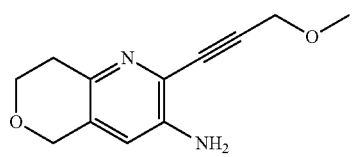 [SMILES: COCC#Cc1nc2c(cc1N)COCC2]

In a sealed tube, a mixture of intermediate 102 (385.00 mg, 1.68 mmol), methyl propargyl ether (170.31 μL, 2.02 mmol), CuI (16.00 mg, 84.0 μmol) and piperidine (498.86 μL, 5.04 mmol) in Me-THF (8 mL) was purged with N$_2$. PdCl$_2$(PPh$_3$)$_2$ (117.97 mg, 0.17 mmol) was added and the mixture was purged with N$_2$ and stirred at rt for 18 h. The crude product was combined with another batch coming from a reaction performed on 30 mg of intermediate 102 and EtOAc and water were added. The organic layer was separated, dried over MgSO$_4$, filtered off and evaporated in vacuo. The crude residue was purified by silica gel chromatography (Irregular SiOH 15-40 μm, 24 g, mobile phase gradient: from DCM 100% to DCM 95%, iPrOH 5%) to give 283 mg of intermediate 140 (72% yield, brown solid).

Example A31

Preparation of Intermediate 96

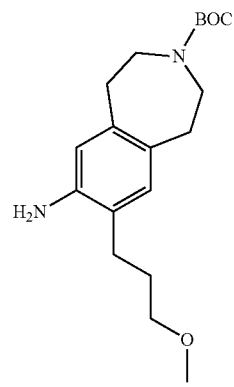 [SMILES: COCCCc1cc2c(cc1N)CCN(C(=O)OC(C)(C)C)CC2]

Intermediate 95 (0.50 g, 1.51 mmol) was diluted in MeOH (12 mL) and was purged with N$_2$. Pd/C (10 wt. %, 161.03 mg, 0.15 mmol) was added and the mixture was hydrogenated under an atmosphere of H$_2$ (1 bar) at rt for 16 h. The mixture was filtered on a pad of Celite® and the solvent was removed under reduced pressure. The crude residue was purified by silica gel chromatography (irregular SiOH 15-40 μm, 24 g, dry load, mobile phase gradient: from Heptane/EtOAc 90/10 to 60/40) to give 352 mg of intermediate 96 (70% yield, yellow oil).

Preparation of Intermediate 104

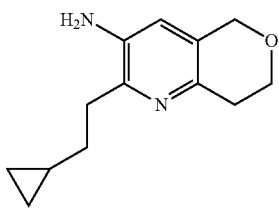 [SMILES: Nc1cc2c(nc1CCC1CC1)CCOC2]

CoCl$_2$ (89.72 mg, 0.69 mmol) was added to a solution of intermediate 103 (740.00 mg, 3.45 mmol) in dry MeOH (13.4 mL) and the mixture was stirred at rt for 30 min under N$_2$. Then NaBH$_4$ (522.64 mg, 13.81 mmol) in dry DMF (7.4 mL) was added and the mixture was stirred at rt for 15 min under N$_2$. The reaction mixture was diluted with EtOAc and water. The layers were separated and the aqueous layer was extracted with EtOAc (twice). The combined organic layers were dried over MgSO$_4$, filtered and the solvent was removed under reduced pressure. The crude residue was purified by silica gel chromatography (irregular SiOH, 15-40 µm, 24 g, dry load on celite, mobile phase gradient: from Heptane/EtOAc 90/10 to 50/50) to give 260 mg of intermediate 104 (34% yield, yellow solid).

Preparation of Intermediate 141

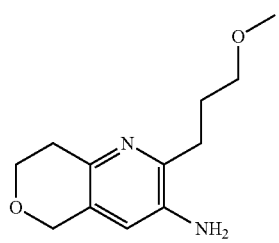 [SMILES: COCCCc1nc2c(cc1N)COCC2]

To a solution of intermediate 140 (250.00 mg, 1.15 mmol) in EtOH (5.50 mL) were added TEA (111.45 µL, 802 µmol) and PtO$_2$ (10.40 mg, 45.8 µmol). The mixture was stirred under H$_2$ atmosphere (1 bar) for 24 h and filtered on a pad of Celite®. The Celite® was washed with EtOH and the filtrate was evaporated in vacuo. The crude residue was purified by silica gel chromatography (Irregular SiOH 15-40 µm, 10 g, mobile phase gradient: from heptane 95%, EtOAc/MeOH (9:1) 5% to heptane 50%, EtOAc/MeOH (9:1) 50%) to give 173 mg of intermediate 141 (68% yield, pale brown solid).

Example A32

Preparation of Intermediate 100

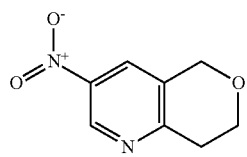 [SMILES: O=[N+]([O-])c1cnc2c(c1)COCC2]

In a sealed tube, a solution of tetrahydro-4H-pyran-4-one (2.00 g, 19.98 mmol) and 1-methyl-3,5-dinitro-1H-pyridin-2-one (3.98 g, 19.98 mmol) in ammonia (7N in MeOH) (34 mL) was stirred at 50° C. for 18 h. After cooling down to rt, the mixture was diluted with DCM and a saturated aqueous solution of NaHCO$_3$ was added. The aqueous layer was separated and extracted with DCM (three times). The combined organic layers were dried over MgSO$_4$, filtered off and evaporated in vacuo to give 1.70 g of intermediate 100 (47% yield, red solid).

Preparation of Intermediate 128

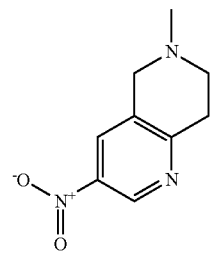

In a Schlenk reactor, a solution of 1-methyl-3,5-dinitro-1H-pyridin-2-one (5.00 g, 25.11 mmol) and 1-methyl-4-piperidone (3.13 g, 27.62 mmol) in ammonia (7N in MeOH) (43 mL) was stirred overnight at 50° C. After cooling down to rt, the mixture was evaporated in vacuo, taken-up in DCM and a saturated aqueous solution of NaHCO$_3$ was added. The layers were separated and the aqueous layer was extracted with DCM (three times). The combined organic layers were dried over MgSO$_4$, filtered off and evaporated in vacuo to give 2.32 g of intermediate 128 (48% yield, reddish solid) which was used in the next step without further purification.

Preparation of Intermediate 200

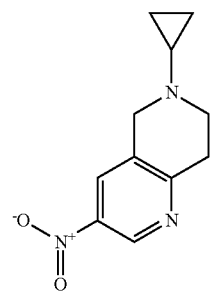

Intermediate 200 was prepared following a similar protocole than the one used for the preparation of intermediate 128 starting from 1-methyl-3,5-dinitro-1H-pyridin-2-one and 1-cyclopropyl-4-piperidinone as reagents (111 mg; 50%).

Example A33

Preparation of Intermediate 102

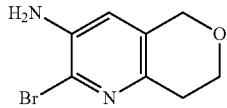

Bromine (351.40 µL, 6.86 mmol) was added to a solution of intermediate 101 (1.03 g, 6.86 mmol) and sodium acetate (1.13 g, 13.7 mmol) in AcOH (25 mL) and the mixture was stirred at rt for 2 h. The mixture was diluted in EtOAc and water and treated with an aqueous saturated solution of NaHCO$_3$ and a 10% aqueous solution of sodium thiosulfate. The organic layer was dried over MgSO$_4$, filtered, evaporated in vacuo and purified by silica gel chromatography (irregular SiOH 15-40 µm, 40 g, dry load on celite, mobile phase gradient: from Heptane/EtOAc 90/10 to 30/70) to give 890 mg of intermediate 102 (57% yield, pale brown solid).

Alternative Preparation of Intermediate 102

A solution of intermediate 101 (550 mg; 3.66 mmol) in of ACN (20 mL) was cooled to 0° C. Then, a solution of N-bromosuccinimide (652 mg; 3.66 mmol) in ACN (20 mL) was added dropwise and the reaction mixture was stirred for 1 h at room temperature. The mixture was concentrated in vacuo and the residue was diluted with ethyl acetate and washed with a solution of NaHCO$_3$. The aqueous layer was extracted with ethyl acetate. The combined organic layers were dried over MgSO$_4$ and the solvent was removed under reduced pressure to give a crude that was purified by flash chromatography eluting with heptane and Ethyl Acetate. The fractions containing the product were mixed to give, after removal of the solvent, 780 mg (93%) of intermediate 102

Preparation of Intermediate 204

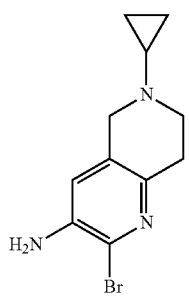 [SMILES: Nc1cc2c(nc1Br)CCN(C1CC1)C2]

Intermediate 204 was prepared following the alternative procedure used for the preparation of intermediate 102 starting from intermediate 201 (477 mg; 75%).

Preparation of Intermediate 137

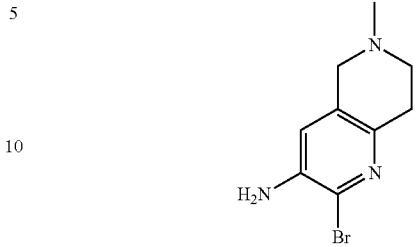

Bromine (665.49 µL, 12.99 mmol) was added to a solution of intermediate 129 (2.12 g, 12.99 mmol) and sodium Acetate (2.13 g, 25.98 mmol) in AcOH (40 mL) at rt and the mixture was stirred at rt for 1 h. The mixture was diluted in DCM and water and treated with NaHCO$_3$ slowly. The organic layer was dried over MgSO$_4$, filtered and evaporated in vacuo to give 2.2 g of intermediate 137 (70% yield, brown solid) which was used in the next step without further purification.

Preparation of Intermediate 201

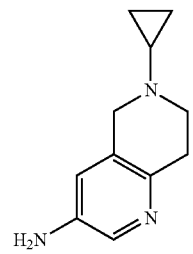 [SMILES: Nc1cnc2c(c1)CN(C1CC1)CC2]

Intermediate 201 was prepared following a similar protocole than the one used for the preparation of intermediate 129 starting from intermediate 200 (94 mg; 98%).

Example A34

Preparation of Intermediate 109

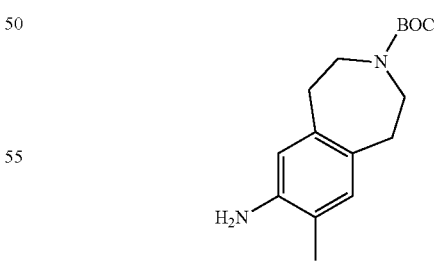

A sealed tube was charged with intermediate 94 (1.50 g, 3.86 mmol), methylboronic acid (693.81 mg, 11.6 mmol), CsF (315.51 mg, 386 µmol) and Pd(dppf)Cl$_2$.CH$_2$Cl$_2$ (2.05 g, 13.5 mmol). The system was degassed and filled with N$_2$ (three times) before addition of 1,4-dioxane (34 mL). The reaction mixture was degassed with N$_2$ for 5 min and heated at 90° C. for 16 h. The reaction mixture was diluted with water, the layers were separated and the aqueous layer was extracted with EtOAc (three times). The combined organic layers were washed with brine, dried over MgSO$_4$ and concentrated under reduced pressure. The crude residue was purified by silica gel chromatography (Irregular SiOH 15-40 µm, 40 g, liquid loading in DCM, mobile phase gradient: from heptane/EtOAc 90/10 to 60/40 over 10 CV) to give 711 mg of intermediate 109 (67% yield, yellow solid).

Preparation of Intermediate 125

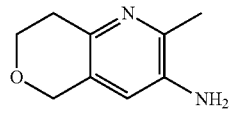

In a microwave vial, a solution of intermediate 102 (250.00 mg, 1.09 mmol), dimethylzinc (546 µL, 1.09 mmol) and Pd(dppf)Cl$_2$.CH$_2$Cl$_2$ (89.35 mg, 0.11 mmol) in 1,4-dioxane (10 mL) was purged with N$_2$ and heated at 100° C. using one single mode microwave Biotage® Initiator EXP 60 with a power output ranging from 0 to 400 W for 10 min. This reaction was performed in two batches from 500 mg of intermediate 102 each. The 2 batches were combined, diluted with EtOAc and water was slowly added. The mixture was filtered on a pad of Celite® and the filtrate was transferred in a separatory funnel. The organic layer was separated, dried over MgSO$_4$, filtered off and evaporated in vacuo. The crude residue was purified by silica gel chromatography (Irregular SiOH 15-40 µm, 24 g, liquid loading with DCM, mobile phase gradient: from Heptane 90%, EtOAc 10% to Heptane 70%, EtOAc 30%) to give 164 mg of intermediate 125 (46% yield, yellow oil).

Example A35

Preparation of Intermediate 113

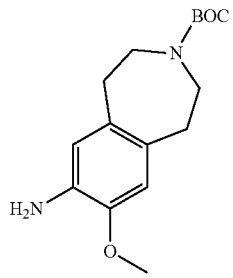 [SMILES: COc1cc2c(cc1N)CCN(C(=O)OC(C)(C)C)CC2]

In a sealed tube, a mixture of intermediate 94 (1.50 g, 3.86 mmol), CuI (73.58 mg, 386 µmol), 1,10-phenanthroline (139.25 mg, 773 µmol) and Cs$_2$CO$_3$ (2.52 g, 7.73 mmol) in MeOH (10.4 mL) was heated at 120° C. using one single mode microwave Biotage® Initiator EXP 60 with a power output ranging from 0 to 400 W for 2 h. The reaction mixture was diluted with MeOH and EtOAc. The mixture was passed through a Celite® pad and the black filtrate was concentrated. The crude residue was purified by silica gel chromatography (Irregular SiOH 15-40 µm, 80 g, dry loading on celite, mobile phase gradient: from Heptane/EtOAc 90/10 to 60/40) to give 576 mg of intermediate 113 (51% yield, orange solid).

Preparation of Intermediate 117

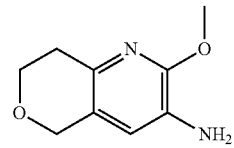

In a microwave vial, a mixture of intermediate 102 (480.00 mg, 2.10 mmol) and Cs$_2$CO$_3$ (1.37 g, 4.19 mmol) in MeOH (5 mL) was purged with N$_2$. CuI (39.91 mg, 209.54 µmol) and 1,10-phenanthroline (75.52 mg, 419.08 µmol) were added and the mixture was purged with N$_2$ and heated at 120° C. using one single mode microwave Biotage® Initiator EXP 60 with a power output ranging from 0 to 400 W for 2 h. The crude was diluted with EtOAc, filtered through a pad of Celite® which was rinsed with MeOH. The black filtrate was concentrated in vacuo. The crude residue was purified by silica gel chromatography (Irregular SiOH 15-40 µm, 50 g, liquid injection (DCM), mobile phase gradient: from heptane 95%, EtOAc/MeOH (9:1) 5% to heptane 70%, EtOAc/MeOH (9:1) 30%) to give 303 mg of intermediate 117 (80% yield, beige solid).

Alternative preparation of intermediate 117: A mixture of intermediate 102 (2 g; 8.73 mmol), CuI (166.3 mg; 0.87 mmol), 1,10-phenanthroline (314.7 mg; 1.75 mmol), Cs$_2$CO$_3$ (5.7 g; 17.5 mmol) in MeOH (20 mL) was heated to 100° C. for 18 hours under nitrogen atmosphere in a sealed tube. The mixture was extracted with DCM (100 mL*3) and the organic layer was dried (MgSO$_4$) and concentrated.

The residue (4 g, dark solid) was purified by column chromatography over silica gel (eluent: petroleum ether/ethyl acetate from 100/0 to 0/100). The desired fractions were collected and the solvent was concentrated to dryness under vacuum to give 950 mg (60%) of intermediate 117.

Preparation of Intermediate 138

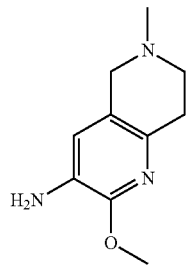

In a microwave vial, a mixture of intermediate 137 (500.00 mg, 2.07 mmol) and Cs$_2$CO$_3$ (1.35 g, 4.13 mmol) in MeOH was purged with N$_2$. CuI (39.33 mg, 0.21 mmol) and 1,10-phenanthroline (74.43 mg, 0.41 mmol) were added and the mixture was purged with N$_2$ and heated at 100° C. using one single mode microwave Biotage® Initiator EXP 60 with a power output ranging from 0 to 400 W for 2 h. The mixture was evaporated in vacuo. The crude residue was purified by silica gel chromatography (irregular SiOH, 15-40 µm, 120 g, dry loading (Celite®), mobile phase gradient: from DCM 98%, MeOH/aq. NH$_3$ (95:5) 2% to DCM 85%, MeOH/aq.

NH₃ (95:5) 15%). The residue was further purified by silica gel chromatography (irregular SiOH, 15-40 μm, 24 g, liquid loading (DCM), mobile phase gradient: from DCM 100% to DCM 90%, MeOH/aq. NH₃ (95:5) 10%) to give 230 mg of intermediate 138 (58% yield, yellow solid).

Preparation of Intermediate 144

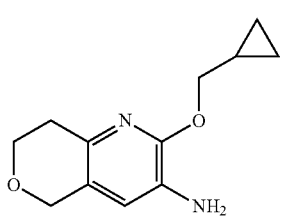 [SMILES: Nc1cc2c(nc1OCC1CC1)CCOC2]

In a microwave vial, a mixture of intermediate 102 (500.00 mg, 2.18 mmol), cyclopropyl carbinol (11.83 mL), 1,10-phenanthroline (78.67 mg, 436.51 μmol) and Cs₂CO₃ (1.42 g, 4.37 mmol) was purged with N₂. CuI (41.57 mg, 218.27 μmol) was added and the mixture was purged with N₂ and heated at 120° C. using one single mode microwave Biotage® Initiator EXP 60 with a power output ranging from 0 to 400 W for 4 h. After cooling down to rt, the crude was diluted with EtOAc and water and filtered on a pad of Celite®. The filtrate was transferred in a separatory funnel. The organic layer was separated, washed with water (three times), dried over MgSO₄, filtered off and evaporated in vacuo. The crude residue was purified by silica gel chromatography (Irregular SiOH 15-40 μm, 10 g, liquid loading (DCM), mobile phase gradient: from heptane 95%, EtOAc/MeOH (9:1) 5% to heptane 70%, EtOAc/MeOH (9:1) 30%) to give 206 mg of intermediate 144 (43% yield, colorless oil).

Preparation of Intermediate 147

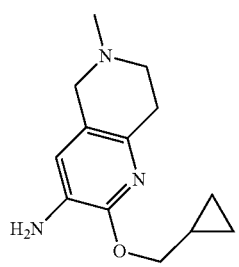 [SMILES: CN1CCc2nc(OCC3CC3)c(N)cc2C1]

In a microwave vial, a mixture of intermediate 137 (415 mg, 1.71 mmol) and Cs₂CO₃ (1.12 g, 3.43 mmol) in cyclopropylmethanol (8.30 mL) was purged with N₂. CuI (32.64 mg, 0.17 mmol) and 1,10-phenantroline (61.78 mg, 0.34 mmol) were added and the mixture was purged with N₂ and heated at 100° C. using one single mode microwave Biotage® Initiator EXP 60 with a power output ranging from 0 to 400 W for 2 h. After cooling down to rt, the crude was diluted with EtOAc and filtered on a pad of Celite®. The Celite® was rinsed with MeOH and the filtrate was evaporated in vacuo to give a brown residue. The residue was diluted in EtOAc, washed with water (three times), dried over MgSO₄, filtered off and evaporated in vacuo. The crude residue was purified via silica gel chromatography (Stationary phase: irregular SiOH 15-40 μm, 220 g, Mobile phase gradient: from 100% DCM to 97% DCM, 3% MeOH (10% NH₄OH)) to give 145 mg of intermediate 147 (24% yield, 66% purity based on LC/MS).

Preparation of Intermediate 205

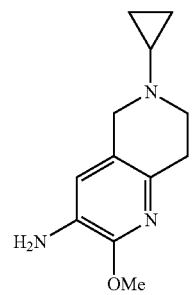 [SMILES: COc1nc2c(cc1N)CN(C1CC1)CC2]

Intermediate 205 was prepared via a similar protocole (T=100° C. and time=1 hour) than the one used for the preparation of intermediate 113 starting from intermediate 204 (65 mg; 17%).

Example A36

Preparation of a Mixture of Intermediate 121 and Intermediate 121'

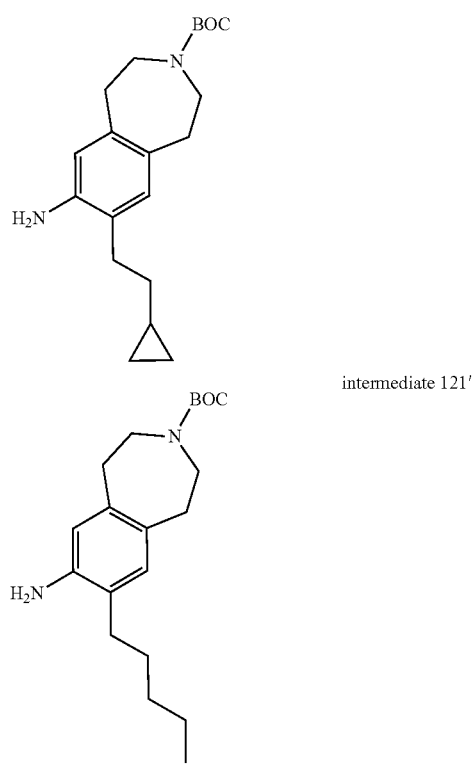

intermediate 121'

In a Schlenk reactor, a solution of intermediate 120 (1.02 g, 3.13 mmol), ammonium formate (11.82 g, 187.48 mmol) and Pd/C (10 wt. %) (1.99 g, 1.88 mmol) in isopropanol (25.5 mL) and Me-TH (12.75 mL) was purged with N₂ and stirred at 70° C. for 35 min. The reaction mixture was filtered on a pad of Celite® and the filtrate was diluted with EtOAc and water. The layers were separated and the organic layer was dried over MgSO₄, filtered and the solvent was evaporated under reduced pressure to give 981 mg of a mixture of intermediate 121 and 121' (95% yield, brown oil) which was directly engaged in the next step without any further purification.

Example A37

Preparation of Intermediate 150

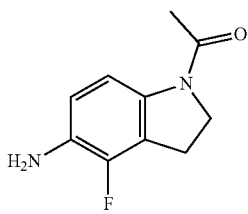

A mixture of 1-(4-Fluoro-5-nitroindolin-1-yl)ethanone (600 mg; 2.676 mmol) was hydrogenated in a pressure vessel reactor at room temperature in ethanol (30 mL) and THF (20 mL) with Pd/C 10% (275 mg) as a catalyst under a 3 bars pressure of hydrogene for 3 h00. The catalyst was filtered off on a pad of Celite® which was further washed with DCM and MeOH. The solvent was removed until dryness to give 470 mg (90%) of intermediate 150.

Example A38

Preparation of Intermediate 153

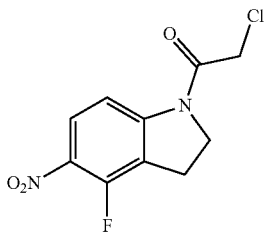 [SMILES: O=C(CCl)N1CCc2c1ccc([N+](=O)[O-])c2F]

Chloroacetic acid chloride (0.7 mL; 8.78 mmol) and potassium carbonate (1.33 g; 9.66 mmol) in DCM (15 ml) was stirred under ice-bath. Then, 4-fluoro-5-nitro-2,3-dihydroindole in DCM (5 ml) was added dropwise. The mixture was stirred at room temperature for 4 hours. Water (10 mL) was added and the organic layer was separated. The aqueous layer was extracted with DCM (20 mL*2). The organic layers were combined, dried over MgSO₄, filtered and evaporated to give 700 mg (59%) of intermediate 153 as a yellow solid which was directly used in the next step.

Preparation of Intermediate 161

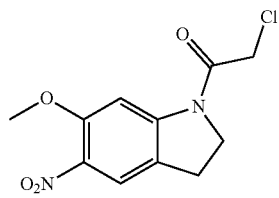 [SMILES: COc1cc2c(cc1[N+](=O)[O-])CCN2C(=O)CCl]

Intermediate 161 was prepared following a similar procedure that the one used for the preparation of intermediate 153 starting from 6-(methyloxy)-5-nitro-2,3-dihydro-1H-indole (1.08 g)

Preparation of Intermediate 154

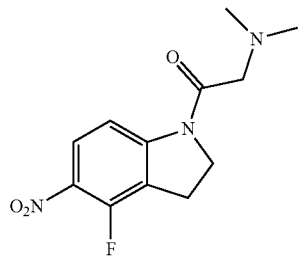 [SMILES: CN(C)CC(=O)N1CCc2c1ccc([N+](=O)[O-])c2F]

Intermediate 153 (700 mg; 2.7 mmol), diethylamine (366 mg; 8.12 mmol) and K₂CO₃ (1.12 g; 8.12 mmol) in THF (40 mL) and water (20 mL) was stirred at room temperature for 16 hours. Water (50 mL) was added and the organic layer was separated. The aqueous layer was extracted with DCM (50 mL*2). The organic layers were combined, dried over MgSO₄, filtered and evaporated to give 600 mg (83%) of intermediate 154 as a yellow solid which was directly used in the next step.

Preparation of Intermediate 162

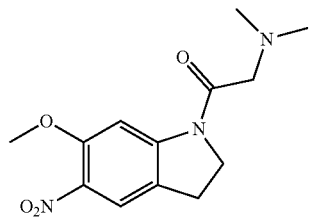

Intermediate 162 was prepared following a similar procedure that the one used for the preparation of intermediate 154 starting from intermediate 161 (950 mg; 85%)

Example A39

Preparation of Intermediate 168

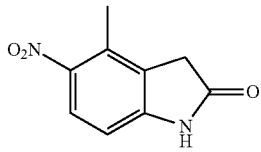

4-methyloxindole (1.23 g; 8.36 mmol) was dissolved in concentrated sulfuric acid at −10° C. Potassium nitrate (844 mg; 8.36 mmol) was added and the mixture was stirred at 0° C. for 1 h. The mixture was poured into ice water and extracted with EtOAc (30 mL*3). The organic layer were combined and washed with brine (30 mL), dried over $Na_2SO_4$, filtered and concentrated. For the purification, the crude (1.93 g) was combined with combined with another crude (1.57 g) coming from a reaction performed on 1.2 g of 4-methyloxindole. The combined mixture was purified by silica gel chromatography (Eluent: Petroleum ether/EtOAc 3/1). The desired fractions were collected and the solvent was removed to give 650 mg (20%) of intermediate 168 as a white solid white solid.

Example A40

Preparation of Intermediate 171: 2

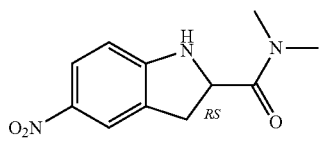

A mixture of 5-nitro-indoline-2-carboxylic acid (1.8 g; 8.65 mmol), dimethylamine hydrochloride (1.41 g; 17.30 mmol), Propylphosphonic acid anhydride (13.8 g; 2162 mmol; 50% in EtOAc) and TEA (5 mL; 346 mmol) in DCM (100 mL) was stirred at room temperature overnight. The mixture was poured into water and extracted with DCM (50 mL*3). The organic layers were combined and washed with brine (30 mL), dried over $Na_2SO_4$, filtered and concentrated. The intermediate product was washed with EtOH and dried under vacuo to give 1.8 g (88%) of intermediate 171 as yellow solid.

Example A41

Preparation of Intermediate 174

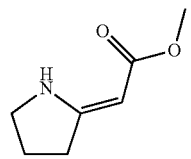

To a solution of sodium methoxide (1.17 g, 21.6 mmol) in dry MeOH (25 mL) under $N_2$ was added a suspension of 2,2-Dimethyl-5-(2-pyrrolidinylidene)-1,3-dioxane-4,6-dione (4.57 g, 21.6 mmol) in dry MeOH (25 mL). The resulting suspension was heated at 70° C. overnight. The reaction mixture was diluted with $H_2O$ (50 mL). Aqueous 1N HCl was added until pH=6 and the mixture was extracted with DCM (3×). The combined organic layers were dried over $MgSO_4$ and concentrated to give a white solid which was purified by silica gel chromatography (Irregular SiOH 15-40 µm, 120 g, dry loading on Celite, mobile phase gradient: from Heptane/EtOAc 70/30 to 50/50). The fractions containing the product were mixed and concentrated to give 2.77 g (91%) of intermediate 174 as a white solid.

Preparation of Intermediate 175

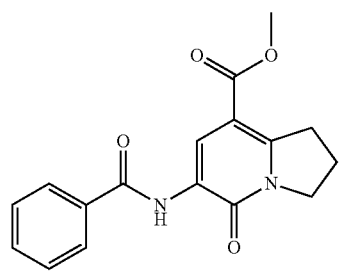 [SMILES: COC(=O)c1cc(NC(=O)c2ccccc2)c(=O)n2c1CCC2]

The reaction was performed twice on 500 mg of intermediate 174.

Typical procedure for one batch on 500 mg of intermediate 174:

A tube was charged with intermediate 174 (500 mg, 3.54 mmol) and 4-ethoxymethylene-2-phenyl-2-oxazolin-5-one (769 mg, 3.54 mmol). Then, ACN (15 mL) and Bismuth(III) nitrate pentahydrate (172 mg, 354 µmol) were added. The tube was sealed and the reaction mixture was heated at 130° C. using one single mode microwave Biotage Initiator EXP 60 with a power output ranging from 0 to 400 w for 25 min. The batches, coming from the 2 reactions performed on 500 mg of intermediate 174, were combined and concentrated to give a dark red residue which was purified by silica gel chromatography(Irregular SiOH 15-40 µm, 12 g, dry loading on Celite, mobile phase gradient: from DCM/MeOH 100/0 to 95/5) to give 2 fractions of intermediate 175:
- 618 mg (30%; 82% of purity evaluated by LC/MS) of intermediate 175 as a beige solid
- 710 mg (32%; 85% of purity evaluated by LC/MS) of intermediate 175 as an orange solid Preparation of Intermediate 176

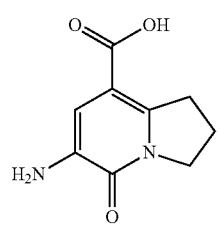 [SMILES: Nc1cc(C(=O)O)c2n(c1=O)CCC2]

A mixture of intermediate 175 (625 mg, 2.00 mmol) and sodium hydroxide (1.60 g, 40.0 mmol) in 1,4-dioxane (8 mL) and water (8 mL) was heated at 100° C. over the weekend. The reaction mixture was concentrated and then, acidified with 1N aqueous HCl until pH=4. The resulting mixture was extracted with DCM/iPrOH (3/1) (8×). The combined organic layers were dried over Na$_2$SO$_4$, filtered and concentrated. The resulting residue was purified by silica gel chromatography (irregular SiOH 15-40 µm, 24 g, dry loading on celite, mobile phase gradient: from DCM/MeOH 95/5 to 85/15) to give 278 mg (72%) of intermediate 176 as a beige solid.

Preparation of Intermediate 177

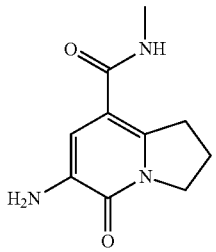

To a solution of intermediate 176 (278 mg, 1.43 mmol) in DMF (14 mL) were added DIPEA (740 µL, 4.30 mmol), methylamine (2.86 mL, 5.73 mmol) and COMU® (1.53 g, 3.58 mmol). The solution was stirred at room temperature for 4 hours and then, concentrated. The resulting residue was purified by silica gel chromatography (irregular SiOH 15-40 µm, 40 g, dry loading (Celite®), mobile phase gradient: DCM/MeOH from 95:5 to 85:15) to give 168 mg (57%) of intermediate 177 as a white solid.

Example A42

Preparation of Intermediate 182

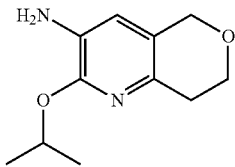

Isopropyl alcohol (10 mL) was added to NaH (419 mg; 10.5 mmol, 60% purity, previously washed with anhydrous heptane) and intermediate 102 (300 mg; 1.31 mmol) was added. The mixture was heated to 220° C. in a steel vessel for 2 h. The reaction mixture was treated with ethyl acetate and washed with aqueous 10% K$_2$CO$_3$ and brine. The organic layer was separated and dried over MgSO$_4$ and the solvent was removed under reduced pressure to give a crude that was purified by flash column chromatography eluting with DCM-MeOH to yield 85 mg (31%) of intermediate 182

Preparation of Intermediate 185

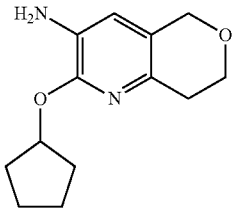 [SMILES: Nc1cc2c(nc1OC1CCCC1)CCOC2]

Intermediate 185 was prepared using a similar procedure than the one used for the preparation of intermediate 182 starting from intermediate 102 (100 mg; 65%).

Example A43

Preparation of Intermediate 189

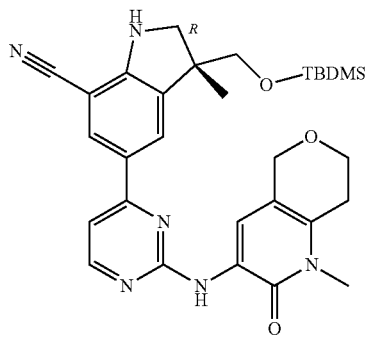

To a solution of intermediate 188 (91.0 mg; 167 µmol) and K$_2$CO$_3$ (46.2 mg; 0.334 mmol) in DMF (910 µL) at room temperature was added iodomethane (12.4 µL; 200 µmol). The mixture was stirred at room temperature for 18 h. Then, EtOAc and water were added. The organic layer was separated, dried over MgSO$_4$, filtered off and evaporated in vacuo to give an orange oil which was purified by silica gel chromatography (Irregular SiOH 15-40 µm, 10 g, liquid loading (DCM), mobile phase gradient: from DCM 100% to DCM 97%, MeOH 3%) to give 74 mg (73%) of intermediate 189 as a pale brown solid.

Example A44

Preparation of Intermediate 190

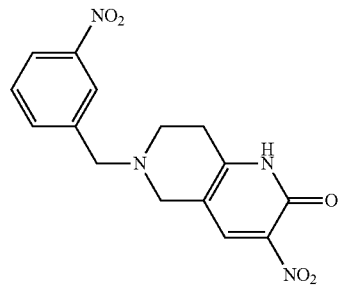 [SMILES: O=c1[nH]c2c(cc1[N+](=O)[O-])CN(Cc1cccc([N+](=O)[O-])c1)CC2]

6-benzyl-5,6,7,8-tetrahydro-[1,6]-naphthyridin-2(1H)-one (1.48 g, 6.16 mmol) was dissolved into sulfuric acid (7.93 mL) and the solution was stirred for 15 minutes at 0° C. Then, nitric acid (8.72 mL) was added dropwise and this reaction was stirred at rt for 18 hours. The reaction mixture was poured onto ice and water, basified with K2CO3 powder and extracted with DCM. The organic layer was dried over MgSO4, filtered and evaporated. The resulting residue was purified by silica gel chromatography (Stationary phase: irregular SiOH 15-40 µm 12 g, Mobile phase: gradient from 100% DCM to 98% DCM, 2% MeOH (2% NH4OH)). The fractions containing the product were mixed and concentrated to afford 660 mg (32%) of intermediate 190.

Preparation Intermediate 191

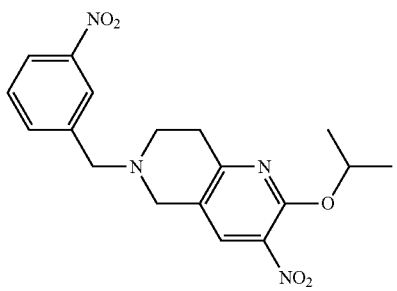 [SMILES: CC(C)Oc1nc2c(cc1[N+](=O)[O-])CN(Cc1cccc([N+](=O)[O-])c1)CC2]

Intermediate 190 (600 mg, 1.82 mmol), iPrOH (278 µL) and cyanomethylenetributylphosphorane (1.2 mL) in toluene (8.71 mL) in a sealed tube were stirred at 90° C. using one single mode microwave (Biotage Initiator EXP 60) with a power output ranging from 0 to 400 W for 20 min. The volatiles were evaporated and the resulting residue was purified by silica gel chromatography (Stationary phase: irregular SiOH 15-40 µm 40 g, Mobile phase: from 90% Heptane, 10% EtOAc to 60% Heptane, 40% EtOAc). The fractions containing the product were mixed and concentrated to afford 298 mg (44%) of intermediate Preparation of Intermediate 192

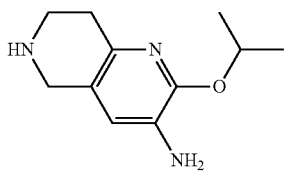

A mixture of intermediate 191 (290 mg, 0.78 mmol) in EtOH (6.82 mL) was hydrogenated at 60° C. under 10 bars pressure for 12 h with palladium hydroxide (26 mg, 0.185 mmol) as a catalyst. The catalyst was filtered off on a pad of Celite® which was with DCM and MeOH. The filtrate was evaporated to give 200 mg of of an intermediate residue which was purified by silica gel chromatography (Irregular SiOH 40 µm 24 g; Mobile phase 93% DCM, 7% MeOH, 0.7% NH4OH to 88% DCM, 12% MeOH, 1.2% NH4OH. The fractions containing the product were combined and the solvent was evaporated to give 100 mg (62%) of intermediate 192.

Preparation of Intermediate 193

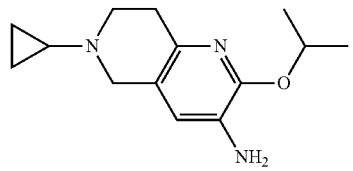 [SMILES: CC(C)Oc1nc2c(cc1N)CN(C1CC1)CC2]

In a sealed tube, a mixture of intermediate 192 (100 mg, 0.482 mmol), (1-ethoxycyclopropoxy) trimethylsilane (0.1 mL, 0.493 mmol) and sodiumcyanoborohydride (0.043 g, 0.69 mmol) in MeOH (1.26 mL, 31.16 mmol) and AcOH (0.04 mL, 0.69 mmol) was stirred at 60° C. overnight. The reaction was cooled down to room temperature. An aqueous solution of NaOH 1N was added and this mixture was extracted twice with DCM. The organic layers were decanted, mixed and evaporated until dryness. The crude product (123 mg) was purified by silica gel chromatography (Irregular SiOH 40 µm 80 g; Mobile phase 99% DCM, 1% MeOH, 0.1% NH4OH to 93% DCM, 7% MeOH, 0.7% NH4OH. The fractions containing the product were combined and the solvent was evaporated to give a first fraction of 80 mg (67%) of intermediate 193 and a second fraction of 20 mg (18%) intermediate 193.

Example A45a

Preparation of Intermediate 196

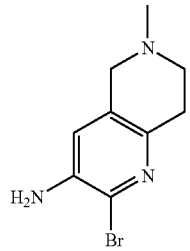

Bromine (665 µL, 12.99 mmol) was added to a solution of 6-methyl-5,6,7,8-tetrahydronaphthyridine-3-amine (2.12 g, 12.99 mmol) and sodium Acetate (2.13 g, 25.98 mmol) in AcOH (40 mL) at room temperature and the mixture was stirred at this temperature for 1 h. The mixture was diluted in DCM and water and treated with NaHCO3 slowly. The organic layer was separated, dried over MgSO4, filtered and evaporated in vacuo to give 2.2 g of intermediate 196 as a brown solid.

Preparation of Intermediate 197

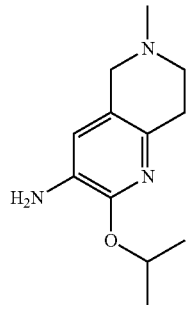 [SMILES: CC(C)Oc1nc2c(cc1N)CN(C)CC2]

Intermediate 196 (2 g, 8.26 mmol) and sodium isopropoxide (5.42 g, 66.08 mmol) in iPrOH (15.2 m) in an autoclave were stirred at 220° C. 10 h. The reaction mixture was diluted with EtOAc, washed with a 10% aqueous solution of $K_2CO_3$, water. The layers were separated and the organic layer was dried over $MgSO_4$, filtered and the solvent was removed under reduced pressure. The residue (6.6 g) was purified by silica gel chromatography (Irregular SiOH 40 μm 330 g, Mobile phase from 100% DCM to 95% DCM, 5% MeOH, 0.5% $NH_4OH$). The pure fractions were combined and the solvent was evaporated to give 720 mg of a mixture of intermediate 196 and intermediate 197 (as the major product) and 80 mg (4%) of intermediate 197. The mixture of 720 mg of intermediate 196 and intermediate 197 was purified via reverse phase chromatography (Stationary phase: YMC-actus Triart-C18 10 μm 30*150 mm, Mobile phase: Gradient from 75% $NH_4HCO_3$ 0.2%, 25% ACN to 35% $NH_4HCO_3$ 0.2%, 65% ACN). The fractions containing the product were mixed and concentrated to afford 377 mg (21%) of intermediate 197.

Example A45b

Preparation of Intermediate 208a

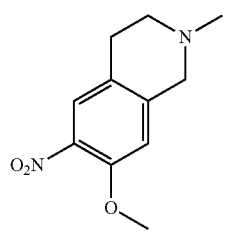 [SMILES: COc1cc2c(cc1[N+](=O)[O-])CCN(C)C2]

And 208b

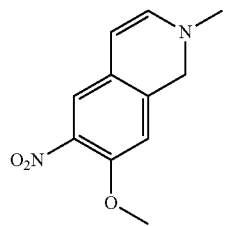 [SMILES: COc1cc2c(cc1[N+](=O)[O-])C=CN(C)C2]

Sodium hydride (91 mg; 2.26 mmol; 60% dispersion in mineral oil) was added portionwise in anhydrous MeOH (1 mL; 24.69 mmol) at 0° C. Then, a solution of 7-fluoro-2-methyl-6-nitro-1,2,3,4-tetrahydroisoquinoline (238 mg; 1.13 mmol) in MeTHF (2 mL). The reaction mixture was stirred at room temperature overnight. The reaction mixture was poured onto iced water and extracted with DCM. The organic layer was decanted, washed with water, dried over $MgSO_4$, filtered and evaporated to give 265 mg of a mixture of intermediate 208a and 208b as a brown solid which was directly engaged in the next step without any further purification.

Preparation of Intermediate 209

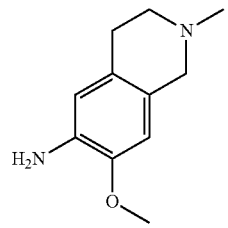

A mixture of intermediate 208a and 208b (265 mg; 1.19 mmol) and Pd/C 10% (55 mg; 0.51 mmol) in MeOH (27 mL) was hydrogenated at rt in a pressure vessel reactor (3 bar) for 4 h. The catalyst was filtered through a pad of Celite® which was washed with DCM/MeOH and the filtrate was evaporated 212 mg of brown oil. This residue was purified by chromatography over silica gel ($SiO_2$, 12 g, eluent: from 97% DCM, 3% MeOH, 0.3% $NH_4OH$ to 90% DCM, 10% MeOH, 1% $NH_4OH$). The fractions containing the product were collected and the solvent was evaporated to give 133 mg (58%) of intermediate 209 as an orange solid.

Example A46

Preparation of Intermediate 211

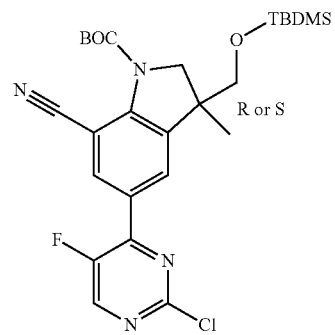

To a solution of intermediate 5R (3.33 g; 4.92 mmol), 5-fluoro-2,4-dichloropyrimidine (0.89 g; 5.32 mmol) and $Cs_2CO_3$ (4.03 g; 12.3 mmol) in 1,4-dioxane (21 mL) and water (2 mL) was added $Pd(PPh_3)_4$ (0.237 g; 0.205 mmol) and the reaction mixture was heated overnight at 95° C. The mixture was poured into ice and extracted with EtOAc. The organic layer was washed with brine, dried over $MgSO_4$, filtered and the solvent was evaporated.

The residue was purified by chromatography over silica gel (240 g, 15-40 μm, eluent: heptane/EtOAc: 1/0 to 0/1). The pure fractions were mixed and the solvent was evaporated affording 1.82 g (83%) of intermediate 211.

Alternative preparation of intermediate 211 A solution in sealed tube of intermediate 5 (1.1 g; 2.1 mmol) in MeTHF (10 mL) was treated with $Na_2CO_3$ (0.4 g; 3.8 mmol) in water (1 mL), 5-fluoro-2,4-dichloropyrimidine (332 mg; 2 mmol), triphenylphosphine (20 mg; 0.076 mmol) and $Pd(OAc)_2$ (8.5 mg; 0.04 mmol) and the mixture evacuated and purged with nitrogen and then heated to 90° C. overnight. The reaction mixture was poured into a mixture of $K_2CO_3$ in water and extracted with EtOAc. The organic layer was dried over MgSO$_4$, filtered and evaporated until dryness.

The residue was purified by silica gel chromatography (24 g of SiOH 15 µm, gradient from 90% heptane 10% EtOAc to 50% heptane 50% EtOAc). The fractions were collected and evaporated until dryness to afford 830 mg (78%) of intermediate 211.

Example A47

Preparation of Intermediate 214

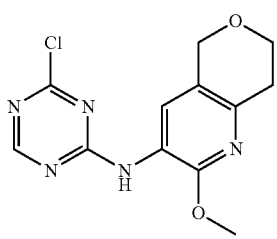 [SMILES: COc1nc2c(cc1Nc1ncnc(Cl)n1)COCC2]

Intermediate 117 (900 mg; 4.99 mmol) was dissolved in acetone (20 mL). Dichlorotriazine (749 mg; 4.99 mmol) and DIEA (2.61 mL; 14.98 mmol) were added and the mixture was stirred overnight at room temperature. The reaction mixture was combined with another reaction performed on 50 mg of intermediate 102.

The solid was filtered and was dried under vacuum to give 950 mg of intermediate 214.

Preparation of Intermediate 215

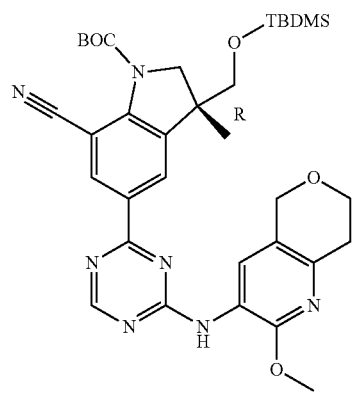

A mixture of intermediate 5R (590 mg; 1.12 mmol), intermediate 214 (453.4 mg; 1.45 mmol), Pd(dppf)Cl$_2$.CH$_2$Cl$_2$ (91 mg; 0.11 mmol) and a saturated aqueous solution of NaHCO$_3$ in dioxane was stirred at 80° C. overnight under N$_2$. The reaction mixture was combined another reaction performed on 50 mg of intermediate 5R. The mixture was evaporated under vacuum. The crude compound was stirred in ethyl acetate (50 mL), and then filtered through Celite®. The filtrate was evaporated under vacuum.

The resulting residue was purified by silica gel chromatographie (eluent: petroleum ether/ethyl acetate from 100/0 to 70/30). The desired fractions were collected and the solvent was concentrated to dryness under vacuum to give 460 mg of intermediate 215 as yellow solid.

Example A48

Preparation of Intermediate 217

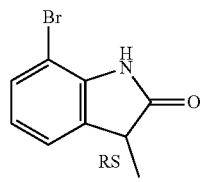

To a cooled (−78° C.) solution of 7-bromooxindole (4.7 g; 22.16 mmol) and N,N,N', N'-tetramethylethylenediamine (10.97 mL; 73.17 mmol) in dry THF (230 mL) was slowly added n-butyllithium solution (19.5 mL; 48.76 mmol; 2.5 M in hexane). The solution was stirred for 30 minutes at the same temperature and then, iodomethane (1.65 mL; 26.6 mmol) was added slowly. The reaction mixture was stirred at −20° C. for 1.5 h, then, quenched with a saturated aqueous solution of NH$_4$Cl and extracted with EtOAc.

The organic layer was stirred over MgSO$_4$, filtered and concentrated in vacuo. The resulting crude material was purified by silica gel chromatography (mobile phase: heptane/EtOAc) to afford, after solvent evaporation, 1.3 g (22%) of intermediate 217.

Preparation of Intermediate 218

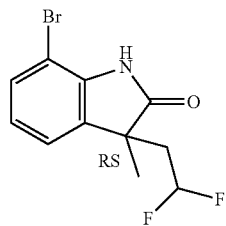 [SMILES: CC1(CC(F)F)C(=O)Nc2c(Br)cccc21]

To a cooled (−78° C.) solution of intermediate 218 (1 g; 4.42 mmol) and N,N,N', N'-tetramethylethylenediamine (2.19 mL; 14.60 mmol) in dry THF (50 mL) was slowly added n-butyllithium solution (3.89 mL; 9.73 mmol; 2.5 M in hexane). The solution was stirred for 30 minutes at the same temperature and then, 1,1-difluoro-2-iodoethane (0.467 mL; 5.31 mmol) was added slowly. The reaction mixture was stirred at −20° C. for 1.5 h, then, quenched with a saturated aqueous solution of NH$_4$Cl and extracted with EtOAc. The organic layer was dried over MgSO$_4$, filtered and concentrated in vacuo. The crude residue was purified by flash column chromatography over silica gel (mobile phase: n-heptane/ethyl acetate from 100/0 to 50/50%). The desired fractions were collected and the solvents were evaporated in vacuo to give 650 mg (50%) of intermediate 218 as a white solid.

Preparation of Intermediate 219

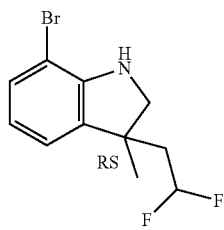

Borane dimethyl sulfide complex (2.12 mL; 22.40 mmol) was added to a solution of intermediate 218 (650 mg; 2.24 mmol) in THF (20 mL). The reaction mixture was stirred at 70° C. for 3 hours. The reaction was cooled to room temperature and MeOH was carefully added. The resulting solution was heated at reflux for 2 hours. The solvents were removed in vacuo and the residue was purified by flash column chromatography over silica gel (mobile phase: n-heptane/ethyl acetate from 100/0 to 80/20%). The desired fractions were collected and the solvents were removed in vacuo to give 605 mg (88%) of intermediate 219 as a colorless oil.

Preparation of Intermediate 220

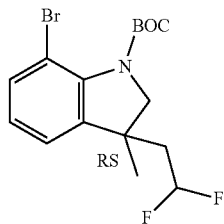 [SMILES: CC(C)(C)OC(=O)N1CC(C)(CC(F)F)c2cccc(Br)c21]

To a solution of intermediate 219 (605 mg; 2.19 mmol) in THF (20 mL) were added trimethylamine (305 µL; 2.19 mmol), 4-dimethylaminopyridine (267.7 mg; 2.19 mmol) and di-tert-butyldicarbonate (717.3 mg; 3.29 mmol) and the solution was stirred at room temperature overnight. The solvents were evaporated in vacuo and the crude residue was purified by flash column chromatography over silica gel (mobile phase: n-heptane/Ethyl acetate from 100/0 to 50/50%). The desired fractions were collected and the solvents were evaporated in vacuo to give 750 mg (90%) of intermediate 220 as a colorless oil.

Preparation of Intermediate 221

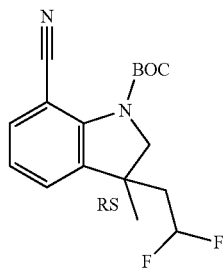 [SMILES: CC(C)(C)OC(=O)N1CC(C)(CC(F)F)c2cccc(C#N)c21]

In a sealed tube a mixture intermediate 220 (700 mg; 1.86 mmol), zinc cyanide (437 mg; 3.72 mmol), Pd(PPh$_3$)$_4$ (430 mg; 0.372 mmol) in anhydrous DMF was degassed with N$_2$ for 10 minutes and then, warmed at 100° C. and stirred overnight. After cooling, the reaction was diluted with a saturated aqueous solution of NH$_4$Cl and extracted with ethyl acetate. The combined organic layers were washed with brine, dried over MgSO$_4$ and concentrated in vacuo. The residue was purified by silica gel chromatography eluted with 20% ethyl acetate in n-heptane. The fractions containing the product were combined and the solvent was concentrated in vacuo to afford 316 mg (42% based on a purity of 80% evaluated by LC/MS) of intermediate 221.

Preparation of Intermediate 222

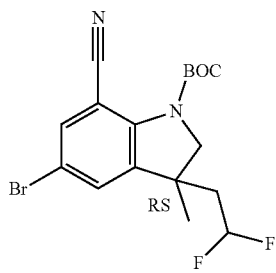 [SMILES: CC(C)(C)OC(=O)N1CC(C)(CC(F)F)c2cc(Br)cc(C#N)c21]

A mixture of intermediate 221 (320 mg; 0.99 mmol) and N-bromosuccinimide (176.7 mg; 0.99 mmol) in ACN (10 mL) was refluxed overnight. The solvent was evaporated in vacuo and the crude was purified by flash column chromatography over silica gel (mobile phase: n-heptane/ethyl acetate from 100/0 to 80/20%). The desired fractions were collected and the solvents were evaporated in vacuo to give 227 mg (46% based on a purity of 80% evaluated by LC/MS) of intermediate 222 as a brown solid.

Preparation of Intermediate 223

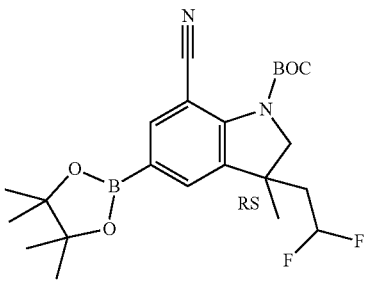 [SMILES: CC(C)(C)OC(=O)N1CC(C)(CC(F)F)c2cc(B3OC(C)(C)C(C)(C)O3)cc(C#N)c21]

To a mixture of intermediate 222 (200 mg; 0.4 mmol) in dioxane (5 mL) was added bis(pinacolato)diboron (253 mg; 1 mmol) and potassium acetate (117.4 mg; 1.2 mmol). After 5 minutes of bubbling nitrogen, Pd(dppf)Cl$_2$.CH$_2$Cl$_2$ (8.1 mg; 0.01 mmol) and XPhos (9.5 mg; 0.02 mmol) were added. The reaction mixture was heated at 60° C. overnight. The solvent was removed in vacuo and the crude was used in the next step without any further purification.

Preparation of Intermediate 224

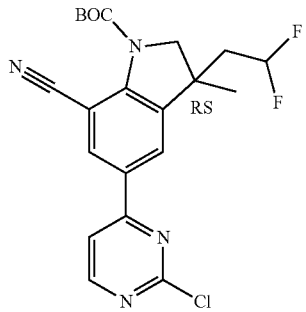 [SMILES: CC(C)(C)OC(=O)N1CC(C)(CC(F)F)c2cc(-c3ccnc(Cl)n3)cc(C#N)c21]

2,4-dichloropyrimidine (59.5 mg; 0.4 mmol), intermediate 223 (179 mg; 0.4 mmol) and Na₂CO₃ (126.9 mg; 1.2 mmol) in 1,4-dioxane (8 mL) and water (2 mL) were degazed for 10 min. Then, Pd(dppf)Cl₂.CH₂Cl₂ (16.3 mg; 0.02 mmol) was added and the mixture was heated at 90° C. for 4 hours. The solvents were evaporated in vacuo and the crude residue was purified by flash column chromatography over silica gel (mobile phase: n-heptane/ethyl acetate from 100/0 to 70/30%). The desired fractions were collected and the solvents were evaporated in vacuo to give 230 mg (99% based on a purity of 75% evaluated by LC/MS) as a brown solid.

Preparation of Intermediate 225

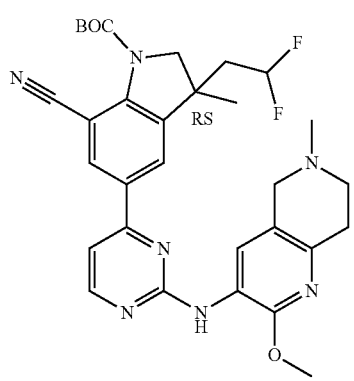 [SMILES: COc1nc2c(cc1Nc1nccc(-c3cc(C#N)c4c(c3)C(C)(CC(F)F)CN4C(=O)OC(C)(C)C)n1)CN(C)CC2]

Intermediate 138 (73.3 mg; 0.38 mmol), intermediate 224 (165 mg; 0.38 mmol), and Cs₂CO₃ (185.5 mg; 0.569 mmol) were dissolved in THF (10 mL) under a nitrogen atmosphere and then, Pd(OAc)₂ (4.3 mg; 0.019 mmol) and rac-BINAP (21.95 mg; 0.038 mmol) were added and the reaction mixture was stirred at 60° C. for 3 hours. THF was removed in vacuo and the crude residue was purified by flash column chromatography over silica gel (mobile phase: DCM/DCM: MeOH (9:1) from 100/0 to 50/50%). The desired fractions were collected and the solvents were evaporated in vacuo to give 153 mg (67%) of intermediate 225 as a brown solid.

Example A49

Preparation of Intermediate 226

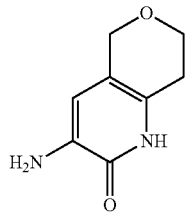 [SMILES: Nc1cc2c([nH]c1=O)CCOC2]

A mixture of intermediate 117 (420 mg; 2.33 mmol), Hydrobromic acid (10.08 mL; 155.5 mmol) and water (1.7 mL) was stirred overnight at room temperature. The solvent was removed until dryness and the crude was directly engaged in the next step without further purification.

Preparation of Intermediate 227

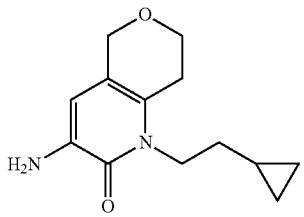 [SMILES: Nc1cc2c(n(CCC3CC3)c1=O)CCOC2]

Cs₂CO₃ (2.3 g; 7.08 mmol) was added to a solution of intermediate 226 (530 mg; 2.14 mmol) in anhydrous DMF (12 mL) under N₂ atmosphere. The mixture was stirred at room temperature for 15 minutes and (2-iodoethyl)cyclopentane was added. The reaction was stirred at room temperature overnight and was diluted with water. The precipitate was filtered off, washed with water and dried in vacuo. The resulting crude was purified by silica gel chromatography (mobile phase: gradient 1000 DCM 0% DCM/MeOH (9/1) to 0% DCM 100% DCM/MeOH (9/1)). The fractions containing the product were mixed and the solvent was concentrated to afford 153 mg (30%) of intermediate 227.

Example A50

Preparation of Intermediate 230

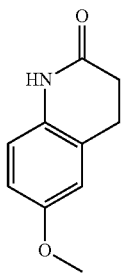

To a solution of 3,4-dihydro-6-hydroxycarbostyril (4.89 g; 30 mmol) in acetone (40 mL) was added of dimethyl sulfate (4.67 g; 45 mmol) and K₂CO₃ (12.44 g; 90 mmol). The reaction mixture was stirred at ambient temperature for 16 hours. The mixture was concentrated in vacuo. The residue was partitioned between a saturated aqueous solution of bicarbonate (10 ml) and methylene chloride (20 mL*2). The organic layer was dried over sodium sulfate and evaporated to give 4 g (75%) of intermediate 230 as an off-white solid.

Preparation of Intermediate 231

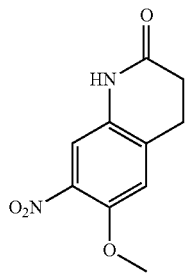 [SMILES: COc1cc2c(cc1[N+](=O)[O-])NC(=O)CC2]

To a solution of intermediate 230 (2 g; 11.3 mmol) in TFA (16 mL) was added sodium nitrite (934.5 mg; 13.54 mmol) at 0° C. The temperature was raised to 25° C. and the mixture was stirred for 4 hours. The mixture was poured into ice and the yellow precipitate was collected affording 1.2 g (41%; 85% of purity evaluated by LC/MS) of intermediate 131.

Example A51

Preparation of Intermediate 235

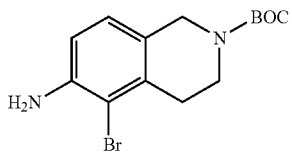 [SMILES: CC(C)(C)OC(=O)N1CCc2c(ccc(N)c2Br)C1]

Preparation of intermediate 235 was performed via 2 reactions as reported below.

Reaction 1: N-bromosuccinimide (716 mg; 4.03 mmol) was added portionwise at 0° C. to a solution of t-Butyl-6-amino-3,4-dihydroisoquinoline-2-carboxylate (1 g; 4.03 mmol) in DCM (20 mL). The reaction mixture was stirred at room temperature for 2 hours, poured onto a 10% aqueous solution of K₂CO₃ and extracted with DCM.

Reaction 2: N-bromosuccinimide (2.08 g; 11.68 mmol) was added portionwise at 0° C. to a solution of t-Butyl-6-amino-3,4-dihydroisoquinoline-2-carboxylate (2.9 g; 11.68 mmol) in C (60 mL). The reaction mixture was stirred at room temperature for 2 hours, poured onto a 10% aqueous solution of K₂CO₃ and extracted with DCM.

The two residues were combined and purified by chromatography over silica gel (irregular SiOH, 80 g; mobile phase: gradient from 20% EtOAc, 80% heptane to 40% EtOAc, 60% heptane). The pure fractions were collected and evaporated to dryness yielding 2.8 g (54%) of intermediate 235.

Preparation of Intermediate 236

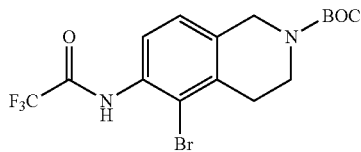 [SMILES: CC(C)(C)OC(=O)N1CCc2c(ccc(NC(=O)C(F)(F)F)c2Br)C1]

Trifluoroacetic anhydride (1.03 mL; 7.43 mmol) was added dropwise to a solution of intermediate 235 (2.21 g; 6.75 mmol) and triethylamine (3.76 mL; 27.02 mmol) in DCM (35.4 mL) and the reaction mixture was stirred at room temperature for 18 h. Additional trifluoroacetic anhydride (0.1 eq.; 94 µL; 0.68 mmol) was added and the reaction mixture was stirred at room temperature for 2 h. Additional trifluoroacetic anhydride (0.5 eq.; 469 µL; 3.38 mmol) was added and the reaction mixture was stirred at room temperature for 30 h. Water was added and the reaction mixture was extracted with DCM (3×). The organic layer was decanted, dried over MgSO₄, filtered and the solvent was evaporated to give 3.18 g of intermediate 236 as a yellow solid.

Preparation of Intermediate 237

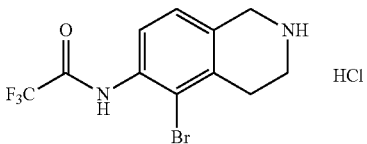 [SMILES: O=C(Nc1ccc2c(c1Br)CCNC2)C(F)(F)F ; Cl]

HCl 4M in dioxane (74 mL; 295 mmol) was added dropwise to a solution of intermediate 236 (3.18 g; 7.51 mmol) in 1,4-dioxane (25 mL) and the reaction mixture was stirred at room temperature for 3 h. The reaction mixture was evaporated to dryness and the solid was suspended in ACN. The precipitate was filtered, washed with ACN and dried to give 2.21 g (82%) of intermediate 237 as a white solid.

Preparation Intermediate 238a

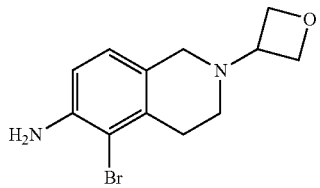 [SMILES: Nc1ccc2c(c1Br)CCN(C1COC1)C2]

And 238b

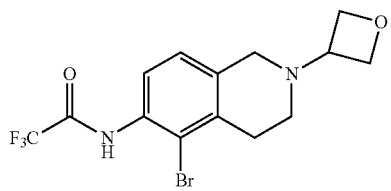 [SMILES: O=C(Nc1ccc2c(c1Br)CCN(C1COC1)C2)C(F)(F)F]

3-oxetanone (942 µL; 15.69 mmol) was added to a solution of intermediate 237 (1.41 g; 3.92 mmol) in MeOH (40 mL). The reaction mixture was heated at reflux for 1 h. The reaction mixture was cooled to room temperature then sodium cyanoborohydride (739 mg; 11.76 mmol) was added. The reaction mixture was refluxed for 2 h. The reaction mixture was cooled to room temperature and allow to stand overnight. The mixture was poured onto a 10% solution of $K_2CO_3$ and diluted with DCM. The mixture was extracted with DCM (3×). NaCl solid was added into the aqueous layer and the product was extracted with EtOAc (twice). The organic layers were combined, then dried over $MgSO_4$, filtered and the solvent was evaporated. The yellow solid residue (2.6 g) was purified by chromatography over silica gel ($SiO_2$, Grace, 80 g, solid deposit; eluent: 96% DCM, 4% MeOH, 0.4% $NH_4OH$). The fractions containing the product were collected and the solvent was evaporated to give 1.25 g of an impure fraction which was purified again by chromatography over silica gel ($SiO_2$, Grace, 40 g; gradient: from 100% DCM to 98% DCM, 2% MeOH, 0.2% $NH_4OH$). The fractions containing the product were collected and the solvent was evaporated to give 363 mg (33%) of intermediate 238a as a pale yellow solid and 694 mg (47%) of intermediate 238b as a yellow solid.

Alternative Preparation of Intermediate 238a

Sodium hydroxide (407 mg; 7.25 mmol) was added to a mixture of intermediate 238b (687 mg; 1.81 mmol) in MeOH (14 mL). The reaction mixture was stirred at reflux for 5 h. The solvent was evaporated, then water and DCM were added onto the residue. The mixture was extracted with DCM (3×) and decanted. The organic layer was dried over $MgSO_4$, filtered and the solvent was evaporated to give 538 mg of intermediate 238a as a yellow oil which crystallized upon standing.

Preparation of Intermediate 239

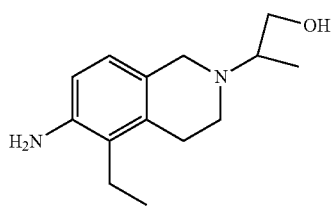

In a sealed tube, triethylborane 1M in hexanes (4 mL; 4 mmol) was added dropwise at room temperature to a previously degassed mixture of intermediate 238a (374 mg; 1.32 mmol), $Cs_2CO_3$ (861 mg; 2.64 mmol) and RuPhos Palladacycle Gen. 1 (108 mg; 0.13 mmol) in THF (9 mL). The reaction mixture was stirred at 60° C. (pre-heated bath) overnight and the reaction was combined with another reaction performed on 50 mg of intermediate 238a. The reaction mixture was then cooled to room temperature, poured onto water and extracted with EtOAc (3×). The organic layer was decanted, washed with brine, dried over $MgSO_4$, filtered through a pad of Celite® and the solvent was evaporated. The resulting residue (590 mg) was purified by chromatography over silica gel (irregular bare silica 40 g, mobile phase: 94% DCM, 6% MeOH, 0.5% $NH_4OH$). The fractions containing the product were collected and the solvent was evaporated to give 122 mg (39%) of intermediate 239 as a yellow oil.

Example A52

Preparation of Intermediate 241

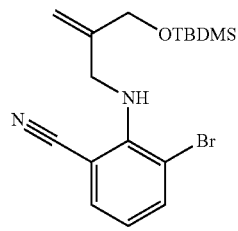 [SMILES: C=C(CNc1c(Br)cccc1C#N)CO[Si](C)(C)C(C)(C)C]

To a solution of 2-Amino-3-bromobenzonitrile (30.0 g) in THF (240 mL) was added sodium tert-butoxide (1.1 eq.) and the mixture was stirred at −5 to 5° C. for 1 hour. A solution of intermediate 3a in THF (85.0 g) was then added dropwise and the mixture was stirred for 2-4 hours monitoring the conversion by HPLC. Water (210 mL) was then added dropwise and the mixture was concentrated to remove most of THF. Heptane (300 mL) was then added and the mixture was stirred for 30 min. After phase separation, the organic layer was washed with water (210 mL), concentrated to 2-3 volumes and filtered through a pad of silica gel (60 g), washing the pad with heptane (300 mL), affording 63.3 g of intermediate 241.

Preparation of Intermediate 242

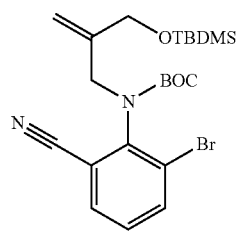 [SMILES: C=C(CO[Si](C)(C)C(C)(C)C)CN(C(=O)OC(C)(C)C)c1c(Br)cccc1C#N]

To a solution of intermediate 241 (50.0 g) in dry THF (500 mL) was added dimethylaminopyridine (0.5 eq.) and the temperature was adjusted to 65-70° C. Di-tert-butyldicarbonate (2.2 eq.) was then added and the mixture was stirred for 2 hours monitoring the conversion by HPLC. Water (350 mL) was added and the mixture was concentrated to 350-400 mL. Heptane (500 mL) was added and the pH was adjusted by addition of 20% aqueous AcOH to 4-6. The layers were separated and water (350 mL) was added. After pH adjustment to 7-8 with aqueous 8% $NaHCO_3$, the layers were separated and the organic layer was washed with water (350 mL) and concentrated to afford 64 g (quantitative) of intermediate 242.

B. Preparation of the Final Compounds

Example B1

Preparation of Compound 21

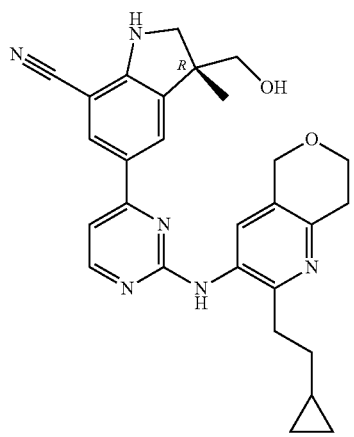

To a solution of intermediate 106 (260.00 mg, 0.44 mmol) in Me-THF (5 mL) was added TBAF (1M in THF) (0.50 mL, 0.50 mmol) and the mixture was stirred at rt for 20 h. The reaction mixture was diluted with EtOAc and water. The layers were separated and the organic layer was dried over MgSO$_4$, filtered, and the solvent was removed under reduced pressure. The crude residue was purified by silica gel chromatography (irregular SiOH 15-40 µm, 12 g, dry load on celite, mobile phase gradient: from DCM/iPrOH 100/0 to 90/10) to give 161 mg of an off-white solid. This product was solubilized in MeCN (1 mL), extended with water (9 mL) and freeze-dried to give 161 mg of compound 21 (77% yield, white solid).

Preparation of Compound 25

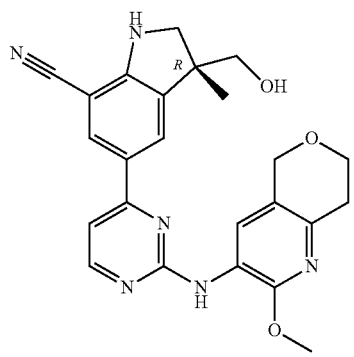

To a solution of intermediate 119 (338.00 mg, 0.50 mmol) in Me-THF (5 mL) was added TBAF (1M in THF) (540.00 µL, 0.54 mmol). The solution was stirred at rt for 3 h and evaporated in vacuo. The crude residue was purified by silica gel chromatography (Irregular SiOH 15-40 µm, 24 g, mobile phase gradient: from DCM 100% to DCM 97%, MeOH 3%). The pure fractions were collected and evaporated to dryness and the residue was triturated in Et$_2$O, the solid was filtered on a glass frit and dried under high vacuum (50° C., 18 h) to give 172 mg of compound 25 (40% yield, white solid).

Preparation of Compound 32

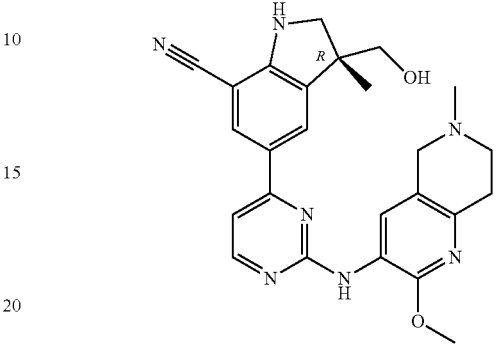

To a solution of intermediate 139 (382.00 mg, 0.67 mmol) in Me-THF (7.5 mL) was added TBAF (1M in THF) (0.75 mL, 0.75 mmol) and the mixture was stirred at rt overnight. The mixture was evaporated in vacuo and purified by silica gel chromatography (irregular SiOH, 15-40 µm, 30 g, liquid loading with DCM, mobile phase gradient: from DCM 98%, MeOH/aq. NH$_3$ (95:5) 2% to DCM 92%, MeOH/aq. NH$_3$ (95:5) 8%) to give a yellow oil which crystallized upon standing. The residue was then triturated in diethylether. The precipitate was filtered on glass-frit and dried under vacuum (50° C., 16 h) to give 143 mg of compound 32 (39% yield, white solid).

Preparation of Compound 34

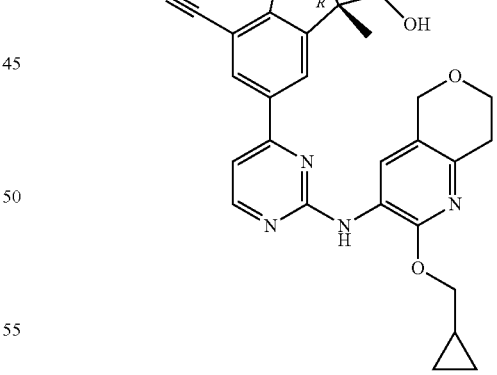

To a solution of intermediate 146 (255.00 mg, 0.29 mmol based on 69% purity 1H NMR) in Me-TH (3 mL) was added TBAF (1M in THF) (320.00 µL, 0.32 mmol). The solution was stirred at rt for 18 h then evaporated in vacuo. The crude residue was sonicated in MeOH, and the filtrate was evaporated in vacuo. The crude residue was further sonicated in DCM. The solid was filtered on a glass frit and dried in vacuo to give 104 mg of compound 34 (35% yield, off-white solid).

Preparation of Compound 35

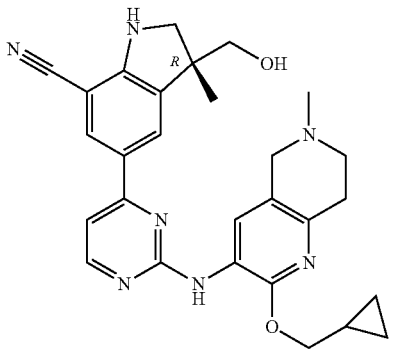

A mixture of intermediate 149 (65.00 mg, 0.11 mmol) and TBAF (1M in THF) (212.47 μL, 0.21 mmol) in Me-THF (1.06 mL, 10.62 mmol) was stirred at rt for 3 h. The reaction mixture was diluted with EtOAc, washed with an aqueous solution of $K_2CO_3$ (10%), water (twice) and a saturated solution of NaCl (twice). The layers were separated and the organic layer was dried over $MgSO_4$, filtered and the solvent was removed under reduced pressure. The crude product was purified by silica gel chromatography (Irregular SiOH 40 μm, 40 g, mobile phase gradient: 98% DCM, 2% MeOH, 0.2% $NH_4OH$ to 88% DCM, 12% MeOH, 1.2% $NH_4OH$). The pure fractions were combined and the solvent was evaporated under reduced pressure. The residue was freeze-dried with $CH_3CN$ to give 33 mg of compound 35 (62% yield).

The compounds in the table below were prepared by using an analogous method starting from the respective starting materials. The most relevant minor deviations to the referenced method are indicated as additional information in the column 'Yield (%)'.

| Compound number | Structure | Mass (mg) | Yield (%) |
|---|---|---|---|
| Compound 5 (mixture of two diastereomers with unknown configuration (DIA A)) | 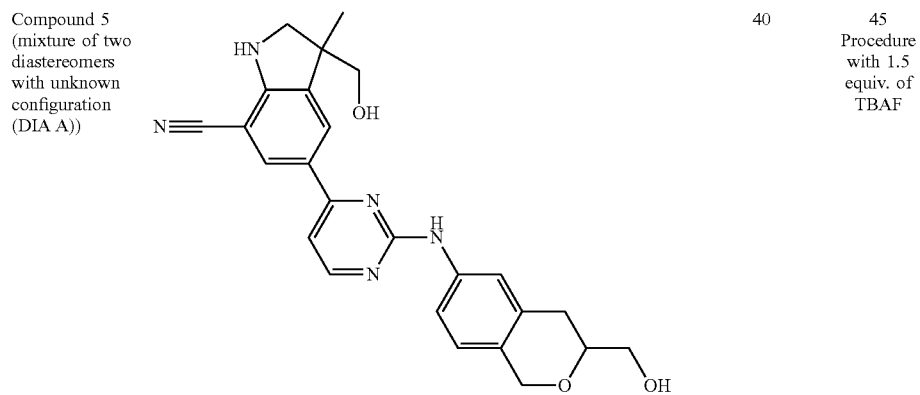<br>From intermediate 35 | 40 | 45<br>Procedure with 1.5 equiv. of TBAF |
| Compound 8 (mixture of two diastereomers with unknown configuration (DIA B)) | 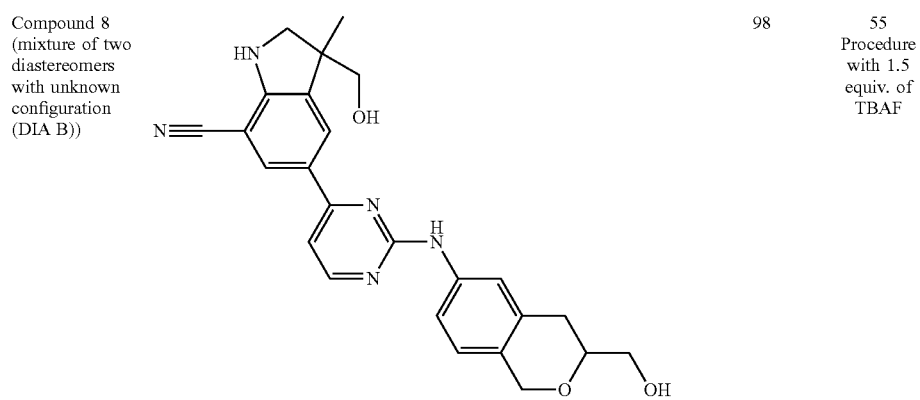<br>From intermediate 41 | 98 | 55<br>Procedure with 1.5 equiv. of TBAF |

| Compound number | Structure | Mass (mg) | Yield (%) |
|---|---|---|---|
| Compound 9 | 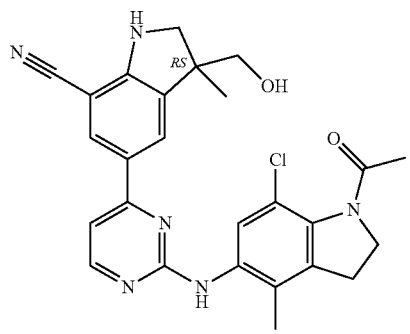<br>From intermediate 47 | 299<br>Off-white solid | 71<br>Procedure with 1.2 equiv. of TBAF |
| Compound 11 | 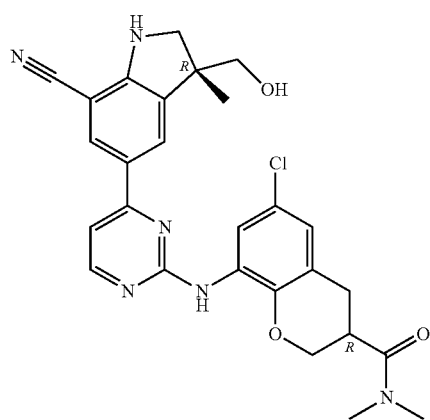<br>From intermediate 59 | 115<br>yellow solid | 37<br>Procedure with 1.1 equiv. of TBAF |
| Compound 12 | 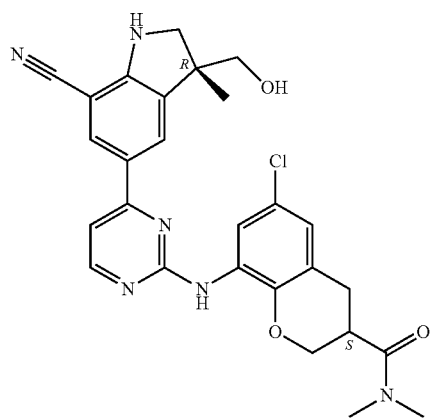<br>From intermediate 62 | 126<br>Pale yellow solid | 61<br>Procedure with 1.1 equiv. of TBAF |

-continued

| Compound number | Structure | Mass (mg) | Yield (%) |
|---|---|---|---|
| Compound 13 | From intermediate 66 | 76 White solid | 68 Procedure with 1.1 equiv. of TBAF |
| Compound 14 | From intermediate 70 | 26 White solid | 13 Procedure with 1.1 equiv. of TBAF |
| Compound 15 | From intermediate 76 | 65 Pale yellow solid | 77 Procedure with 1.3 equiv. of TBAF |
| Compound 16 | From intermediate 82 | 82 Off-white solid | 45 Procedure with 1.5 equiv. of TBAF |

| Compound number | Structure | Mass (mg) | Yield (%) |
|---|---|---|---|
| Compound 17 | 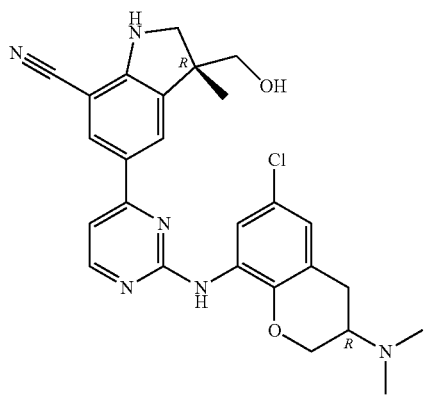<br>From intermediate 87 | 100<br>white solid | 34<br>Procedure with 1.1 equiv. of TBAF |
| Compound 18 | 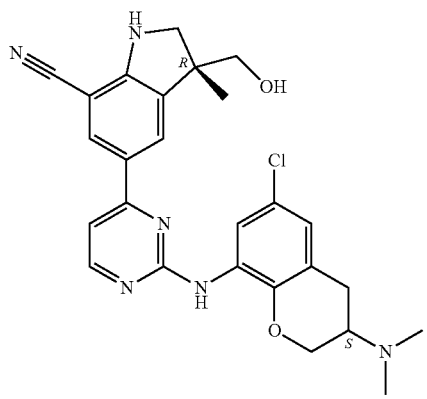<br>From intermediate 87 | 86<br>white solid | 29<br>Procedure with 1.1 equiv. of TBAF |
| Compound 19 | 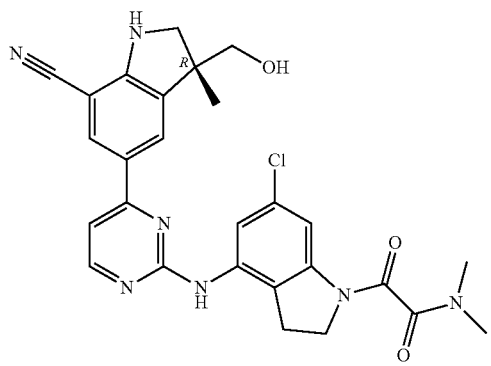<br>From intermediate 93 | 41<br>Off-white solid | 37<br>Procedure with 1.1 equiv. of TBAF |

-continued

| Compound number | Structure | Mass (mg) | Yield (%) |
|---|---|---|---|
| Compound 22 | From intermediate 108 | 85 white fluffy solid | 65 Procedure with 1.15 equiv. of TBAF |
| Compound 23 | From intermediate 112 | 126 yellow solid | 65 Procedure with 1.1 equiv. of TBAF |
| Compound 24 | From intermediate 116 | 132 yellow solid | 54 Procedure with 1.1 equiv. of TBAF |

-continued

| Compound number | Structure | Mass (mg) | Yield (%) |
|---|---|---|---|
| Compound 26 | From a mixture of intermediate 124 and 124' | 155 Pale yellow solid | 23 Procedure with 1.1 equiv. of TBAF |
| Compound 27 | From a mixture of intermediate 124 and 124' | 36 white solid | 5 Procedure with 1.1 equiv. of TBAF |
| Compound 28 | From intermediate 127 | 202 Yellow solid | 49 Procedure with 1.1 equiv. of TBAF |
| Compound 29 | From intermediate 131 | 263 Pale yellow solid | 64 Procedure with 1.1 equiv. of TBAF |

-continued

| Compound number | Structure | Mass (mg) | Yield (%) |
|---|---|---|---|
| Compound 30 | From intermediate 134 | 167 Pale yellow solid | 68 Procedure with 1.1 equiv. of TBAF |
| Compound 31 | From intermediate 136 | 72 White fluffy solid | 39 Procedure with 1.1 equiv. of TBAF |
| Compound 33 | From intermediate 143 | 133 Yellow solid | 57 Procedure with 1.05 equiv. of TBAF |
| Compound 36 | From intermediate 152 | 170 | 31 Procedure with 2.5 equiv. of TBAF and THF as solvent |

-continued

| Compound number | Structure | Mass (mg) | Yield (%) |
|---|---|---|---|
| Compound 39 | From intermediate 160 | 44 | 16 Procedure with 1.5 equiv. of TBAF and THF as solvent |
| Compound 40 | From intermediate 165 | 80 | 37 Procedure with 4 equiv. of TBAF and THF as solvent |
| Compound 44 | From intermediate 179 | 122 | 79 |
| Compound 46 | From intermediate 184 | 62 | 57 Procedure with 1.2 equiv. of TBAF |

-continued
| Compound number | Structure | Mass (mg) | Yield (%) |
|---|---|---|---|
| Compound 47 | 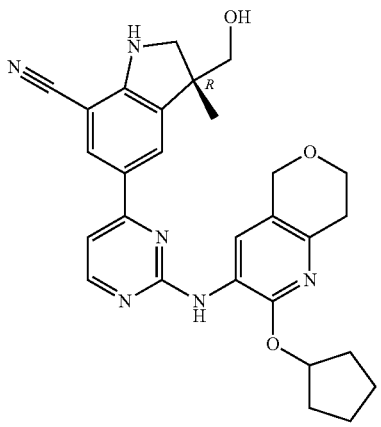<br>From intermediate 187 | 57 | 41 |
| Compound 48 | 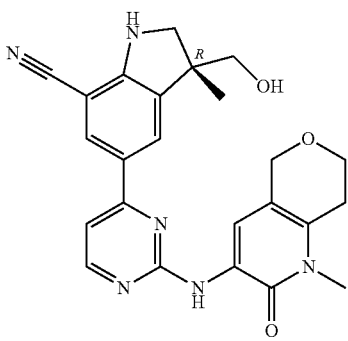<br>From intermediate 189 | 43 | 57<br>Procedure with 1.05 equiv. of TBAF |
| Compound 49 | 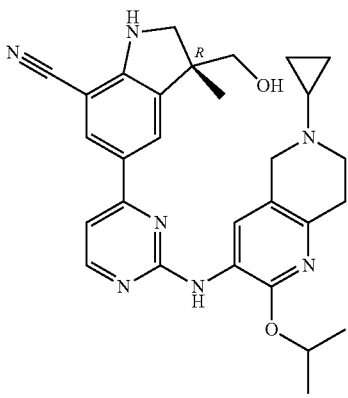<br>From intermediate 195 | 47 | 48<br>Procedure with 2 equiv. of TBAF |

| Compound number | Structure | Mass (mg) | Yield (%) |
|---|---|---|---|
| Compound 50 | 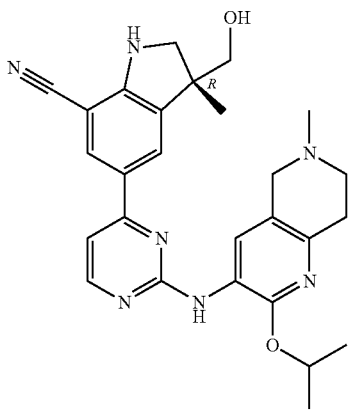<br>From intermediate 199 | 296 | 55<br>Procedure with 2 equiv. of TBAF |
| Compound 51 | 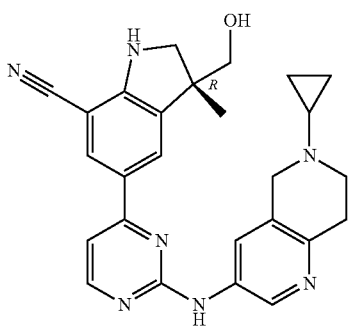<br>From intermediate 203 | 53 | 60<br>Procedure with 2 equiv. of TBAF |
| Compound 52 | 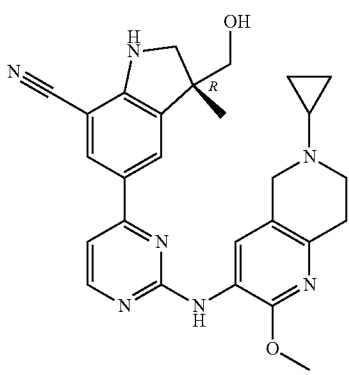<br>From intermediate 207 | 36 | 37<br>Procedure with 2 equiv. of TBAF |

-continued

| Compound number | Structure | Mass (mg) | Yield (%) |
|---|---|---|---|
| Compound 53 | From intermediate 210 | 43 | 67 Procedure with 2 equiv. of TBAF |
| Compound 54 | From intermediate 213 | 97 | 94 Procedure with 4 equiv. of TBAF and THF as solvent |
| Compound 55 | From intermediate 216 | 48 | 31 Procedure with 1.6 equiv. of TBAF and THF as solvent |
| Compound 58 | From intermediate 229 | 100 | 68 Procedure with 1.2 equiv. of TBAF |

-continued

| Compound number | Structure | Mass (mg) | Yield (%) |
|---|---|---|---|
| Compound 60 | *From intermediate 240* | 8 | 25 Procedure with 2 equiv. of TBAF |

Example B2

Preparation of Compound 1

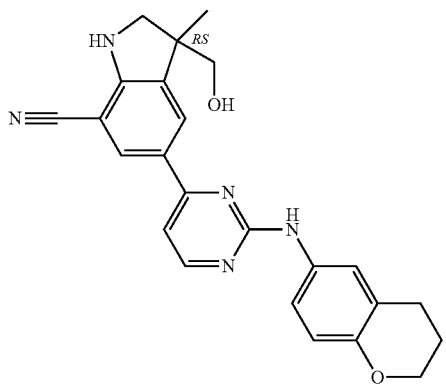 [SMILES: CC1(CO)CNc2c(C#N)cc(-c3ccnc(Nc4ccc5c(c4)CCCO5)n3)cc21]

To a solution intermediate 15 (126.00 mg, 0.24 mmol) in DCM (3.79 mL) was added TFA (0.88 mL, 11.56 mmol) at 0-5° C. The reaction mixture was stirred at 0-5° C. for 1.5 h. The reaction mixture was poured in a mixture of crushed ice, water and NH$_4$OH. After extraction with DCM (twice), the organic layers were combined, washed with brine, dried over MgSO$_4$ and evaporated. The crude residue was taken up into Et$_2$O, filtered and dried under vacuum to afford 70 mg of compound 1 (69% yield).

The compounds in the table below were prepared by using an analogous method starting from the respective starting materials. The most relevant minor deviations to the referenced method are indicated as additional information in the column 'Yield (%)'.

| Compound number | Structure | Mass (mg) | Yield (%) |
|---|---|---|---|
| Compound 3 | *From intermediate 22* | 120 yellow solid | 28 Procedure with DCM/TFA (3:1, eq./eq.) |

| Compound number | Structure | Mass (mg) | Yield (%) |
|---|---|---|---|
| Compound 4 | 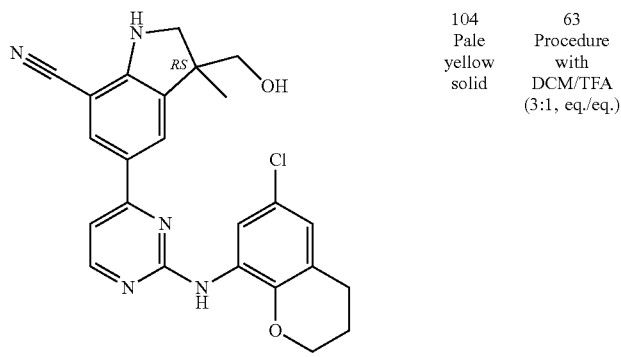<br>From intermediate 27 | 104<br>Pale yellow solid | 63<br>Procedure with DCM/TFA (3:1, eq./eq.) |
| Compound 7 | 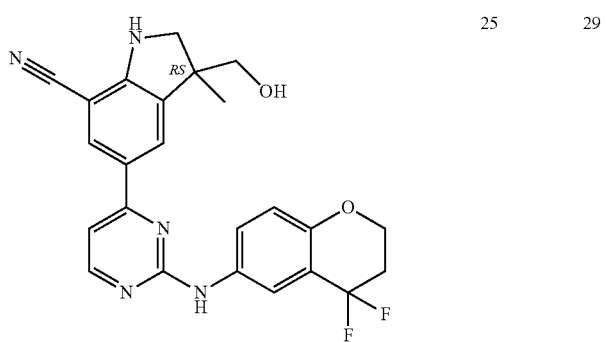<br>From intermediate 40 | 25 | 29 |
| Compound 10 | 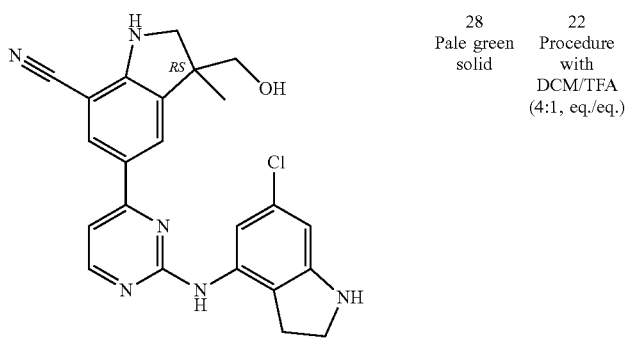<br>From intermediate 51 | 28<br>Pale green solid | 22<br>Procedure with DCM/TFA (4:1, eq./eq.) |

-continued
| Compound number | Structure | Mass (mg) | Yield (%) |
|---|---|---|---|
| Compound 20 | 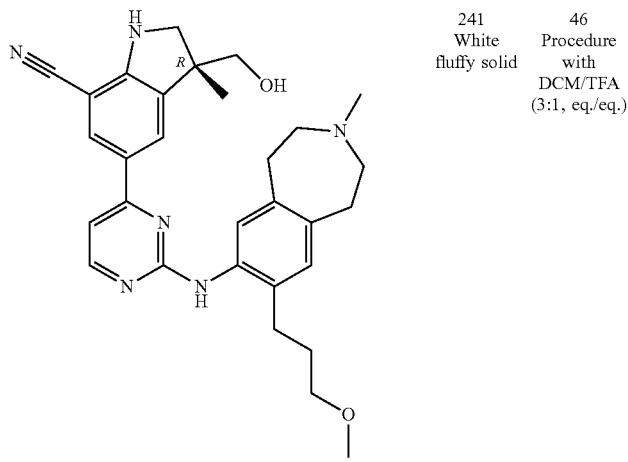<br>From intermediate 99 | 241<br>White fluffy solid | 46<br>Procedure with DCM/TFA (3:1, eq./eq.) |
| Compound 38 | 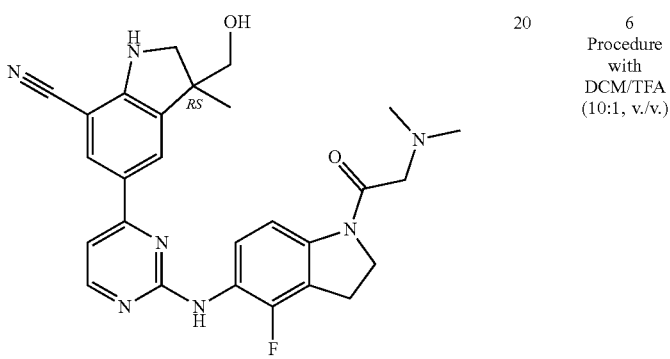<br>From intermediate 157 | 20 | 6<br>Procedure with DCM/TFA (10:1, v./v.) |
| Compound 41 | 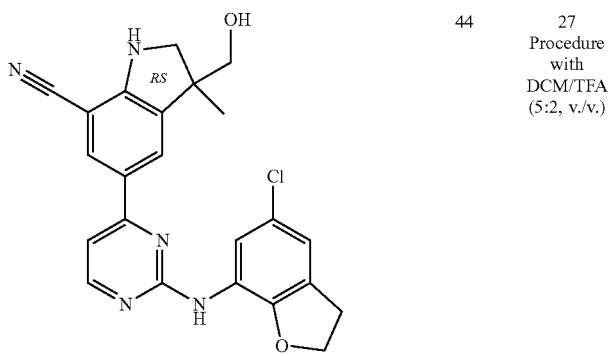<br>From intermediate 167 | 44 | 27<br>Procedure with DCM/TFA (5:2, v./v.) |

-continued
| Compound number | Structure | Mass (mg) | Yield (%) |
|---|---|---|---|
| Compound 43 | 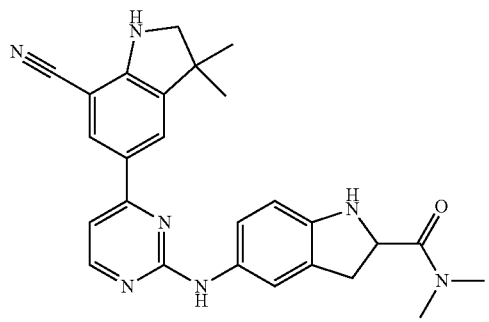<br>From intermediate 173 | 35 | 8<br>Procedure with DCM/TFA (1:1, v./v.) |
| Compound 45 | 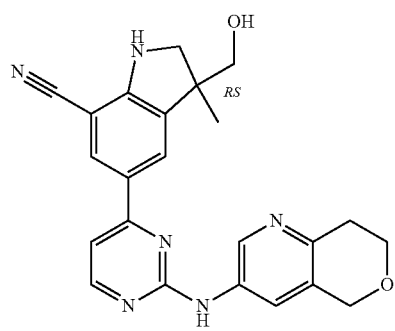<br>From intermediate 181 | 110 | 27<br>Procedure with DCM/TFA (2:1, v./v.) |
| Compound 59 | 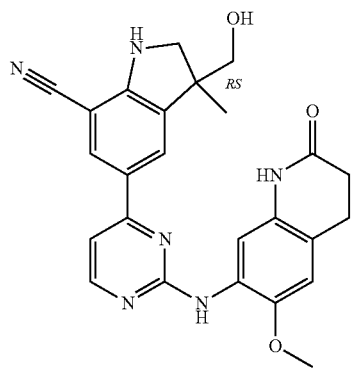<br>From intermediate 234 | 50 | 31<br>Procedure with DCM/TFA (10:1, v./v.) |

Example B3

Preparation of Compound 2

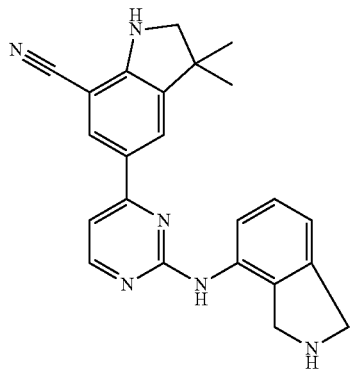 [SMILES: CC1(C)CNc2c(C#N)cc(-c3ccnc(Nc4cccc5c4CNC5)n3)cc21]

HCl (3M in H₂O) (3 mL, 9 mmol) was added to a solution of intermediate 16 (378.76 mg, 0.65 mmol) in MeOH (10 mL) and the reaction mixture was stirred 5 h at 65° C. The reaction mixture was cooled to room temperature, poured onto a 10% aqueous solution of K₂CO₃ and extracted with DCM. The organic layer was decanted, dried over MgSO₄, filtered and evaporated to dryness. The residue was taken up with DCM/MeOH (90/10) and the precipitate was filtered, washed with DCM and dried. The filtrate was evaporated and dissolved in DCM/MeOH (330 mL, 10% MeOH) and a 10% aqueous solution of K₂CO₃ was added. The organic layer was decanted, dried over MgSO₄, filtered and evaporated to dryness. The residue was purified by chromatography over silica gel (irregular SiOH, 25 g+5 g solid deposit, mobile phase gradient: from 0.5% NH₄OH, 5% MeOH, 95% DCM to 1% NH₄OH, 10% MeOH, 90% DCM). The pure fractions were collected and evaporated to dryness. The residue was further purified by reverse phase chromatography (X-Bridge-C18 5 μm 30*150 mm, mobile phase gradient: from 60% NH₄HCO₃ (0.5%), 40% MeOH to 20% NH₄HCO₃ (0.5%), 80% MeOH). The pure fractions were collected and evaporated to dryness. The residue was crystallized from CH₃CN and the precipitate was filtered and dried to give 53 mg of compound 2 (21% yield).

The compound in the table below was prepared by using an analogous method starting from the respective starting materials. The most relevant minor deviations to the referenced method are indicated as additional information in the column 'Yield (%)'.

Example B4

Preparation of Compound 42

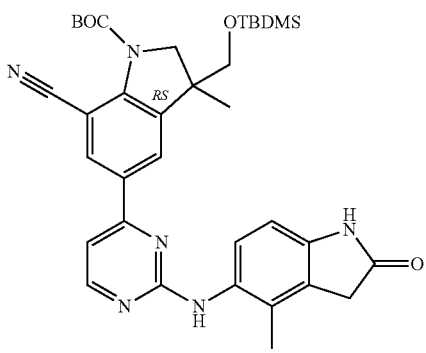 [SMILES: Cc1c(Nc2nccc(-c3cc(C#N)c4c(c3)C(C)(CO[Si](C)(C)C(C)(C)C)CN4C(=O)OC(C)(C)C)n2)ccc2c1CC(=O)N2]

Intermediate 170 (200 mg; 0.15 mmol) in TFA (5 mL) and DCM (20 mL) was stirred for 1 hour. Then, aqueous NaHCO was added to the mixture until pH superior to 7. The organic layer was separated, dried over MgSO₄, filtered and evaporated to give a sticky gum which was diluted in THE (5 mL) and treated with TBAF 1M in THE (2.5 mL; 2.5 mmol). The solvent was removed, and the reaction mixture was partioned between DCM (20 mL) and water (20 mL). The organic layer was separated, dried over MgSO₄, filtered and evaporated.

The residue was purified by high-performance liquid chromatography (column:Phenomenex Synergi C18 150*30 mm*4 um, eluent: 0.1% aqueous TFA-ACN from 20% to 30%, v/v). The desired fraction was collected and the solvent was concentrated. The intermediate fraction was basified by aqueous NaHCO₃ (5 mL) and extracted with DCM (10 mL*3). The organic layers were combined, dried over MgSO₄, filtered and evaporated to give 10 mg (15%) of compound 42 as a yellow solid.

| Compound number | Structure | Mass (mg) | Yield (%) |
|---|---|---|---|
| Compound 6 | From intermediate 36 | 26 | 28<br>Procedure with MeOH/HCl (3M in H₂O) (28:1, eq./eq.) |

Example B5

Preparation of Compound 56

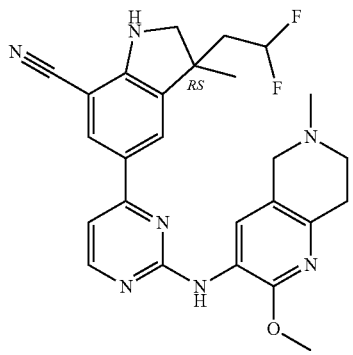 [SMILES: COc1nc2c(cc1Nc1nccc(-c3cc(C#N)c4c(c3)C(C)(CC(F)F)CN4)n1)CN(C)CC2]

And Compound 57

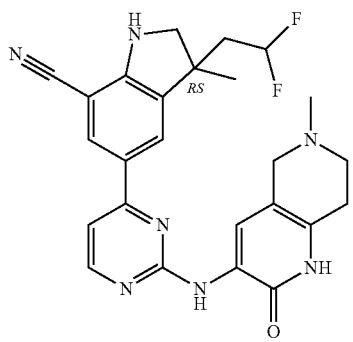 [SMILES: CN1CCc2[nH]c(=O)c(Nc3nccc(-c4cc(C#N)c5c(c4)C(C)(CC(F)F)CN5)n3)cc2C1]

To a mixture of intermediate 225 (153 mg; 0.259 mmol) in DCM (4 mL) was added TFA (2 mL) and the reaction was stirred at room temperature for 2 hours. The solvents were evaporated in vacuo and the crude was purified by reverse phase (Stationary phase: Phenomenex-Gemini C18 (5 μm) 21.2*100 mm; mobile phase: from 90% of $H_2O$ (0.1% HCOOH)—10% (MeOH) till 54% of $H_2O$ (0.1% HCOOH)—46% (MeOH). The desired fractions were collected, washed with a saturated solution of $NaHCO_3$ and extracted with ethyl acetate to afford 2 fractions. The respective organic layers were dried over $MgSO_4$, filtered and the solvent was evaporated in vacuo to afford—fraction A (clear oil) which was dissolved in a mixture of ACN-Diethyl Ether and evaporated until precipitation. The white solid was filtered to afford 30 mg (23%) of compound 56.

Fraction B (impure compound 57) which was purified again via reverse phase (Stationary phase: Phenomenex-Gemini C18 (5 μm) 21.2*100 mm; mobile phase: from 95% of $H_2O$ (0.1% HCOOH)—5% (MeOH) till 63% of $H_2O$ (0.1% HCOOH)—37% (MeOH) followed by a third reverse phase purification (Stationary phase: Phenomenex-Gemini C18 (5 μm) 21.2*100 mm; mobile phase: from 70% of $H_2O$ (25 mM $NH_4HCO_3$)—30% (ACN: MeOH 1:1) till 27% of $H_2O$ (25 mM $NH_4HCO_3$)—73% (ACN: MeOH 1:1). The desired tubes were collected and the solvents were evaporated in vacuo. The resulting yellow solid was dissolved three times in ACN and then, the solvent was concentrated under vacuum to give 22 mg (18%) of compound 57.

Conversion

Conversion C1:

Preparation of Compound 37

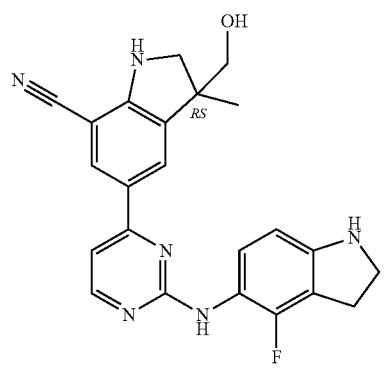 [SMILES: CC1(CO)CNc2c(C#N)cc(-c3ccnc(Nc4ccc5c(c4F)CCN5)n3)cc21]

A mixture of compound 36 (300 mg; 35% of purity), HCl 3M (5 mL) in MeOH (10 mL) was heated to reflux for 1 h. Then, the solvent was removed. The reaction mixture was basified by aqueous solution of $NaHCO_3$ and of a solid (300 mg) was collected.

It was then purified by preparative high-performance liquid chromatography (column: Gemini 150*25 5 u, eluent: 0.05% HCl-ACN from 0%/100% to 25%/75%, v/v). The desired fraction was collected and the solvent was removed to give 120 mg of an impure intermediate fraction A. Fraction A was further purified by preparative high-performance liquid chromatography (column: Phenomenex Gemini 150*25 mm*10 um, eluent: water (0.05% ammonium hydroxide, v/v)—ACN from 35%/65% to 65%/35%, v/v). The desired fraction was collected and the solvent was removed to give 40 mg (14%) of compound 37.

Example B1b

Preparation of Compound 1b

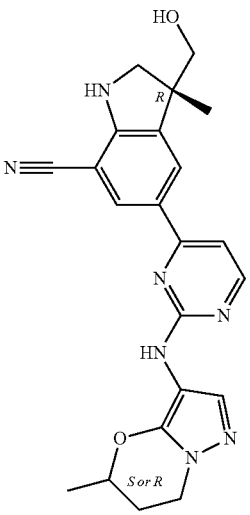

A mixture of intermediate 11b (140.00 mg, 0.26 mmol) and TBAF (1M in THF) (0.53 mL, 0.53 mmol) in Me-THF (2.64 mL) was stirred at rt for 8 h. The crude residue was purified via silica gel chromatography (Stationary phase: irregular SiOH 15-40 μm, 80 g, mobile phase gradient: from 100% DCM to 90% DCM, 10% MeOH, 0.1% NH₄OH). Product containing fractions were collected and concentrated under reduced pressure. The residue was taken up into CH₃CN. The precipitate was filtered and dried under vacuum to give 44 mg of compound 1b (40% yield).

Preparation of Compound 2b

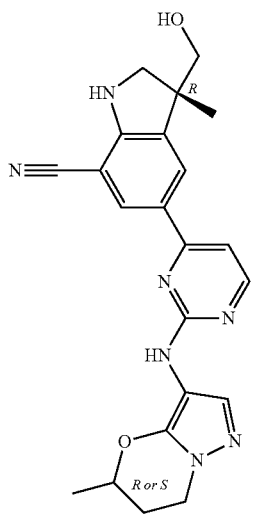

A mixture of intermediate 13b (252.00 mg, 0.47 mmol) and TBAF (1M in THF) (0.95 mL, 0.95 mmol) in Me-THF (4.75 mL) was stirred at rt for 8 h. The crude residue was purified via silica gel chromatography (Stationary phase: irregular SiOH 15-40 μm, 80 g, mobile phase gradient: from 100% DCM to 90% DCM, 10% MeOH, 0.1% NH₄OH). Pure fractions were collected and evaporated to give 77 mg of compound 2b (39% yield).

Preparation of Compound 3b

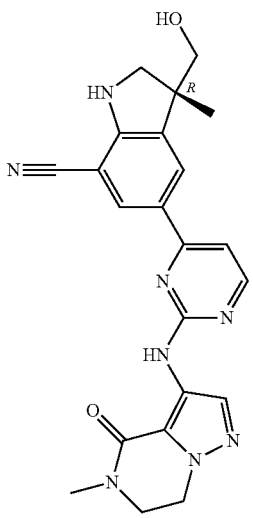

TBAF (1M in THF) (0.35 mL, 0.35 mmol) was added to a solution of intermediate 17b (0.13 g, 0.23 mmol) in THF (4.00 mL) and the solution was stirred at room temperature overnight. Water and a 10% aqueous solution of K₂CO₃ were added and this mixture was extracted twice with EtOAc. The organic layers were combined, dried over Na₂SO₄, filtered and the solvent was evaporated until dryness. The residue was taken up into CH₃CN, triturated and filtered. The precipitate was washed once with DCM and dried until dryness to give 77 mg of compound 3 (77% yield).

The compounds in the table below were prepared by using an analogous method as described for the preparation of compound 3b, starting from the respective starting materials. The most relevant minor deviations to the referenced method are indicated as additional information in the column 'Yield (%)'.

| Compound number | Structure | Mass (mg) | Yield (%) |
|---|---|---|---|
| Compound 4b | ![structure] From intermediate 21b | 66 | 71 Procedure with 1.1 equiv. of TBAF |

-continued

| Compound number | Structure | Mass (mg) | Yield (%) |
|---|---|---|---|
| Compound 5b | From intermediate 23b | 198 | 74 |
| Compound 9b | From intermediate 52b | 44 | 68 Procedure with Me—THF as solvent |
| Compound 10b | From intermediate 57b | 44 | 23 Procedure with Me—THF as solvent |

-continued

| Compound number | Structure | Mass (mg) | Yield (%) |
|---|---|---|---|
| Compound 11b | From intermediate 60b | 65 | 67 Procedure with 1.6 equiv. of TBAF and Me—THF as solvent |
| Compound 12b | From intermediate 68b | 12 Off-white solid | 4 Procedure with 1.1 equiv. of TBAF and Me—THF as solvent |
| Compound 13b | From intermediate 74b | 30 | 25 Procedure with 2 equiv. of TBAF and Me—THF as solvent |

-continued
| Compound number | Structure | Mass (mg) | Yield (%) |
|---|---|---|---|
| Compound 14b | 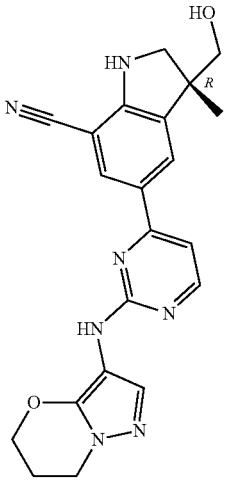<br>From intermediate 79b | 76 | 18<br>Procedure with 2 equiv. of TBAF and Me—THF as solvent |
| Compound 15b | 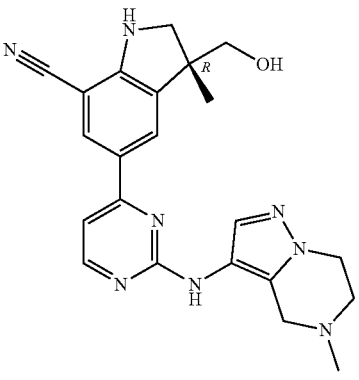<br>From intermediate 83b | 95 | 68<br>Procedure with 2 equiv. of TBAF and Me—THF as solvent |
| Compound 16b | 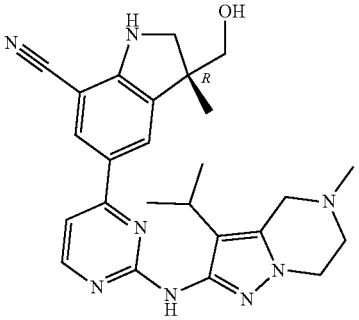<br>From intermediate 88b | 136 | 46<br>Procedure with 2 equiv. of TBAF and Me—THF as solvent |

-continued

| Compound number | Structure | Mass (mg) | Yield (%) |
|---|---|---|---|
| Compound 18b | 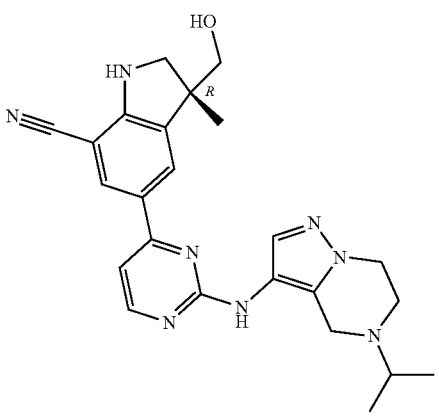<br>From intermediate 100b | 62 | 23<br>Procedure with 2 equiv. of TBAF and Me—THF as solvent |
| Compound 19b | 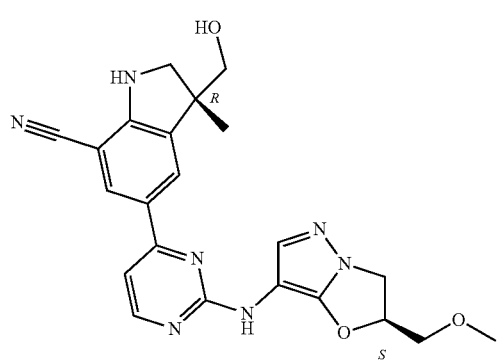<br>From intermediate 105b | 297 | 50<br>Procedure with 2 equiv. of TBAF and Me—THF as solvent |
| Compound 20b (methyl groups Cis in bicyclic pyrazole) | 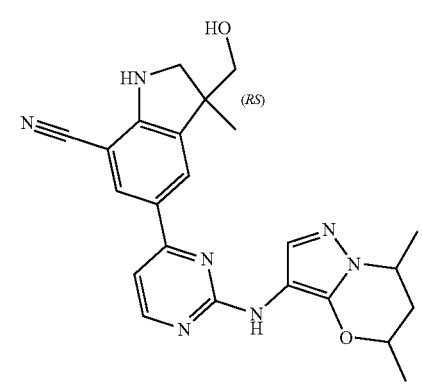<br>methyl groups CIS:<br>mixture of (R,S) and (S,R)<br>From intermediate 110b | 185 | 56<br>Procedure with 2 equiv. of TBAF and Me—THF as solvent |

-continued

| Compound number | Structure | Mass (mg) | Yield (%) |
|---|---|---|---|
| Compound 21b (methyl groups trans in bicyclic pyrazole) | (structure) methyl groups TRANS: mixture of (R,R) and (S,S) From intermediate 114b | 54 | 35 Procedure with 2 equiv. of TBAF and Me—THF as solvent |
| Compound 22b | (structure) From intermediate 122b | 92 | 64 Procedure with 2 equiv. of TBAF and Me—THF as solvent |
| Compound 23b | (structure) From intermediate 123b | 24 | 15 Procedure with 2 equiv. of TBAF and Me—THF as solvent |

| Compound number | Structure | Mass (mg) | Yield (%) |
|---|---|---|---|
| Compound 24b | 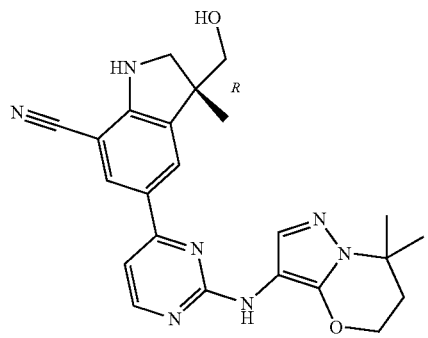 From intermediate 128b | 157 | 46 Procedure with 2 equiv. of TBAF and Me—THF as solvent |
| Compound 25b | 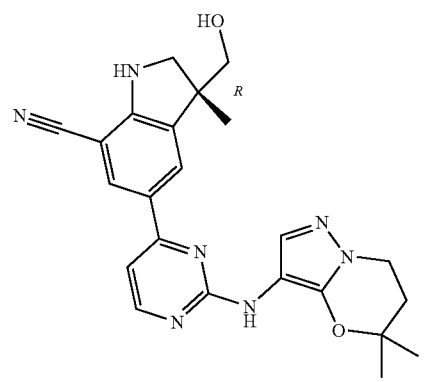 From intermediate 132b | 185 | 39 Procedure with 2 equiv. of TBAF and Me—THF as solvent |
| Compound 26b | 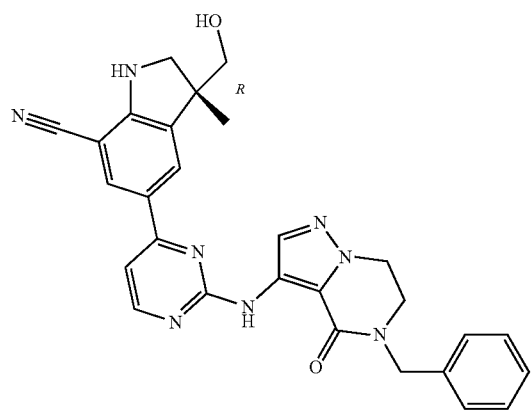 From intermediate 136b | 486 | 53 Procedure with 2 equiv. of TBAF and Me—THF as solvent |

-continued
| Compound number | Structure | Mass (mg) | Yield (%) |
|---|---|---|---|
| Compound 27b | 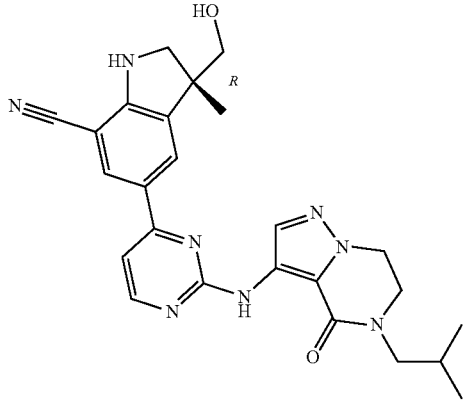<br>From intermediate 140b | 63 | 62<br>Procedure with 2 equiv. of TBAF and Me—THF as solvent |
| Compound 28b | 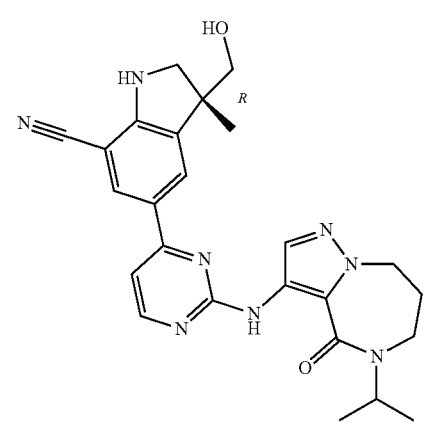<br>From intermediate 144b | 320 | 63<br>Procedure with 2 equiv. of TBAF and Me—THF as solvent |
| Compound 29b | 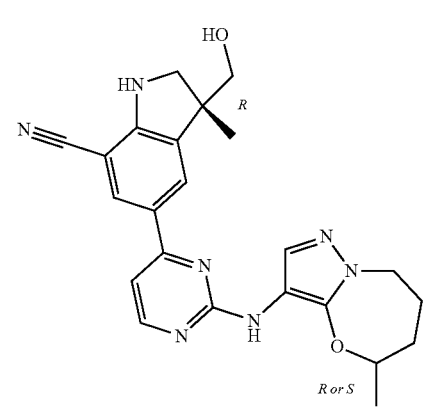<br>From intermediate 151b | 77 | 65<br>Procedure with 2 equiv. of TBAF and Me—THF as solvent |

-continued

| Compound number | Structure | Mass (mg) | Yield (%) |
|---|---|---|---|
| Compound 30b | From intermediate 153b | 42 | 35 Procedure with 2 equiv. of TBAF and Me—THF as solvent |
| Compound 31b | From intermediate 157b | 111 | 46 Procedure with 1.9 equiv. of TBAF and Me—THF as solvent |

Preparation of Compound 17b

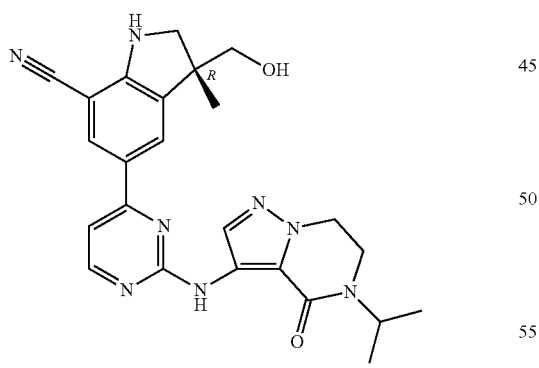

A mixture of intermediate 93 (450 mg, 0.786 mmol) and TBAF (1M in THF) (1.57 mL, 1.57 mmol) in Me-THF (7.87 mL) was stirred at rt for 3 h. The reaction mixture was diluted with EtOAc, washed with a 10% aqueous solution of $K_2CO_3$, water and a saturated solution of NaCl. The layers were separated and the organic layer was dried over $MgSO_4$, filtered and the solvent was removed under reduced pressure.

The crude product (460 mg) was purified by silica gel chromatography (Irregular SiOH 40 μm 40 g; Mobile phase 99% DCM, 1% MeOH, 0.1% $NH_4OH$ to 93% DCM, 7% MeOH, 0.7% $NH_4OH$. The pure fractions were combined and the solvent was evaporated to give 272 mg of an intermediate compound which was crystallized from ACN to give 183 mg (51%) of compound 17. M.P=212° C. (Kofler).

Example B2b

Preparation of Compound 6b

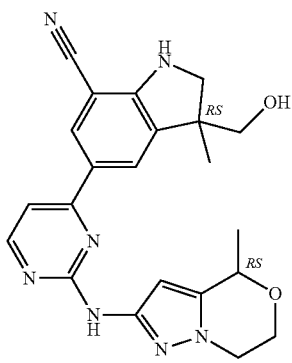 [SMILES: CC1OCCn2nc(Nc3nccc(-c4cc(C#N)c5c(c4)C(C)(CO)CN5)n3)cc21]

TFA (2 mL) was added to a solution of intermediate 33b (100.00 mg, 0.084 mmol) in DCM (5 mL) and the mixture was stirred at room temperature for 17 h. The reaction mixture was evaporated under vacuum and the resulting residue was combined with another batch carried out on 0.040 mmol of intermediate 33b. The resulting mixture was purified by high-performance liquid chromatography (gradient elution: acetonitrile/0.05% ammonia in purified water). The desired fractions were collected and the solvent was concentrated under vacuum. The crude residue was further purified by preparative TLC plates (eluent: EtOAc/MeOH: 9/1) to give 14 mg of compound 6b (38% yield; mixture of 4 diastereoisomers).

The compounds in the table below were prepared by using an analogous method as reported for the preparation of compound 6b, starting from the respective starting materials. Minor deviations to the referenced method are indicated as additional information in the column 'Yield (%)'.

| Compound number | Structure | Mass (mg) | Yield (%) |
|---|---|---|---|
| Compound 7b | 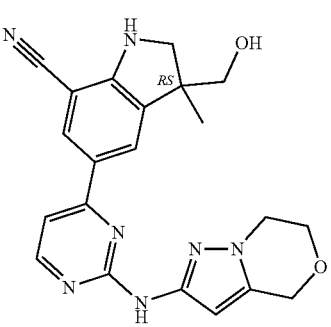<br>From intermediate 40b | 38 | 84 |
| Compound 8b | 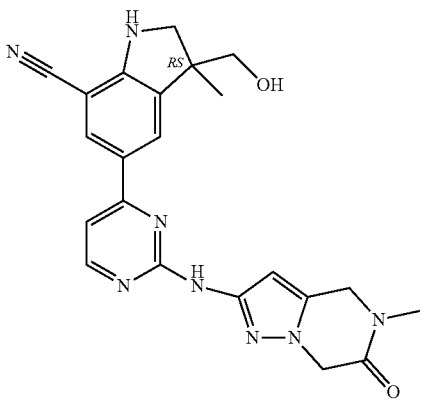<br>From intermediate 47b | 28 | 40<br>Procedure with TFA/DCM 1:4, v/v |

Example B3b

Preparation of Compound 32b

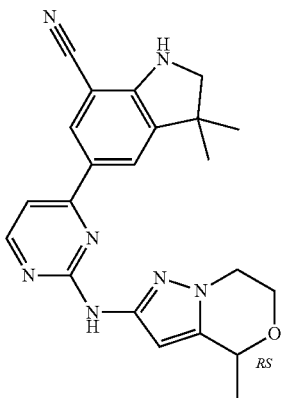 [SMILES: CC1OCCn2nc(Nc3nccc(-c4cc(C#N)c5c(c4)C(C)(C)CN5)n3)cc21]

TFA (1 mL) was added to a solution of intermediate 162b (200.00 mg, 0.196 mmol) in DCM (5 ml) at 0° C. The mixture was stirred at 0° C. for 1 hour. The reaction was concentrated to give the crude product. The crude product was purified by preparative high-performance liquid chromatography. (Column: Waters Xbridge 150*25 5 u. Condition: A: water (10 mM NH$_4$HCO$_3$); B: MeCN; at the beginning: A (60%) and B (40%); at the end: A: (30%) and B (70%); Gradient Time (min) 12; 100% B Hold Time (min) 2; Flow Rate (ml/min) 25.) The pure fractions were collected and the solvent was evaporated under vacuum. Water was added and lyophilized to dryness to give compound 32b as yellow solid (45 mg; 57.2%).

Example B1c

Preparation of Compound 3c

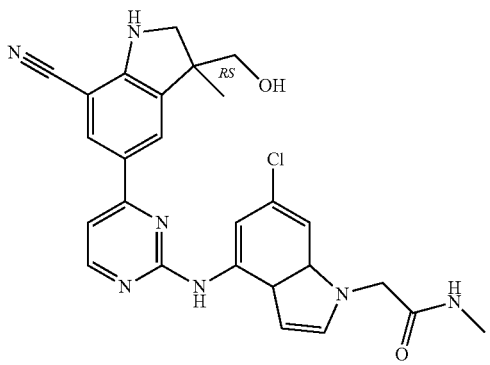 [SMILES: CNC(=O)CN1C=CC2C(Nc3nccc(-c4cc(C#N)c5c(c4)C(C)(CO)CN5)n3)=CC(Cl)=CC21]

A solution of intermediate 22c (241.00 mg, 0.26 mmol based on 65% purity determined by LC/MS) in TFA (3 mL) and DCM (3 mL) was stirred at rt for 0.5 h. The reaction mixture was concentrated under vacuum and coevaporated with toluene. The residue was purified by reverse phase semi-preparative HPLC (Stationary phase: X-Bridge-C18, 10 μm, 30×150 mm, mobile phase gradient from 10% CH$_3$CN, 90% H$_2$O, 0.1% NH$_4$OH to 98% CH$_3$CN, 2% H$_2$O, 0.1% NH$_4$OH). The relevant fractions were freeze dried overnight to give 43.7 mg of compound 3c (34% yield, pale orange solid).

Alternative Preparation of Compound 3c

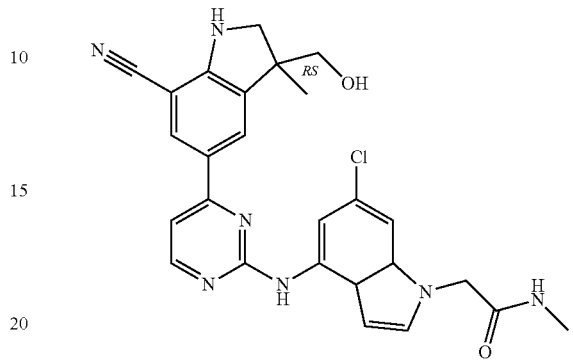

A solution of intermediate 21c (817.00 mg, 1.14 mmol) in TFA (12.2 mL) and DCM (12.2 mL) was stirred at rt overnight. The reaction mixture was poured into ice, basified with K$_2$CO$_3$, filtered and extracted with DCM. The organic layer was washed with brine, dried over MgSO$_4$, filtered and the solvent was concentrated under vacuum. The residue was crystallized from ACN, filtered and dried under vacuum to give crude compound 3c. The residue was purified by reverse phase (stationary phase: X-Bridge-C18, 5 μm, 30×150 mm, mobile phase gradient from 50% aq. NH$_4$HCO$_3$ (0.5%), 50% MeOH to 0% aq. NH$_4$HCO$_3$ (0.5%), 100% MeOH). The fractions containing the product were combined and evaporated to dryness under vacuum to give 130 mg of compound 3c (23% yield).

Preparation of Compound 8c

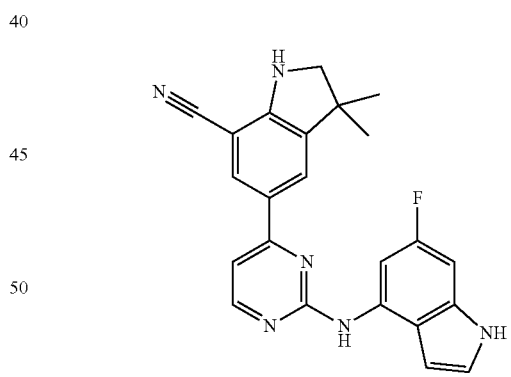

A solution of intermediate 35c (397.00 mg, 0.605 mmol based on 76% purity determined by LC/MS) in TFA (3 mL) and DCM (3 mL) was stirred at rt for 1 h. The reaction mixture was concentrated under vacuum and coevaporated with toluene. The residue was triturated with cyclohexane and a minimum of ethyl acetate and the solid was collected by filtration, washed with cyclohexane and dried under vacuum. The crude product was purified by a Mass Directed Auto Purification system (basic column) to give 31 mg of compound 8c (10% yield, beige solid).

The compounds in the table below were prepared by using an analogous method starting from the respective starting materials.

| Compound number | Structure | Mass (mg) | Yield (%) |
|---|---|---|---|
| Compound 1c | 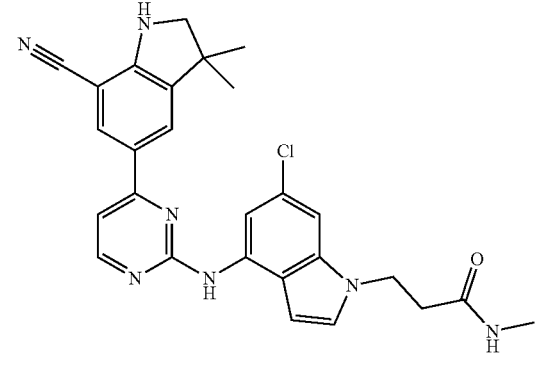<br>From intermediate 15c | 35<br>off white solid | 28 |
| Compound 2c | 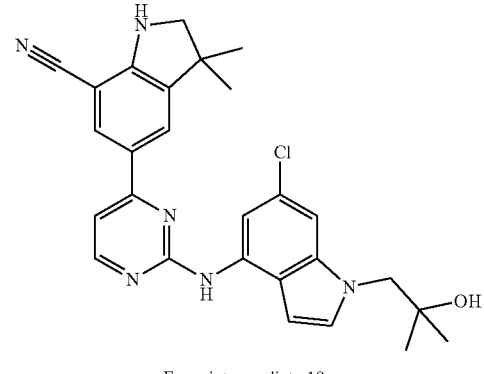<br>From intermediate 18c | 45<br>off white solid | 35 |
| Compound 7c | 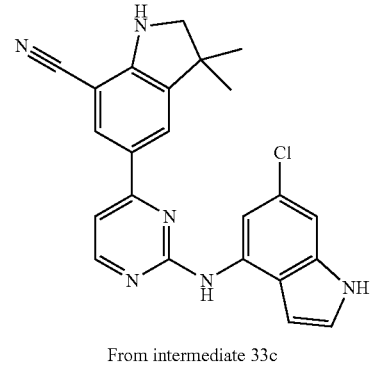 [SMILES: CC1(C)CNc2c(C#N)cc(-c3ccnc(Nc4cc(Cl)cc5[nH]ccc45)n3)cc21]<br>From intermediate 33c | 2.2<br>light brown solid | 1 |
| Compound 12c | 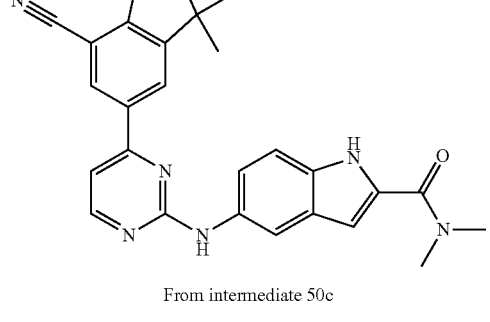<br>From intermediate 50c | 20 | 54<br>Procedure with DCM/TFA: 1/1 (v/v) and T = 0° C. |

Preparation of Compound 4c

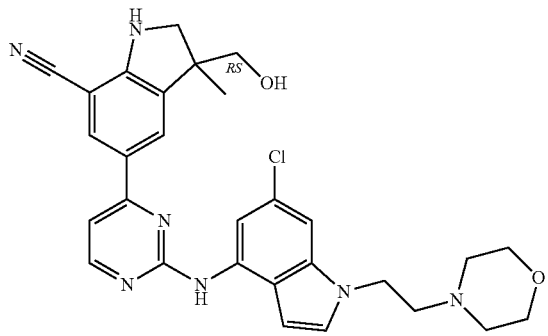 [SMILES: CC1(CO)CNc2c(C#N)cc(-c3ccnc(Nc4cc(Cl)cc5c4ccn5CCN4CCOCC4)n3)cc21]

A mixture of intermediate 25c (77.00 mg, 0.117 mmol) and TBAF (1M in THF) (0.129 mL, 0.129 mmol) in Me-THF (2 mL) was stirred at rt for 2 h. The residue was directly purified by silica gel chromatography (irregular SiOH 15-40 µm, 24 g, liquid injection with DCM, mobile phase gradient: from DCM/MeOH (+10% aq. NH$_3$) 100/0 to 80/20). The product containing fractions were combined and evaporated to dryness. The residue (35 mg) was recrystallized from EtOH, filtered on a glass frit and washed with EtOH. The solid was collected and was dried at 50° C. under reduced pressure for 16 h to give 24 mg of compound 4c (38% yield, pale yellow solid).

The compounds in the table below were prepared by using an analogous method starting from the respective starting materials.

| Compound number | Structure | Mass (mg) | Yield (%) |
| --- | --- | --- | --- |
| Compound 5c | 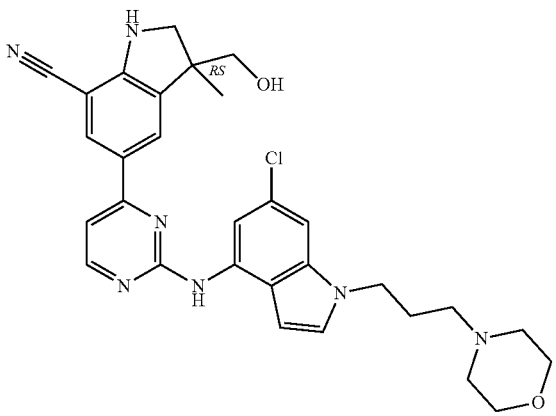<br>From intermediate 28c | 192<br>yellow green solid | 45<br>(over 2 steps) |
| Compound 6c | 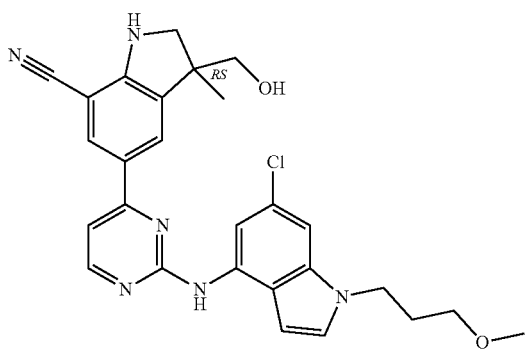<br>From intermediate 31c | 132<br>brown solid | 34 |

-continued

| Compound number | Structure | Mass (mg) | Yield (%) |
|---|---|---|---|
| Compound 10c | From intermediate 46c | 180 light brown solid | 56 |
| Compound 11c | From intermediate 47c | 1127 yellow solid | 30 |
| Compound 13c | From intermediate 54c | 6.7 | 2 Procedure With 1.5 equiv. of TBAF and THF as solvent |
| Compound 14c | From intermediate 58c | 48 | 62 |

Example B3c

Preparation of Compound 9c

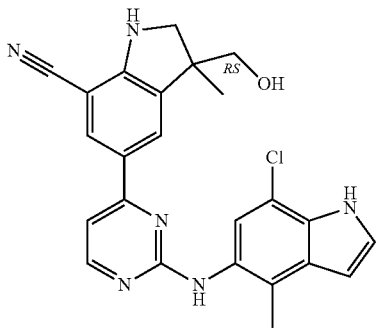 [SMILES: Cc1c(Nc2nccc(-c3cc(C#N)c4c(c3)C(C)(CO)CN4)n2)cc(Cl)c2[nH]ccc12]

A solution of intermediate 42c (155.00 mg, 0.317 mmol) in sodium ethanolate (20% in EtOH) (30 mL) was stirred at 40° C. for 1.5 h. The mixture was neutralized (pH: 7) with HCl 1N and extracted with EtOAc. The organic layer was dried over $MgSO_4$, concentrated under vacuum and purified by silica gel chromatography (irregular SiOH 15-40 μm, 40 g, liquid injection with DCM, mobile phase gradient: from DCM/MeOH (+1000aq. $NH_3$) 100/0 to 90/10 in 10 CV). The pure fractions were combined and the solvent was evaporated. The residue (45 mg) was purified again by reverse phase (Stationary phase: X-Bridge-C18, 5 μm, 30×150 mm, mobile phase: gradient from 60% $NH_4HCO_3$ (0.2% in $H_2O$), 40% MeOH to 20% $NH_4HCO_3$ (0.2% in $H_2O$), 80% MeOH). The product containing fractions were combined and evaporated to dryness to give 26 mg of compound 9c (18%, light yellow solid).

Analytical Part

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow (mL/min) T (° C.) | Run time |
|---|---|---|---|---|---|---|
| Method 1 | Waters: Acquity UPLC ®-DAD and Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| Method 2 | Waters: Acquity UPLC ® H-Class-DAD and SQD2 | Waters: BEH C18 (1.7 μm, 2.1 × 100 mm) | A: 95% $CH_3COONH_4$ 7 mM/5% $CH_3CN$, B: $CH_3CN$ | From 84.2% A to 10.5% A in 2.18 min, held for 1.94 min, back to 84.2% A in 0.73 min, held for 0.73 min. | 0.343 40 | 6.1 |
| Method 3 | Agilent 1200 equip with MSD 6110 | Agilent TC-C18 (5 μm, 2.1 × 50 mm) | A: $H_2O$ (0.1% TFA), B: $CH_3CN$ (0.05% TFA) | 90% A held for 0.80 min, then from 90% A to 20% A in 3.7 min, held for 3.00 min, back to 90% A in 2.00 min. | 0.8 50 | 10 |
| Method 4 | Agilent 1200, MSD 6110 | Agilent TC-C18 (5 μm, 2.1 × 50 mm) | A: water (+0.1% TFA), B: $CH_3CN$ (+0.1% TFA) | From 100% A for 1 min, to 40% A in 4 min, to 15% A in 2.5 min, back to 100% A in 2 min, held for 0.5 min. | 0.8 50 | 10 |
| Method 5 | Agilent: 1100-DAD and MSD | YMC: Pack ODS-AQ (3 μm, 4.6 × 50 mm) | A: HCOOH 0.1% in water, B: $CH_3CN$ | 95% A to 5% A in 4.8 min, held for 1 min, back to 95% A in 0.2 min. | 2.6 35 | 6 |
| Method 6 | Agilent 1290 Infinity DAD TOF-LC/MS G6224A | YMC-pack ODS-AQ C18 (50 × 4.6 mm, 3 μm) | A: 0.1% HCOOH in $H_2O$ B: ACN | From 95% A to 5% A in 4.8 min, held for 1.0 min, to 95% A in 0.2 min. | 2.6 35 | 6.0 |

TABLE-continued

LCMS Method codes (Flow expressed in mL/min; column temperature (T) in ° C.; Run time in minutes).

| Method code | Instrument | Column | Mobile phase | gradient | Flow (mL/min) T (° C.) | Run time |
|---|---|---|---|---|---|---|
| Method 7 | Agilent 1200 equip with MSD 6110 | Phenomenex Luna-C18, 50 × 2 mm, 5 μm | A: $H_2O$ (0.1% TFA, B: ACN (0.05% TFA) | 100% A held for 1 mn then 100% A to 40% A in 4 mn then 40% A to 15% A in 2.5 mn then back to 100% A in 2 mn held for 0.5 min. | 0.8 50 | 10 |
| Method 8 | Agilent 1260 series equip with an Agilent G2120B ESI-SQD set in positive mode | ACE C18 (50 × 3 mm, 3 μm) | A: 0.05% TFA in $H_2O$ B: ACN | From 95% A to 0% A in 1.3 min | 2.2 50 | 1.3 |
| Method 9 | Waters: Acquity UPLC®-PDA and SQD | Waters: BEH C18 (1.7 μm, 2.1 × 100 mm) | A: $H_2O$ + 0.1% HCOOH/B: $CH_3CN$ + 0.1% HCOOH | From 95% A for 0.40 min, to 5% A in 5.2 min, held for 0.80 min. | 0.40 40 | 6.4 |
| Method 10 | Agilent 1200 equip with MSD 6110 | XBridge Shield RP18 (5 μm, 2.1 × 50 mm) | A: $H_2O$ (0.05% $NH_3 \cdot H_2O$), B: $CH_3CN$ | 100% A held for 1.00 min, then from 100% A to 40% A in 4.00 min, then from 40% A to 5% A in 2.50 min, back to 100% A in 2.00 min. | 0.8 50 | 10 |

Melting Point (DSC, MP50, or K)

For a number of compounds, melting points (MP) were determined with a DSC1 (Mettler-Toledo) (indicated with DSC in the analytical table). Melting points were measured with a temperature gradient of 10° C./minute. Maximum temperature was 350° C. Values are peak values.

For a number of compounds, melting points were obtained with a Kofler (K) hot bench, consisting of a heated plate with linear temperature gradient, a sliding pointer and a temperature scale in degrees Celsius (indicated with K in the analytical table).

For a number of compounds, melting points were obtained with a Mettler Toledo MP50 apparatus (indicated with MP50 in the analytical table). Melting points were measured with a temperature gradient of 10° C. per minute starting from 50° C. (waiting time 10 seconds) to a maximum value of 300° C.

TABLE

N°. means compound number; MP means melting point (° C.); Rt means retention time (min).

| No | MP (° C.) | MP Method | Rt | [M + H]+ | LC/MS Method |
|---|---|---|---|---|---|
| 1 | 221 | K | 2.73 | 414 | Method 1 |
| 2 | 230 | K | 2.42 | 383 | Method 1 |
| 3 | 171 | DSC | 2.10 | 441 | Method 1 |
| 4 | 235 | DSC | 3.30 | 448 | Method 2 |
| 5 | 152 | K | 1.97 | 444 | Method 2 |
| 6 | — | — | 2.19 | 397 | Method 2 |
| 7 | 245 | K | 2.45 | 450 | Method 2 |
| 8 | 168 | K | 1.96 | 444 | Method 2 |
| 9 | 221 | DSC | 2.52 | 489 | Method 1 |
| 10 | 196 | DSC | 2.67 | 433 | Method 1 |
| 11 | 205 | DSC | 2.81 | 519 | Method 1 |
| 12 | 153 | DSC | 2.80 | 519 | Method 1 |
| 13 | 225 | DSC | 2.44 | 518 | Method 1 |
| 14 | 265 | DSC | 2.43 | 504 | Method 1 |
| 15 | — | — | 2.13 | 498 | Method 1 |
| 16 | — | — | 2.43 | 532 | Method 1 |
| 17 | 224 | DSC | 2.98 | 491 | Method 1 |
| 18 | 224 | DSC | 2.97 | 491 | Method 1 |
| 19 | 278 | DSC | 2.56 | 532 | Method 1 |
| 20 | — | — | 2.29 | 513 | Method 1 |

TABLE-continued

N°. means compound number; MP means melting point (° C.); Rt means retention time (min).

| No | MP (° C.) | MP Method | Rt | [M + H]+ | LC/MS Method |
|---|---|---|---|---|---|
| 21 | — | — | 2.64 | 483 | Method 1 |
| 22 | — | — | 2.64 | 479 | Method 1 |
| 23 | — | — | 2.21 | 455 | Method 1 |
| 24 | 296 | DSC | 2.29 | 471 | Method 1 |
| 25 | 136 | DSC | 2.81 | 445 | Method 1 |
| 26 | — | — | 2.69 | 509 | Method 1 |
| 27 | — | — | 2.86 | 511 | Method 1 |
| 28 | 202 | DSC | 2.20 | 429 | Method 1 |
| 29 | — | — | 2.07 | 428 | Method 1 |
| 30 | 232 | DSC | 2.19 | 427 | Method 1 |
| 31 | — | — | 2.24 | 427 | Method 1 |
| 32 | 139 | DSC | 2.52 | 458 | Method 1 |
| 33 | 122 | DSC | 2.37 | 487 | Method 1 |
| 34 | 219 | DSC | 3.22 | 485 | Method 1 |
| 35 | — | — | 3.00 | 498 | Method 1 |
| 36 | — | — | 3.98 | 459 | Method 4 |
| 37 | — | — | 2.54 | 417 | Method 3 |
| 38 | — | — | 2.53 | 502 | Method 3 |
| 39 | — | — | 4.06 | 471 | Method 4 |
| 40 | — | — | 3.63 | 514 | Method 4 |
| 41 | — | — | 4.73 | 434 | Method 4 |
| 42 | — | — | 3.51 | 427 | Method 4 |
| 43 | — | — | 2.87 | 454 | Method 3 |
| 44 | — | — | 2.04 | 472 | Method 1 |
| 45 | 253 | DSC | 2.19 | 415 | Method 1 |
| 46 | 199 | MP50 | 2.99 | 473 | Method 6 |
| 47 | 170 | MP50 | 3.21 | 499 | Method 6 |
| 48 | — | — | 2.31 | 445 | Method 1 |
| 49 | 138 (gum) | Kofler | 3.63 | 512 | Method 1 |
| 50 | 199 | K | 2.96 | 486 | Method 1 |
| 51 | 176 (gum) | K | 2.33 | 454 | Method 2 |
| 52 | >260 | K | 3.02 | 484 | Method 2 |
| 53 | 159 (gum) | K | 2.35 | 457 | Method 1 |
| 54 | — | — | 0.68 | 447 | Method 8 |
| 55 | — | — | 4.91 | 466 | Method 7 |
| 56 | 156 | MP50 | 2.72 | 492 | Method 5 |
| 57 | 238 | MP50 | 2.34 | 478 | Method 5 |
| 58 | 166 | MP50 | 4.13 | 499 | Method 5 |
| 59 | — | — | 4.00 | 457 | Method 4 |

TABLE-continued

N°. means compound number; MP means melting point (° C.); Rt means retention time (min).

| No | MP (° C.) | MP Method | Rt | [M + H]+ | LC/MS Method |
|---|---|---|---|---|---|
| 60 | — | — | 2.16 | 499 | Method 2 |
| 1b | >250 | K | 2.01 | 418 | Method 2 |
| 2b | gum at 244 | K | 2.02 | 418 | Method 2 |
| 3b | 315 | DSC | 2.27 | 431 | Method 1 |
| 4b | — | — | 2.27 | 402 | Method 1 |
| 5b | >260 | K | 2.23 | 402 | Method 2 |
| 6b | — | — | 3.86 | 418 | Method 4 |
| 7b | — | — | 3.70 | 404 | Method 4 |
| 8b | >260 | K | 2.02 | 431 | Method 1 |
| 9b | 162 | K | 2.08 | 417 | Method 1 |
| 10b | 212 | K | 2.36 | 432 | Method 1 |
| 11b | — | — | 2.42 | 446 | Method 1 |
| 12b | 201 | DSC | 2.04 | 404 | Method 1 |
| 13b | >260 | K | 2.09 | 431 | Method 1 |
| 14b | >250 | K | 2.03 | 404 | Method 1 |
| 15b | 258 | K | 2.00 | 417 | Method 1 |
| 16b | 235 | K | 2.33 | 459 | Method 1 |
| 17b | 212 | K | 2.42 | 459 | Method 2 |
| 18b | 247 | K | 2.21 | 445 | Method 1 |
| 19b | 233 | DSC | 1.92 | 434 | Method 2 |
| 20b | 246 | K | 2.14 | 432 | Method 2 |
| 21b | 279 | DSC | 2.11 | 432 | Method 2 |
| 22b | >260 | K | 2.28 | 446 | Method 2 |
| 23b | >260 | K | 2.28 | 446 | Method 2 |
| 24b | 209 | DSC | 2.24 | 432 | Method 1 |
| 25b | >260 | DSC | 2.09 | 432 | Method 2 |
| 26b | 174 (gum) | K | 2.67 | 507 | Method 2 |
| 27b | 164 (gum) | K | 2.60 | 473 | Method 2 |
| 28b | 173 | DSC | 2.40 | 473 | Method 2 |
| 29b | 266 | DSC | 2.36 | 432 | Method 1 |
| 30b | 258 | DSC | 2.36 | 432 | Method 1 |
| 31b | 179 | DSC | 1.95 | 448 | Method 1 |
| 32b | — | — | 3.94 | 402 | Method 4 |
| 1c | — | — | 4.54 | 500 | Method 9 |
| 2c | — | — | 5.07 | 487 | Method 9 |
| 3c | >250 | K | 2.24 | 502 | Method 2 |
| 4c | 216 | DSC | 2.73 | 544 | Method 2 |
| 5c | 220 | DSC | 2.88 | 558 | Method 1 |
| 6c | 182 | DSC | 3.06 | 503 | Method 1 |
| 7c | — | — | 4.95 | 413 | Method 9 |
| 8c | — | — | 4.69 | 399 | Method 9 |
| 9c | 217 | DSC | 2.67 | 445 | Method 1 |
| 10c | 260 | DSC | 2.58 | 513 | Method 1 |
| 11c | 217 | DSC | 2.51 | 516 | Method 1 |
| 12c | — | — | 5.15 | | Method 10 |
| 13c | — | — | 2.74 | 427 | Method 3 |
| 14c | 209 | DSC | 2.85 | 486 | Method 1 |

NMR

The NMR experiments were carried out using a Bruker Avance 500 III using internal deuterium lock and equipped with reverse triple-resonance ($^1H$, $^{13}C$, $^{15}N$ TXI) probe head or using a Bruker Avance DRX 400 spectrometer at ambient temperature, using internal deuterium lock and equipped with reverse double-resonance ($^1H$, $^{13}C$, SEI) probe head with z gradients and operating at 400 MHz for the proton and 100 MHz for carbon. Chemical shifts (δ) are reported in parts per million (ppm). J values are expressed in Hz.

Compound 21:
$^1H$ NMR (400 MHz, DMSO-$d_6$): δ 8.79 (s, 1H) 8.31 (d, J=5.1 Hz, 1H) 8.02 (s, 1H) 7.88 (s, 1H) 7.61 (s, 1H) 7.35 (s, 1H) 7.25 (d, J=5.6 Hz, 1H) 4.94-5.00 (m, 1H) 4.69 (s, 2H) 3.97 (br t, J=5.6 Hz, 2H) 3.67 (br d, J=9.6 Hz, 1H) 3.39-3.46 (m, 1H) 3.32-3.38 (m, 1H) 3.23-3.28 (m, 1H, partially obscured by solvent peak) 2.79-2.89 (m, 4H) 1.46-1.56 (m, 2H) 1.26 (s, 3H) 0.60-0.76 (m, 1H) 0.27-0.35 (m, 2H) −0.09-0.00 (m, 2H).

Compound 25:
$^1H$ NMR (400 MHz, DMSO-$d_6$): δ 8.42 (d, J=5.6 Hz, 1H) 8.26 (s, 1H) 8.08-8.12 (m, 1H) 8.07 (s, 1H) 7.95-7.98 (m, 1H) 7.41 (s, 1H) 7.37 (d, J=5.6 Hz, 1H) 5.00 (t, J=5.3 Hz, 1H) 4.68 (s, 2H) 3.94-3.98 (m, 2H) 3.93 (s, 3H) 3.68 (d, J=9.6 Hz, 1H) 3.42-3.49 (m, 1H) 3.36-3.42 (m, 1H) 3.28-3.30 (m, 1H, partially obscured by solvent peak) 2.76 (br t, J=5.6 Hz, 2H) 1.29 (s, 3H).

Compound 32:
$^1H$ NMR (400 MHz, DMSO-$d_6$): δ 8.41 (d, J=5.1 Hz, 1H) 8.26 (s, 1H) 8.08-8.13 (m, 1H) 8.05 (s, 1H) 7.92-8.00 (m, 1H) 7.42 (s, 1H) 7.36 (d, J=5.6 Hz, 1H) 5.00 (t, J=5.6 Hz, 1H) 3.91 (s, 3H) 3.69 (d, J=9.6 Hz, 1H) 3.49 (s, 2H) 3.42-3.47 (m, 1H) 3.36-3.41 (m, 1H) 3.27-3.30 (m, 1H, partially obscured by solvent peak) 2.74-2.81 (m, 2H) 2.65-2.70 (m, 2H) 2.36 (s, 3H) 1.30 (s, 3H).

Compound 34:
$^1H$ NMR (400 MHz, DMSO-$d_6$): δ 8.43 (d, J=5.1 Hz, 1H) 8.29 (s, 1H) 8.04-8.12 (m, 1H) 7.90-8.00 (m, 2H) 7.42 (s, 1H) 7.39 (d, J=5.6 Hz, 1H) 5.01 (t, J=5.3 Hz, 1H) 4.68 (s, 2H) 4.18 (d, J=7.1 Hz, 2H) 3.95 (t, J=5.6 Hz, 2H) 3.68 (d, J=9.6 Hz, 1H) 3.42-3.49 (m, 1H) 3.36-3.42 (m, 1H) 3.31-3.34 (m, 1H, partially obscured by solvent peak) 2.73 (br t, J=5.1 Hz, 2H) 1.25-1.35 (m, 4H) 0.50-0.59 (m, 2H) 0.29-0.44 (m, 2H).

Compound 35:
$^1H$ NMR (500 MHz, DMSO-$d_6$): δ 8.43 (d, J=5.4 Hz, 1H) 8.29 (s, 1H) 8.07-8.13 (m, 1H) 7.96 (d, J=8.2 Hz, 2H) 7.45 (s, 1H) 7.38 (d, J=5.4 Hz, 1H) 5.02 (t, J=5.4 Hz, 1H) 4.15 (d, J=7.3 Hz, 2H) 3.69 (d, J=9.8 Hz, 1H) 3.51 (br s, 2H) 3.43-3.48 (m, 1H) 3.37-3.41 (m, 1H) 3.29-3.32 (m, 1H, partially obscured by solvent peak) 2.73-2.78 (m, 2H) 2.65-2.72 (m, 2H) 2.37 (s, 3H) 1.25-1.35 (m, 4H) 0.51-0.59 (m, 2H) 0.35 (q, J=4.8 Hz, 2H).

Compound 56:
$^1H$ NMR (300 MHz, DMSO-$d_6$) δ 8.44 (br d, J=5.4 Hz, 1H) 8.26 (s, 1H) 8.14 (s, 1H) 8.07 (br d, J=3.8 Hz, 2H) 7.51 (s, 1H) 7.39 (br d, J=5.1 Hz, 1H) 5.90-6.43 (m, 1H) 3.91 (s, 3H) 3.69 (br d, J=10.2 Hz, 1H) 3.48 (br s, 2H) 3.41 (br d, J=10.7 Hz, 1H) 2.65-2.86 (m, 4H) 2.18-2.43 (m, 5H) 1.37 (s, 3H).

Compound 1b:
$^1H$ NMR (500 MHz, DMSO-$d_6$): δ 8.14-8.30 (m, 2H) 8.04 (br s, 1H) 7.89 (br s, 1H) 7.27-7.36 (m, 2H) 7.13 (d, J=5.0 Hz, 1H) 5.00 (t, J=5.4 Hz, 1H) 4.33-4.46 (m, 1H) 4.00-4.19 (m, 2H) 3.66 (d, J=9.8 Hz, 1H) 3.39-3.46 (m, 1H) 3.34-3.37 (m, 1H, partially obscured by solvent peak) 3.28 (d, J=10.1 Hz, 1H) 2.16-2.28 (m, 1H) 1.91-2.05 (m, 1H) 1.35 (d, J=6.3 Hz, 3H) 1.26 (s, 3H).

Compound 2b:
$^1H$ NMR (500 MHz, DMSO-$d_6$): δ 8.17-8.31 (m, 2H) 8.04 (br s, 1H) 7.89 (br s, 1H) 7.27-7.38 (m, 2H) 7.13 (d, J=5.4 Hz, 1H) 5.01 (t, J=5.4 Hz, 1H) 4.34-4.45 (m, 1H) 4.02-4.15 (m, 2H) 3.67 (d, J=9.8 Hz, 1H) 3.39-3.46 (m, 1H) 3.35-3.39 (m, 1H, partially obscured by solvent peak) 3.28 (br d, J=9.8 Hz, 1H) 2.16-2.27 (m, 1H) 1.92-2.07 (m, 1H) 1.36 (d, J=6.3 Hz, 3H) 1.27 (s, 3H).

Compound 3b:
$^1H$ NMR (500 MHz, DMSO-$d_6$): δ 8.61 (s, 1H) 8.47 (d, J=5.4 Hz, 1H) 8.24 (s, 1H) 8.10 (s, 1H) 8.00 (s, 1H) 7.46 (s, 1H) 7.39 (d, J=5.4 Hz, 1H) 5.04 (br s, 1H) 4.36 (t, J=6.0 Hz, 2H) 3.81 (t, J=6.0 Hz, 2H) 3.69 (d, J=9.8 Hz, 1H) 3.44-3.51 (m, 1H) 3.37-3.43 (m, 1H) 3.29-3.33 (m, 1H, partially obscured by solvent peak) 3.04 (s, 3H) 1.31 (s, 3H).

Compound 17b:
$^1H$ NMR (500 MHz, DMSO-$d_6$) δ 8.65 (s, 1H), 8.46 (d, J=5.4 Hz, 1H), 8.23 (s, 1H), 8.10 (s, 1H), 7.99 (s, 1H), 7.46 (s, 1H), 7.38 (d, J=5.4 Hz, 1H), 5.03 (t, J=5.2 Hz, 1H), 4.77 (spt, J=6.7 Hz, 1H), 4.33 (t, J=6.0 Hz, 2H), 3.65-3.76 (m, 3H), 3.43-3.51 (m, 1H), 3.36-3.43 (m, 1H), 3.31 (d, J=9.8 Hz, 1H), 1.30 (s, 3H), 1.18 (d, J=6.6 Hz, 6H).

Compound 3c:
$^1$H NMR (500 MHz, DMSO-d$_6$) δ 9.44 (s, 1H) 8.50 (d, J=5.0 Hz, 1H) 8.15-8.21 (m, 2H) 7.98-8.07 (m, 2H) 7.39-7.46 (m, 2H) 7.26 (d, J=3.2 Hz, 1H) 7.14 (s, 1H) 7.00 (d, J=3.2 Hz, 1H) 5.00 (t, J=5.4 Hz, 1H) 4.79 (s, 2H) 3.73 (d, J=9.8 Hz, 1H) 3.44-3.52 (m, 1H) 3.37-3.43 (m, 1H) 3.31 (d, J=9.8 Hz, 1H) 2.63 (d, J=4.7 Hz, 3H) 1.31 (s, 3H).

Compound 8c:
$^1$H NMR (400 MHz, DMSO-d$_6$): δ 11.13 (br s, 1H) 9.38 (s, 1H) 8.50 (d, J=5.6 Hz, 1H) 8.16 (s, 1H) 8.10 (s, 1H) 7.97 (br d, J=12.1 Hz, 1H) 7.37-7.52 (m, 2H) 7.23 (br s, 1H) 6.96 (br s, 1H) 6.83 (br d, J=8.6 Hz, 1H) 3.44 (s, 2H) 1.31 (s, 6H).

Or

Optical Rotation is measured with a polarimeter such as e.g. 341 Perkin Elmer, an Autopol IV automatic polarimeter (Rodolph research analytical) or a P-2000 (Jasco).

Specific rotation (OR): $[\alpha]^\theta_\lambda = (100 * \alpha)/(c*1)$

α (measured rotation) is the angle through which plane polarized light is rotated by a solution of mass concentration c and path length 1. Concentration is in grams per 100 mL; path length 1 is in decimeters and is 1.000 decimeter.
θ is the temperature (° C.) and λ the wavelength of the light used.
Unless otherwise indicated, temperature is 20° C., and the sodium D line is used (589 nanometer).

OR data: Solvent: DMF (unless otherwise indicated); temperature: 20° C. (unless otherwise indicated); wavelength: 589 nm (unless otherwise indicated); Concentration of the sample in grams per 100 mL; 'OR' means optical rotation (specific rotation); 'N' means compound number.

| No | OR (°) | Concentration (g/100 mL) |
|---|---|---|
| 11 | +58.08 | 0.260 |
| 12 | −11.38 | 0.290 |
| 13 | +19.80 | 0.227 |
| 16 | +19.04 | 0.236 |
| 17 | +63.93 | 0.280 |
| 18 | −5.00 | 0.260 |
| 19 | +18.93 | 0.280 |
| 20 | +6.15 | 0.260 |
| 21 | +9.95 | 0.342 |
| 22 | −19.03 | 0.242 |
| 23 | +11.28 | 0.293 |
| 24 | +9.62 | 0.312 |
| 25 | +11.78 | 0.221 |
| 26 | +12.44 | 0.225 |
| 27 | +9.78 | 0.225 |
| 28 | +9.92 | 0.222 |
| 29 | +10.87 | 0.230 |
| 30 | +15.71 | 0.280 |
| 31 | +17.04 | 0.270 |
| 32 | +18.71 | 0.278 |
| 33 | +12.37 | 0.291 |
| 34 | +10.73 | 0.261 |
| 35 | +22.40 | 0.250 |
| 44 | +17.69 | 0.39 |
| 46 | +18.6 | 0.10 (MeOH; 23° C.) |
| 47 | +13.3 | 0.06 (MeOH; 23° C.) |
| 48 | +8.52 | 0.27 |
| 49 | +37.83 | 0.23 |
| 50 | +23.33 | 0.24 |
| 51 | +11.2 | 0.25 |
| 52 | +33.85 | 0.26 |
| 53 | +13.62 | 0.257 |
| 58 | −2.3 | 0.18 (DMSO; 23° C.) |
| 3b | +23.73 | 0.295 |
| 11b | +16.46 | 0.243 |
| 12b | +14.55 | 0.275 |
| 13b | +16.80 | 0.250 |
| 14b | +9.55 | 0.220 |
| 15b | +6.80 | 0.250 |
| 16b | +6.40 | 0.250 |
| 17b | +16.97 | 0.330 |
| 18b | +9.60 | 0.250 |
| 19b | −18.75 | 0.240 |
| 22b | −34.34 | 0.335 |
| 24b | +10.83 | 0.240 |
| 25b | +15.00 | 0.200 |
| 26b | +17.41 | 0.270 |
| 27b | +18.57 | 0.210 |
| 28b | +22.31 | 0.260 |
| 10c | +14.55 | 0.220 |
| 14c | +16.3 | 0.227 |

Pharmacological Part

Biological Assay A

Inhibition of Auto-Phosphorylation of Recombinant Human NF-kappaB-Inducing Kinase (NIK1/AP3K14) Activity (AlphaScreen®)

NIK/MAP3K14 auto-phosphorylation activity was measured using the AlphaScreen® (αscreen) format (Perkin Elmer). All compounds tested were dissolved in dimethyl sulfoxide (DMSO) and further dilutions were made in assay buffer. Final DMSO concentration was 100 (v/v) in assays. Assay buffer was 50 mM Tris pH 7.5 containing 1 mM EGTA (ethylene glycol tetraacetic acid), 1 mM DTT (dithiothreitol), 0.1 mM Na$_3$VO$_4$, 5 mM MgCl$_2$, 0.01% Tween® 20. Assays were carried out in 384 well Alphaplates (Perkin Elmer). Incubations consisted of compound, 25 microM Adenosine-5′-triphosphate (ATP), and 0.2 nM NIK/MAP3K14. Incubations were initiated by addition of GST-tagged NIK/MAP3K14 enzyme, carried out for 1 h at 25° C. and terminated by addition of stop buffer containing anti-phospho-KK Ser176/180 antibody. Protein A Acceptor and Glutathione-Donor beads were added before reading using an EnVision® Multilabel Plate Reader (Perkin Elmer). Signal obtained in the wells containing blank samples was subtracted from all other wells and IC$_{50}$'s were determined by fitting a sigmoidal curve to % inhibition of control versus Log$_{10}$ compound concentration.

Biological Assay B

Effect of Compounds on P-IKKα Levels in L363 (NIK Translocated Multiple Myeloma) Cells All compounds tested were dissolved in DMSO and further dilutions were made in culture medium. Final DMSO concentration was 1% (v/v) in cell assays. The human L363 cells (ATCC) were cultured in RPMI 1640 medium supplemented with GlutaMax and 10% fetal calf serum (PAA). Cells were routinely maintained at densities of 0.2×10$^6$ cells per ml—1×10$^6$ cells per ml at 37° C. in a humidified 5% CO$_2$ atmosphere. Cells were passaged twice a week splitting back to obtain the low density. Cells were seeded in 96 well plates (Nunc 167008) at 2×10$^6$ per ml media in a volume of 75 μl per well plus 25 μl 1 μg/ml recombinant human B-cell activating factor (BAFF/BLyS/TNFSF13B). Seeded cells were incubated at 37° C. in a humidified 5% CO$_2$ atmosphere for 24 hr. Drugs and/or solvents were added (20 μl) to a final volume of 120 μl. Following 2 hr treatment plates were removed from the incubator and cell lysis was achieved by the addition of 30 μl 5× lysis buffer followed by shaking on a plate shaker at 4° C. for 10 min. At the end of this incubation lysed cells were centrifuged at 800×g for 20 min at 4° C. and the lysate was assessed for P-IKKα levels by sandwich immuno-assay carried out in anti-rabbit antibody coated Mesoscale plates. Within an experiment, the results for each treatment were the mean of 2 replicate wells. For initial screening purposes, compounds were tested using an 8 point dilution curve (serial 1:3 dilutions). For each experiment, controls (containing MG132 and BAFF but no test drug) and a blank incubation (containing MG132 and BAFF and 10 μM ADS125117, a test concentration known to give full inhibition) were run in parallel. The blank incubation value was subtracted from all control and sample values. To determine the $IC_{50}$ a sigmoidal curve was fitted to the plot of % inhibition of control P-IKKα levels versus $Log_{10}$ compound concentration.

Biological Assay C

Determination of Antiproliferative Activity on JJN-3 (NIK Translocated) and KMS12-BM (NIK WT) Multiple Myeloma Cells All compounds tested were dissolved in DMSO and further dilutions were made in culture medium. Final DMSO concentration was 0.3% (v/v) in cell proliferation assays. Viability was assessed using CellTiter-Glo cell viability assay kit (Promega). The human JJN-3 and KMS12-BM cells (DSMZ) were cultured in RPMI 1640 medium supplemented with 2 mM L-glutamine, and 10% fetal calf serum (PAA). Cells were routinely kept as suspension cells at 37° C. in a humidified 5% $CO_2$ atmosphere. Cells were passaged at a seeding density of $0.2 \times 10^6$/ml twice a week. Cells were seeded in black tissue culture treated 96-well plates (Perkin Elmer). Densities used for plating ranged from 15000 (JJN3) to 20000 (KMS12BM) cells per well in a total volume of 135 medium. Drugs and/or solvents were added (15 μl) to a final volume of 150 μl. Following 96 hr of treatment, plates were removed from the incubator and allowed to equilibrate to room temperature for approx 10 min. 75 μl CellTiter-Glo reagent was added to each well that was then covered (Perkin Elmer Topseal) and shaken on plate shaker for 10 min. Luminescence was measured on a HTS Topcount (Perkin Elmer). Within an experiment, the results for each treatment were the mean of 2 replicate wells. For initial screening purposes, compounds were tested using a 9 point dilution curve (serial 1:3 dilutions). For each experiment, controls (containing no drug) and a blank incubation (containing cells read at the time of compound addition) were run in parallel. The blank value was subtracted from all control and sample values. For each sample, the mean value for cell growth (in relative light units) was expressed as a percentage of the mean value for cell growth of the control.

Data for the compounds of the invention in the above assays are provided in Table A (the values in Table are averaged values over all measurements on all batches of a compound). ('n.c.' means not calculated)

TABLE A

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
| --- | --- | --- | --- | --- |
| 45 | 2.7 | n.c. | ~186 | ~60 |
| 1 | 5.9 | n.c. | 550 | 96 |
| 2 | 4.3 | n.c. | ~177 | 112 |
| 3 | 1.4 | n.c. | 85 | ~24 |
| 4 | 26.9 | n.c. | >10000 | 107 |
| 5 | 1.9 | n.c. | 151 | 21 |
| 6 | 12.6 | n.c. | 794 | 263 |
| 7 | 5.9 | n.c. | 525 | 48 |
| 8 | 2.0 | n.c. | 162 | 41 |
| 39 | 2.5 | 3 | n.c. | n.c. |
| 36 | 3.7 | 16 | n.c. | n.c. |
| 41 | 11.8 | 3 | >10000 | 138 |
| 9 | 2.0 | n.c. | ~2754 | 25 |
| 10 | 4.9 | n.c. | ~5754 | 42 |
| 11 | 9.1 | n.c. | 1175 | 36 |
| 12 | 14.1 | n.c. | ~6606 | 22 |
| 37 | 4.3 | 9 | n.c. | n.c. |
| 13 | 1.3 | n.c. | ~3548 | 18 |
| 14 | 3.0 | n.c. | 251 | 54 |
| 40 | 4.3 | 3 | n.c. | n.c. |
| 42 | 8.9 | 36 | n.c. | n.c. |
| 15 | 2.5 | n.c. | 96 | 89 |
| 43 | 6.6 | 5 | n.c. | n.c. |
| 16 | 1.6 | n.c. | ~339 | 26 |
| 17 | 3.3 | n.c. | 182 | 5 |
| 18 | 4.1 | 16 | 9 | 1 |
| 19 | 5.0 | n.c. | ~692 | 6 |
| 38 | 3.4 | 12 | n.c. | n.c. |
| 59 | 12.9 | 37 | n.c. | n.c. |
| 20 | 20.4 | n.c. | 1479 | 372 |
| 21 | 3.0 | 21 | 3890 | 81 |
| 22 | 2238.7 | >10000 | n.c. | n.c. |
| 23 | 4.8 | ~79 | ~550 | 162 |
| 24 | 3.0 | ~74 | ~288 | ~214 |
| 25 | 1.7 | 10 | >10000 | 174 |
| 26 | 5.1 | 501 | ~525 | 692 |
| 27 | 7.1 | ~1202 | 1380 | 871 |
| 28 | 1.1 | 14 | >10000 | 851 |
| 29 | 3.4 | 16 | 51 | ~27 |
| 30 | 0.8 | 2 | 10 | 4 |
| 44 | 4.5 | 35 | >10000 | >10000 |
| 31 | 1.4 | 2 | ~31 | 4 |
| 32 | 1.7 | 10 | 525 | 195 |

TABLE A-continued

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
| --- | --- | --- | --- | --- |
| 33 | 8.1 | 17 | >10000 | 776 |
| 34 | 10.5 | 23 | >10000 | 1738 |
| 48 | 1.6 | 31 | >10000 | ~2344 |
| 35 | 4.3 | 69 | n.c. | n.c. |
| 50 | 3.4 | 56 | 3981 | 240 |
| 46 | 13.0 | 20 | >10000 | 778 |
| 51 | 3.4 | 4 | ~174 | 52 |
| 53 | 1.8 | 1 | ~468 | 12 |
| 47 | 35.5 | 51 | n.c. | n.c. |
| 49 | 34.7 | 115 | n.c. | n.c. |
| 54 | 4.2 | 2 | ~9 | ~7 |
| 52 | 7.8 | 20 | >10000 | 200 |
| 58 | 35.5 | 204 | >10000 | 2399 |
| 56 | 12.0 | 76 | ~5754 | 3236 |
| 57 | 17.4 | n.c. | >10000 | 11220 |
| 55 | 3.8 | 11 | >10000 | 107 |
| 60 | 4.8 | 17 | 603 | 100 |
| 1b | 2.8 | 2 | ~2818 | 58 |
| 2b | 2.0 | 4 | >10000 | 93 |
| 3b | 1.0 | 3 | >10000 | 91 |
| 4b | 8.5 | n.c. | ~6456 | 1905 |
| 5b | 20.4 | n.c. | >10000 | 468 |
| 6b | 5.9 | n.c. | ~851 | 398 |
| 7b | 11.8 | n.c. | 6310 | 1698 |
| 8b | 4.0 | n.c. | 6166 | 1148 |
| 9b | 6.8 | n.c. | 1660 | 204 |
| 10b | 9.6 | n.c. | 2399 | 1023 |
| 11b | 39.8 | n.c. | ~1820 | 1585 |
| 12b | 1.5 | 4 | ~549 | 251 |
| 13b | 2.0 | 29 | ~1862 | 457 |
| 14b | 2.0 | 6 | 3981 | 155 |
| 15b | 3.5 | 11 | ~4467 | 200 |
| 16b | 363.1 | n.c. | n.c. | n.c. |
| 17b | 3.0 | 3 | >10000 | 309 |
| 18b | 6.2 | 7 | ~5495 | 288 |
| 19b | 11.7 | 19 | ~5495 | 316 |
| 20b | 6.2 | 2 | n.c. | n.c. |
| 21b | 5.9 | 5 | 2512 | 269 |
| 22b | 7.1 | 3 | >10000 | 166 |
| 23b | 6.9 | 2 | ~2239 | 45 |
| 24b | 4.9 | 28 | ~5888 | 676 |
| 25b | 8.1 | 7 | >10000 | 3020 |
| 26b | 9.5 | 25 | ~9550 | 1698 |
| 27b | 4.47 | 13 | >10000 | 1585 |
| 28b | 17.0 | 251 | >10000 | 3388 |
| 29b | 3.9 | 6 | >10000 | 85 |
| 30b | 5.2 | 13 | >10000 | 263 |
| 31b | 5.0 | 63 | ~7762 | ~2138 |
| 32b | 5.9 | 8 | n.c. | n.c. |
| 1c | 30.2 | 23 | 1380 | 26 |
| 2c | 87.1 | 78 | ~6026 | 123 |
| 3c | 4.3 | 4 | 204 | 12 |
| 4c | 9.6 | n.c. | ~1023 | 9 |
| 5c | 12.0 | n.c. | ~692 | 23 |
| 6c | 34.8 | n.c. | 1622 | 10 |
| 7c | 148.0 | 72 | >10000 | 537 |
| 8c | 38.0 | n.c. | >10000 | 85 |
| 9c | 10.5 | n.c. | 5623 | 1175 |
| 10c | 4.3 | n.c. | >10000 | 63 |
| 11c | 4.3 | n.c. | 427 | 16 |
| 12c | 10.5 | 14 | n.c. | n.c. |
| 13c | 6.2 | 3 | n.c. | n.c. |
| 14c | 5.6 | n.c. | >10000 | 63 |

Prophetic Composition Examples

"Active ingredient" (a.i.) as used throughout these examples relates to a compound of Formula (I), including any tautomer or stereoisomeric form thereof, or a pharmaceutically acceptable addition salt, or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (I):

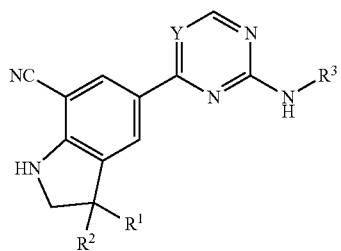

(I)

a tautomer or a stereoisomeric form thereof, wherein
$R^1$ represents $C_{1-4}$alkyl;
$R^2$ represents $C_{1-6}$alkyl, $C_{1-6}$alkyl substituted with one $R^5$, or $C_{1-6}$alkyl substituted with one, two or three fluoro atoms;
Y represents $CR^4$ or N;
$R^4$ represents hydrogen or halo;
$R^5$ represents $Het^{3a}$, $-NR^{6a}R^{6b}$, or $-OR^7$;
$R^{6a}$ represents hydrogen or $C_{1-4}$alkyl;
$R^{6b}$ represents hydrogen; $C_{1-4}$alkyl; $C_{3-6}$cycloalkyl; $-C(=O)-C_{1-4}$alkyl; $-C(=O)-Het^4$; $-S(=O)_2-C_{1-4}$alkyl; $-C(=O)-C_{1-4}$alkyl substituted with one substituent selected from the group consisting of $-OH$ and $-NR^{16a}R^{16b}$; or $C_{1-4}$alkyl substituted with one substituent selected from the group consisting of $-OH$ and $-S(=O)_2-C_{1-4}$alkyl;
$R^7$ represents hydrogen, $C_{1-4}$alkyl, $-C_{1-4}$alkyl-$NR^{8a}R^{8b}$, $-C(=O)-R^9$, $-S(=O)_2-OH$, $-P(=O)_2-OH$, $-(C=O)-CH(NH_2)-C_{1-4}$alkyl-$Ar^1$, or $-C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of $-NH_2$, $-COOH$, and $Het^6$;
$R^{16a}$ and $R^{16b}$ each independently represents hydrogen, $C_{1-4}$alkyl or $C_{3-6}$cycloalkyl;
$R^3$ represents
a) a fused bicyclic ring system of formula (1a-1) or (1a-2):

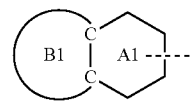

(1a-1)

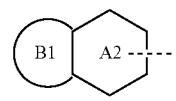

(1a-2)

ring A1 represents phenyl or a 6-membered heteroaromatic ring containing 1 or 2 N-atoms;
ring A2 represents 2-oxo-1,2-dihydropyridin-3-yl;
ring B1 represents a 4- to 7-membered saturated heterocyclyl containing one or two heteroatoms each independently selected from O, S, $S(=O)_p$ and N;
wherein (1a-1) and (1a-2) may optionally be substituted on the ring carbon atoms with in total one, two or three substituents each independently selected from the group consisting of halo; cyano; oxo; $-OH$; $C_{1-6}$alkyl; $-O-C_{1-4}$alkyl; $-C(=O)-R^{10}$; $-S(=O)_2-C_{1-4}$alkyl; $-S(=O)(=N-R^{20a})-C_{1-4}$alkyl; $-O-C_{1-4}$alkyl substituted with one, two or three halo atoms; $-O-C_{1-4}$alkyl-$R^{12}$; $C_{3-6}$cycloalkyl; $-O-C_{3-6}$cycloalkyl; $Het^{1a}$; $-O-Het^{1b}$; $R^{18}$; $-P(=O)-(C_{1-4}$alkyl$)_2$; $-NH-C(=O)-C_{1-4}$alkyl; $-NH-C(=O)-Het^{1g}$; $-NR^{17a}R^{17b}$;
$C_{1-4}$alkyl substituted with one, two or three halo atoms; $C_{1-4}$alkyl substituted with one, two or three $-OH$ substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;
wherein ring A2 may optionally be substituted, where possible, on the N-atom with a substituent selected from the group consisting of $C_{1-6}$alkyl; $C_{3-6}$cycloalkyl;

Het$^{1a}$; R$^{18}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; and C$_{2-6}$alkenyl substituted with one R$^{13}$; provided that when Het$^{1a}$ or R$^{18}$ are directly attached to the N-atom of ring A2, said Het$^{1a}$ or R$^{18}$ are attached to the N-atom via a ring carbon atom; and wherein ring B1 may optionally be substituted, where possible, on one or two ring N-atoms with a substituent each independently selected from the group consisting of C$_{1-6}$alkyl; C$_{3-6}$cycloalkyl; Het$^{1a}$; R$^{18}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; —(C=O)—C$_{1-4}$alkyl; —C(=O)NR$^{14g}$R$^{14h}$; —C(=O)—C$_{1-4}$alkyl-NR$^{14i}$R$^{14j}$; —C(=O)—C(=O)—NR$^{14k}$R$^{14l}$; C$_{2-6}$alkenyl; and C$_{2-6}$alkenyl substituted with one R$^{13}$; provided that when Het$^{1a}$ or R$^{18}$ are directly attached to the N-atom of ring B1, said Het$^{1a}$ or R$^{18}$ are attached to the N-atom via a ring carbon atom; or b) a fused bicyclic ring system of formula (2a-1):

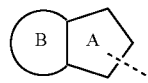

(2a-1)

ring A represents pyrazolyl optionally substituted with one substituent selected from the group consisting of C$_{1-4}$alkyl, —C$_{1-4}$alkyl-O—C$_{1-4}$alkyl, and C$_{1-4}$alkyl substituted with one, two or three halo atoms;

ring B represents a C$_{5-7}$cycloalkyl or a 5- to 7-membered saturated heterocyclyl containing one or two heteroatoms each independently selected from O and N;

wherein said C$_{5-7}$cycloalkyl or 5- to 7-membered saturated heterocyclyl may optionally be substituted on one or two ring carbon atoms with one or two substituents each independently selected from the group consisting of C$_{1-4}$alkyl, —C$_{1-4}$alkyl-O—C$_{1-4}$alkyl and —C$_{1-4}$alkyl-OH, or one ring carbon atom may optionally be substituted with oxo; and wherein said 5- to 7-membered saturated heterocyclyl may optionally be substituted on one or two ring N-atoms with a substituent each independently selected from the group consisting of C$_{1-6}$alkyl; C$_{3-6}$cycloalkyl; C$_{1-4}$alkyl substituted with one, two or three halo atoms; C$_{1-4}$alkyl substituted with one, two or three —OH substituents; C$_{1-4}$alkyl substituted with one R$^{13}$; —(C=O)—C$_{1-4}$alkyl; —C(=O)NR$^{14g}$R$^{14h}$; —C(=O)—C$_{1-4}$alkyl-NR$^{14i}$R$^{14j}$; or c) a fused 6- to 11-membered bicyclic heteroaromatic ring system containing one or two heteroatoms each independently selected from O, S, and N;

wherein said fused 6- to 11-membered bicyclic heteroaromatic ring system may optionally be substituted on the ring carbon atoms with in total one, two or three substituents each independently selected from the group consisting of halo; cyano;

C$_{1-6}$alkyl; —O—C$_{1-4}$alkyl; —C(=O)—R$^{10}$; —S(=O)$_2$—C$_{1-4}$alkyl; —S(=O)(=N—R$^{20a}$)—C$_{1-4}$alkyl;

—O—C$_{1-4}$alkyl substituted with one, two or three halo atoms; —O—C$_{1-4}$alkyl-R$^{12}$;

C$_{3-6}$cycloalkyl; —O—C$_{3-6}$cycloalkyl; Het$^{1a}$; —O-Het$^{1b}$; R$^{18}$; —P(=O)—(C$_{1-4}$alkyl)$_2$;

—NH—C(=O)—C$_{1-4}$alkyl; —NH—C(=O)—Het$^{1g}$; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; and C$_{2-6}$alkenyl substituted with one R$^{13}$; and wherein said fused 6- to 11-membered bicyclic heteroaromatic ring system may optionally be substituted, where possible, on one ring N-atom with a substituent selected from the group consisting of C$_{1-6}$alkyl; C$_{3-6}$cycloalkyl; Het$^{1a}$; R$^{18}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; —(C=O)—C$_{1-4}$alkyl; —C(=O)NR$^{14g}$R$^{14h}$; —C(=O)—C$_{1-4}$alkyl-NR$^{14i}$R$^{14j}$;

—C(=O)—C(=O)—NR$^{14k}$R$^{14l}$; C$_{2-6}$alkenyl; and C$_{2-6}$alkenyl substituted with one R$^{13}$; provided that when Het$^{1a}$ or R$^{18}$ are directly attached to a N-atom, said Het$^{1a}$ or R$^{18}$ are attached to the N-atom via a ring carbon atom;

R$^{10}$ represents —OH, —O—C$_{1-4}$alkyl, —NR$^{11a}$R$^{11b}$ or Het$^2$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^{1b}$, Het$^{1e}$, Het$^{1g}$ and Het$^4$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$ and Het$^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^2$ represents a heterocyclyl of formula (b-1):

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and
wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

R$^{11b}$ represents hydrogen; Het$^{1e}$; $C_{1-4}$alkyl; $C_{1-4}$alkyl-Het$^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

R$^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, —S(=O)$_2$—$C_{1-4}$alkyl, —S(=O)(=N—R$^{20c}$)—$C_{1-4}$alkyl, or —C(=O)—Het$^{1f}$;

R$^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;
Ar$^2$ represents phenyl optionally substituted with one $C_{1-4}$alkyl;
Het$^{3a}$, Het$^{3b}$, Het$^5$, Het$^6$ and Het$^{1f}$ each independently represents a heterocyclyl of formula (c-1):

(c-1) represents a N-linked 4- to 7-membered monocyclic saturated heterocyclyl optionally containing one additional heteroatom selected from O, S, S(=O)$_p$ and N;

wherein in case (c-1) contains one additional N-atom, said additional N-atom may optionally be substituted with $C_{1-4}$alkyl or $C_{3-6}$cycloalkyl; and
wherein (c-1) may optionally be substituted on one or two ring C-atoms atoms with one or two substituents each independently selected from the group consisting of halo, $C_{1-4}$alkyl, and $C_{3-6}$cycloalkyl;

R$^{11a}$, R$^{14a}$, R$^{14c}$, R$^{14g}$, R$^{14i}$, R$^{14k}$, R$^{15a}$, R$^{17a}$ and R$^{19a}$ each independently represents hydrogen or $C_{1-4}$alkyl;
R$^{14b}$, R$^{14d}$, R$^{14h}$, R$^{14j}$, R$^{14l}$, R$^{15b}$, R$^{17b}$ and R$^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

R$^{20a}$, R$^{20b}$ and R$^{20c}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;
and the pharmaceutically acceptable addition salts, and the solvates thereof.

2. The compound according to claim 1, wherein R$^3$ represents a fused bicyclic ring system of formula (1a-1) or (1a-2):

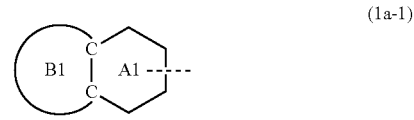

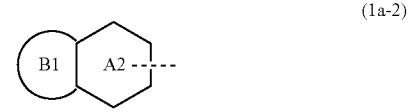

ring A1 represents phenyl or a 6-membered heteroaromatic ring containing 1 or 2 N-atoms;
ring A2 represents 2-oxo-1,2-dihydropyridin-3-yl;
ring B1 represents a 4- to 7-membered saturated heterocyclyl containing one or two heteroatoms each independently selected from O, S, S(=O)$_p$ and N;
wherein (1a-1) and (1a-2) may optionally be substituted on the ring carbon atoms with in total one, two or three substituents each independently selected from the group consisting of halo; cyano; oxo; —OH; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; R$^{18}$; —P(=O)—($C_{1-4}$alkyl)$_2$; —NH—C(=O)—$C_{1-4}$alkyl; —NH—C(=O)—Het$^{19}$; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; and $C_{2-6}$alkenyl substituted with one R$^{13}$;
wherein ring A2 may optionally be substituted, where possible, on the N-atom with a substituent selected from the group consisting of $C_{1-6}$alkyl; $C_{3-6}$cycloalkyl; Het$^{1a}$; R$^{18}$; $C_{1-4}$alkyl substituted with one, two or three halo atoms; $C_{1-4}$alkyl substituted with one, two or three —OH substituents; $C_{1-4}$alkyl substituted with one R$^{13}$; $C_{1-4}$alkyl substituted with one R$^{18}$; $C_{2-6}$alkenyl; and $C_{2-6}$alkenyl substituted with one R$^{13}$; provided that when Het$^{1a}$ or R$^{18}$ are directly attached to the N-atom of ring A2, said Het$^{1a}$ or R$^{18}$ are attached to the N-atom via a ring carbon atom; and wherein ring B1 may optionally be substituted, where possible, on one or two ring N-atoms with a substituent each independently selected from the group consisting of C$_{1-6}$alkyl; C$_{3-6}$cycloalkyl; Het$^{1a}$; R$^{18}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; —(C=O)—C$_{1-4}$alkyl; —C(=O)NR$^{14g}$R$^{14h}$; —C(=O)—C$_{1-4}$alkyl-NR$^{14i}$R$^{14j}$; —C(=O)—C(=O)—NR$^{14k}$R$^{14l}$; C$_{2-6}$alkenyl; and C$_{2-6}$alkenyl substituted with one R$^{13}$; provided that when Het$^{1a}$ or R$^{18}$ are directly attached to the N-atom of ring B1, said Het$^{1a}$ or R$^{18}$ are attached to the N-atom via a ring carbon atom.

3. The compound according to claim 1, wherein

R$^5$ represents —OR$^7$;

R$^7$ represents hydrogen, C$_{1-4}$alkyl, —C$_{1-4}$alkyl-NR$^{8a}$R$^{8b}$, —C(=O)—R$^9$, —(C=O)—CH(NH$_2$)— or C$_{1-4}$alkyl-Ar$^1$;

R$^9$ represents C$_{1-6}$alkyl, or C$_{1-6}$alkyl substituted with one substituent selected from the group consisting of —NH$_2$, and —COOH;

R$^3$ represents a fused bicyclic ring system of formula (1a-1):

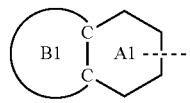

(1a-1)

ring A1 represents phenyl or a 6-membered heteroaromatic ring containing 1 or 2 N-atoms;

ring B1 represents a 4- to 7-membered saturated heterocyclyl containing one or two heteroatoms each independently selected from O, S, S(=O)$_p$ and N;

wherein (1a-1) may optionally be substituted on the ring carbon atoms with in total one, two or three substituents each independently selected from the group consisting of halo; cyano; oxo; C$_{1-6}$alkyl; —O—C$_{1-4}$alkyl; —C(=O)—R$^{10}$; —S(=O)$_2$—C$_{1-4}$alkyl; —O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; —NH—C(=O)—C$_{1-4}$alkyl; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{2-6}$alkenyl; and C$_{2-6}$alkenyl substituted with one R$^{13}$; and wherein ring B1 may optionally be substituted, where possible, on one or two ring N-atoms with a substituent each independently selected from the group consisting of C$_{1-6}$alkyl; C$_{3-6}$cycloalkyl; C$_{1-4}$alkyl substituted with one, two or three halo atoms; C$_{1-4}$alkyl substituted with one, two or three —OH substituents; C$_{1-4}$alkyl substituted with one R$^{13}$; —(C=O)—C$_{1-4}$alkyl; —C(=O)NR$^{14g}$R$^{14h}$; —C(=O)—C$_{1-4}$alkyl-NR$^{14i}$R$^{14j}$; —C(=O)—C(=O)—NR$^{14k}$R$^{14l}$; C$_{2-6}$alkenyl; and C$_{2-6}$alkenyl substituted with one R$^{13}$;

R$^{10}$ represents —OH, —O—C$_{1-4}$alkyl, or —NR$^{11a}$R$^{11b}$;

R$^{11b}$ represents hydrogen; C$_{1-4}$alkyl; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;

R$^{13}$ represents —O—C$_{1-4}$alkyl, —C(=O)NR$^{15a}$R$^{15b}$, —NR$^{19a}$R$^{19b}$, C$_{3-6}$cycloalkyl, or —S(=O)$_2$—C$_{1-4}$alkyl;

R$^{12}$ represents —OH, —O—C$_{1-4}$alkyl, —NR$^{14a}$R$^{14b}$, —C(=O)NR$^{14c}$R$^{14d}$, —S(=O)$_2$—C$_{1-4}$alkyl, C$_{3-6}$cycloalkyl, or Ar$^2$;

4. The compound according to claim 1, wherein

R$^5$ represents —OR$^7$;

R$^7$ represents hydrogen;

R$^3$ represents a fused bicyclic ring system of formula (1a-1):

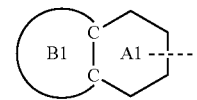

(1a-1)

ring A1 represents phenyl or a 6-membered heteroaromatic ring containing 1 or 2 N-atoms;

ring B1 represents a 4- to 7-membered saturated heterocyclyl containing one or two heteroatoms each independently selected from O and N;

wherein (1a-1) may optionally be substituted on the ring carbon atoms with in total one, two or three substituents each independently selected from the group consisting of halo; C$_{1-6}$alkyl; —O—C$_{1-4}$alkyl; —C(=O)—R$^{10}$; —O—C$_{1-4}$alkyl-R$^{12}$; —NR$^{17a}$R$^{17b}$; C$_{1-4}$alkyl substituted with one, two or three —OH substituents; C$_{1-4}$alkyl substituted with one R$^{13}$; C$_{2-6}$alkenyl; and C$_{2-6}$alkenyl substituted with one R$^{13}$; and wherein ring B1 may optionally be substituted, where possible, on one or two ring N-atoms with a substituent each independently selected from the group consisting of C$_{1-6}$alkyl; C$_{1-4}$alkyl substituted with one R$^{13}$; —(C=O)—C$_{1-4}$alkyl; —C(=O)—C$_{1-4}$alkyl-NR$^{14i}$R$^{14j}$; and —C(=O)—C(=O)—NR$^{14k}$R$^{14l}$;

R$^{10}$ represents —NR$^{11a}$R$^{11b}$;

R$^{11b}$ represents C$_{1-4}$alkyl;

R$^{13}$ represents —O—C$_{1-4}$alkyl, —C(=O)NR$^{15a}$R$^{15b}$, or C$_{3-6}$cycloalkyl;

R$^{12}$ represents C$_{3-6}$cycloalkyl;

R$^{11a}$, R$^{14i}$, R$^{14k}$, R$^{15a}$, and R$^{17a}$ each independently represents hydrogen or C$_{1-4}$alkyl;

R$^{14j}$, R$^{14l}$, R$^{15b}$, and R$^{17b}$ each independently represents hydrogen or C$_{1-4}$alkyl.

5. The compound according to claim 1, wherein

R$^2$ represents C$_{1-6}$alkyl substituted with one R$^5$;

R$^5$ represents —OR$^7$;

R$^7$ represents hydrogen;

R$^3$ represents a fused bicyclic ring system of formula (1a-1):

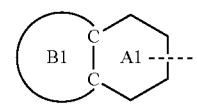

(1a-1)

ring A1 represents phenyl or a 6-membered heteroaromatic ring containing 1 N-atom;

ring B1 represents a 4- to 7-membered saturated heterocyclyl containing one heteroatom selected from O and N;

wherein (1a-1) may optionally be substituted on the ring carbon atoms with in total one, two or three substituents each independently selected from the group consisting of —O—$C_{1-4}$alkyl; —O—$C_{1-4}$alkyl-$R^{12}$; and $C_{1-4}$alkyl substituted with one $R^{13}$; and wherein ring B may optionally be substituted, where possible, on one N-atom with a $C_{1-6}$alkyl substituent;

$R^{13}$ represents $C_{3-6}$cycloalkyl;

$R^{12}$ represents $C_{3-6}$cycloalkyl.

6. The compound according to claim 1, wherein $R^3$ represents a fused bicyclic ring system of formula (2a-1):

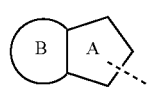

(2a-1)

ring A represents pyrazolyl optionally substituted with one substituent selected from the group consisting of $C_{1-4}$alkyl, —$C_{1-4}$alkyl-O—$C_{1-4}$alkyl, and $C_{1-4}$alkyl substituted with one, two or three halo atoms;

ring B represents a $C_{5-7}$cycloalkyl or a 5- to 7-membered saturated heterocyclyl containing one or two heteroatoms each independently selected from O and N;

wherein said $C_{5-7}$cycloalkyl or 5- to 7-membered saturated heterocyclyl may optionally be substituted on one or two ring carbon atoms with one or two substituents each independently selected from the group consisting of $C_{1-4}$alkyl, —$C_{1-4}$alkyl-O—$C_{1-4}$alkyl and —$C_{1-4}$alkyl-OH, or one ring carbon atom may optionally be substituted with oxo; and wherein said 5- to 7-membered saturated heterocyclyl may optionally be substituted on one or two ring N-atoms with a substituent each independently selected from the group consisting of $C_{1-6}$ alkyl; $C_{3-6}$cycloalkyl; $C_{1-4}$alkyl substituted with one, two or three halo atoms; $C_{1-4}$alkyl substituted with one, two or three —OH substituents; $C_{1-4}$alkyl substituted with one $R^{13}$; —(C=O)—$C_{1-4}$alkyl; —C(=O)NR$^{14g}$R$^{14h}$; —C(=O)—$C_{1-4}$alkyl-NR$^{14i}$R$^{14j}$.

7. The compound according to claim 6, wherein $R^1$ represents $C_{1-4}$alkyl;

$R^2$ represents $C_{1-6}$alkyl substituted with one $R^5$;

$R^5$ represents —OR$^7$;

$R^7$ represents hydrogen;

$R^3$ represents a fused bicyclic ring system of formula (2a-1):

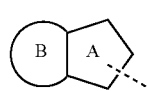

(2a-1)

ring A represents pyrazolyl optionally substituted with one substituent selected from the group consisting of $C_{1-4}$alkyl, and —$C_{1-4}$alkyl-O—$C_{1-4}$alkyl;

ring B represents a $C_{5-7}$cycloalkyl or a 5- to 7-membered saturated heterocyclyl containing one or two heteroatoms each independently selected from O and N;

wherein said $C_{5-7}$cycloalkyl or 5- to 7-membered saturated heterocyclyl may optionally be substituted on one ring carbon atom with one or two $C_{1-4}$alkyl substituents, or one ring carbon atom may optionally be substituted with oxo; and wherein said 5- to 7-membered saturated heterocyclyl may optionally be substituted on one or two ring N-atoms with a $C_{1-6}$alkyl substituent.

8. The compound according to claim 6, wherein $R^1$ represents $C_{1-4}$alkyl;

$R^2$ represents $C_{1-6}$alkyl substituted with one $R^5$;

$R^5$ represents —OR$^7$;

$R^7$ represents hydrogen;

$R^3$ represents a fused bicyclic ring system of formula (2a-1):

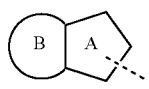

(2a-1)

ring A represents pyrazolyl;

ring B represents a 6-membered saturated heterocyclyl containing one heteroatom selected from O and N;

wherein said 6-membered saturated heterocyclyl may optionally be substituted on one ring carbon atom with one $C_{1-4}$alkyl substituent, or one ring carbon atom may optionally be substituted with oxo; and wherein said 5- to 7-membered saturated heterocyclyl may optionally be substituted on one N-atom with a $C_{1-6}$alkyl substituent.

9. The compound according to claim 8, wherein $R^3$ represents a fused bicyclic ring system selected from the following structures:

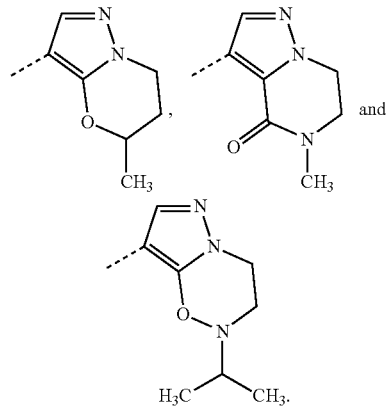

10. The compound according to claim 1, wherein $R^3$ represents a fused 6- to 11-membered bicyclic heteroaromatic ring system containing one or two heteroatoms each independently selected from O, S, and N;

wherein said fused 6- to 11-membered bicyclic heteroaromatic ring system may optionally be substituted on the ring carbon atoms with in total one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; R$^{18}$; —P(=O)—(C$_{1-4}$alkyl)$_2$; —NH—C(=O)—C$_{1-4}$alkyl; —NH—C(=O)—Het$^{19}$; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; and C$_{2-6}$alkenyl substituted with one R$^{13}$; and wherein said fused 6- to 11-membered bicyclic heteroaromatic ring system may optionally be substituted, where possible, on one ring N-atom with a substituent selected from the group consisting of C$_{1-6}$alkyl; C$_{3-6}$cycloalkyl; Het$^{1a}$; R$^{18}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; —(C=O)—C$_{1-4}$alkyl; —C(=O)NR$^{14g}$R$^{14h}$; —C(O)—C$_{1-4}$alkyl-NR$^{14i}$R$^{14j}$; —C(=O)—C(=O)—NR$^{14k}$R$^{14l}$; C$_{2-6}$alkenyl; and C$_{2-6}$alkenyl substituted with one R$^{13}$; provided that when Het$^{1a}$ or R$^{18}$ are directly attached to a N-atom, said Het$^{1a}$ or R$^{18}$ are attached to the N-atom via a ring carbon atom.

11. The compound according to claim 10, wherein
R$^5$ represents —NR$^{6a}$R$^{6b}$, or —OR$^7$;
R$^{6b}$ represents hydrogen; C$_{1-4}$alkyl; C$_{3-6}$cycloalkyl; or —C(=O)—C$_{1-4}$alkyl;
R$^7$ represents hydrogen, C$_{1-4}$alkyl, or —C$_{1-4}$alkyl-NR$^{8a}$R$^{8b}$;
R$^3$ represents a fused 6- to 11-membered bicyclic heteroaromatic ring system containing one or two heteroatoms each independently selected from O, S, and N;
wherein said fused 6- to 11-membered bicyclic heteroaromatic ring system may optionally be substituted on the ring carbon atoms with in total one, two or three substituents each independently selected from the group consisting of halo; cyano; C$_{1-6}$alkyl; —O—C$_{1-4}$alkyl; C$_{1-4}$alkyl substituted with one, two or three halo atoms; C$_{1-4}$alkyl substituted with one, two or three —OH substituents; C$_{1-4}$alkyl substituted with one R$^{13}$; C$_{2-6}$alkenyl; and C$_{2-6}$alkenyl substituted with one R$^{13}$; and
wherein said fused 6- to 11-membered bicyclic heteroaromatic ring system may optionally be substituted, where possible, on one ring N-atom with a substituent selected from the group consisting of C$_{1-6}$alkyl; C$_{3-6}$cycloalkyl; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; and C$_{2-6}$alkenyl substituted with one R$^3$;
Het$^{1d}$ represents a 4- to 7-membered monocyclic saturated heterocyclyl containing one or two heteroatoms each independently selected from O, S, S(=O)$_p$ and N;
wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and O—C$_{1-4}$alkyl; and
wherein said 4- to 7-membered monocyclic saturated heterocyclyl may optionally be substituted on one, two or three ring C-atoms with one or two substituents each independently selected from the group consisting of —OH, halo, C$_{1-4}$alkyl, cyano, —O—C$_{1-4}$alkyl, —NH$_2$, —NH(C$_{1-4}$alkyl), and —N(C$_{1-4}$alkyl)$_2$;

R$^{13}$ represents —O—C$_{1-4}$alkyl, —C(=O)NR$^{15a}$R$^{15b}$, —NR$^{19a}$R$^{19b}$, C$_{3-6}$cycloalkyl, or Het$^{1d}$.

12. The compound according to claim 10, wherein
R$^1$ represents C$_{1-4}$alkyl;
R$^5$ represents —OR$^7$;
R$^7$ represents hydrogen;
R$^3$ represents a fused 6- to 11-membered bicyclic heteroaromatic ring system containing one or two heteroatoms each independently selected from O, S, and N;
wherein said fused 6- to 11-membered bicyclic heteroaromatic ring system may optionally be substituted on the ring carbon atoms with in total one, two or three halo substituents; and
wherein said fused 6- to 11-membered bicyclic heteroaromatic ring system may optionally be substituted, where possible, on one ring N-atom with a substituent selected from the group consisting of C$_{1-4}$alkyl substituted with one, two or three —OH substituents; C$_{1-4}$alkyl substituted with one R$^{13}$;
Het$^{1d}$ represents a 4- to 7-membered monocyclic saturated heterocyclyl containing one or two heteroatoms each independently selected from O, S, S(=O)$_p$ and N;
R$^{13}$ represents —O—C$_{1-4}$alkyl, —C(=O)NR$^{15a}$R$^{15b}$, or Het$^{1d}$;
R$^{15a}$ represents hydrogen or C$_{1-4}$alkyl;
R$^{15b}$ represents C$_{1-4}$alkyl.

13. The compound according to claim 10, wherein
R$^1$ represents C$_{1-4}$alkyl;
R$^5$ represents —OR$^7$;
R$^7$ represents hydrogen;
R$^3$ represents a fused 9-membered bicyclic heteroaromatic ring system containing one N-atom;
wherein said fused 6- to 11-membered bicyclic heteroaromatic ring system may optionally be substituted on the ring carbon atoms with in total one, two or three halo substituents; and
wherein said fused 6- to 11-membered bicyclic heteroaromatic ring system may optionally be substituted, where possible, on one ring N-atom with a substituent selected from the group consisting of C$_{1-4}$alkyl substituted with one, two or three —OH substituents; C$_{1-4}$alkyl substituted with one R$^{13}$;
R$^{13}$ represents —O—C$_{1-4}$alkyl, or —C(=O)NR$^{15a}$R$^{15b}$;
R$^{15a}$ represents hydrogen or C$_{1-4}$alkyl;
R$^{15b}$ represents C$_{1-4}$alkyl.

14. The compound according to claim 13, wherein
R$^1$ represents methyl; and
R$^2$ represents methyl or —CH$_2$—OH.

15. The compound according to claim 14, wherein Y represents CR$^4$.

16. The compound according to claim 15, wherein R$^4$ represents hydrogen.

17. The compound according to claim 14, wherein Y represents N.

18. The compound according to claim 1, wherein the compound is selected from compounds

465 466
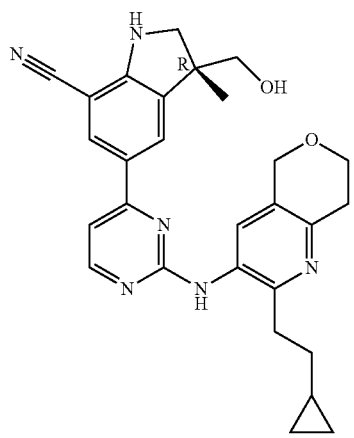 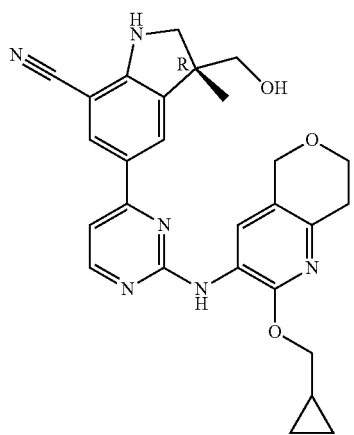
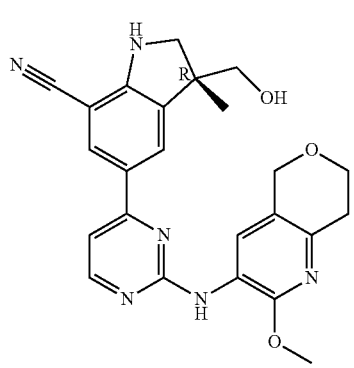 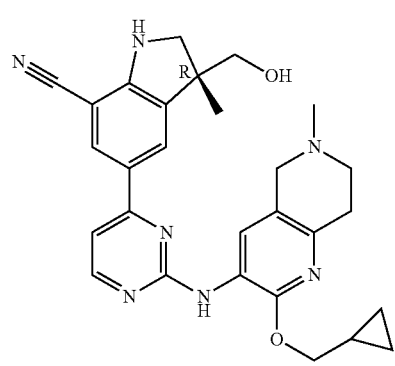
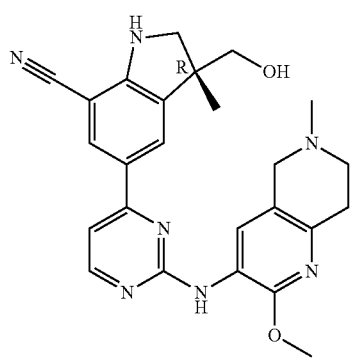 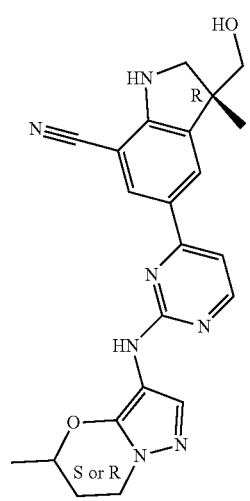

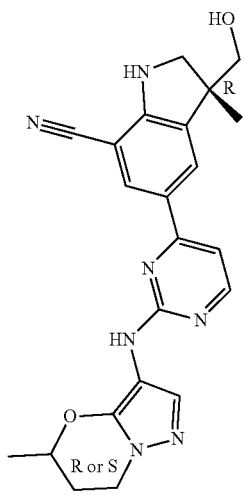

and tautomers and stereoisomeric forms thereof, and the pharmaceutically acceptable addition salts, and the solvates thereof.

19. A pharmaceutical composition comprising a compound as claimed in any one of claims 1 to 18 and a pharmaceutically acceptable carrier or diluent.

20. A method of treating leukemia, lymphoma, or myeloma in a warm-blooded animal comprising administering to the said animal an effective amount of a compound as claimed in any one of claims 1 to 18 and a pharmaceutically acceptable carrier or diluent.

* * * * *